United States Patent
Safadi

(10) Patent No.: US 9,469,855 B2
(45) Date of Patent: Oct. 18, 2016

(54) MODULATION OF NLGN4 EXPRESSION, NK CELL ACTIVITY IN NON-ALCOHOLIC FATTY LIVER DISEASE (NAFLD)

(71) Applicant: HADASIT MEDICAL RESEARCH SERVICES AND DEVELOPMENT LTD., Jerusalem (IL)

(72) Inventor: Rifaat Safadi, Nazareth Elit (IL)

(73) Assignee: Hadasit Medical Research Services and Development Ltd., Jerusalem (IL)

(*) Notice: Subject to any disclaimer, the term of this patent is extended or adjusted under 35 U.S.C. 154(b) by 0 days.

(21) Appl. No.: 14/963,319

(22) Filed: Dec. 9, 2015

(65) Prior Publication Data

US 2016/0115485 A1   Apr. 28, 2016

Related U.S. Application Data

(63) Continuation of application No. 14/501,160, filed on Sep. 30, 2014, now Pat. No. 9,243,294.

(60) Provisional application No. 61/884,153, filed on Sep. 30, 2013.

(51) Int. Cl.
| | | |
|---|---|---|
| A61K 48/00 | (2006.01) |
| C07H 21/02 | (2006.01) |
| C07H 21/04 | (2006.01) |
| C12N 15/113 | (2010.01) |
| A61K 31/7088 | (2006.01) |
| A61K 45/06 | (2006.01) |
| C12Q 1/68 | (2006.01) |
| A61K 31/713 | (2006.01) |
| A61K 31/7105 | (2006.01) |

(52) U.S. Cl.
CPC ....... *C12N 15/1138* (2013.01); *A61K 31/7088* (2013.01); *A61K 31/713* (2013.01); *A61K 31/7105* (2013.01); *A61K 45/06* (2013.01); *C12Q 1/6883* (2013.01); *C12N 2310/11* (2013.01); *C12N 2310/14* (2013.01); *C12Q 2600/158* (2013.01)

(58) Field of Classification Search
CPC .......................... A61K 48/00; C12N 15/113
See application file for complete search history.

(56) References Cited

U.S. PATENT DOCUMENTS

| | | | |
|---|---|---|---|
| 4,816,567 A | 3/1989 | Cabilly |
| 5,641,870 A | 6/1997 | Rinderknecht |
| 5,910,573 A | 6/1999 | Plueckthun |
| 7,579,392 B2 | 8/2009 | Gan |

FOREIGN PATENT DOCUMENTS

| | | |
|---|---|---|
| EP | 0404097 | 12/1990 |
| WO | 93/11161 | 6/1993 |
| WO | 93/15210 | 8/1993 |
| WO | 96/13583 | 5/1996 |
| WO | 96/37621 | 11/1996 |

OTHER PUBLICATIONS

Bian and Ma (2012) Liver fibrogenesis in non-alcoholic steatohepatitis. Front Physiol 3: 248.
Bird et al., (1988) Single-chain antigen-binding proteins. Science 242(4877): 423-6.
Björkström et al., (2010) Expression patterns of NKG2A, KIR, and CD57 define a process of CD56dim NK-cell differentiation uncoupled from NK-cell education. Blood 116(19): 3853-64.
Bolliger et al., (2001) Identification of a novel neuroligin in humans which binds to PSD-95 and has a widespread expression. Biochem J 356(Pt 2): 581-8.
Bolliger et al., (2008) Unusually rapid evolution of Neuroligin-4 in mice. Proc Natl Acad Sci U S A 105(17): 6421-6.
Clackson et al., (1991) Making antibody fragments using phage display libraries. Nature 352(6336): 624-8.
Cooper et al., (2001) Human natural killer cells: a unique innate immunoregulatory role for the CD56 (bright) subset. Blood 97(10): 3146-51.
Holliger et al., (1993) "Diabodies": small bivalent and bispecific antibody fragments. Proc Natl Acad Sci U S A 90(14): 6444-8.
Huston et al., (1988) Protein engineering of antibody binding sites: recovery of specific activity in an anti-digoxin single-chain Fv analogue produced in *Escherichia coli*. Proc Natl Acad Sci U S A 85(16): 5879-83.
Kohler and Milstein (1975) Continuous cultures of fused cells secreting antibody of predefined specificity. Nature 256(5517): 495-7.
Lopez-Vergès et al., (2010) CD57 defines a functionally distinct population of mature NK cells in the human CD56dimCD16+ NK-cell subset Blood 116(19): 3865-74.
Marks et al., (1991) By-passing immunization. Human antibodies from V-gene libraries displayed on phage. J Mol Biol 222(3): 581-97.
Melhem et al., (2006) Anti-fibrotic activity of NK cells in experimental liver injury through killing of activated HSC. J Hepatol 45(1): 60-71.
Moreira (2007) Hepatic stellate cells and liver fibrosis. Arch Pathol Lab Med 131(11): 1728-34.
Moretta (2010) Dissecting CD56dim human NK cells. Blood 116: 3689-3691.
Muhanna et al., (2007) Lymphocyte-hepatic stellate cell proximity suggests a direct interaction. Clin Exp Immunol 148(2): 338-47.
Muller et al., (1998) A dimeric bispecific miniantibody combines two specificities with avidity. FEBS Letters 432(1-2): 45-49.
Sans et al., (2000) A developmental change in NMDA receptor-associated proteins at hippocampal synapses. J Neurosci 20(3): 1260-71.
Seki et al., (2011) Antitumor immunity produced by the liver Kupffer cells, NK cells, NKT cells, and CD8 CD122 T cells. Clin Dev Immunol 2011: 868345.

(Continued)

*Primary Examiner* — Amy Bowman
(74) *Attorney, Agent, or Firm* — Roach Brown McCarthy & Gruber, P.C.; Kevin D. McCarthy

(57) ABSTRACT

The present invention provides a method of treating, attenuating or preventing a liver disorder by inhibiting NGn4 expression and thereby modulating the activity of NK cells. The present invention further relates to diagnosing a liver disorder by evaluating NLGn4 expression in NK cells.

6 Claims, 7 Drawing Sheets

(56) References Cited

OTHER PUBLICATIONS

Wang et al., (2010) Delivery of siRNA therapeutics: barriers and carriers. AAPS J 12(4): 492-503.

Zapata et al., (1995) Engineering linear F(ab')2 fragments for efficient production in *Escherichia coli* and enhanced antiproliferative activity. Protein Eng 8(10): 1057-62.

Zelber-Sagi et al., (2011) Nutrition and physical activity in NAFLD: an overview of the epidemiological evidence. World J Gastroenterol 17(29): 3377-89.

Clinical Trial No. NCT01133184: Improved Prevention of Perinatal Hepatitis B Transmission. Updated May 27, 2010, http://www.clinicaltrials.gov/ct2/show/NCT01133184?term=nct01133184&rank=1.

https://en.wikipedia.org/wiki/Small_interfering_RNA.

Page 661 left column of Microbiol Mol Biol Rev. Dec. 2003; 67(4): 657-685 http://www.ncbi.nlm.nih.gov/pmc/articles/PMC309050/).

Wittrup et al., Knocking down disease: a progress report on siRNA therapeutics, Nat Rev Genet. Aug. 18, 2015; 16(9):543-52 (10 pages).

SEQUENCE LISTING

```
<160> NUMBER OF SEQ ID NOS: 20

<210> SEQ ID NO 1
<211> LENGTH: 338857
<212> TYPE: DNA
<213> ORGANISM: Homo sapiens

<400> SEQUENCE: 1
atctctcttt ttcttgcaga accgtctctc tcccttctct gtctcttagc acagagctct      60
tattcagcca ctagcttggc ccttcctgct tcaattgtaa tgcttgttct gcccgtccac     120
agactattgg cggcagaaac aacgaatttc ctccaaacta ggcggtgttg gtggctcttg     180
cattcctctg gatgaggaaa tctagttggg gggttccaga aggggaaggc tcctgggctt     240
tcaatacatc ctcctgaatc atacctcgtt tcgggttccc tagaaaaatc tggacgtgta     300
aaaagaactc ttaacggccg atgcagctct tccaaagcta aggtaggtgc agttttaaga     360
cctgtctctg ggacattatt ctcattttaa aaagccgttt aaacattttg acttgcagca     420
aaggatggaa agcctcactg cagatacttg agcttcactt catctgatct ttattttttc     480 ctttatgat tattaatatt attttggaa aatttggaca ggactttctc ccatctgtct      540
cgctgcattt cttaggtgtg ggtgggagtg tagaccttca tacggttttt acatgcaacc     600
tctccacaga aatatttggt tttatttca cttaaagaga aaaatccaga ccaccgttgt      660
ttggaagcgt tttgctgcaa tcagctattt gaacggctct ggggccgtgt gtgatgtgtt     720
tacaaagtag cgctgccttc cacacaaata aacagaagac tgtggcgggg agaggaggaa     780
aaaaatatat atgtatctgc agtacaggga gaagaaggag agaagcggcc agggctggag     840
atggtgaagg caggaagact tctgcaaact gtgaggcatg ggaggctttt cttttctttt     900
tctctccccc cccaccccc cccttattc tttaagaaaa ctgtcagcta ccaccgcctg       960
gggtgctttt ttgagggggtt ggggggggtgc tgttaaccag aaagaaaaag ggaaaaccgg    1020
cttggttggg gtcgcattta agcgatttt tttccctcct tcatctccgg gcctcggata     1080
agatgacggc ttgggtgatg cacgaaataa cgcacgtgat tgattagacc tggcttggct    1140
tggctaggga acgatccagg cgcgctggag accccgcgtg aagatgaaat gacggtagct    1200
ccgggctgct tctgtaaacc ggggagcggg ctccatgcac ccctttcccg tgtgtgtggg    1260
tttcgaggcg ggtgggaagg gtgaggcaag ccgcagaagg agggtagagc tggtggtttt    1320
gcttctttcg gagcctttga gtgtagtctg aacctttgag gggggcgcgg gggggcttgc    1380
agctgccgcc ctgggaacca tctctgaact gcccgctttt ccgaaggagc ggaaaagttg    1440
gaagctgcga ggacagacta ccggagccct ggtctggtc tcgggggatc tggagcccta    1500
gtcggtgccc actgagaaca cccttctcg gagcgagggt gtcgggggga gtgttaagcc     1560
```

```
tgcggggcgc acggtccgcc agtccccgag gtggggacgg gggaggaggc tgaggagtcg    1620
gttccaatag gcgcaccacc tctacagccc tggaaaacgc aaccgccacc ccctcttccc    1680
ttccatccca tcccaagcct ctctgctgtc ccgggccgat ttcatctcgt ctcttccccc    1740
gcctccccgc ttccccgcct cccaattccc gcgcggctcg gctcagcccc ttcccactcc    1800
agtgggcaga actgatggag aagatccgcc aagcgcgcag ccggcggcgg aggagacagt    1860
gcggggtggg cgaggggctt cgagaccacg cagagagaga gtgaacttca gtcctgaccc    1920
ctccccaagg ccgcggctgg ggcgcccaca gcccgcgctg gcacccgcgt ggcctgacct    1980
gcggaagcgc gagcggggat gaggtaggga gaggaggta ggtgccgctc ggctgcagat    2040
gatgcgtggg tgggggcttt gctgtgggag gagaggccca ggtcccggcc tgcgccctcc    2100
actccgcggc tgctccctcc gcctctggtt ttccaagagg ccggtcgcta ccccggagga    2160
cactctcatc cttcagtcag tctcctggac acccccttcct cctcctgtcc ctcaacctga    2220
cctggctctt tcgcccctcc gagaaccggt aggctggggt ccctcggcgg ggttctcctg    2280
ggccgcaccc gaagctttgc gccccggta tccgggccca gtgctccgtg caaccctggg    2340
cccgagcgca cgattccggc gcctgctcgc cgccagacac agcgcccttt cttcccggag    2400
cggcggggc gggagcaggg gggtcaggcc aaccccttgca cccccgaggc ctggcccggg    2460
ccaccctggg aacggatgtt ctgcatggag agcgaggggc agccggagga cgtcctccgc    2520
atcataccccc tccccttccc cagaaggctt ttttttttc cggactgcgg gttttctttt    2580
ctctgccttc ttcctctgaa cctacggcag gtgtcagcct cttttgtgt atgtgctgct     2640
gctatctcgg ggatgcgggg ggaggggtg caggaggcag cgtgaagggg tcctaggagg     2700
ttccggcggg gttttggccc ctgcggtgcg ccggggcttg caactcgccc gggtgctggg    2760
cgcgcgcgtc acgaattcag cctagggctt gggcgagtct gcggggagtg aggacagagg   2820
atcccgatct gtcatttgga cccaacttaa gaaatttggg gtgggggttg ggtggggggtt    2880
ttggaactaa gcaggtgatg ttcttgcgag ctggatccac aaggtggtag tatgcttct     2940
ttttatttt atttttattttt attttctattt ggtcattttt tttgggggg gcggtggttt   3000
gttgttgttg ttgttgctct tatcttatgc ttttttgaagg catccgttgc ccgtagggtt   3060
tacatcggag cgcgttgcat tatattttct tgaaggggg tggtgtgcgt gagctcccat    3120
ctcagaatca gcccttccgg tgatgtgagg aaggcaaaag caaaaaaaaa aaaaaaaaa    3180
aaaaaaaaa aagaaaaaa agaaagaaaa aaaaggaaaa gaaaaagttt agggagacct     3240
cgttatcctg acgaagcaga attgccagtt tgtgtgggcg ttctgcgggc aacatagaag    3300
tgcatgctta agaaatccgg ggtagcttcc ttctccagct agaaattaaa tggccagggt    3360
gcaaacacct gactttgatg agaacaaagc ggcagaaact gcaagagacc tgcatggttt    3420
gaatggacgc actgagcctt ttcctagggg atggcagagc ggggtgaaat cagatagcaa    3480
agaaatctgc cgttttgtgg gggcagattt ggagagtgga gaattatttc atacctttag    3540
ttggctgtgg ggaagatgtt agcagtaatc cattaaatcc tcagcataga tttttcctgtg   3600
gaaatgagca aaatgttaag tgggggaggg atggctaatg gcacatggtt gcattaatcc   3660
ctgtatttcc agaaaaaaat atggaatttc tgtgtatcct aaaattaaga atacaggaat    3720
ttcatggaga actctgcaag catgtatttt ctcagattag aaattcagta ttttattact   3780
caatgaaatg tagaatgcgt gtgtgtgtat gtgtgtatac agacatacac acacgcattc    3840
tacatttcta catatatgtg tgtgtgtgtg tatatatata tatatatata tatatatata    3900
tatatggcca ttttaaagag tattttcttt gacatgtaag aacataatca gggccagttg     3960
```

```
tagcaagtgg aaaattactt catcagtttt aagtcagtag attaaaatgg aaggcttcat    4020
ttttttttga aatcagaata ataattgcat tttcataata atgcctgtgc gtggatgcag    4080
ttttaaagat gctttgatgt tttcttctcc agtggaagaa ttgctacttt tctttgcgtt    4140
ttatttaaat aaactaatgc cgagtataca gttggccctc aaaccagtaa cctagctgat    4200
ttttacccaa acctgagaat gtaacagata cttgataagg gactggtggc tgcataaggt    4260
agataatgaa gttatcttga tgctgtgaaa tttacaagca gacttgaaag aatttgaaag    4320
ttcatagttg ttggcctgga atgtagccta atggtaaata tatagatttt ttaaaatttg    4380
tgaacttggc tatttcattg ttttgtgtgt agtaatttgt ggaaagctta tagtctctcc    4440
acaaagatga gagtgttgac tgactccgca acagagactt gcttttggaa gtgcaggggt    4500
ctctttaaaa gccatttgga atactgtgct tttatttcta gaccacaacc aaaaggttct    4560
caaaaaacta acattcaag tgcacgaggg aatgacctcc gtttaacatt ctttcttttt    4620
aattggtacg ccacatttca aaccttttgt aatactgttg aatattgcca ataatgcaac    4680
ttgttgagcg aatgcattgc attcaaatga agtagcaata tacaaatatt ttaagtcctt    4740
tagtatcctc cttctaaaga taggcttatc tggttaaaat atacttatat tccaaataag    4800
gtgagagttg gtcttaagat gtgaatgtca agtgtaagag acacgatttt agtttgtaaa    4860
ccagaatgta ttctttctgt actgcttttct gccttttaac aatatgtatt ctattcccaa    4920
atggggaaat atgttcagtt tagtttaaat ctgttgctct ttttgtgtgt gttttttgtct    4980 gagtactgta ctttttcaga ggagagactt cgtctcctat ttaattatgt gaatggatat    5040
tcagacagat ttgaatagcc accactgatt tcttaaactc ctgagctacc agttttaaat    5100
caaagataca tcttttgcac agtcaattag aggaagtgag aatcaaaatt gaagcccagg    5160
ctgctgaggc aattaggtca tctgctgtgc tctctactac cattcactca acgaatattt    5220
tccagttctg tcatttttct ctaaacaacc tacatttgga ctttgaaagg ctccactgtt    5280
ctttgttaag tgaacggcag tgtaggaagc ccttcctcat ttttcttgga gcacagtagc    5340
acacatgaac aagaaaaaaa agaaggtgat agctcctagc agtttgtcat tgtgccattt    5400
ataggctttg aataaatgta tagatgaaaa ggctttccct ctgcaggtgg ttacattaaa    5460
caaaaaataa gtaaataaaa gcctcataaa atcattacgg gagtggaagg ttggtggtgg    5520
aaaacagccc atctacctcg ggctgagatt tcaaacttta gacatctcgt gttcagttca    5580
cgtgtcccag gtgtgtgcgg aacacctcca tacaccacat cttcccaagg cactctcatc    5640
ttcccagaaa tggtacctga aggagaacag acctaacccc aacaatacta aaatacgtat    5700
ataaaaaact atatatagta agatatgtat cctactatat aatatatata tggtaataca    5760
tattatagta aggtctgcat catgtatata aaaatacact atatatctta ttattatata    5820
tatagtgaga tgaggtgtat taatccattc tcaggctgct aaaaaagaca tacccaagac    5880
tgggtaattt gtaaaggaaa gaggtttaaa tgactcacag ttcagcatgg ctggagaggc    5940
ctcaggaaac ttacaatcat ggtggaaggg gaagcaaata cttccttctt cacatgatgg    6000
caggaaggag aggaatgaga accgagtgaa gggggaaacc ccttataaaa tcaacagatc    6060
ttgtgagaac ttactcacta tcataagaat agcatggggc aaactgcccc catgattcaa    6120
ttacttccca cccacatccct ccacgacacg tggggattat gggagctaca atccaagatg    6180
aggtttggtg gggacaaagc caaaccatat catgaggttt tattgaattt atttgagaca    6240
ggaaaagagt aatcctccat aatttagaaa ggagatgaag tacaatgaac atttaggtcc    6300
```

```
tcattagttg aggaatacat ttcaaagaga gaaatgttaa tttcagtata gtgctaatga    6360
aacgatctag gctttcactg ctctctggaa atgtggataa atggcccaga attttgtttg    6420
ggttgtttta tttaaaatgt atattatata aagaaatcat ggtttgtcaa agtaacagag    6480
tgctattttt ggcttacaac aggactttct tagctccacc tgttaatatc ggtgatcatt    6540
ttggttttaa gaggctggta cctgattgga tgatgaaaac ttggatctca aagccatcac    6600
cccagacatg tgattttatt aacatctgtg gcatctgtc cggctcccac atcaacccctt    6660
catccaggct cattttctgt tgttttttgt ttggttgttt gtatgctttg gttggggaga    6720
ggggacacgg attttgctaa gggcacctt tcaggagtg aaacttagcc tgtcatataa       6780
gctgaaaagg aacttgggtt gtttcaagtt gcattacttg gtaagttttt ggatccttta    6840
aaaaagaaag gactgaggtt actaaaagtg ttattggcac tgataaaaga gctatggtga    6900
attgtggttt gttttgtaa agtgcagaaa aggcctcttt ggttctgtga tgatggctgt    6960
ggtgaagttg catgcggtgc cattttccat gtttagtatt tcaacaccac caatatgtgg    7020
ctctggagta tgggacgggc aagtccaaga actcagtgag gcatgccgtg tgactccaat    7080
ggtcagagct gttcagcatg gaactgtggt ctcaaaagca tgggggatgg gggcagaaga    7140
agctcgctgc aactgagtgc ctttaactta ttccactctt cagtactctc tgtgactata    7200
actctgtgaa tgggttaggt ggggaaactc acaaaagtaa atgcatgttt tcacaaacaa    7260
aatatgtcat tgttaactgt tttcctaagt gagacaatat gccctcatgc cctgaagcta    7320
catggtaaga atggcagtgt gtatgagcgg gtgtatacac atacatgtat gcatatgcta    7380
acacattaac taggaactag tctttgctga aaatgttttt ctcagccatt gcaacacatt    7440
agataaaagc aaatatatat atatatatat atatatatat atatatatat aatataagaa    7500
ggaaaaatgt ggttttccat tattttcttt ttcttatcct catcattcac caaatctata    7560
ttaaacaact cataacatct ggcctgggta atagagtgag accccaactc cacaaagaaa    7620
caaaaattaa aaacaaatta gccgggcctg atggcaagta cctgtggttc cagctgaggt    7680
gggaggatca cttgagccca ggagttcagg gctgcagtga gctatgatta cgccagtgta    7740
ctccagcctg ggagacagag caagacccta tctctaaaaa tataaataaa taaataaata    7800
aataataaat aaaaatagaa aatgtacaat gaaagttata aagttggcca ggcgtggtgg    7860
ctcacgcctg taatcccagc actttgggag gctgaggtgg gcgaatcacc tgaggtcagt    7920
agttcaagac tagcctggcc aacatggcga atcctgtct ctactaaaaa tacaaaaact    7980
agctgggtgt ggtggtgtgt gcctgtaatc ccagctatac aggaggctga ggccggagaa    8040
ttgcttgaac ctgggagggg gaggttgcag tgagccaaga tcgtgccatt gcactgtagc    8100
ttgggtgaca gagcgagact ctgtctcaaa aaaaaaaaa aaaaaaaga aagttataaa      8160
gttacctatg atgggtctgg atgtactcct tatttaggag tgaagacatt cgttaacatg    8220
agacctaagt aagtagaaag tatgtgttta agggacaggt gtccattttc tctaggtctc    8280
ctggaagctt ttttttttcta atttgagtac tagttccaaa aaaggtgtta ccgcctatgt    8340
ttatagtgaa actatctatg tgtgacaaaa ttctaccctc tcttgtccat caatattgtg    8400
caatgttgtg tacttgtatg gagaaataga caacttttac aaagatcaaa ctaggcaccc    8460
tttaccaacg ctaaactcat aacccttta tctgcctttg tagaagattc tcacctttat     8520
ttctcttggt ccctctgaga aatattttcc tctgagacaa tgcaatctat gcctcatctt    8580
taagcaatcc tagctcacca gtatgagtaa tgttgtctat ttttaaggtt atctcattat    8640
tctaaaagac tttaaattgt tgaaaaataa attgtgtgag gggtggtaga gtttgaaaca    8700
```

```
attatctgtg atgttaccag atattttaga ctaaaatata ttagaatcca aggtattgtt   8760
catgccttaa aaatgctgaa atatctgact gttgcttatt aattttaaaa agaatatagg   8820
aaatagccat taattaatga ggctgttttcc actaccacat aaaaaaaaaa aaagctcaca   8880
ggtgcctgta tgttttttgtc gaatcaaagt aatctgcttt atgtatgcat ttattcatag   8940
aatttactaa aatcaaaatc aaggttttat aaatataggg tttgacaaag ttttaaaata   9000
taaccagcta tacaaatatg gcatgtggga aattctatta aattgtcatg aacatgcttc   9060
tttgtcattc caggagtctt tcttttcatt actctttcct atttgatctg ttattctata   9120
gaattatctt cattttctct ttaatacttt aaggatccct gagaccttgt cactcatcca   9180
aatagaataa aggaatgagg gaagaaagaa ggaagggaag aaggaaggaa gaaaggacgg   9240
aaggaagaag gaagggatgg aggaacgaag ggaggaaggg agggaaggaa agaaggaagg   9300
aaggaaggaa gaaagaaaga aagaaagaaa gaaagaaaag agaaaggaa ggaagaaagg   9360 aagcagggag ggagggagaa ggatgataga tcgaagggaa ggagagaagg agggaaggag   9420
ggaaagaaga aaggaaggaa agaaagaaga gaaaaaggaa ggagagaggg agggaatgaa   9480
ggaaagaagg aaagaaggaa ggaaagaaag aagagaaaaa gaaggaagga aggagggaag   9540
gaaggaagga aagaagaaag gaagggaaga gggaaggaag ctgtggtttc tgtgcaccat   9600
taactaacaa tagctcctgt gaaccagcct ggaagttcat tcaccacata caatatagtt   9660
tcttttggaa aatgcatgtc aaactatata tatggtttgt gtgtgtgtat atatatatat   9720
acacacacac acatacatat atatacgtat atatgtatat acatataaaa tttgcatgta   9780
cttttcatac aaaagaacaa gaactatata tatacaatat atatacattg gaatatattt   9840
attatagatg tatatggatt ttactatata ttatttcttg aaaaagtata agaactcccg   9900
aatcagggat tctttcttga agaggctgcc tggtccaata ttttttggaaa accatatatc   9960 atttgcctct cttcaattat atcctgaaaa tggacacatt atggccttaa agtctcctgt  10020
actaatgggt ttagcagctg tgacggataa cttagggttc ttttgtaatga gttttaacca  10080 aattaaccac aagagtgttg agaatacttc tgttgacaca gagcagaaag aagtactaac  10140
agggtatgaa gatacttgaa agtgtttaaa ttaccaagac tacttggaga tatgaacttg  10200
ttggtttttt tctttatttc acgaatttat tcaaaacttg ttgagtacca ataagtgggg  10260
tacaaagaag atgaaattgc ttatcttccc tatattaacc atacactaat gttattttgc  10320
acctctggtt ttatgtttaa gaacaaataa gttttaccag aattttttctt ctggtgtgtg  10380 tgtgtgtgtg tgtgtgtgtg tgtgtgtggg tttaatctct catgtcctat ttcaaaagtt  10440
aaggaaaaca acagcttgat tcagtcttca tacatctttc ttaaatagtt aagggcaaaa  10500
tcatcagagc tacatagccc aaatattagg aattaggttc atgttcgaat tctcagaggg  10560
taattatata gttcgatttt aacttcttca acagaccgac tactacagtt gatgagcaag  10620
gagatgaaag tatttgataa acatcatgga gttaatatga ttcttgaggg aggggagaag  10680
gctgcttgtc ttaggtaatg cttttgaggg taggtttgtc ctagccttga ggtagcaggc  10740
ttgctctgtt ggctgaagaa gccttaacat gcatgcccgt attgcaaatt tacccacatg  10800
ccaactgtat gctgtgggaa gaaatgaata atgtagatgc cattacaggg aattaggcgg  10860
aacggataga cttagtgcat cagaaccaat gagaagtaga caagacattt agaaaatagc  10920
aacagcaatg aaaacaaata taagtaaacc acaatcaaaa cccttacatt tgggtttcta  10980
gttgcctgtt accacagagg gttctggtta ctagctaaaa tgtaacccag taggaaggtc  11040
```

```
aagacaaggc ccctcatgct gtctcaaaca gtaacaaaca gtaaggatga cccagggaga   11100
aagggtaaca agttacatgg aagttaaata ccagttacct gtgcagagac tgaaaacata   11160
aagcagacac aggaatggca gtagtagaaa gtggggaaaa tctgaatttg ttgcagcata   11220
aaaccaacca accaacccta gtgagggaat caatacctca aaaaaaaaat cttctgacaa   11280
tctaggttca tggtagagat taaacggtac catattatga ggacagaaca ataaatcaca   11340
catggcttcc catagaattt gtgtgacagt ggttgtgtac tatgattcag tctgtcatga   11400
caatttcacc agtaaaataa ccttccagga tttatttgat atctcaattg ataagcctcc   11460
cgtaagtgaa taaccagaat atgacataat ttataaaaat taacttaaaa ttacacaaga   11520
agttatgtgt ctagtcattt cacaatcaaa tgtatttagg catttaatct agtaagatcc   11580
caaataataa aaaattgttt ctttctagac caacatgtat cctgatgtta taaatacata   11640
tgtaaattat atacatatat ttgtatatgt aaaatacaca tacatttaca tatgcataca   11700
tagctcactt tttattgggg agcacatctt cctgaaggtt tttcaaagaa taattattct   11760
acctgtaatg ctgtagcagt atttgtaaaa agttcaaatg tggctgggta cagtggctca   11820
tgcctgtaat tccagcattt tgagaggcca aggaaggagg gttacttgag cccaggactt   11880
tgagaccagt ctaggaaaca ccatccatac gaaaaaaatt taaaaataag tcaggtgtgg   11940
tggtgcatgt ctgtagtccc tgttactcag gaggctgagg tgtaaggctc acttgaggag   12000
tatatcagga gtttgaggct gcagtgagct atgacctcac tactgcattg cagcctgggc   12060
aacagagtga cactccatct cttaaaaaga attcaaatgc ctcatttatc tggacagaat   12120
ttgattggtg ttattctatt gctgaataat tccagggtat gcatttacct tttctctatt   12180
gactttaaac atagcttatg aaaacaaac aaacaaaaac caaacagagg agtttgcaaa   12240
actatattta aaagtaaacc atactccctc accctgact ccacaaaaat actgtttaat   12300
gtagagaaac cacagacggt gcagccccca aatctggagc atcctcaggt acctggggc   12360 attctggagt gaggggctga gcctcagagg catttggtca cacttgggtg gggatgcctc   12420
attggctagt gaagaagcag ctgtctcttc catgtagtgg tcagttgtgg cctctcctgg   12480
aagggaattt atccagcagt gtgtgttcct gaagatgcta atagcaaatt atgttcagtg   12540
aagccagctg catcctgttg gtcttgctag tcccgggatt cttgccacag caggtcagaa   12600
tggaagggag ctgcttatct ttcctcctta cttcctctcc ccatcccagc tctcatctga   12660
catccttcca acacctatat gacaggaaaa aaattctctc ttcaaattaa gaaaagggtc   12720
tggtctgggt acgatggctc atgcctgtaa tcccagcact ttgggaggac gaggtgggtg   12780
gatcatatga ggtcaggagt tcaagtagtg aaaccccatc tctactaaaa atacaaaaat   12840
tagccaggtg tggtggcacg tgcctgtagt cccagctact caggaggctg aggcaggaga   12900
atggcttgaa ctcaggagtc ggaggttgca gtaagctgat atcacgccac tgcactccag   12960
cctgggcgac agagcaagac tctctctcaa aaaaaaaaa aaagtgtttt gagtatttac   13020
tctccacatc tttcagctat ttcacttcac tgggagtaga caggacagga tggctccagg   13080
gacagtgcta ttgttacctt gttatccact tccaatttgg aaaggtaaaa atatgcttca   13140
gtgtctacta aattgcctgc attgaatttg aagtacagtt tgttgggata ctcatgatga   13200
aattggaaaa cagaatcaca gattgttagg acttgaatgt acttgagcaa tcatttgtat   13260
tccctcatgt acacaaggaa attgagtcac agagagtttc agtgattat cctcatcctt   13320 tttttttttt tttgagacgg agtttcgctt tcgttaccca cgctgagtg caatggcgca   13380 gtctcggctc accgcaacct ctgcctccca ggttcaagtg tttctcctgc ctcagtctcc   13440
```

```
caagtagctg ggattacagg cacacaccac cactgctggc taattttgta tttttagtag    13500
agacagggtt tctccatgtt ggtcagctgg tctcgaactc ccgacctcag gtgatccacc    13560
tgccttggcc tctcaaagtg ctgggattac aggcgtgagc caccatgccc ggccgtgatt    13620
tatctccata attttaaaca ctatccctgc aatgaaaaag gaatacccccc aattttttaac  13680 atatctgctt acgccagttc atgacaagct tacaaaatta gaagtaattt taaatgggca    13740
aaataaagca aagtgcatta tttaatttttc aaaacagact tttctttatt atgcagcagc   13800
gatttaaaca gataaatcat ttctatgaaa gggactagca gagaaagcag gaaaagacat    13860
gtcccacatt aaaagctgaa cttgttggtg ggaactcatt ttgttttatg agttatgatg    13920
aatgcacctt agctgtttct aaccccgctc ccattccctg ttttttatttg taagtcagaa   13980 cccagcattt ttacattttt tgaagtgtta attaattgcc tttgtttaat gcaccttgct    14040
gtgtctcaag cattgttaag aaaggataag atcttttttca gggatgattc tttcctttcc   14100
ttacagggct ttgtctgtga tgagaacttt ctatacacat attttttcttt ttaagagacg   14160 gggtctcact atgttgcgca ggctggtctc gaacgcctgg gctcaaggga tccttcggac    14220
tgacctcctg aaatactggg attactggtg cgagccaccg cacttggctc tatctttctg    14280
caaaaactgg tggattctac ttctctctcc atctatgttt agtcctggga gatataatca    14340
agagaaaaga aacatctacc ttcattagat taagagtcaa acaaaagggc ctagaggcaa    14400
agaggctcca cgaccctctt ttgcgggtga gcctgtgcat tgaaatcctc agcttcaaag    14460
agacacagaa ggcaaaatag gaagttggat ttgcaggagt tagtctcttg gagggtcttg    14520
taaaattgaa gggttcacat atgccctgtc aactctccaa gagagagatg acttggtgaa    14580 atctgtatttt tgtgatgatt agtctttctc agagggctgg ttcaagggca aacgaagggc   14640
agaataagga cttgcagatg tgttaagaac agaacccgct gtgttgtgcg tcaacgacaa    14700
aagcccactc cactcctgac attcatattt tggggtaact gttttttgca gtgcagacct    14760
gtgaaacctg gagtatttcc agtcacagct tttatcgaga tgctttctgt tgacctgaga    14820
attaattatg gtttgtcaaa cagcttgacg accttgtcag tggtgttttt tggtttttac    14880
aactccccat ctaaggattt gagaatgccg cagtggataa aactgtgtga ctgacgttca    14940 ttatttttttt ccacaatgct ttaaagtaag tgcgctggga atgctccatt tattatgtag   15000
aggagagaca tttccaaact ttaacttttgt tgctgttgct tttgtacact gaggcattga   15060
ttctgcagga ttaaaagaag gtgctgatta ttccatttgg tggaaagttt caggagtgga    15120
agccagcaga attgttccac tgagatgata attctgactc tttgattctt acacattgac    15180
tacttttaca aaatacaaac ctgttttaat ctttttaaag gacatttgtg cgctactgtt    15240 ttcattttttt aaaataacct tttaaaaatt ttaggatagt ttcaggtttg ctgaaaggtt   15300
gcaaagatag tacagagagt tactctttaa ctccacacgc atatcgcatc ttacgtgacc    15360
atctgttaca cttaaggaac caacattagt acgttactaa gaactgacat cacaatttgt    15420
ttggatttca ctggtgtcca cctaatgtcc ttttttctctt ctgaggtacc atctgaaata   15480
ccacactgca tggatttgcc ctattttctt agcctcatct agtctgtgac agtttctcag    15540 ttttttccttg ttttttcatga ccttaatagt tttgaggtat taatgtcatg gagaatgtcc   15600
accaactaga gccagtctga tgttttagac aggggtatgt gtttgggggga ggaaatccac   15660 agagatgaag gttccttcca tctcacccta gcaacggtga ctactgtcca gaagactttt    15720
gctgctggtg ttggctttga tcacctggct gacagagagt ttgtcacttt tctctgctgt    15780
```

```
aaagttgtac tctcccctcc ctgcccaagt ctagtctttg aaaccaagtc cctaaagtgg    15840
ggtgggggtg ggagaagagg cagaattaag ctccactttc cggatggtgg aatatcgata    15900
aattatttgg aattcttctc taagaaagat gggtctctcc cctttattta cttaatcaat    15960
catttatatc agtatggaca catggatatt ttagatatgc tttgggctac attgctgtga    16020
cttattccac tttatattcc ttgtggccat gatgtagaca ccagagagtc tattcacttg    16080
aatagcaagt aaatgagggg actcaatggt aaatgactct tagagaaact ctcagccctg    16140
ctggttcatg gatgctcagc ttgcaaaaac accttcttcc atcaggaaac ctcagtggat    16200
gggcaaacat tacagcgtcc ttgaatatgc ttcattgctt taatctacga acttcctatg    16260
cagtaagcaa aaccacccat accacagctt aagagtgggg ctttcctccc aacactcatc    16320
ctagtgtctt ttgataaaga ggtataaagt tgaaggaaca tgttactaac cagaagactt    16380
ccagaggacc ccattgatca gggtagatga atggctgtgt gcgtcttgtc acaaccatca    16440
gtatttcaaa aggtgatatc atcctcttaa ccttatgatg tgttttaaca taaaattta    16500 atatgcatac aggcggttat tacttaagca ttgcttaaga agcagtcttt ttttttttaat    16560 tcatgtaact ggatctattc tctgaataag gaatataagc aaatcgtagc catttcaagg    16620 actcttttt tttttttta aatggagtct tgctctgtcg cccaggctgg agtgcagtgg    16680
cgcgaccttg gctcactgca acctccacct cctggttcaa gccattctcc tgtctcagcc    16740
tcccaagtag ctgggattac aggtgcccac gagcacacca ggctgatttt tgtgttttta    16800
gtagagatgg tgtttcacca tgttagccag gctggtctcg aactcctgac ctcagatgag    16860
ccgcccacct caacctcctg acgtgctggg attacagaca tgagccactg tgcccagcct    16920
caaggaggct tttaagggca ggatgttttt ttttcttatg gtgaaggaat gaagagtagt    16980
atgggaaaga aatacagaaa ctttgaaaaa agaaatgtaa aactggatca tcattccata    17040
ggctagtagt taatagtaaa taactgtata gtttgttcaa gggattttgt gaatatttta    17100
aacacagatg ataattctct atctacatct acgtgtttac ctgcatttat atcatatgta    17160
cgtatggaca tatatatttg cctgtagatc acatctttgt atggtatctg taccaatatt    17220
agagtctata gctacagcat atcaataaca gtatctattc ttatctatat cttaatcata    17280 tctattttg tatctgtaca catatcttta ccgatattca cattatattt ctatgtctag    17340
atctatatat atctctatct ataccatttt gaactttaca tttcctacag tatgatagca    17400
taagctattt taggattatt aaaaatcttc ataagcattg ttttttcatgg ttaattttct    17460 caaaagacta tgctttaaca tacccagttc tttatatatt ttttgacatt tggcttattt    17520
taatgttttt gctcctctaa tgtattttc ttttttact ccacacccct cccgcctcta    17580
attttcaaat tgggcattct tcattatagg ggcattgctt attttctttt gtatgtttca    17640
aaaaacattc tgcattggtc tgtacacatt tttccctctt gtatcccttc tgtaaacatt    17700
tgtattcact tgaaacctta tggaatattt tactacagaa aatttctggt tatgataaaa    17760
aaaggcagag aagatagaat aaaggatccc atgtgcccat cagttggctt cagcaattat    17820
gaatggatag cctaatcttt agtatctaac ttcattcata tttccattct tattatggca    17880
tgatgtaatt catttaaaga tatgtctgta cgttgctcta aaatatagga accattttat    17940
tttacacagc tgcagaatct tttccatgcc taaaattatc aacagtagtt cctctgtatc    18000
atccactata aagttgtaac tgtcaaaatg atcttctcgt agttttgtaa ctcacgcaag    18060
gtcaaggtct agcactgcaa taggttgatt tgtcttttac atttctttta attgatatag    18120
cttccctatc tttttatgca cattcttgtt gaaaaaactg ctctttttac tctacatgaa    18180
```

```
agtgggtttt agaattggaa aatgtagttg tcaagttatt ttagaaggaa cgtgtgtatt    18240
ttccgtaatg cacagtctta agttactaac tccttaggag caaacgctgt gtgacttggt    18300
agtgttctac ccagaaggaa tgctgctggg taaatttggc cagctacgtg acagctcttt    18360
ggactcagta tatctcagtt ttatctattt ttaacaaggt tttattttga agacagggtc    18420
tcgctctgtc gcccatgctg gagtgcagtg atgcaatcat agctcgatgc ggtcttgaac    18480
ttctgggctc aagcaatctt cccacctcag cctcatatta tctagtacct ggcagagata    18540
cagatctgat gagaagcaaa gatagagggg tgtcagaagg tagcttttgt tgcaccatta    18600
catacataca cacacacaca cacacacaca cacacacaca aacgggcgca cacgcacgca    18660
caaagaatca actgcaattt tttcctcttt gccaacccac agttaagtaa aattattagt    18720
tctattgaac tccacattgc atgtgatatt ttgaatgata gaggctaaag agaggccaaa    18780
gagggaggat tgcttgaggc caggagttca agacgagctt cgacaacata atgagaccgc    18840
gtttctacag aaaaaaagaa aaaaaatagc cagatgtgat ggctcgctcc tgtaatccca    18900
gctactggag aggctgagac aggaggatgg cttgagccga ggagttggag gctgcagtga    18960
actctgatag tgccactgca ctccagcctg ggtgacagag agattctgtc tctaaaaaac    19020
aggaaaaata tgactaaaga aaaccaaact aatctaatct atacagttat agatagttgg    19080
ctatcattct tatgctaatg taagtatgcc tcattttaag aagagttgtg tgtgtgtatg    19140
tgtgtgtatc tgtgagtgtg tgtgtatgca tgatataaat ccagacttct aagcgagtat    19200
cagggatggt gaactattat tagtagatca ttggaacctg ttacacaagg atgcactaga    19260
gaattttaca aactattaaa ttctgtataa tttaaaatgt gacttgattt actcagatat    19320
tttaaaagga tgcatgtctc ttacaaaaca agatttacta actttggtgc tcttgacgtt    19380
gaggctggat aattctttgt tgtggtggct gtcctgtgcc ttgcgtgatg ctgaatggta    19440
ttgctggact caagcttcta ggtgcccgtt gtatacacgt tcctgtttta aaaaaaactt    19500
atataaattt aacgggcaca agtgctgttt tgttacatgg atatattgca tagtgatgaa    19560
atctgggttt ttagtgtaac caccacccaa ataacataca ttgtatccat taagtaattt    19620
ctcattcctc atcatcctac caccctccca cctttttgat tctccagggt ctattattcc    19680
actctctgtg tccatgtgta cacattattt agctcccact taggagtgag gacatgtggt    19740
ttttgacttt ctgtttccga gttgtttcac ttaaggtaat ggcctccagt tccatccatg    19800
ctcctgcaaa agagatagtt tcgttctttt tatggctgaa taatatttcg ttattcatat    19860
ataccacatt ttctttattc atttatccat tgatggatgc ctagctggat tccatatctt    19920
tgctattgtg aatagtgcgg tattaaacgt atgcgtgcag gtatcctttt gacatagcga    19980
tttcttttta tttgcgtaga tacccagtag tgggattgct agataagatg gtagttctat    20040
ttttagttct ttgaggactc tccatactgt tttccataga acttatacta atttacattc    20100
ccatcaacag tgtatgtgga ttcccttctc tctgcatcct catcaacctc tgttatgttt    20160
tgagtttgac atccacaatg tctgcagaca gtctcagata tccccttggg agtaaaatcc    20220
atcccagtta aaaagctctg ttatgaaatg aggtgtactt attccaagtt ttacatgggg    20280
aatttcactg gttttgggt tctagtagcc ccgacgtgta tactgggcat gaccagataa    20340
gataaactgg gcaaagagtg caatgagaga tagtaaccac attattttgg aagatgtttt    20400
tcataaccag aatagacttt atgaattcta tcaattgtaa tgagaatcgg attgacattt    20460
ggggacagtt aatataacgc acgttatccg aaaggaggtg gcattgattt atataagtga    20520
```

```
gagcttacga gaaaacaaag actggaaata aagaaaaaga aaatccttga taagtatctg   20580
atagaacaaa gtgcagaacg aaatgcagct agcttatcta aaattgggca aaatcatgtt   20640
ccaaatgaaa gctcagtaga tgggaagaga gtatttgaac atttgatgtg aaaaatgaga   20700
tttactgttc cacagatatg aacacattga tgagagctgt cagttattag aacttattaa   20760
catcaatggg aacaccagaa atgtgctgca cagaaaatta aatttaagac tgtttgaaaa   20820
tggtgttata ttttctgaac tgttacattg attgattaaa attagattat ccaacaaaat   20880
aagaactttt gatattctgt gagtgaatat gagatgaatt tatgtggcag atgtgttttt   20940
aaaagatgta ttattaaccg cagagattca gaattaatgt cgccaacccc aaagaatgca   21000
gtataacatt tgtcataagt gacctcataa taggttattt tataatatcg ttttttaattt  21060
tgataataaa tggacacctt ttacatcttt aataataaaa ggatatatgc aaaaccagtt   21120
atttttattc caatgttaat aaaatagcaa taagcctcat ttcatttgaa gcaccaactt   21180
tcactccata tcaaatttct aaaagtctgg gagatactca ccaactagtc aagaagattt   21240
tcattctata aaattgtata atgcagtgaa tcctgttctt ttcccatatg catttattta   21300
atatttatat ttgatacaag gaatctatat tattttcatt aagccactca taaacgtaag   21360
tgttttactt cttcttgggt acattttttaa aaatttggtt acattttttga gatgttgatg   21420
ccatggttaa aatattccaa ctaagtaatg ggatgggttt acaataagtt tttgctctac    21480
aaggaaaatg gtcaataaat caggctccag ccaattatag gagaaaagga aaagttaact    21540
tattatacat tattgcacac agtgtttgat gtatgtatgc aaattgctcc caaatacagt    21600
ttggttgcag ttgtgctcca catttatggt ggatgcagtt ttgaatatgt gcagagagaa    21660
tatattctga cctcattcat caatgtgatg caaatgtgta gaaatggcaa ggtcattttt    21720
gtatgatgat aaaatgcctg tttgaaagta aactcatcca cccatccatc caaggttgc    21780
attttctcaa ttcccaattc taaatatgtc tgtgtgtgtg tgtgtgtatg tgtgtgtgag    21840
agagagagag agagaatcta gtgcaatttt attgttctac tttgttccag gcttgacatt    21900
ttagtgattg aaactaaaat accttgattc ttaccctcta attttacaaa taaaatctgg    21960
tttactgtta tggattgaac tgtgttacag attgaattgt gttccccaaa aagatatatt    22020
gaaatcctaa tgcccagcac ctcagaatgt gatcttattt tgaaataagg tctttgcaga    22080
tgtaattaca atgaggtgat taaggtggcc cttattccgt acaactggtg tcgtaaccac    22140
catgtgaaga cacagacact cacagggtga agacggccat ctgatgatgg aaggttggca    22200
tgatgcagct acaaaaaggg aatgccaagg attactggca actccctgaa tttagaagag    22260
acaggaaagt atcctcacca agaaccctca gagggagcat ggccaacatc atgatttttgg   22320
acttctagac ttcagaactt tgagagagta tattcctgtt tcctgagaca taagccttgt    22380
gattcttttt gatagtaact ctaggaaact catacaccaa gacacagagt tatttattta    22440
aattcatttt ttttcattta aaaatactta tttgacaaag actgtaatat ggaaagtgtc    22500
cagtgtgatg actggatgta cgtatacatt gtgtaacaat gatcacaatc aaattaatga    22560
acatatcact catagcccat gtggtacata atggatggac ctgaagttat gcagccagct    22620
tggggcagag ctgggtttga agggcagact cctcacccag ccacacttgt cttccagaat    22680
cactttcaca tcgtcatgag gattttagag actccactgc tccatgtcac tgcatcaaca    22740
cattgtggag tgggggggtct cataattcat tgcaggtgtc tgaagatcaa cagttgggtt    22800
tcccttccct caactgtaaa atgagtgagt tggacctgtc tccagggcct ttctaagcta    22860
tatgatttga gaacaatgat cattgtaatt aagacgcttg acttgaatac tgctcatttt    22920
```

```
aaaccatgat tagggatatg agatgctccg tgtgttttct aaataaactt cattgtgacc  22980
tggttaagtg ttggatatga attggcaaga ggaggcttgc tagtagaaat ggtgtaattt  23040
aaaacccatt cacaagtatt tacacactgc aagacatcta gatcctcaga agtcaggtag  23100
tatcctaaaa gcacagtgtg taatttatgg tagataattg aaattgcact gaaattgaac  23160
ttggtggtgg ggagtacact tcatagtatt caattttgc cttcacttta ttctatgtct  23220
gactctcagg aaataggaac tgcaacgttg gtttctccca gtgtatttc aacttcaaac  23280
ttgtgaattg taaaccatta aacaaatgat caaacactac atctttccct gctcttgtat  23340
ggacatagag ttttgttatt catgccttct cttttcttat ctgggaagag atctttctta  23400
acctttagaa attggattaa tgcgaccctc tttaacctca catttgatgt gaatgtcaga  23460
actttttgaa acttagctgt gcttttagta cactgatcac tgagtgcccg ttgactggca  23520
ggcactgggc tgctcagtga ggtaggtgaa gaagagacac cagctccctc ctggagtgtg  23580
tgctctgctg gaggataaag acacttatca agcaatagca taaatgcttc tgacaccatg  23640
actctaatca gagtggcaca gccaatgggc atggggctag gagaatatga gaattcgtag  23700
gtatggggat gctgtcaggg ttcatgaaag gtcttcccaa tgatgagaaa actgcaagtt  23760
gggaggaggt agaaataact gaaagaaatg gttgtagaga tgaatacatt gggggatgat  23820
cgtgttgcag ggtgacatct tttagtgata aaagggatag agtttgagct cctgctgcag  23880
accctcagcg atgtgttgta atggtaagaa ttggctcatg gtttcctggt ttgcctgatt  23940
gctgcatcca caaaccatg ggttctgggg ttaattccca tccatttgt tgctgaattt  24000
ctcagaatga tagtcttcgg tacattgtta ctgaaaggag gtgctaaacc caatgtcttc  24060
attgcttttg aagcagatgg tccagtgtag tgtttctcaa acataagcat cagagtgtcc  24120
tagaggtctt gttaaaggca aattgctggg atccatccca ggagtttctg agtcagcaga  24180
tctgagatgg gacccataat tccccagttg aagttgccgt tactggtctt gggatcactc  24240
ttttagaact actgccttag ggtatttctg ggttacatgt gcacacatga cctgcttaag  24300
ttttgagctc aacattctgt tttattcctt cctgttcaga ggccggcatc cacagctctg  24360
ggtctcatca tttgcttttt gtcatccagt tgtgctctac tgatttataa gttatcttta  24420
tgttttcagt ttcccagtca attcaagcca atgcatattt attgggcatc taccatgtgc  24480
tatgactgt gagggactta agattaata acaacaacca taaaaactca ttgacgtgct  24540
gggcattatt tatttcccca tggccccccaa atgctaggct tatcattcaa aacactacag  24600
caacttgaag gcagcagatt gtttctcatt tcagggatcc acaggtatat ggcttctcaa  24660
acgaaggtct ggtaattcca ggctgcatgc agctattctt cctttaaaga ctgagaaacc  24720
atgcatacaa catcttttct tccttcttcg tttatacatt tgataactat gtactgacat  24780
cttactttga gaaggtcacc atgccagata ccgtcagtga tagaaacaca gataagattc  24840
aacctctgat cccagggaga ctctcagtaa ggaagagaaa atgagaaatg aaagtaccta  24900
tactacaagg catgcacgtc acacattcca taagtgggta aaaacacaga ccttggcagc  24960
acagaatctt gttttccatt tgtgtcattt aggacactgc attggttatc tattgctgca  25020
taaaaaattc ttctaaacct taggttaaaa ctgcaaacat ttatcatctc atgcatttct  25080
atacatcagg gatttaggag cagtgtagct ggccagttct agctcagggt ccgtcatgat  25140
gttgtggtca agttgtagac agggcttgca gttttatgac ggtgttggag aatctcactt  25200
atgtgtcact tggcaggagg cttcagttct tggccacatg ggcttctccc tagggctaga  25260
```

```
cgtgtgacat taacagctgg cttttctgaa agtgaggaga gaaagaggga ggctgaaaga    25320
gagtctaagg tgaaagccac acactcttag aacttgatct tggaggtgac accttgtcac    25380
ttttgcactt gatttggagg tgacaccttg tcacttttgc tacatgctat tggttgttca    25440
aatcaaatct ggcaccatgt ggatgaggat tccaggaagg tgttaattgc aggtgtcagt    25500
tggccatctc agaagctaga ctatcaccag aagctcttcc aaaggaggtg gcttatgagc    25560
tgcatagaat tttgtcataa ggacaaagga gaaagtgtga acaaacacat aggtacagca    25620
agtgttgagg aatgggctgt gttgtgttga gtgttgtctc aagggcatgt tgagtttggg    25680
tgatgaaatt gaaatcagat catttcaggt ggtgcaactt gatggtaagc catatagatg    25740
ttattctgta ggcaatgggg caatcatatt aggactttg cagaattatt taaggaatag    25800
cagtttcatg atagtagagg tagggataga agacagaagg tcagtaatgc aagttgagat    25860
ctagttatag attcaactgt ggtagagatt gaggaaatgg ggatggcatg aggctctgca    25920
gaggcattgg aaggatgata ctgatagaat cttgcaaact attggataga ggccaagaca    25980
atgaataacc atccaaggtt gcagttatgg gtggagttgt ccagttaaga aaagggagag    26040
agttcagagg taggtgaagg tcagcattat tagatgcttt ggagacacat gagactgaca    26100
gagatgttta ctattttttt tggtgattat aaggtaatca atagactttg agagattact    26160
gtttttcagt cttccatatt atgttgcttg gatgcatttt tctttttcc tgaaacttgg    26220 cagacatatc cattatcaag acgttttcag aggggcatgg tggctcatgc ctgtaaatcc    26280
agcactttgg gaggctgaag caggattgct tgagctcagg agttggagac cagccggggc    26340
aacatggtga aactccatct ctacacaaag tacaaaaatt agtcaggcat ggcagcatat    26400
gcctgtagtc ctacctactc gggaggctga ggttggagga ttgcttgagc ctgggaggcg    26460
gaggctgcag tgagcccaga tcacactact gcactccatc ttgggtgaca cagtgagacc    26520
ctgtctcaaa aaaaaaaaa aaagaaaat gaaagacct tttcaaccat tctaatcata    26580
attccaagac ctatttgtgt cctgacttca agagcaggta ctcttattga gaaacatttc    26640
tgtaattgtt cccacttccc ttatacctt ttttctgaca gcaggtggca tccctcagt    26700 tgtctagctg accactggaa gggctgaccc ctcaacaaac ccatatcctg cttggagttt    26760
ctctataggc cctgtcttat ttattgctcc tgctttgagt aacttctcc ttcctcaaat    26820 ctattcttct aattttcctt cactgcctat taattgaact gactttttctg attgtctgtt    26880 cctcctgcct ttgcagttac tgtcgctccc taaattccat cctcgaatca ctcctcttcc    26940
ttccgtactg tcctatgtag cttgtcatct actcatggtt tgatgattat ttccatcgga    27000
gagaccacag gggtctctat cttctgctct cacttctctt ccaagttcct tcctgccctt    27060
acagctcccc tttcaacaac attgcctata tgctctggcc aaaactcaat tcagtgttcc    27120
caaaattgtc ccatcatctt tcttgccaag cttaccctgc tccctgctca tggcatcttc    27180
tcctctcaat tcctcatctt ggatttgaat cccctctctt tcccatcccc agtgtaaatc    27240
actttcagaa ataacaggtc ctgtcatttc ttcttctgag atacatctgt actttccttg    27300
gtcatcttct cactttatgt gttactattt taatcatatc ctgtctatga cttgtacact    27360
ctccaatcta tttttaaagc tattcttct tcatcttcac aaataattga ttatgtaaga    27420
ctactatctc gttcaaaatt cataaacaag catccactgt gcttcaccac ctgccccatc    27480
tccgccgtta caactgcagt catcatttta ctcctctggg tgttatactt catcctccac    27540
ccaacctgag tatggatagg aatcactgca tttcaccttg gtttcttgct ttttctcatt    27600
cttctcaggc tctctttcaa cctggaatac tgttattttc ccatctccac accttattca    27660
```

```
tgactgaggg ctaaaatgct gtttctttca ctgctctctc taacatgcat tgtttgtatt   27720
cctctgtggt agtcatcaat ttccattaca gaggccagga gacctgatac tttcttgagt   27780
gtgaatttca gtagttgacg tcttgtgtct cagtttcctc agctgttgag ggctgtgaga   27840
agagtaccta cctcgaggga tgtttgcaaa ataaataagt taaggtcagg cactgtggct   27900
catgcctgta atccaagcac tttgggaggc tgaggcagga ggactgcttg atcccaggag   27960
ttcgagacca gcctgggcaa catagggaga ccctgtctgt acaaagaata ataataataa   28020
taataaaaat taggcaggta tgatggcaca tgcctgtgat cccagctact gggaagctg    28080 agacaggagg attgcttgag cctgggtatt caaggttata atgagctagg attgcaccat   28140
tgcactccag cgtgtgtgac agagcaagat cttgtaaaaa aaaaaaaaaa aaaagaaaa    28200 ggaaaggaat aaattaagca tataaagcac tttaaaacag gtatttagaa agtgttgaag   28260
gcggccttga cattacttat ctttggccca tccttgtctt tctccttcgt agtctaaaat   28320
gttttacaaa ggactgtttc tcatgacact gagaatgaac cccaaattcc tttcactgac   28380
ctattccact tttatacagt aagcctcttg ctcacttctc caccttcatc ccaggccatc   28440
ctcttctcac tgaactgctg tcccagtcct cttttggttt tgtgatctga gtggataccg   28500
tgttaggaca ttttttgtgtg ccactccctc tgcccagagc accctgtcct gttcccattt   28560
aaagtgggtt ccaccctcga ttgtgttctt atttaaccca ttatttactt tcttctctga   28620
gctcacctga tctcaaaggc ttttttattc tttgtctact tatggatatg tgtggaggat   28680 ctgggggggtt agtgaatttt tctctgcatt ctctaaacat gtgtattgca tgaatctgga   28740
atagatcagc ccttactggg tatttattaa agaaatgagt agttgtaaga cactctatag   28800
atattcattt aatgaatgag aaaatcaaat gttgcctggt aaaaacaagt gttaagtcag   28860
ctatcacagt tttctgagat atgcagccaa gccaggagga ctgagggaag gatgtctttc   28920
attgtaaaat caacgcactg taggggaaag ttcctctctc acctaaggga atatcgatct   28980
tccttgattg tttgctttgg tatttctaaa ttagcatgat ttaccaaaaa tgtttggatc   29040
actcagtaca tgcatgtgat ttttttctaaa tggctatctt taaaaaaact tcctcatctg   29100
tattaatgtc cctagagttt ttacattttt tgcctgtatt tcattaaaga tgatgtcata   29160
gaaaattttt gtcaaatttc tcattctggt ccgtgcctgg aagattgaca gtgatgcagt   29220
ctaagaaagt tcaggatttt gaggtttaat catttacatt ctaacactaa agctacaaat   29280
ctgccgtgca gtgttgctta cttctactgc tcactggatg gatgagtcta tgtgcttttt   29340
aaattcctta taaagatgtg ggtcaaaact agcagtgtgg tcaataaatt aatttcttga   29400
gagtttatca gaattgtggg atgatttggg aggagcaaaa ttgtgtaaaa tcaatcctct   29460
atttttaaac ttattcttct aaaattctaa atagaatttt tttattcatt aatatttct    29520 tgatttcata atgctaaaaa ttaagtaaga tgaatgttgt gttgagaaat gggagcaaat   29580
ccaagaccaa aaatcagatg atttattaaa tttgcaagtt aaaaaaataa atacagtttg   29640
aaagattgct ctgtttgagg aaaggacata caatttgtt gagataactt agggtacaaa    29700
tcaaggtcat ttatgttcat ttgaacattc atattcacat ccggaaatat ccagaatgac   29760
tacactaaaa cctgcaggta aattcttttc tcagctgagc ataccatatt gttgtagtta   29820
atcaagaaat ctaccaaaat taaatttgtc ctcctacttt ttagtttaga aatttagggg   29880
gtcactggga ctcaaaagaa aattcaataa ataatggacc atcctagaga tacttctttt   29940
taacttaaaa atccctctga gatatcctca ggttttaaaa ataccttgt atttttcctgt    30000
```

```
ttttgtgtgt gtttgtgtag gcctacatct tcatattagt catcagtgtt gtcagaacct    30060
tggctagaat catagtctag acctcttgag gtcactgggt ggttggctac attttccacc    30120
tcttgctttt catgggtccc actctgagaa acatgctcct tctctctctc tcctctttca    30180
aggtcatctt tgaggacatc ttctgaagct ttttctgaga tgctgcctct tctgagcacg    30240
acactgtcta ttcttgtatc accagtatag gagctcatgc aatttgtaag cacttgcctt    30300
aatgatgcgc tccctgaaag accctgagga gagggatcag gtggcgttca tctttaggat    30360
cccttccctg tcctcacagc acattcatgg tccacgttca gcaaacactt gtacaatgac    30420
atgacttagg gtttctagac aatctgtatt gtaatttctg ttgatataaa gggataacat    30480
tagcatcata tgaaaagtca gagttctatc aatgtcatct tgatgaaaat atttatatcg    30540
ttatatctta tgtcctaggt gtcttcttga ctgactaccc agggcgagtt ggaatggcta    30600
tgtgcatctc tctgaacccc caaatcttta gttgtaatga tgaacttaca tggagaggct    30660
tattcgaaac gtcattatag tgtggatgat aaccttctta gtttccacag ctgatattcc    30720
tccaaagttt tgtatgcttt gactaatgta ttctctttat gctaagcttt ctttaaaatg    30780
atatgaatgt tccataaatg ctgattttt ttgttttttg agacagggct tcactctgtc    30840
acccagggtg gagtgcagtg gcgtaactac agctcactgc agcctctgct cctgggctca    30900
agcaatcctc ccacctcagc ctgtggagta gctgggacta caggcgtgca ccaccaaacc    30960
tcgctaattt ttgtattttt ttgtagagac agagtttcgc catgttgccc aggctggtct    31020
caaattcctg agctgaagca atcctccctc ctcagcctcc cgaagtgctg ggattacagg    31080
catgagccac cacgcccggc cccataactg ttagtttaat tagcaccttt ctgctttagt    31140
tcatgttgac tattgaaaat ctatcatcct gtataattaa tgttttttaaa agatactttt   31200 agatagtgat caaaaactta tttattaagt agaatgtaaa ttattacaaa tgatatgaat    31260
accataggat aaagttttta tatgacaact tagattataa aatgcaattc tagccaggca    31320
cattggctca tgcctgtaat cccagcactt tgggaggccc agcaggcacc aaccgcttgc    31380
ttccaggagt tcgagagcaa ccagggcaac atagtgagac tccgtctcta taaaaaatac    31440
aaaaaaaaaa aaaatagct gagcatggtg gtgcatgcct gtagtcccag ctattcagga    31500
gactgaggtg agaggattgc ttgagcctgg gaggttgagg ctgcagtgat ccaaggttgc    31560
accgttgcac tccagtctag gcaacagata aatatgagta caaatggctg atcatcttca    31620
tattaatatg aaattgcatt ttttgataca ggatctcgtt ctgtcttgtg gccttctgta    31680
ataggttatc ttgtccaaat tctggaataa agtccagaag aattttaatc tagataattt    31740
attctttaac ctttgaaata ttgtatcagc tacatgacaa tggcttataa ctagctctaa    31800
ataaatgaaa taacgtttgc gagagtgaat cacatcactg agaaccaagg ggaaacatga    31860
aatagtgatt atttgaacag agagtgttag tggtctgcat tctgccttgc acccaaatgg    31920
catcacctat gggtgtgata aaagcccct gcctttctct ccctcctcag tgcttgggat    31980
ttccaacaac agcaaaagag aagccaggaa gaatgctgtg ttgtgagtac ccccaggaag    32040
ggttttcctt tatgaagagg cagacctagt taggaaatac ataaccatgg actgcaggaa    32100
agacagttga gtctgcatgg aggatagaga ccagggaccc cataaaagga gaggtggtga    32160
ccgaggcctg caggatgcat ggaaacattc ctgacctcaa gggcagcaac tgtgaacaca    32220
ctcctactag gcagaactag aatgatgaa cagagttctt ttcagggaga ctcaccaggt     32280
agatgactac acatgagaca cttttttttt tttttttttt tttttttttt tgagacagag    32340
tctcgctctg tcgcccaggc tggagtgcag tggcgccatc tcggctcact gcaagctccg    32400
```

```
cctcccgggt tcacgccatt ctcctgcctc agcctcctga gtagctgaga ctacaggcgc    32460
ccgccaccac gcccggctaa ttgttttgta tttttagtag agacagggtt aaaccgtgtt    32520
agccaggacg tcttgatct cctgacctcg tgatccgccc acctcggcct cccgagtagc    32580
tgggattaca ggcgtgagcc accgaaacac tttcagtggg aatattttgt tccatcagat    32640
tttagcaata tcggatttga aaataggggga agcacacaca gatacaatta gtttcaccat    32700
ctcacttgtg tatttaaaca aacctgtaaa caaagctaag cgaaccaaga aacaaacaaa    32760
acctcaaacc taatacagta ataataggct gggggtggtg gctcatgact attattaatc    32820
tcagcacttt ggtaggctaa tacagaagaa ttgcttgagc ccagagttcg agaccagcct    32880
gggcaaaata gtgagatcct atctctataa agattattta aaaaattagc caggtttcga    32940
ggcatccacc tgtagtccca ggtacttggg aggctgagag gcaggggat cacctgagcc    33000 taggaatttg agattacagc cagctgtgat cgtgccattg aattccagcc tgggtaaaag    33060
agtgaggtct gtctccaaag ttaataaata agtaaaataa taataataat ttttaccgta    33120
tcacaaaaaa tatagccagt cagatacaat gcacactaat tattgtaaaa ttttctgaaa    33180
cacacataca tcactaactt gataattgta aatttaacac tgattggagg gtgtgaacaa    33240
aggtatgatc aagtaaaata aatgtatagg caatttcaaa gtcttaataa tacaatttca    33300
agagctaata ttaattgagc atttactata tgcacactca tgcatcatgg gactgtgttt    33360
ggtgctaata tcacaaaact ttatttttc ttccactggt aattttgtc actgttgaaa    33420 actgtttcag ccatggatcc ccacagtgcg gagattgcgg gatgtgggag agaaatgatg    33480
gtctcaatcc ccacctgagc cagtgtccta tggcaggcag gtgaaagcca agccacccag    33540
cttgagttct ggctccactt ttatagttct gtggtgttgg gcaggttagc taatctgtcc    33600
ctgcattagt gttctcaact aatggggata aagctcacat ataccttata tgttttgga    33660 gacaattaag agttagtata tgtaaagaat tcagcaagtt agatgctgac ccactatgta    33720
catattagct attataactt attattcgga caaacagcta atgcatgtgg agcttaatac    33780
ctaggtgacg ggttgatagg tgcagcaaac cactatggca cacgtttacc tatgtaagaa    33840
acctgcacat tctgaacatg tatcccggaa cttaagtaa aataaaaata aaaataaaa    33900 aaataactat tattactact attattagaa ttgtttggat gaggaggtag cttgatatct    33960 tgaaaaatg catggtcttt ggagtcaaga taggtcttac tccctgcttc agtgagctgc    34020
gttacttaac acctggatat cattttttc ccaatgtaaa ataagatgtc ataataactc    34080
ctgcccttgg ctgtagaagg gtcagtgaag atgaatgtta ttatgattgt tgttaaatat    34140 aaattcatt ttacaaatac agtttcatca acaatattta tgataatgcc tattaataac    34200
aaaatgtgct aggtgttatg agaaatcaaa aacatagtta aaatatgatc ttgtcttcct    34260
gtaatttaat aatgtgctgg ctcattagct atgaaaccca aaggccttat ctactttgta    34320 ttaattttt ttcaagcatg gaagtaagcc cagaagggta ttgagtgatg tatcctcttc    34380
ttcccttacc atctttccta tagatgcaaa atcctgagtg tgaaaggcca cgtggtactc    34440
tgttagatat ctcgcaggtg ttacttatcg atggttcttg cttaaaagta gaaggaggag    34500
tgtcgcatga gacgcatcct ataaagagag cattccgggt gagatggcaa gaaaaactcc    34560
gaatggtcct gagatgataa ctgatccaat ggagatgata tatctgttca gttgacgcaa    34620
acataattgc ggtttatacc cgtgaatgta aggcaaaaac tgcaattacg cttgcaccaa    34680
cctaatatat atatcttttg gagacagggt cttgctctgt cgcccaggct gtagtgtagt    34740
```

```
ggtgcgatca cagctcactg cagcctcaac ctcccaggct caagtgatcc tcccacctca   34800
gcttcctgag tccgctggga ccatagacac atgccgccac atccagctaa ttttgagata   34860
agttttcttg cagtagagtc aatggcagtg ttgttctgac cttctgccac agcaaaacat   34920
ctctgcaggt tgaggattag ttcttgcaaa taagtgattt ctaaatgatt gattggttct   34980
tttcacacat tttgcagatt tcttttatta aacaagttat atctaatgga gaaatacagt   35040
gagttgatga tctccaacaa aactttaatg ccacccagat caatgccaac cagattatga   35100
gttgcccatt ggaaacctca aggagtcttc attgattttg tattctcaaa ctgcatgtgt   35160
gtgctaaaat ggttgcatag agattccaca tgcagccatg catgtgtgta ggtgctccca   35220
ctagactagt tccttgactt attagggaac aagttaagaa ttacttcatg tcatgatcgg   35280
ctagttcttg taactaccca taagaaagct tataaggaat gtcacattgg ttttgaaaca   35340
atatcatctc ttttactgat ggagagaggt atgttttttct tttttttttt aaatagggaa   35400
caatgtgcta agatgaaaaa aaaaaatcaa gtaggtttcc agggaggcat tttttttttt   35460
tttttttttt ttttgagacg gagtctcgtt ctgtcgccca ggcggagtg ctgtggcgcg    35520 atctccgctc actgcaagct ctgccttccg ggttcacgcc attctcttgc ctcagcctcc   35580
cgagtagctg gactacagg cgcccgccac tgcgcccggc taattttttg cattttttagt    35640 agagacgggg tttcaccgtg gtctcgatct cctgacctcg tgatccgccc acctcggcct   35700
cccagagtgc tgggattaca ggcgtgagcc accgcgcccg gcccagggag gcattttaa    35760 aggcaccatc tcagaaggac gaggcaatgg taagtatcag gaatagttat tggcgagtcc   35820
agcacagcag tcaatgactg tgttctggac tgcaccgttg gactcgggaa ccactgtgtg   35880
gccaggctgt gggctccggc agttgttcaa aaccctgaac ctggagctca gaccagaggg   35940
ttgtatggga ggctcactgt cattcattgt aaccctaaga acctcatcct tccttgagcc   36000
cgattgttcc catctgatca gagcttagat gcaagattgg gaagaaaggt ggtggagttg   36060
gggtctgcct ggaggacagc ccaggtgagt catgcatggc tgggagagca gtaggttcat   36120
tctcaccacc tcattttttct aaggggaaac agatccacaa gggagggtca gccccagatc   36180
attggccaca cttatgggaa acatgtgctg ctgttacgca ggccccttca ttctgtttgc   36240
atgctctcct tgtaaccect gggcctatca ggacgccagg gtgtctgttg aagaggcat    36300 ccaagaagga tctttaggct gcaggatgga agcacacact acagcatgac cttaggtaga   36360
tggttcattc attaccttt aatatcttcc tctttctttg ctgtcaaaca tgggtaataa    36420
aatacctaac ctgtcatatt ataagaagta attgaggcca ggtgcagtgg gtcatgcctg   36480
taatcccaac acgttgggag gctgaggagg gagaatcact tgggttcagg agttcgagac   36540
cagcctgggc cacacagtga gacttcatct ctacaaaaaa tttaaaaatt agccagacat   36600
ggtgatgcac acctgtagtc ccagctactt gggaggctga ggtgggagga tcgcttgagc   36660
tcaggagttt gaggctgtgt agctgtgatt gctccactgc actccagcct ggccaacgag   36720
caagaccctg tctcaaagaa aaaaaaaatt aggtgaaaac aatgtctatg caacgctcag   36780
tgcctggtga tgtctaagga atgcccaaac tttctaggta aggggtaggg gatgcattgg   36840
gtgagagtcc cattggatga gcatgaatgg gaactcatca atattgctga aagtgcctga   36900
tccagaatta aaatatttca acagaaaatt cagaggaaac tttagaatgc tgaaaaatgc   36960
catattggtc agtcttactg gttaatcgac ttttctgaag tacatacaca cttttttttt   37020
atttgagata gaatctcgct ctttcatcca ggctgtagtg cagtggcaga atttcagctc   37080
actgcaacct ccacctccca ggttcaagtg attctcctgc ctcagcctcc cgagtagctg   37140
```

```
ggattacagg cacccactgc aacgctcagc tagtttttgt attttttagta ggggtgaggt    37200 tttaccatgt tggccaggct ggtcttgaac tcctgacctc aggtgatctg cctgcttttg    37260
cctcccaaag tgctgggatt acaggtgtga ccacaactt ccttcccacc cagctaattt     37320
ttgtattttt agtagaggca gggtttcacc atgttgacca ggctggtctc gaactcctga    37380
cctcaagtga tccatccgct tggcctcca aaagtgctgg gattacaggc atgagccact     37440
gtgcccagca cacacttcac tttggatcaa gcccccttta gagcatctga acttcttttc    37500
cagtcccttg ttccacccag gcaatcccaa gcctggtgcc ttcctatctc tagcctttga    37560
tttaggctat tctgtctgcc tgtgtgcaac atttcctttc cctccttact gaagttctac    37620
cccatcctgt gttgcatgag ttgatggata attttgaaaa ataattatt ggtaatcatt     37680 aacctctact gacttatttc attgatgcat ttttgagcct ggttaaacca agtctagcag    37740
tgctttcgga ttactttggt ggtgaaaatt gtttacttaa aaaaaaaaaa acaatttgaa    37800
acaaataaaa gtagaaagca gtggtttcaa gctcatttgg agtgtccaaa gtgacatgcc    37860
tggaaattta ggattttgaa ataattgtct gctcctcctc atggccacac ttcggggtac    37920
atctcataaa gtagacaaac acagatgaag gtcacctgtc tgactcactg tatgtaaacc    37980
tctcagaaat tcacccttgg ctgcactgct caccggaagt ccatttttctt ctagagtaaa   38040 gatttgcaat gatctaggac tcaaaaagtc catcttgggc catttgaatg accccagcat    38100
ctcattttac cctttgtatt tgtagcccct gcagagtggg gttcaaaatg tcagacaggt    38160
actactagta caggcagagg ggacactcag accatgagat ccttctcact gtctggacat    38220
tagaaagaga gcagagccca aggaaaagat atgggtagaa tacttttgtg atatacagct    38280
gtgagcccat gttagtggag atatttcaca attgaaaatc tggacccttc cccacaaact    38340
caaattttag aaaggttcat ctgatgcttt catacatctc aagtaaatgg ctctgtcttt    38400
tcatggttca gctgcaaatc tgaagtcttt acaatttgat tgcttaaata ttggttattg    38460
acaaattttc ttatcaattt gaatgttgta gcttccaaac ttttgtcaaa atttagacca    38520
caaaggcctt ttgagtatct ctttaatgat tgccagataa ttttcctatc catggctttc    38580
tctttacaga ataaaacttc agtattttc cttgattcta gaagattgtc aaggtcatgt      38640
cctttatgga actcttgttt ccaacaaagt tgattttaa acatctctcc atatttcctg     38700
ccataaacaa atactaggtt ttgttttca aagataattt gtaatttata aagaaagatt     38760
aatgctgtcc cacctccccc atttgatcat taacatacaa attggaagaa atcatactt     38820 ggaaaaatga ttgatcagct gttttgctatt tttatctagt atagatttat ttgtcttatc   38880
aaaggtaaaa cgaataaagg tacacatcat ttttcatcag catatacagc taaataatca    38940
ataatgatac attatgtaaa tccctttggc tcctgaatta cacgactttc ttttttttcca   39000 ttttctttt tttcaaacctg gatgagtctt aataaataat caaggcctga agctaagaa     39060 atgtttgtct tctctctcac acttacagcc tttggaacag gaacccaatg cagcattggt    39120
tgtaattatt tcagtagctg cagtgcaaag cacattcagg tgaatataat cagactgtcc    39180
tagttccaag gagaagcagt agtaacaggt ctggcatcag gctcagagct atagacgagt    39240
cacagcttat aatatgatag actcacttta tgaaacccaa agggaacatt atataaagtg    39300
cacaatcatg agaaggaaat gagaacttct gaacctagga cttttttaaa attgttttac    39360
catatgcact taggttcaaa ctacatttga aaccactggg cattatcagt atgtctctgc    39420
aagagtcagc tactgctttt gcttaattgg tagctgcatt ttctcttaag gggggaatgc    39480
```

```
tttggagtgt gttttcctga taatttggag tggtctttgc tgaatggtga tcctaggttg    39540
gaatttccta cattgtacac caagaatcag ttggctggat gaaaaacaag tgacaaaggg    39600
tttttccttt cccagtattc tcaaaatcct cagtaagaac tgaaggcatc atgactcttc    39660
agtgacatca gttgtccttg aggaggggtg gaggatttcg tggagacaca cataggcctg    39720
ataatgagga catctatgct gtaatccagc tctgctgcta attagttgtt tgcaattact    39780
aggttttttgg tatgtttaaa gactgcagag acaggcattc attccttttc actatgaaga    39840
atgtgtgaat gtaaattaag aaccacagct agctgagaag tacaaataat ttgtgaagcc    39900
tatttaatac tcgaaaattt caatttatgt cagttcattc aattttttcta catacagttg    39960
actgaacact ttctggtttt gtaaccccta ttagggaaaa ttctttgcaa tggattttca    40020
tgataatctg gatagtctta gtgatcttat gttagaattt attttattgc taggatgact    40080
tagtccaatt caaaactgat gatcaagaaa aattccttc atggcattcc tgaaaacata    40140
attttttaagt caagggatga tcaggataat tctaggggcc tgtaagtttg aacattgaga    40200
ttgttgatac taagttctga acacatatta cccaaatgaa tcttttatta aacatttttgt    40260
ggtttcaaag gacatagagt agttatgcaa atcaatgtgg tgcagcaact acagtataac    40320
cttcagatgt tagggaatca acgactaaaa aaaaaaaagg acagtatttg aatgttatta    40380
caaagacacc tgcgattctt gaaggacatt tcaaaggcag acaatggggt aaattgtgat    40440
tgaaatacac gcgcaatctc tatgatatgc tccttccact tagaaagtgg gatgaaagct    40500
catcaattga agagtaattg ctaaaaaaga tttctcctct atctagcttg ggagtattta    40560
ggagctaatc agagtatttc gtcttctcgg aaattaaaag agatgaacag agttgtgcag    40620
acatggggaa aataaagttt agtttaatat ttagatttta aaattagtac ttgatggaca    40680
ttttaaaaag tgtacaatta tcaaaacttc aatatctaat ccttttatgt aaactatggt    40740
ggatacatgg aaacaccagg gacgggtgct ggttcttgtt aacttttctt tctctgtcag    40800
ccacaagagt gcctgtccca tagcagtaaa ctaataagta tttgctaaat taagaagtgg    40860
gaagggcgtt gtaggttatt gatcaaacga aaataaatat attttgttgt ttattcaaaa    40920
atttccccga cttaattttt ttaaaatgta acttaatttt ttaaagctca tctgtgtttc    40980
tttgttttgt gtcgagtcaa agattatttt atgtcaatta ccttttcatg ctgaggcaac    41040
agtttcagtt ttcccattct gcaaaactaa tttcctgatt cctctctcac cagggaccat    41100
tcccctccaa aatcctacaa ggtgggtcca tgacatctgc tagagaaaaa gagggacatg    41160
ttggagcgat aggattccca tgggcactga catactggcc tctggggata ggaagattaa    41220
tgcttagtac aagaaagaag gaaaagaagg ccttggcgag gactgtttta tctcagcatt    41280
tctcagaagc tccttcagtg gagacttcgc ctgggacctt cgccccacct tcttctaatg    41340
gcacttcctc cctgtggggc tccacgcggg acattacgtc ggtgatgcgt agggcatcgg    41400
gtgcggaaat gtgtgcgtgc ctcctggcgt gtgcgtgcct tctggcgtgt gcctgtgcgt    41460
gtacgtgcgc atgcgtccgc ctcccgggtt cacgccattc cctggcctca gcctccgggg    41520
tagctgggc tacgggcgct cgcttttttt ttttttttt gtattttttag tagggacggg    41580
gtttcaccgt gttagccagg acggtctagg aaattttttaa gccactctga ctaaagaagg    41640
tggagttggc cgggcgcggt ggctcaaacc tgtaatccca gcactttggg aggccgaggc    41700
gggcggatca ctaggtcagg agatggagac catcctggct aacgcggtga aaccccgtct    41760
ctactaaaaa tacaaaaaaa ttagccgggc gcggtggcgg gcgcctgtag tcccagctac    41820
tcgggaggct gaggcaggag aatggcgtga acccgggagg cggagcttgc agtgagctga    41880
```

```
gatcgtacca ctgtactcca gcctggttag agtttatatt tcctttaaat ttctagagaa   41940
aacagattgt catgtatttt tatagagaca aaatactgat gaaggtgata tacaggtagc   42000
ttaattatga ttttttctaag atttaattag atggtaaatt tacagtaatt attaatatgt   42060
tcactgcttt tattaaaaac catcaattct gaatccacaa tgacacaaat ggtgagtaag   42120
gcttatgtct tgtatctgtg ttctttcagt gcttaaatgt caagagaaaa acaaagactt   42180
ttaacatgat ttttaaggaa cgttttcatt ctatggtggt ttctaatgta tgtgtttgtc   42240
tttagacttc ctttatcctt ttcctttcat ctctttctca aactcataag gtttcctttg   42300
tgcagatact tttttgcctg tttttcctcc ctagtttatg ctgcttttct gtcaagaggc   42360
tatatttcag aatgggaaaa aagggcaagc atatatagtt aaatgaatca ttttacactg   42420
tttgtaagtt attatacata agctaatgtt tgatctctgg aggataaaaa tgagctcaag   42480
tttgagcaaa tgatggtgcc gcacacatgc cctacctat ggtgagtcaa ctatggccta   42540
tgggtggtgg ccaattttg taaataaaat gttttgcaac ccaaccacac acttaaattt   42600 acatttcat atatggttct tttatactac agtgccagag tggaatggtt gccccagaca   42660
ctgcatggcc tacaaagcct aaaatattta tcatgtgatc ctttaccaga aaacattggc   42720
aatgcatact ttggcaattc atggtgatca tcttgggcct atgagttaat gcatccgtgc   42780
atacatttta aattagaaat atgtaataca ttagcattaa caacagagca tatgcttttg   42840
tattaggaat tctatgaatg catgcactac aactcttaaa cacagagcaa gtttaaagcc   42900
tggcatctgg ggtgtatgga tgagtgggggc ctgggaacac ccttgaattt tacctgtaaa   42960
atttatgtgc accagggaaa gattcagtgg cgttcaacaa cacaagaagc tgcagctggt   43020
tcgtgtgggt tttcattggt ggtctctagc tgctcaagtg atggattcca gttgctggtt   43080
gatctctctt agggctaagg ttcattattg cacagattga tcttggagaa acatcttgac   43140 tgttttttc acactccaat ccatttgttt tatgatctag aagaaaggaa cgcttaaatg   43200
caaacaatta ttgtgatttt tattccgctt cactgaactt tttaatgaag tgcattttgt   43260
acagttaaaa ccaggggtt cctggattct attttttgtg ggaattttg agagagaagt   43320 aattctgact cagtacgctt ccttggagtg gataattaat attaatgggg aatgaaattg   43380
ttttgtcttt cgctggcatg ttgttctctg ccacacctgg catgctgtgg acctgtagta   43440
aatattaact aaatatattt tagacacaga tgattaagga tcttttgctg aaaaacattc   43500
tcttaatctt ttatacttcc ctttccacag tgcctgctga aaacatgaat ttcaattgtg   43560
tttctaagtc ttggtcaatt taagtgtgac atggggtgat ggggaaatag cagttaggac   43620
taaaggtaga aggtaacatg atccatgtga attgtggtca gtgcaaaggc ctggaacagc   43680
ggtcactctt tcctgtccat gaacctttgt gctattcctc tttgtacaca gtttaaaata   43740
taaataagaa aatgtcatgc tgccaagtat gtatcacagt gcaggccacg tagaagatgc   43800
tttatatgtg ttggatgcag gccagtgttc tcaactcagc agtttcagag gaagtgaaac   43860
aagccctggc tggaaaccag tagccgtaag gtctaagtcc tggctgagca gtccaaatgg   43920
gttccctaac ctattgccca tcccctcagc taagaagggc aggcagtgcc cctgggcaat   43980
gctggtttta tccaactctc agaaggcgcc attctttgcc tacgctctcc cgtgtattgg   44040
tccaaagccc accaacttcc tgagtggagt tccttcacat tctgcagaaa accttctgtg   44100
gtgctttaac attggatggg aagatgaagt tatcttgggc tctgggctat gttagtcatg   44160
ttttggtaaa cgaagcattc tgttttcacc aggggatgag taggtataat tttccttctt   44220
```

```
gagttttgca aacctgggtg gagaagaaaa tcagtgcaat gtcttatgaa tttttttttt   44280
aatagaagat agcaacttgg aagcaattga gtgttgagtc taagagattc cccaccccc    44340 ccagcatttg ttctgatctc atatatatgt acagaaaaat ataaattatt tagcattgac   44400
ttatctgtaa ttaagtcttc taaaaggact actgttttag ctgctatatt ttcttctcaa   44460
ttacttggaa aatttaaacc ttccttgggg aatgtttagt ctttcacttg tccttttaat   44520
ggtaattgat tggattgttc aaattatgct gttctgagaa aagttaaca aataaaatct    44580 ggcaaagtaa taagcaaatg gcatcaggta aatgaaaaga acagcacact gtgtccagtg   44640
atatgtgtct tcactaattt cttacctttc aaaagttgaa gattgataat caaggtaaac   44700
tttaaaatgg aaaatttgcc agctacagat tttaaagttc ataaaaggtg gttttttgat   44760
agcttttgtt gctactattt ccatttagcc ttttataata attagttaaa aatctcaact   44820
aattcttttg ataagatatc ataggttgta tttttcaatg tttaagccag atacttgctt   44880
aaaaatcagt taattaactg agagtgaata attgtcattt attattttat atttgaaata   44940
ttaggttata gtttaaacat tttacttaaa gtgtaactag aatactggac acattttgct   45000
aacactcagt gttttcaggt gttttttaaa tcatcaccat ttctatggtt aagtcttaga   45060
acaacactct gaaatgatgt ggcatcaacc atctgagaaa gtaattaaaa gggataaaat   45120
agtaccacat gagttgggat tccttgacta tccaaccaaa aaattaccga tttttaggaaa   45180 cattctatt aatctaatta tccttcaaag tgagtggacc tttgacgtca ttttcaacag    45240
cagtgccatc ttgttttgt gtagttgaag atcagttcat tgatcttatg tctcaggaag    45300
aaattgcagt atttcttttt tgtcttttt tttttgaga cggagtcttg ctctctcgtc     45360
caggctggag tgcagtggcg cgatctccgc tcactgcaaa ctccgcctcc cgtgttcatg   45420
catatctcct gcctcagcct cccaagtggc tgggactaca ggcgcccacc accactcctg   45480
gctaattttt tgtattttta gtagagacag ggtttcacca tgttagccag gatggtctcg   45540
atctcctgac ctcgtgatct gcccgcctca gcctcccaaa gtgctgggat tagaggcgtg   45600
agccaccgtg cccggccagt atttattttt ttggtgttta aaaggttaaa ctgctttgga   45660
aagaaatttc aaaatgattt gggttttccg ggcttagaaa gcagactcca gctctaatag   45720
tatatgcttt ttttctacaa atgttttcca ctagatggtt atagagaatc gtttcaattg   45780 atttcttttct gatgtcttct ctatttggaa atgcagtcgt tcacatctaa tggacacttt   45840
ctagcagccc tgtttcatcc ctcctgtata cttcttaact aggattccag aaggagcagt   45900
cacatttgtt tttccttact ttccactcct tcttcagcat gttcatgttc tcagctgtaa   45960
cacataatca caaacttaat ggtttgaaga acactcattg gtaaacatgg ttctggaggc   46020
cactttctga aatggacctg gtggagctac aatcttagtg tcagcagggc tccttccttc   46080
ggaaggctcc aagggagaat ctttctcctt gtcgttttcc cccatggagg ctacctgcgt   46140
tccttagctg ttgtggcagg tcacatctcc ctctctgact ctgaccctcc tgcctccctc   46200
ttgtaagggc ccttgtaatg ccactgggct cacccagcta acccaggatc atctctttat   46260
ctcaaaatcc ttaacttaat cacatctgca aagtcccttt gccgtgaaag gtcacatatt   46320
cacagactct ggggattaag atgtggatag ctttggggac agtgcattat tcagcctcag   46380
gatgctataa tcgtatgatt gatgcatctc agggggtcatc ttagttggcc tctgcaacat   46440 cttttctccct cttgatacct ttcctgggat gctttcctca acatctttga caacactctt   46500 gttttcccctt tttctcccctg atggctgctt ttctcttttat tttccttctt cccttgtctc   46560
tttccctcct ccttgctcca tctcccttgg gaatcccatt gtacattgta tactcgatgg   46620
```

```
aaggtatgtt tggaatatta tcacgtgtgt gaccaaagac tgatggccag tgaaatggtc    46680
ttaggtgatt tggccctaag ttcccttttc tatcccattt catgacatct gtctacatat    46740
cctgtgtctc aggcatgttg aaggacacac aaccttctgg taccagcagt gtttagccac    46800
agacctccgt gtcactgtta ttgctacctt cctcccttgc ctgactttc tccctgcagt     46860 ggaggtccta atgattccac attcacctga aagtcatttc tcaagggagc cttccatgac    46920
ctgctccccc tctataatca tgtatccaaa agagtacccc catgataacc ctctttcctc    46980
tcttgttaat ttcaatgcct tacttcccta ccagactaaa aattcccctg aatacaggaa    47040
atatcttacg ttattgtaat caccactccg tctaatgcag tgccccactg ctatggtttg    47100 aatatccct ccgaaactta tgttgaaact taattctcag tgtggcagta ttaagaggtg     47160
ggcctttaag aggtgattgg atcaaggatt aatggattaa tgtgtaaaag gattaattgg    47220
ttaagaagaa ggagagagac ctgaggtagc actgagccct ttggctatgt gataacatgg    47280
gccacctcag gaatcagcag agagtcccta ttagcaagaa gcttctcatc agatgcagcc    47340
ccttaacctt ggacttctca gcccccagaa ctttaagaaa taaattcctt ttgttcataa    47400
agttactcag tttcagatgt tctcttataa gcagcgggaa acaggactac taagacacac    47460
agtcaaaaat tatttattaa attaataata ttaccataaa atcatagtag ttaaatctgt    47520
gtttagagat agtttcactc cttttagtct atcacttta aatctacgta ttcatgttag      47580
ttccgtggta tgagcgtctg tgtgcatagc tgtaattata gtgtaataga ttactaaagc    47640
agtcatgaaa cacttgaggg ttctttgtac caccgctcaa atttatttac atccatacac    47700
acttgtcaaa agaggtagag agtttcagat gcccttaact atccttattc cccacaggcc    47760 tacccctcata tttctgatag cagctgatat accaggagag ctgaaaatta agttccatcc   47820
taagcacaga gacttaagag ttgctgtcac ttagagagag agagaagcaa actattggtg    47880
cctccgaatg caatattggt tttccccaaa gaatgcttta tcttcgcttt acttaaagaa    47940
aaaagcaggg cagggcagtg gaaatgaact gataaccttg tgtctgtgga tataactctg    48000
ctccagggaa gacattaaag ggtaatgctt tgaaaataac atcaagaaat gaaagttaac    48060
ataaaaaaaa aaaagctgtc agtactttag gtgttccaaa gtcctgtgga gagtggctta    48120
actggagttt atagcaactc tgagacattt ttttttagta cagttctgcc actactttct    48180
atgtttataa acaatgaaca gatgcattca gtgctagtta cctagaatca actctcatac    48240
ccagcattac actcgaacgt tgaatgttgt attagtccgt tcttgcattg ctttaagaaa    48300
atacctgagg ctgggtaatt tataaaggaa agaggtttaa ttggttcatg gttctgcagg    48360
atgtacagga agcataggg ttttgcttc tggagagtcc tcagggaact tacaatcttg       48420
gcggaaggta aaggggagt gagctttctt acatggccgg agcaggagga agagagagag      48480
aggggcaagg tgctgcacac ttttaaacaa ccagatctca tgagaactca ctcactatac    48540
agtaccaagg gggccgatgc taaaccattc atgagaactc cgcccccatc atccagtctc    48600
ctcccaccag gccccacctc catcactggg aattacagtt cgacaggaga tttggatagg    48660
gacacatttt catcttaatt tgtatttttgg tatagtttca taggaaagat ttaggttggt   48720
gttctctcgc atggaaattc acttagagct tttacttgct tgttacttgt tttaaagcct    48780
ttccaattga accaatttat taagggcatc tatttaatt tctatggtaa atgtactaaa     48840
aactagaaga gatcttactg ccttgatact agttttattgc ttgtttatta ggtgccctga   48900
aaagataact ttagcatcca ctgcttgcta accatccttg tcttcagcat cattagaaga    48960
```

```
tacgaaggag taaggaacgt gcttatgaga aaacagaagc tatggcatcc cccatcatag    49020
ccacatgagt cttgaatagg ccgcctgctt ctctgtcttc tttttgcaag tgggttgcat    49080
cctagctttg gtggtgtcct tgtaactttg gaattgcctt tgagagaaga ccagtctgtc    49140
tctttccagc tgctggacct gagagattgg gctgcaggtg gcaaatggtc gctactgaga    49200
aaactgaaag caatgacagc catataatat ggtgtgaaca ccatatggat caaactggga    49260
catcacagtc agcacacact catccaattc tcagaccaag gcacaccatg aaattctgac    49320
atttaggttt cctgcctctt aggaattcca tcaaaattat ataagtagca ctattctaaa    49380
ttttaaccta ctatcatttt aaaaaatgac ttactcacag ccctaacact catcggagca    49440
ggttgatatt gtagaaaact ctagccctat gcaactggag tgatcttgat gctaagacaa    49500
tatgacccaa agccttgtcc tttcctcttg gctatatgaa tattttctaa cttttgtgaa    49560
caaaatatgc ctcttttttcc tcatgatggt gtttcaaaat gagtcgatgg gtgttttttca   49620 gttattagtg gataggagct ctcttagctt agtccttcaa aagcttgtgt ttgatgttgt    49680
agctttgtaa attatctcaa tgtatgcata cacacatact cccctaccaa aaaaggtcaa    49740
tagatgctta gaattccttc cttccttcct tccttccttc ctttttttca gggtcttgct    49800
ttgtcgctca ggctggagtg tagtagtaca atcatagctc actgcagctt tgagttcctg    49860
ggctcaagta atcttcccat ctcacacctc agcctctcct gggaccacag gcatgcacca    49920
ccacacccag ctgatttaaa atttgttttt ttagagacac ggttttccta tgttgttcag    49980
gctggtctcg aactcctgga ctctagtgat cctcctgtct tgtgctcctt ggattacagg    50040
cataagccgc cacgcccagc cacgtagtat ttctatattt tacttttagc ataagtccgt    50100
gaaagaacta tatttctcat gctttgttca actgtgcaca tcatgatgtt gaaggatttg    50160
cacgatggct atgatggtgg ctgtcactgc actacaatac tttttttgaa ataagtgaa    50220 atattcattg ttcactagaa tagtcttaca ggcatttgtt tctttagaat tggaaacttt    50280 cttttttatat tcatggtcgt atttcattct gctagcagtt taggcagatt caatctgtcc    50340
cactttccag tggtagaaac agtgtgaaga agtgaagtag ttgttggaaa atcactgtgg    50400
tttgcttccc aggggttgcc ttgtccactg attacaaaag tatcataaca catggcatct    50460
tcccacaagg agtttagagt ttgaaaagtc aatgtattaa tgtacatagg ggacccactt    50520
ccactcaaag caaacattga gtcaggtatc agagctcggt gggtgaacac gatggcattt    50580
aattatccta aattacttta tataatcaat atctactaac tgcctttgtt atgatgctac    50640
ccatcatttt tggagtcaca agctttcaac ctttgtctaa ctaaaagatg gatatctgca    50700
ttttatatta ggtggtctgg aagccatagt aatattagag agcacatagg gaatgttta    50760 gtccatttgg gctactataa ggaaatacca tagactgtgt agcttataaa caacagacat    50820
ttattgctca attctggagg ctgggagtcc aagatcaagg tatggcagat tcagtgtctg    50880
gtgagcaccc acatcctggt ttgtagatgg tgccttctcc ctgtatcctc atgtggtaga    50940
aggggtgagg gagctgagtt cccttttatg agggcactaa tcccattcat gaggctccaa    51000
cctcatgacc tcatcacctc ccaaggacct cgcctcctga taccatcatc ttggggtca    51060 caatttcaac ataggaattt ggaggggcac aaacattcag atcatagcag ggagagagat    51120
gagccttgcc caactccatg aagccatcta gattttttca gtctcagtcc tatttccatt    51180
ttttaatgtt gagttttgaa ctctattaat gtctcctggt attttcaaaa ctttgtagag    51240 cttttcatcat caatattaaa cctttcacat tcaaaggaca tgattatttt gtgtgagtag   51300
cgtgttgtta tttgacaaat gagtacaatt ataaataaat cttgaccatc ttgatagagg    51360
```

```
aaataaatgc acgtgtcaag atatactata atgcttttgt aatcaaaaca atgatggggc    51420
caggcgcagt ggctcacgcc tgtaatccca gcactttggg attacaccca ctgaggtggg    51480
tggatcactt gaggtcagga gttcgagacc accctggcca acatggtgaa accccatctc    51540
tactaaaaat acaaaaatta gccaggcatg gtggtgcacg cctgtaattc cagctactca    51600
ggaggctgag gcaggagaat cgcttgagcc caggaggcag aggttgcaat gagtcaagat    51660
ggtgtcactg cattctagcc tgggcaacag agtgagactc tgtctcaaaa acaaaacaat    51720
caaacaaaaa gcaatgatgg atagaacagg gtattattta aatgaaaact gtaaggggag    51780
ttgtatgctc tcaaatgtca ttatgcacag tctaatattt tcccttttac tttgtcactc    51840
tacctgctaa tttgcttcct taattcagag ttatgtcttt ggttattagt tataatatag    51900
gctgacagtt atgtagcgtt tcttctgtgc taggacctgt tccaagtgct tttttatatta   51960 actcattggt ctcaaccact ctacctgata gttaccatta gtattagttt cctatctgtg    52020
ctgcagtaac aagttactac agacttagtg gctgcttaca gctctagagg tcagaagtcc    52080
aaaatgagcc ttaggaggct aaaatcaagg tatcatcagg acaccgttct ttttggaggc    52140
tctaggagag gacagatttc cctgcctttt ccagattcta gagacttctt actctccttg    52200
gctcataagt tcctttctgc accttcaatg ccagtagatt gagtccttct cattctgtca    52260
tctttctggt tcttcctctt ttcttttttcc cttttctact tataaggatc cttgtgatta    52320
tgtggaccca ctggataacc tggaatcatc tccccatttc gaggtctgct gactgggaac    52380
cttaattcta cctgcctctt tcatttgaat ctcttttcca tgtaaggtca cacaaagtca    52440
caagttcttg tattaacaca tggtcatccc gggggtccg ttattctgca gaccacacag     52500
ttgttatctt cattttacag acaagaaaga caaacagtga gagttaaatc acttactcag    52560
ggttgttggg ctgctaaatg gtagagccag ttaaaattag gagtgtacac agggaagcta    52620
ggcagtgttg tggtcaaggg ccttggcccc ctgaaggttc aatgaaaaat catggagaca    52680
aagtgatttt tactgtccac tcaactggat tgcacagagg gagagagaga ccaggagcct    52740
ggctggctgg tgagaaattc ttacccttttg gccagcagtg tgggttcctg ggttctctgc   52800
actgtggctt ccaaaagagc agagcgtctt tgttgacccc gctcgctgtg tcataactgt    52860
aggggccaag gctctttact ccctaaaatt ttaatgaaaa atcactgact aggcagactg    52920
attaacagga gaaatgacat tacaagtgta tttaatgcag atacacagga gcctttggaa    52980
tgaagatcta ccctccaaat gaggtccaga agcttataca ccatcctgag gttacagaaa    53040
gagtgggggc ttggatccca gtaaaacagg tgatgggagg gggaggtgag gaattctgtt    53100
gaggagatta ttagaacaga gattaacttg taaagagttc tctttgaaaa ttaaatgatc    53160
cttggagaca cccttggaaa actgtctgct caggtgtggt tttatcttgt tttttttttt    53220
tttttttctg taatagataa tgatataact tgaagggggtt gaaaaacaac tgtaggttgt    53280
caaatgtatc ccatatccta gccctcactt ctggttccat cttactttttc tatgtaagtt    53340 ttcacttcta gttctatttc ttacttagaa attgtgttaa tcactggtat aagtagcatc    53400
tttgccagat aaaaggaaa aacaaaaaca aatgctttat gacgatatgt gggagaaaag     53460
aatgtaatag tacttgagaa atattggaac tggttaaata ctagatggtg ttgggtagtg    53520
tttaataaaa tgattatatt tcatagagaa cattttctct acgctgaggc agaaatacag    53580
agataatttt atactatact catcctttct cctaatcata ttattttta aaattcaagt     53640 tagaatttga gtgattgtat tgctgctgtg ctgttttttct cagaggaaaa atcatagcaa   53700
```

```
attatttcaa agatagatgg agaacatggt gtttctctat atccaggttg gattgaatgt    53760
tgtattagcc aatggaaacc ttcctcttca ccctctggag ggtcacggaa atcatgtca    53820 caaaaggcag attaatagaa agcaatacat atttattaag ttgtagattt gtgtaacaca    53880
ggagccttca gaatgaggac acaaagatac aggggagact gtccaatttt tttttttatt    53940
caacttattt tagattcagg gggtacatgt gtaggtttgc tagatgggaa tattgcgtga    54000
tgctgaggta tagggtacaa ttgatcccaa tcaatggtgg taagcatagt gaccaccagc    54060 tagttttca gtcctcaccc tactcacttc ccattctagt agtccctgt gcctattgct    54120 cccgtcttta tttccgtgtt ttctcaagct cccacttata agtgagaaca tgcagtattt    54180
ggttttctgt ttttatgttg actcacttag gataatggcc tccagcagta tccatgtttc    54240
tgcaagggac ctgattttgt tctttttcat ggttgcatag tattccacag tgcatatgtg    54300
gagaccacat tttctttatt tattccaccc accactgatt ggcatctagg ttgattccat    54360
gtctgtcttt gctattgtga atagtactac agtgaacata caaatgcatg cgtctttttt    54420
gtagaacgat ttatttcct ttgagtatat acccagtaac gggattgctg ggtcaaatgg    54480
tagttttgtt tcatttaagt cctttgagaa atctccaaac tactttccac agtggctgaa    54540
ctaatttaca atctcagcaa gaatgtataa gtgttccctt tttctctgca aactcactgg    54600
catctgttat atattttttt ttttgactat ttaatgatgg cctttctgac tggtgtgaga    54660
tggtttctca ttgtggtttt gatttacatt tccctaatga tcaatgatgt ggagcatttt    54720
tcagatgttt attgattgct tatatgccct cttttgagaa gtgtgtgttc atgttctagg    54780
cacagttttt ttttgttttt tgttttgttt tgttttgttt tgtttgagac agagtctagc    54840
tctgttgccc aggctggagt gcagtagcac catctcggct cactgcaacc tctacctcct    54900
gggttcaaaa aatcctgcct cagcctccta agtaggtggg attacaggtg cccaccacca    54960
tgcctggcta attattttgt atttttttag tagagacagg gtttcaccat gttggccagg    55020
ctagttttga gctcctgacc tcaagtgatc tgctgcctcg gcctcctgaa gtgctaggat    55080
tacaggcgtg agcgaccact accagccctt ggcacagttt ttaatggggt tatttggaaa    55140
ctcagttttt atgctaaggt tcaactaact gtggacaacc cagtagaaat agggttggac    55200
aaaaagggcc tgatctaaag ctaatggact gagtggggaa acccagccag gtctgtctgc    55260
ctagattctt cttggcctct ctgagcagca ttccttctgg gtgtgaggta ggaccctctg    55320
tggaatgggg ggtcttagga cctacagtca aaaaggcagg tcagaggatt tatttatggc    55380
cagtgtttac agaaaggcag gggaaagttg aggtcatctt ttttggttt catgggtgct    55440 ttgtggggaa ggggtctggt ttgtatgacc tgctttaggg aggagggatt ccagttccta    55500
tggccagcct tcggggagaa tggaattgag agacaacagg tcaggggagg gtcagagaaa    55560
aaccttttgc ctctgaggct gctgaagcct tcattttgtg gtatcattct ctgagcccca    55620
acaacacaaa ttttttttaac ttcatgcaaa actcttaggt cagttgagcc tagaatacag    55680
gtttctacgc tgtgtggcta aagtacggtc cttccctcct ctccacaggg agcagatgaa    55740 atttatttg gaggaagtta actcagaata gaaggaccca gagatgtcag agagtggagt    55800
gggggcgaga gcccagactc cgtatctgtc ctgagaaagt taggacataa ggacccacag    55860
acatcagaga gtggagtagg ggtgagggcc cacgctctgt gtctgtaagg gaattgtcta    55920
cactctgcat actcacagcc atcagctttc ttgttcttcc ttccaagttg aaagtcactg    55980
gactccttca agtccatcct ggaggatccc tttcttggta aactgaactg gcagagaaaa    56040
gtattccata actggcattt ggaggccatt tgggcctatt acttatttac tgtacaatat    56100
```

```
gttcacctgc tgaggaagga cccctggcta tccacacaga cctgattctt aagtgagaaa   56160
agacagtctt acatcctaga tattttgag aagctttcaa taagaaattc tttttaaaaa    56220
ttgaaaaaag aatcatctgg aggtagcaca gacaacacca accaagaaaa caagagacaa   56280
aatttctaat ctgtaacttg taggagatat gatgaaatag tgactcataa aaaacatggg   56340
aattctatta aaatgtgaca tattaggcaa attaaataat cagattggag aacgattatg   56400
aggatatctc caatgacaa aactttaatg agagagagat agcaaaatgg aaggaacga     56460 atatggagac tctaggaatc tgacattcga agagtatttt caggaaggac aacagaatac   56520
aaataagcaa aagtgactta tgaataattt ttaaaataat cccagcattg agggatctac   56580
acttccaggc ttatgaaaca acactcaggg ctcaccatag tgaatgaatt gaaactccaa   56640
actacaaaag cacattgcga gatttcagaa gaacaaatat atagggaaga tcctaagagc   56700
ttggaggctg tattaggccg ttcttgcatt gatataaaga aatacccgag actgggtaat   56760
ttacaaagaa aagaggttta attggctcat ggttctgcag gccgtacagg aagcatggcg   56820
gctcctgggg aggcctcagg aacgtgtcaa tcatgacaga aggtgaaggg aaagcaggca   56880
catcttacat ggctggagca cgaggaagag agagagagga cgtgctacag cctttcaaac   56940
caccaggtct cctgagaact cactcactat acagtaccaa ggggtgtgta cagtaccatt   57000
caagagaact ctgctcccca tgatgccatc acctcccacc aggccccatc tccaacactg   57060
gggattacaa ttcaatatga gatttgggca gggacacaga tccaaatcat atcagaggca   57120
aagaaaaaaa acttattaag aatcaagaat ttgtaatgtc atagaatgct tcatgtcttc   57180
actgaacgtt aaaagataga aactttcaca attctaagaa aaaacaattt actacgtaga   57240
actcttggag caaactgtcc atgggcaggc agggtcaagg catttacact gatgtagcat   57300
ttccgaaaat ttacctttg tgcacccttt cttggaaagc tgtgtgatta tgtcttcctt     57360
caaacagcgg aataaatgac aaatagaaag atggggaatc caaggaacag tggccttcac   57420
agaagagagc tgaaagaatg caggtctcag attaatgccc agagcaggct gggacagctg   57480
gaatcctaga gtgagacttc aaggagaaag tacataaaag aaaaggaaat gagccatttg   57540
accatgtaga aatagtactt gagatgggct ttagttccct tggaacattc agaaaaattg   57600
aacaatagac acacagaaaa gcatgaaatg aaaatgtgaa gttgttgttg tctccagata   57660
aaacaggagg caattcaatg aaggagattt aattagagta gaatgcttca ttcaggagtg   57720
attattaatt gcacagttac aataaagtta aagagagaag gccaggtgta gtggctcacg   57780
cctgtaatcc cagcactctg ggaggccaag ataggcagat ctcttgagtc caacagttcg   57840
agaccagcct gggcaatgtg gcgaaatccc acctctacaa aaaattcaaa aattatctgg   57900
gcatggtggt gtgtggctgt agtcccagtt actgcagagg ctgaggtggg aagattgctg   57960
gagcctggaa ggttgggct gcggtgagtt gtgactgtac cattgcactc cagcctgggc    58020
aacagagcaa gaccctgtct cgaaaaaaca aaaaggcaga aggggcaaat agagtggtgg   58080
ttgcccattg ataatttata ggtaatatct aaaaataata tatcaagaaa aaatagcata   58140
aactattact tagaaaatatc atagagcata tatttggaga ggagaagcta agaaatctga   58200
aagcatttgc tttctaaagc aagtgtggtc atgggatgtt gtatgttggg caagaaagtg   58260
ctgtttgttg tgcaaataac acttgtagta gtttgacctt taaaacttca tgcatgcctt   58320
tctttattga aacaaaattt tttcaaaaga aaaatgataa ggccaagatt gaatggtatg   58380
tgaatgtgaa tatgacagtt aaaagcatga tttctcaaat gtacctgccc attggaatca   58440
```

```
cctggagaat gtaataggta ttaatgcctg tgctgtggtc ctccagagat tctgacttgc    58500
tcggtctgca atgcagactg ggcagtgaaa ttttttcaatt ctccttaggg attctaagat   58560
gcagcagagt ttaggaagca tggatctagg tagctcagat tcttacttga atttaaaaat    58620
ctctagctgg gtgcagtggc tcatgcctgc aatcccagca ctttgtgctg ggctgaggtg    58680
ggaggattgc ttgagcccaa gagttccaga ccagcctggg caacatagcg tgcctgtgtt    58740
cccagctatt caggagactg aggtgggagg ttcgcttgag ccctggaggt caaggctgca    58800
gtgagctgag attataccgc tgcactcaag cctgggcaac agagtgagac cctgtttcaa    58860
aaaaaaaaaa aatcttgtcc agtgttctct tcaccaagat acagtggttt cagtaataaa    58920
ctactactaa catgatgatt tagattgagc caacttcatc actcagtcat ttctttgtta    58980
tctgatatgt tctttatgga aaggctttaa ttgcttgaaa atgacctaat gcttctccca    59040
agcttcccat tttttttttcc ctttcttaac tgaagtcaca gaatgttctc gtgtgtggaa   59100
tgctttgtct atcctacggg aagccaattg tgcatggctc atggcgccat gctggcttaa    59160
ttgttccaat tcctcctgtt tctccgacca cacatgaggt tgaattaaat ataatttcct    59220
cagtttgcat ttcccaggca gtcgtcctaa gtggcttctt ggaggagctc tgtgcattcc    59280
actggtctaa ttctgtgatg ccctttaact cgagggccaa ggacataatt accagctcta    59340
gaaattcgtt ccgtggtcaa ggatgcttgt gcagaggcca aattttcttt cattataatt    59400
tggcctttgc caagcttcaa agtgaagggg attgagttcc tactaaagag tattggcacc    59460
taggaagtga atgcttctc tatcttttgc agctagtgtg ttctacattt cttcaatgta     59520
ccttctgcct ggtaaatgtc agattatttg ttgatcatcc tcagggtgta gttctttgtg    59580 ttgttaaaata agaacccagt ggcttaaaag cattggcttt tgagaagtca tttttatcct   59640
ggatgataac tcaaatccat gcagtgctga tatttacagc tgggaggtga catgatctta    59700
tcctttggtc tgttgctcaa attattgatt tcagtaggac ttactggctc ccttctgtct    59760
tggggatacc tttgatctgt cttgccttgg gggaccctcc ctctgacctg gaatagcagc    59820
ctatttccac aagaagggac cctctgagag aggacagtct tcataccgcc tcttccgatt    59880
ttcctttatc ttttatgggt tttggcttta aactttact cttagaatgt ccttaaagct      59940
aatgattttt taatgttctc tagtgtatta ctaaaagctc ttcatctact tgaaagactg    60000
gggcaggaag attgcttgag cccaaaaggt cgaggctgca gtgagttgtg atcctgccac    60060
tgtattccag cctgggtgac agagcaagac cctgtctcaa aaaataaaa aggacaggtg     60120 cagtggctca cgcctataat cccagcactt gggaggctg aagcaggagg attgcttgaa     60180
gccagagttc tagaccagcc tgcaacatag agagacccat ctcttcaaaa aataaaaaaa    60240
aaatagctgg acatgatggc acacccctgt agtcccagct tcttgtgggg ctgagaccag    60300
caggaggact tctagagcct aggaattcca ggatgcagtg agcaatatgt atgtgttaat    60360
acatagtgaa accagttatt ggagaattag tatatgtcct cccacaaatt cagtatgttt    60420
tcctaattat ccaattaatt caagggcat aaacataata gatgcaaatt attttacgtt     60480
ttttgtttaa aaaccttttt gactgaatca gtctatgacg ctttagtatt tgaagttgcg    60540
gacagaactt agtcttaaga tagcactcgc tttgttgata gatttccatg gagggaattt    60600
ttgccagatg ataatttagc ttgaagatgt tatagatgtg gacagtcaca ccctctaagt    60660
tacacagtct ggggtgggcc aattgaaaag aacatgcaga aacacaggct tgttaaggga   60720
taattaaacg tgggggaaat agaacagtca tggcagagga tttaataggg tttaattggg    60780
ttaggaagaa taggccggag tgaaagaata gctcttaata ggaggtctag aaatagccaa    60840
```

```
ggaaagcatt aattgcagaa aatctgtgac atctgattac tgtagtgaaa gaaagatcca   60900
cctttaaaaa tcctatctat acagaaagaa gtgatagggga gaaggaaatc ttcccacgga   60960
catatttaag aaaaacagtg gggaggtttg agatttcaaa gggccatggt tcaggttata   61020
attcaaaaga gaggcaaatg atagtcctac tcttcttgag tttcaggaag ggggaggatt   61080
ttgccacttg ctgtgaaata attttggagc ttctataacg ttgatccttt catcctattt   61140
tttcttggac ttgggatgtg gggagtggat aagatgggga tggagaagaa cagggtttg   61200
aaatgcctct tttgattctg ttcattcccg gaattcttct ccatgggcct taaagagtag   61260
agactccttc ccggtgcatg acatccagtg gccaattaat gaaactttat ttcctcagat   61320
aagttccctt cctccattaa tttgtgggaa ttcagatgaa aacttacttg gactgtggtt   61380
ttctatgtgt ttgtgaatgg aaggacatgt ttgtctttga ccttccttta gtttcacgtc   61440
ttagtcttga tatttaagta gctttggttc agacagagaa ggaccatgtg tgcagttgct   61500
gggactgctc tctagcttgg aggttccctg gtcttgggaa agatctccct gcccctatgca   61560
ggtggcatag atgtttaatt ttctacatga gagaagcgct agagtttttt tattcattac   61620
ttgtgtgcac agctgtggcc tctagggaag ctcagctgag gtggtctcag gttccaccaa   61680
aggttaccgg ggagagatga ctaggaagac aggaagacct gtctcacttg ggagggtatg   61740
gcaagagcta ggcaagacct cctggtggag atatttgcct tttattcttt cttttttttt   61800
tttttttttt tttgagacag tttcactctg tcacccgggc tgaagtgtag tggtgcgatc   61860
atggctcaca ccaacctccc cgtctcgagc tcaagccatc ctcccacctc agcctcttga   61920
gtagctaggg ctacaggcat gcaacaccat gtccagctaa ttttttaaatt attttttagaa   61980
acaaggtttt gccatgttgc ccagactggt cttgaactct taggctcaag tgatcctccc   62040
gcctcagcct ccgaaagtgt tgggattata ggcatgagcc atgttgcctg acccatttat   62100
tctcaagtac ttatgctcag ggcaggtctt ccaagggaag agaacagcca gataagactc   62160
gtatgagata gctgaggagg tggcatttca tccttccatg cacatgctcc ttatccacaa   62220
gcagaaagct gtaaccttgg ctgtccccac taggtcatga taggtagata cgcaggtgat   62280
gaccacagac tggcaattag ccaaggattc tcagctgtgc acgctacatg tgtgagtgtg   62340
tgtgacagat cccttttggcg gtttggtgga aaattgatac attttgtaaa aatgatatgt   62400
ttaagtcata caataaggta aataacgcat aaaaggaaat cggttttatt gaaatagtta   62460
ccaaggtata ttaatattaa tatttaaagt tggtgcagtg gctcatgcct gtaaacacca   62520
gcatttgggg aggctgaggt gagaggattg cttgaggcca ggagttcaag accagcctgg   62580
ccaacaaagt gagactctgt ttctacaatc aataaaataa aaaataaaaa taaaaagata   62640
tatttaaact gggctacagt aatacatgtg catctttatt gtgtgctaag tacctggatc   62700
tacttaagag gttcgtaata gtcacaattt caaagtacaa taagcgtaaa cagtatttg   62760
ggatatctgt gataacagtg ttaagtgtcc tacctcacg ggtaatggaa gcaaatacta   62820
aatttcagtg catggtagtg aaactaaaga tgtaattact tttgcccatt gcaatttgta   62880
gaacccatgg aatctatcta aagactcctg ggtggcaaag gataaatgct tgagggtatg   62940
atacccccatt cttcatgatg tgattattac atattgcatg cctgtatcaa aacaactcat   63000
gtgcccccata tatatatata tgtatatgta tatacacctg ctatgtactc acaaaaaaat   63060
aaataaagac acctgggtgg gattgggggtt tttggactta gggtgagaa catctgcatt   63120
tagaattgtg tagaggaaag gttttgattt atttattata cctctgtttt ctttaaaaaa   63180
```

```
cctgcatgtg tagtaggaat tttgccagag gtgggaatgt gagagtcact agtttgcagc    63240
atagagcatt ctatactgag ataattattt ttatgtcaaa aagaaagtga agaatctggc    63300
agattagaat cttcatgtta ttttcattta aaaagcttgg aagtgtcaat atcaattaat    63360
attgactgct atttactgac attttttggca aaaaacattt cattttaatg aattttgtct    63420
tgtttgaatg tttgtaaggc tttggaggta gttttaggag atagttgcct ttgattcctg    63480
aggtatattc ttgggtctac cctgattctg tctcttgact ttgcacctct ttccttcctg    63540
aaccctgttt aaaagagcct tccttttacg actcttttct tccatcctat tcttccttcc    63600
catgctaatg tgagacacag aggtttttat gagaagcctg ttgtctatat gctggatctt    63660
ggaagccttg gttatttcct agagatggaa ggtctgatct cagttaagtt ctgaccccag    63720
gacaagaagc ctctctggag taactgactc actgggatag agcctgtttt cacaaaattaa    63780 tattcctgtc tggggagggc agaggaaaca ttttggggag tgggtggagg tgatgaggtt    63840
caagcctgag gatgaagctt gccttttcctg ggagcttgta cagtgtcata ctcaggaaat    63900
aaactgtgtg ggaaaggtgg tgtttagtaa tctagagccg aacaccttgt aaggccctca    63960
ccttgtcatt ctgcactgtc agaagcacat gagaaaagag tgtaggctgc cagagcaagc    64020
atcacaccga aataggaact tctcagatag agccgtctgc ctaaaacaaa gtaaccttag    64080
caaataggat ctgtgctaca gaaaatggag cactctagcc agggttgtga gatggagctg    64140
gtcctggggt cacaggtggt gtcttgggaa acgttctgaa gacactcagc ttttcggata    64200
ttgcacagtt cattaggaga ggtatgggca gtggttatga agctccttat gtaagagaca    64260
tagagataca ctcaacagta ttactccaga gggtctggc tcctgtcttg cacttgggag    64320
tacacacttg ttcttgtcca cattaacctc caactgtcca catgatcaac catctgcaga    64380
cccactgcca gttgagggtc gtgccaggtc agaagtacta actgcaggtt aaactgtgct    64440
atttagaaat tgagtgtttt tttcttactc aaactgacag ttttcctttg tagaagaact    64500
cactcagctt ccactctggc ttaaatattt ccttttacatg atcaatatta tctctgtcca    64560
tcagatacag caatgagaaa gccttttaaa ggaaatgagg ttaaaagtga ctgggtatct    64620
agaattcttt attttgtttg ctaaattgca ggcaaatata ttcccagaac tagttgtgat    64680 acctttttcag aaactggctt atttgacatt ggctgaaagt aatactctaa cactttactg    64740
ctgtgtcaat gagtgaaatt cctgcaggca aaaacaatag ggactacatc gtgaagccta    64800
tgagaatttt atggtggaaa catgagtgga gcaggtggtg gaagtagctc atcttctgtg    64860
gttgtggtac ccacaggaga tgagctaagg agaatgccct gaaacctaac cttgccaatt    64920
ttctgtcttc tgtgtcctgg ttccttctgg tttccttgtg tctcttttct tccttttaat    64980
ttaatagtgt ttactgaaga ccttctgtct tccaagttca agtattagtc atctctgggc    65040
tttgccctta gatacttatc atagtctagc aatgaatgta agcattgagg aagtaatggt    65100
gacataatgt gaatgttcag tgtggtatca tcttccccac tctttgtaaa tcttggtggt    65160
cttaattctt gaatgtcaat gcttaccccc tctatgctgt ctttacagaa gtcctctggc    65220
ctagctctct ctacatgtct aaaattgtag aagcatcttc tgggcactcc attgcaaagt    65280
ccattctgca gaagcccacc atcccacaga aggagcaggt gggaggcagt ggaccacagg    65340
ctggctgcat ggtagcaatt gaaaagcaat ggagcacagg ctggcttcat ggtaacagtt    65400
gaaaagcaat ggagcacagg ctggcttaat tgtagcaatt gaaaggcaag cttcatctca    65460
tcagctggag tgtttactac ttgagggatgg gtacttgatt ggtgtatctt tacattttat    65520
caaaatgggt ttcaccttgg aagcattcag tggtacctca gtgaataatt gtaattagct    65580
```

```
aggatttctt tggggaatac ttattgttct aaatttatat gtgtttacat atatgtactg   65640
tattagtctt ttttcacact gctgataaag acataccgga gactgggtaa tttataaaga   65700
aaaagagatt taatggactc acagttccat gtggttgggg aggcttcaca attatggcaa   65760
aaggcaaggt aagaacaaag gcatgtctta catggcggaa ggcaaaaaga gagagcttgt   65820 tcagggaac tcctcattat aaaaccatca gatctcatga gacttactat cacgagaaca    65880
gtatggggga aactgccctc ttgattcagt tatctcccac agggtccctc tccctatacg   65940
tgggaattat gggagctaca attcaagatg agatttgtgt ggggacacag tcaaaccata   66000
tcacatacat atgcatatct ttatgtaagg tgtgtgaata taggtgtgta tattcatata   66060
ctcttgtact ttctcaaaca caaaccatag cacgtgcaat aatatccttg agttacatct   66120
gctactctgc ccattttaca cataagagat ggaagcattg atggttatat taggtagggt   66180
tctctagagg aacagaacta ataggacaga tagatatata aaggggagtt tatcaagtag   66240
tatttgttca cacgatcaca aggtcccaca acaggccatc tgcaagctga ggagcaagga   66300
agccagtccg aatcccaaag ctgaaggact tggagtctga tgtttgaggg caggaagcat   66360
ctagcacagg agaaagatgt agacttagag gctaagctag tctagtcttt tcatgttttt   66420
ctgtctctgc tttatatttg ctggcagctg attagatggt gcccacccag attaagggtg   66480
ggtctgcctt ccccagccct ctgactcaaa tattaatctc ctttggcaac accctcagag   66540
acacacccag gatcaatact ttgcattctt caatccaatg aagttgacac tcagcattaa   66600
ccatcacaat ggtgtataca cccttctctg gttgctgatg gagttaaagt gagagccagg   66660
atttgaatca tagtcataaa actgcacaaa acctctgccc catactacct cccagataca   66720
taatacacac atgagtaggt gtttttgtgc ctgttatagt gcatttgagc ctgttgttct   66780
tagtttgctc ttatgtagga ccatctctct gaaaacagat gatcagcatc atatgcaaca   66840
ggtagtattg attatctgta gcataaaggc atggaacacg ggattttcag ggaatggagt   66900
aggaaaaatt cctgaaccta agcagcttaa tagtttaata tttcacttgg ttagttcgaa   66960
tatatatgtt catatgcaca tgcatgaaat gacatggata aaataagttt taatgtattg   67020
tatctatata aatctcttta aacctcaaaa aatgtatata tccaaactaa ttatttgtca   67080
gtctctccct ctctttctcc ctctctctct ttccacgtat ttatatataa atatttctgc   67140
aaactaacca actgaaatat taagctccta tctatgtttt atatgtattt ctgcaaatag   67200
ccaaccaaaa tattaaagca attaaactcc taaatataat atttctttta tctattatat   67260
tatttcttca aactaaccaa ttgaaatatt aagcttctat gttttatata tataaagtat   67320
ttctccaaat aaccaagcaa aatattgagg tattaagctc ctgtgaatgt tttatattat   67380
tctatgtata tagaataata tattttatat gttttttatt atattttata ttattctata   67440
tgtagaataa tatattttat atcctatatt atatatagaa taatatattt tatatcctat   67500
attatatata gaataatata ttatatatcc tatattatat atagaataat atattttata   67560
tcctatatta tatatagaat aatatatttt atatcctata taatatatag aataatatat   67620
tttatatcct atataatata tagaataata tattttatat cctatataat atatagaata   67680 atatattttta tatcctatat aatatataga ataatatatt ttatatccta tataatatat   67740
agaataatat attttatatc ctatataata tatagaataa tatattttat atcctatatt   67800
atatatagaa taatatattt tatatcctat attatatata gaataatata ttttatatcc   67860
tatattatat atagaataat atattttata tcctatatta tatatagaat aatatatttt   67920
```

```
atttatatttt tattttttata atatattttg taatatatat gttttttata tatagaataa    67980
tatatttttat attattctct ctctatatat agcaggttag tttgaagata tctatacgta    68040
taatatatta aaatttattt ttggccaggc gcgttggctc acgcctgtaa tcccagcact    68100
ctggaggcc  aaggcgggcg gataatgagg tcaggagttc aagactagcc tggccaatat    68160
ggtgaaaccc tgtctctact aaaaatacaa aaaattagct gggcatgggg gcatatgctt    68220
gtagtcctgg ctactcagga ggctgaggca agataatccg ggaggcagaa gttgtagtga    68280
gccgagatct caccactgca ctccagcctg ggtgacagag tgaaactctg tctcaaaaaa    68340
aaaaaaaatt attttataga tataatttca tatatgataa gttaaagtac aaactcttga    68400
aacaactcct cttatatatg aggggaaaga agaagattat ttgtacagta caattagtac    68460
agtgaattct gggaaaaagt cagtaaatac tcatttcaaa tcctcatgta caattcaagt    68520
aaagaaaaat ctggtggcat ttttatatcc tgctaataaa ggttatctgg tgttggaaaa    68580
catattttat ttttacatgt acatagtagg tgtatatatt tgtgggtaca tgagatattt    68640
tgatataggc atatgtgtaa aaatcacatt agaataaatg gagtatacat cacctgaagc    68700
atttatcatt tctttgtgtt acagactttc caattatgct tttagttatt taaaaatata    68760
cagtaaatta atgttgactg cagtcaccct gttgtgctat caaatactag atcttattca    68820
ttctgtctat attttgtgc ccattaacca tcctcacttc tctctctctc ccattaccct     68880
tcccagcctc tggtagccat cattctactc tctgtctccc tgactgcaac tgaaagaaat    68940
attttttaaag aataggctgg aaggccacac tgactctcac tgtttctggc acactaaacc   69000
ttgccatttt ctgcagtagg gattgtctcg cttcagttat gccttgctac ttcagtgaag    69060
gactttctgt tcccactggg ctcctatact gagtctgctt tggagataat agtctgagat    69120
gtcagagcgt cttagtggtg aaagcaactt aagaggtcac tggcacaagc cctcgttttg    69180
cagtggaggg agttgatggc gagggcactt ggctaattag tgaccagggc tatagcaggc    69240
tcaggttcca tgactgtgct taccatggct ggcaggatcc cagggctttt ctgtgtaata    69300
tgtgggtgga tggtctattg ccttgggctt gtcgcataat catggagaaa acagtttata    69360
ttttcccttc aattttttaaa tccaagatag tttgatagca catgggaaaa taaagtcatt    69420
gagtaaaact tatacggatg agaatctttt gattaaattt tcattgtaaa ataatcatag    69480
tcataaaaag tgtatcaaaa tgtgtatttg gatattcatt ttaaagagta aaaataatc     69540
agatacatag tattgtaccc actgacagac aaggaaagag aacattccca ctgtttttat    69600
atatcagtgt gagttgcttc cctctctcct acctttcagt gaaatctaat cccccaagat    69660
ttggttttca tactgtcctt gctgtatatt tcaggacaaa catagctctg agcaatatat    69720
tgtttagttt tactattatg taaataaaat cacactattt gtagtcttct gtgacttgcc    69780
ttttatgttt gagattttcc catttttcctc catatatctg tattttattc attttttgact  69840
gttttgtaaa gccttctgtt ttaatatgcc aacatttatt tattcattat cctatttatg    69900
gatatctgga ttgtggcaat attttttgca attataattg gggcttattt atcctcagca    69960
aactaacgca ggaacagaaa accaaacacc gcatgttctc actcataagt gggagctgaa    70020
tgatgagaac acatggacac atgggggagg gaaacaacac acagtgggc  ctgtctgggg    70080
atgcccggag gggagagcat caggaagact agctaataga tgctgggctt aatacatagg    70140
tgatgggttg atttgtgcag caaaccacca tggcacatgt ttacctatgt cacaaacctg    70200
cacatcctgc acatgtacct tggaacttaa aagttgaaga aaaaaaaatg gggctgcagt    70260
ggacatttcc gtgcatgttt cctgatgcat gggagttcta gttgctccac atcgttgctc    70320
```

```
agtacttggt atcattgttt gtttgtattt ttattaatcc tattgtgatt tcatctgcat    70380
ttcaccaata atgaatgaca ttgagcctct tgtcctatgt tgaggctatc tgtagatttg    70440
aggactcctt cctggatgtg gatttatggt ggagaaacca acaaagatgg ctttgagtgt    70500
aggctgaatt actagaaaag taatgatcta gttatccaaa tatgaaacaa agcatggaa     70560 gcagtttggg gattggagaa tgagattttt aggagcacca aagatgtct atctgactat     70620 attcttgaag agaaaatagt catggcacta caggcatggt ggcacatacc atgttatcag    70680
ctggcactac aggtgtatgc ctccatgacc ttgaggacat atgactttga gttcggtgag    70740
agagatgaac acaaagccta gagagatctg caaatcattt gatttagatt tagaaattgt    70800
gtctggaaaa catttaattt cacacagaaa atcaagcatt aacgcacttt tattatttgc    70860
cagtccttgt gctagcttta gatatgcaga agatgaataa aagaaaaaaa tgcatcacag    70920
gtagggatag ataccttcat gagaatgtaa gctcctagtg ggcaggaact ccttctttac    70980
cccattacgt accottacct agcatagtga tctttacggg atacttctgt ggtctgaagg    71040
cttgtgtctt tccagaatcc ccatgttgac gttgtaaccc caaagtgatg gtgctaggag    71100
gtagggcctt tggagctgat gagatcatga gggtggatgc cccagaatgg tattaatgac    71160
attttaaaag ataccccagg gagattcctt gcccttttcc ccttttccaa agttataagg    71220
aaaatacagc cctctaggaa gcaggccctc accatacact gaatctacca tgccttgatc    71280
ttggacttcc agcctccaga gctgtgagca atgaatatct gtggtttata agcccccaa    71340 gctatgatat tttgttacag cagcctgaat ggactaagcc aacttctaag ttttggtgtt    71400
gtcttatttc tttggtcggt gtaggatctt tctgtccaca tagtttactc tagaaagatg    71460
tatgccctat tcctcatggt atatttgtct ttcctatctg tggaatatcc tcttatccaa    71520
ttcgtcttgg ctgggcaaca tataagccat taactcttta cccttgggtt tagtttgggt    71580
tctgctgagg cccctgctga aaattctggt ttctacaatt atggctcatg catgttcctg    71640
acccattaaa cttcagtgga agaacagaaa tggtgaggga ggtgatggag ttgatacctt    71700
gagctgccat atggtgcaag atcatcttga agatagaaca tttggcatcc tttttttttt    71760
taagagatgg ggtcttgcta atttgcccag gctaaactca aactcctggg ctcaagtgat    71820
gctcctggct cagcctccca attacctggc aatacaggca tgtgccacca tgcctggcca    71880
catttttact ctccaattgc ttaatatata gtaaagataa tggttcaaaa tggtaaattt    71940
tttttgtgtg taccaata acatttttt ttaccttaaa catattcaat cttatttga      72000 caatttttta aaatttcaac tttttttttt tattcatggg atatatctgc aggatttttt    72060
acctgggtgt attggatggt gctgaggttt gaggtacagt tgattctgcc acacaggtat    72120
ggagtatagc acccaacagg tagttttct accttttccc cctccctctc cctgctgtag    72180
tagtcccaag tttgttattg ctttatgtcc atgagtaccc aatgtttagc tcccacttct    72240
aagtgagaac atgtggtatt tgattttctg tttctgcatt aattaactta aaataatggc    72300
ttccagctgc atccatgttg ctgcaaagga catgatttca tttgttttt tttgtttgtt     72360 tgttttgttt ttttgagacg gagtctcgct ctgttgccca ggctggagtg cagtggcgcg    72420
atcttggctc actgcaagct ccgcctcctg ggttcacgct attctcctgc ctcagcctcc    72480
tgagtagctg ggactacagg tgcccgccac cacgcccagc taattttttg tatttttagt    72540
agagatgggg tttcactgtg ttagccagga tggtctcgat ctcctgacct cgtgatccac    72600
ctgcctcggc ctcccaaagt gctgggatta caggcgtgag ccaccgcgcc ggctgatttg    72660
```

```
tttttatggc tgcatagtat tccgtggtat atacgcatca cattttcttt attcaatcta    72720
ctgttgatgg actcttagat tgattccatg tctttgctat tgtgaatagt gctgtgatga    72780
gcatacatgt gcatgtgtct ttttggtaga acaatttatt ttcctttgta tatataccca    72840
gtaatgtgat tgctaggtca aatggtagtt cctcttttaa gttccttgag aaatctccat    72900
actgctttac acaatggctg aactaattga cgttctcacc aacggtgtat atagccttct    72960
cttttctctg cagccgcaac agcatctgtt gttttttgat gttttatgaa tagccattct    73020
gactagtgtg agatggtatc tcattgtggt tttgacttgc atttctctgg tgaaaaatgg    73080 tggatttttta aatgggattt cattttagga tttaatagaa actgcatagg tgactgtgca    73140
aagaactctt aagatttgac aaaaggcaaa ttagattgta atctccttta tgtaggaggg    73200
gaaataaaaa ccagaatatt aaaatatcta catgtacaaa aatagacaaa gtggcagatt    73260
gctggtgttg gatggatgtt gagcagggat ggaggacttg tgtgtgcatg catgcatggc    73320
catgcgtgga gagtggtcat tcattttggt aacagcatag agctttgggc ttcagaacaa    73380
aagataagcc catcccact caggtaccct aaaatgttgt ctccactaga cacaaaagaa    73440
aaggaagcca gagatgtctg tagcttatgc agagttttgg gaatagctat tctagacttt    73500
cttagtgaac agtatagaag gattattgta caagcccagt aatttgggca aggatcagat    73560
tctgttgctt ttgttttctg gatgctccgt aatgaatgtg agatggaagc ggatgtctca    73620
agtgcttctt gttctcagaa acctcctggc agcagacatc tcagtgggcc cagacgttca    73680
gcgtggctgg aagtaaaaca cagggaaggg tgctctttct cagttatcct atttttttt    73740 aaaagcatct acaaagcttc ctgttttcta atatattccc aggcctttga agacaaggc     73800 cataaacacc caggagatgt gactttattc ttttttaaggt ccagatacca aaatgcctgt    73860
catcagggct caccttaatt aaatacgtat cttaaaatta aaccaatctc aatttaagga    73920
atgtatactt tggggagaaa tttattacaa tttttattca gaacacttta aattctgata    73980
ggcctgaaga gtgtgagcct caccttaatt gcaacctgag tcagaataac tgccctgcag    74040
agaatcattt aaaataccca atcaagttat aaattagtca aatgccatt ctgagatatt     74100 attattttat gcagtctttg cagagaatac atgctatata gcccttcttc actcccaaag    74160
tatatgtata tatttaatga agttttcacc ttttttatta aaattttaa tccattaaca     74220 attttagaat tcattttgta gcatatcctc tttatcttag agatattaaa tatctaccta    74280
tttatgaata actatcaata accacgtttc acccttttgtg aaatccttttt cagttttgta   74340 aactcacatg ggagatcttg tttttttttt tccccacaag gatgtaggtt ggttaaattt    74400
acagtggttc tttaatgatg ataatgcaca tttgattgat atcaataata aatattgata    74460
tcttcaatat caacatttct tgtaatgcta aaaatttaca agttgccaat tttttgaata    74520
tgactatatt ttcacacaca cacacataca cgacagcact aattatattc actaaatata    74580
cctacagata cttaatcatt tacacagcca ctataatttt atacttgatg ccttaaacca    74640
gtaattctcc cttgagggtg gttttggccc ctgggctacc tagcactatc tagagacatt    74700
ttccatagtt aaaactgggt aggaggtgcc actatcatct agtgagtaga ggtcagggat    74760
gctgcaaaat actgtacatt gtacaggcga cgccccacac acaaagaatt atatggttca    74820
caatgtcatt tatactgaga tggggaaacg ctgggcttta attatagcaa ttttgtgcaa    74880
attagccaaa tttcaaaaaa caagggagtg aaaaagata gctctcaacc tgtgaatatt     74940
gtgaatgccc aatctagacc tagtaagtgt acagatgccc ttgggcgcgt cttcttaggt    75000
tgctgctgct tcataatcgc tcactgccca tcaggacctt gtgggatgta gatttaggca    75060
```

```
gaggagggtt tgatcatac agctggatca gtcataacca ataagtgact catagtctca    75120
ttcacattga gtttgagaat ttaaggtgtg ggctggaatt ccttatggaa ctaactttat    75180
ataccttgga agaagtccac ccactgaatt ctacatttat tgagctctgt gtttcaggga    75240
atgtgcaata ccttgaggat acatactatc tcatttagtc ccaagtagct tttaaatatt    75300
tgagagtggt tttggccccc aggctgaaag taacagctac ctctggttaa aaatctttca    75360
ggaaagaagc aaccaaacag gacatcacct ctttgttttt cttgtctgtc tcttaattat    75420
tcagaaatgg gattgctgta tggcagacat ccaaatgttg tctacagtag aattcagaga    75480
tagaagcaaa cacctaaatc agtcattggt gagatgctat ttgtcacttt caaagttata    75540
atccagattt tcagtgcgtt ttcatccaac tctggtgaac ttttcccagg atgtcatgta    75600
ctatggaatt tcccccccatt gtattattgt tctgtgatag atccagctcc aatatgtttt    75660
atttaaaaaa aaaaagccat gtgatgtatt ctgttcaact gattacttaa atgaaatgga    75720
taattatttt ctgatgcaga tgctctgaat aacccacaaa atccttagaa acacatttgt    75780 atatttgag ttgaagaaca tgctaaaggc accctccttg caacacctag tgaaatattt    75840
tctgttccta ggggatcatt taacaacata atgtccattc ctgcacagca ttcttttatt    75900
gtcacaggag cagcgactta tgtagggata gttatattat ctatgtaaag acaaattgag    75960
gtggtgaccc tttaaaagtt gactccaggc tcaatgggaa agtaactcaa atgcagcctc    76020 agcttttttaa atgggctgaa gggtgaagag gataccctct aaggcatgca gtggcttact    76080
ggaaagtcag gataattgta tcaacacttt taattatgaa tgaagtcttc aagaaactag    76140
cactacagca tgtacttgaa atgcaccatc ttgtatagtg ttttacaagg aaactgagat    76200
tcagagcagt gaagtgtgta gcctaaatat atatgcactt gaccagacca aggagaattt    76260
gtgtccaaag tctacactct tttcatttga tgatgttccc tttgtggcct gataaatatc    76320
cacatcatga tgccagattg acttggatgc atgcttccat cttctctccta ctggaaaact    76380 tttagagctc catgcatgtc tccttaggaa aatgtgacaa tttccttaaa catttgagaa    76440
acagtgtttt ggaagtaccc atgtattgat aaccagtctg gtaaacaata gcaaaactgg    76500
gaggtgttgt tactataatc tgcataacct gtataactct tgaacatctg tttgatcatt    76560
caacacagat ttgtttagtg ttttctaaat gtcaggcatt gttcatggtg ataggatgta    76620
cagaggaatt aagacaagtg gtggctgcta ggcatggtga ctcatgcctg taatcccaac    76680
actttgaaag gtcgaggggt aggatcccctt gaggccagcc tggacaacat agggtgaccc    76740
aatgtctaca aaaaaatcca acgaattagc cggacatagt ggtgcatgct tgtggtccca    76800
gctactcggg agggtgaggc gggaggatgg gttgagccca ggagttggag gctgcagtga    76860
gctatgacag caccactgca ctgcagcttg gcaatatag caagcaccaa tctctaaaaa    76920
aaacaaaata aataaagaca ggtgatgttc ttgctgttgc ctactatgtg gagatggcac    76980
tatacacatt tctatacaaa tgaataggaa tttcatagag agatgttgtg gatttcgtgg    77040
aagagccagc cagtgttcta ggtggtcgtt gtgtggcttc attattcttg tctgctttct    77100
tcctctttta ggctgccttg gagttttcat aagaaattgt ccctggaggt gttggatgat    77160
cacagcttcc ttggagcatt gcagttgctg gaatccagtt tcaggattaa gggagggctg    77220
cctccttgca atgggctgcc aagaaaacgg ctgtgcttgt tcttaacctc aggctctgtc    77280
tgtgatcagt ctgagagtct ctcccaggtc tactgctccc tggaaagccc tatctctctg    77340
caggctcgcc tctgggcttt gtctccttgg agccacatca ctgggacagc tgtggatgtg    77400
```

```
gatgcagatt tgaaccatgt cacggcccca gggactgcta tggcttcctt tgttgttcac   77460
cccggtctgc gtcatgttaa actccaatgt cctcctgtgg ttaactgctc ttgccatcaa   77520
gttcaccctc attgacagcc aagcacagta tccagttgtc aacacaaatt atggcaaaat   77580
ccggggccta agaacaccgt tacccaatga gatcttgggt ccagtggagc agtacttagg   77640
ggtcccctat gcctcacccc ccactggaga gaggcggttt cagcccccag aaccccgtc    77700 ctcctggact ggcatccgaa atactactca gtttgctgct gtgtgccccc agcacctgga   77760
tgagagatcc ttactgcatg acatgctgcc catctggttt accgccaatt tggatacttt   77820
gatgacctat gttcaagatc aaaatgaaga ctgcctttac ttaaacatct acgtgcccac   77880
ggaagatggt gagtacctca ctggaacaga aaacaatacc tcttgtgcag tgtgtagaga   77940
gatttgctag gagggtttta taatgtctca tgcatgatct cttctataac ccgtttattt   78000
tattttaatt tattttttcat attccaaatg caattcttgc agcaacttac cacatgttcc   78060
acttgtatgt attgggccat ctactgactg gacaaaacta taaataataa ctttaattat   78120
tttcatatat tgccttctta acttttata atgcttattt gcagatgaaa ataaatgaa     78180 gcatataatg ttgcatgtta tacctgaatc atctgtaaag gaatgaatct atagaaaaat   78240
aatagaatta agtacactat tatgctccag tttgcaaact gaaagataga gaaatggtt    78300 cttctgcct taatgactta agatattagc accttttttg agttttcaaa gaaaacttg     78360 attgttttta atatacaagt aggggatagt tcatacaatg gttggatttc attgtttaga   78420
atcggttttc ttaacgtaaa tttggatgtt cttttcttcc aatattcgct gcaatcaagt   78480
ggcaaaatgt aatcagatga ttctagctac attagagatg aatgcgtttg tattttaaa    78540 aatttccttt tttatataaa acaacaatga aagtctgtag acacaataac gtttaatata   78600
ttaacctaat gttagtaaaa catgaatagt tttatgtctg tatagatttc aaattcagat   78660
ttccttggaa gaataaccag actaaagtat gccataatgg tatcacattt cccagttagc   78720
atttccatat gccgttttta gatgaggaga agaacaaca gagaataaaa tatacctgga    78780
aagaaaggaa gttaatttgt gggaatgata gatgtatcta atgtagaaac tagagtgtgt   78840
cctttgtata aagttcttcg tggaaagtgt gataaatttc ttttatggag aaatttcttc   78900
ttcttctttt tttttttttt taaacttcaa tccctggaaa acattttca gtaagatttg     78960 gctgaaaata gtaaatcaac aacgacgtta atccactgat ctccaaaatt gttttgcatc   79020
tatcagatta ctctttctcc atataaatgc cagatagttt aagtagagtg tcatgaaaaa   79080
ccataccagg gttgtgtgtc actgaggtta caaattgtca ttgagattac aaagaacagc   79140
ccagagaaag aaattaaagg attctgcttc attatattag tggtttctgg catattgccc   79200
ttgtcgttat ggtgacagac ctctcaatta tctcataaag tccaggtctg aatgtgattc   79260
aaggagttaa actgacattt ggacgctgta cttccatggg gtgttctgag ctgtctccgt   79320
gcctaacagt ccctctttgt gtgtgtgtgt gagatgaata agagctctca aaagcaatta   79380
gggttctcat ttgagcagcc acctgggttg agatctttct cataatgaac tattcaaaca   79440 aaaccaaaa agaaaggaag acaaaaatgg ggagaaaacc ccccaaacag gacaagggt     79500 taaaattgct ttcataatac tttggatgtg ctagagtctg gtgattttgt agagctagcc   79560
ttggcaacaa tgaatgcact tcaaatagaa ggcctcctca tataggagtt ggacagaatg   79620
agaccaccca tgaaaagaa tcaatagcct ccctgactgc agagccctgt atgtacaatt    79680
gtgtggatgg agaccacaaa cggtgtggcc gtttcattgc aattcggtat tgaattaaaa   79740
tttgaggaat gtaaatatgt gaaaaatgct attcagtgaa aaagtaatcc aaacttcata   79800
```

```
ataaacccag ttccacttgt ttagatcttt aggcttttg aagcaatatg tgcatatgat    79860
cttgacaagg gaatcagaaa tctaatagtg actgaaaagg tagaatcgat ctccccacga    79920
tgtgtaaact ttagaatttt gctggtgaga gttcaaagct acagccctgc atgtttgtac    79980
catccacaag tcagccta ttgggttagg agtttttatt tttggttgct tgcttgtttt    80040
cttaactcta tcaacgaaga accagtgcag gccaggcgcg gtggctcacg cctgtaatcc    80100
cagtactttg ggaggccgag gcaggcagat cacgtggtta ggagatcgag accatcctgg    80160
ccaacatggt gaaaccccat ctctactaaa aatacaaaaa ttagctgggc atggtggcgc    80220
gtgtctgtaa tcccagctac tcaggaggct gaggcaggag aattgcttga accaaggagg    80280
tggaggttgc agtgagccac aatcgcgcca ttgcactcca gcctggcaac atagcaagac    80340
tccgtctcaa aaaaaacaa aaacaaaaaa agaaccaatg cagagcttta gatgtttaat    80400
tattaattat tcactaaatg aatgaactcc gcatccacaa catattgaaa tgttggcatc    80460
atgctgattc tctccaaagg ccttctctta gggagtatct cagttcagat caatgctttt    80520
atttagcagg agagagagca atattattat ttggaattca aaattccact ctgaccagtc    80580
tgacaaagcc agaaagacaa atctaaacaa taacaacagc aaaaatctac tttttttgtt    80640
tagctttgtc tttctgcctt gatcagattg gctcaaattt ctatgtttct actttcataa    80700
aatgtgtagg tatattaaaa atacaaaaat agactatttt agatacgtac ttatccttac    80760
atttaagaac taacttgcat gaggaaaagt gttggaaatt tcttcgtagt acaatagttt    80820
atgaaacata tatttttttt ctgtagaaaa caatactttt tataattccc tttaaaataa    80880
atcaggtctt gctgaaggtg agtcttttca tttaaactgg catcatgatc tactaaactt    80940
aggcttgggt ctttataact atttcctacc ttacaaattt ctttatttaa attttcatag    81000
gttattaatt tctctttgtt gttagacaac aggctaatta attaacttga attgcatatt    81060
taaccttttg ataggtgctc aaataaggtc aaagtcagtc aagccagtcg gaagctctag    81120
taggacacgt gggccattgt tgacaaggaa cagttggaga ccgattgacc gaatctgcat    81180
ggtgtgtgtg tgtgtgtgta tgtgacagag agagagagag agagagatag cagagagagt    81240
gtgactgagt gactactttg aggaagcaat gcagaatatg gcttggtagc ttgattaaac    81300
ataaattgtg aaagtcaagc cgagaagttc cagtctcaca tactaagtcc acttgagttc    81360
atacatgagg ggatggcagt acagttcgtg attcgtcttg gtccccaagg agactgaaca    81420
cagaaagatg agttatggaa acacttaagg ttttaatga gaaccagtga tactgtttag    81480
aagtgaggtt aaaagtaag ggaaaaataa agcacacatt ttgaaggagt tgctcagaca    81540
agatatcata ttaaatataa agcttggagg agaaagagcc acaagtgagt ccagattgcc    81600
ttgggaaatg gacagaccca tggaaccact tcctgagtga cctacacctg tgcttttct    81660 ctggatcctt ggacatacat cttaaggtct tattcttgaa agatttcagg ggcgagaagc    81720
ccttccattc ttcatcatgg gactaaaaat actgggaaat ataaggaaa atataaatga    81780 aagtcattat cgcccaggca cagtggctca tgcctctaat ccgagcactt tgggaggtca    81840
tggtgggtgg atcacttgag gtcaggaatt cgtgaccagc ctggccaata tggtgaaacc    81900
ccgtctttac tacaaataca aaaaattagc tgggcatggt ggtgtgcgcc tgtaatctca    81960
gctacttagg aggctgaggc aggagaatga cctgaactcg agaggtggag ggaggttgca    82020
gtgagccgag atcgcaccac tgcactccag cctgggcaac agagtgagaa tccctctcaa    82080
aacaaaacaa agcaccactc attatcattg tattttcatt gtagcataac agcaaatgcc    82140
```

```
attatgatttt ctagaaaagt gaaattttgg gttgtttttt ttttttgcta gcaatacaat    82200
tgaaaaagga agatattaaa aaagaacaga ttattggatg caaggtgtcc ctatcatctt    82260
tttcccccaa gatgacacct gactctttga atactatgac ttaagtaagc ttgctatgat    82320
tgttgattga ggacctattt ggtgaaaaca tggagcttta tgatgaaata taaacagaca    82380
cgacatggac aatgacctgt aggagtttgc acagttaata aacctagagg tagataataa    82440
gccagagcat cctagttagg gaacaaagaa agctctgtga cagctcaggg acaggctatt    82500
ttttgaggaa aaacttgatg gaagctgtta agttgttgag ctgtgccatg aagaatatat    82560
gggtgatgga agggattcat ctattaaagc atctgatgaa tggaacattt gaacacagaa    82620
atctatgtta agcagtttgg tgtcaatcgt tgctgttgtt actacttggg tgttaagtgt    82680
ggcgtggtaa cagaagctgt gctttagcat gggctgtttc tggcagtgcc atatcatgaa    82740
agttcttttt tttttttttt cccttttaga aacaggatct tgctctgtca tccagggtga    82800
agtacaatgg tgcactcata gctccctgca gcctcaacct cctgggctca agggatcctt    82860
ccatctcagc ttcctgagta gctgggacta caggtgcact ccaccatacc tggctaatct    82920
ttttagtttc tgtagagatg gggtgtcact atgttgctct ggctggtctt gggttcaagt    82980
gatcctccca cctcggcctc ccaaaatgct ggcattacca gcataagcca ttgcactggg    83040
cccataaact tttttatgtt atccacagct gctgacccta tactttctag ggtagacaag    83100
ctacctaaga tgaaagggtg gcaggagaac aacagggaaa gaagctggaa agtcaaccag    83160
ctttgctagc gattttacaa aaaaaaaatg tattcgcttc ttttatagat accactggat    83220
ctaattcaag atataattta tagcatggtt ttcatccttg aatagctccc atcttttctg    83280
agggtcttac aaacttttct ggcattctgc attagtcaag agatatttgt gttcaaatgg    83340
tagaaggcaa cctagcctca atctgacttt gagggaaaaa atggaaattt attagaaggg    83400
ctatgggata tccaaactta ctgtaaaagt tgagaaatca gattggcaga atggcaggga    83460
tgcagctaga ctttagacac acctggaagc attgaatcca aggacatcac caatcttcat    83520
atctcgttct ttgcttcttt ctggaaatag gcttgcttta aatggcagta agagggttct    83580
ctgcagtttt tgttagttgc attttgtttt tctcagtacc accagtgagg acaaagttc    83640 cataattcca tactaaaaat cccagggcgg ggttttgatt ggcccacttg actcaggagt    83700
aagaagagat aaaactgggc tgttcttgtg tataccagtt ggcaggggga gaaggacagt    83760
tctcaccata aggtgtctgg aatgagcagg cactacttca cttcactgtc caaatatttt    83820
ttgagcatcg attatatgcc agacatgcct tagaggctga gattgtgaga gatacaagca    83880 ttcctaatttt tgagagatag gtacttgtag gcagaaaagt catggtccct gagagatgtg    83940
caagcaccgc cctccacccc taccccccag ccaactcgcc cattcctgga acctgggaat    84000
aggttggagg catggcacct gacttcttca atactctgcc ttaaataatg acttcaaatg    84060
gcaaagggga attaaggttg ccgattgaat taggtttgct aatcagcaga ccttccaata    84120
gggagaatct atcctggatt ctcatatata ttaacagaga ccctccactg tggatgcaga    84180
agactcaaaa ggagatcaga gttggtgtaa agcaacgtga gaaagagata cctggacatt    84240
gctggctttg aatatgagag agccaggaga aggaacgca ggtggcagtc tctagaagcc    84300
ggaagagaca gggaaacaga ttttcctta gagcttccag caaggagccc gacagccctc    84360
ctgatacctt gattctagcc ccatggaaga aactctgacc ttagaactgt aaaagaataa    84420
atgtgtgctg ttctaagctt actaagtttg tggagatttg tcttagtggt aatagaaaac    84480
taaggaagag ttttatcacc ctgtaatatt atttgaaatt cataatgaag tattactctg    84540
```

```
aaaacaaaag ttcagagtct ctgaagttgt ttggtttcgg gccttctgga cccctctcca   84600
ttctgggatt ctacttccaa gaatttctag ttgaaaacac ccttgggcac ttagagcttt   84660
ctaccttgct caagcatgct aaggagatca tatcaattct tattttaggg cagacatttt   84720 tcagatttt aaaaatgtat ttttaaaaa tttgagagat aggtaccctg tctctgaatg    84780
gggtcttgca ctgtggccca tgctgcagtg cagtgtcaca gtcatagctc actgcagcct   84840
cgaactcctg gccgcaagtg atcccccaac ttcagcctcc tgagtgtctg ggactatagg   84900
ctgagactac tatattgagg ttcagagaag aagcatgtcc aggtgtctgc aaattagaaa   84960
atggtggcag atttttaaa aagaaacga tgaaaaatta ccctgatta gatttacatt     85020 acaattttca gccaccatga ctggctagtt tttaaattt taaagagttg gagccttcct    85080
atgttgccca gactggtctg gaaccctagc ctcaagtgat cctttcatct caaactccag   85140
agttctggga ttacaggtgt gagccaccac gcccagtgac attttgcaaa tttgacattt    85200
tgcatcatgt taatatagcc tcatggccaa ttgtcctaaa tggtatattc aaagataat     85260 actgttttga cacagaaagg taccaaaggg tcatttagaa ttttttcagg aagctataac   85320
agatttccag agtagatggc tttgaatgac atataacaaa ataccgaaat tgttctttcc   85380
tcatctgtct ccacagagtt tcactcaaga tcgcggctgc acctttacat gtcttatttt   85440
cctacttaca aacactgctg acaaaatcct ctgtgttccc cactccttcc ggctacacct   85500
taagctgtgg tctcttctgg gcaaagtgat tctctgacct tttcaagcta caccttgttt   85560
cctcctccaa ccaaaacttg tttgctggag ttgaaatgcc agtttagccc cttagcagat   85620
cagtcattat gggcaagtga cccagcttgc ttgggccaca gtgtccttat gtctaaaata   85680
gaggcggctg agaggtttaa ggttttaatc catataaagt gcttagtagc cagcacgtac   85740
aagcaccctg taatctgatg ttagtgcagc atcattaata acagaaaagg gaacccgaaa   85800
atttcagcaa aattgcatgt gcatagtggg tctggtatgt atattagtct aggcataata   85860
aatgttgaac gtctgtgaca taactattgt agtagtagag gggtaagctt aagaagtaag   85920
accaataaat agcccatcat ttctggcagt ttctagtatg gttttaacaa agggaatt     85980 tgggaggaat aacatttta aaagagccc actattatca ttctgcttta ttcctaactt     86040
tagtcctttt gagcctgtgt tatcaaatgg attttgagca tatgtgaatt agagaaatta   86100
atcactagga aaggattaga attaactttt ttggaaaagt tccttaaacc gtgaaaaggc   86160
agtaacacca ttctttgtgt gtgagattaa agagaaatta attttctttc tcttcttgtc   86220
tagacacaca aagtccaatt gtacgcatac agtcacaaaa tataggtgaa aaacgaaaac   86280
tgtgttaaca cggtgagaca gatgttttaa ccaatcaaca tcaacatgca actaggtgaa   86340
aataattaaa ttactccagt tttcatctgt cagttggatg tttgacattg tgtagacaca   86400
gcttataagt aaagataatt atgaaagatt attaaataaa gatctccctg acacggatta   86460
attgaaaagt atttagtatt ttttgtaagc acagttaaac tggagtggat ttccgatagc   86520
atgtgtctct cccccagctc aaaaagcttt cagcaatttg aatactgagt aataatctta   86580
ttgagggttt agaaattaca tatgtttgga ataatactat ttagtagtat gaattatgcc   86640
tgtttgaata attaagaaat atcttttcct aacaaagaac attttccctt atgtacataa   86700
tcttccaata catgaatttt aattcaattc aatttgcaat ttagattctt gtcataattt   86760
gaacaaatac agattaccta gaatatatta aaaatcaaat tttcacatag tgcatatcat   86820
aagaattttt ttttagaaat tgtcagagat agaaactta ggtacaacta gtccactgga    86880
```

-continued

```
atatttggcc atttaaaaca attagctcat tatttatttg tggagtcttg cttcctaaga   86940
tgttgtagtc ttatttgttg tcaattaata ttgctggttt gaacatggtt atttattttc   87000
cgtactattt tagccaagct attaattttt attatttatt tttttaattt tatttttttt   87060
atgtttgaga cagtcttgct ctgtcaccca ggctggagtg cagtggtatg atctctgctc   87120
actgcagcct ccacctccca ggttcaagtg attctcctgc ctcagcctgc cgagtacctg   87180
ggactatagg tgcccaccac cacacccagg taattttttgt attttttagta gagatagggg   87240 ttcaccatgt tagccaggct caaactcctg acctcaggtg atcctcctgc cttggcctcc   87300
caaagtgctg ggattacagg tgtgagccac cgtgcctggc ctagccaagc catttaacct   87360
ttaaatattt agtgtcctca gctattaaaa ataagagtaa tatgattata catcctatga   87420
atttgtttta taattattgt gatttgggag taaacaacta tataagaaat aattataaaa   87480
gagataagat tagtgcatat taagactttg atgtcaggtt aattgaatgt taatcccatg   87540
actttatctt tcattgcaag attctttgcc tgagtgggt actggaagcc attgttgaga    87600
gtagatccga tcttactaga ctgttggctg gttctcctaa aaccaggctg ttttcataat   87660
gagttagttt aacattttgt ctttatgttt aagcacccct ttccttggtg cagtcacagc   87720
caaactgcaa acagaaatcg agaagttgtg agctccagat ttgagagcca cagagagttt   87780
gtgagatcaa aaacatccac tctcagtaaa taaatcagag ctacctaaat cacacagtca   87840
gcttaaaggc aagggaacca gagggaaaaa ctccaaagga gtgatctctt catgcaattg   87900
ctactggtaa aataaagcaa agatgagaca gtgtagtctc caccttatta tttcaatcta   87960
atattctata ttgaggttca gagaagcagg tccagatttc cacaaattag aaagtggtgg   88020
cttgctcttg taatcctagc acttggggag gtctaggtgg gtggattgct tgagcccagg   88080
agttaagacc agcctgggca acatgacaaa accctgtcct taccagaaaa aaaaaaaatt   88140
agctgggcat ggtggtgctg gcctgtagtc ccagctactt gagggatga ggcgggagga     88200 tcacttgtgc ttgggagatc aaggctatgg tgagctgaga tcacagcagt gcactccagc   88260
ctgggtgaca cagtgagacc ctgtatctaa aaaagaaata aaagagaaac atttccttgt   88320
tagactttac gtatctgacg atgacttttg atggtgaagg taggcattgg tatgtggtct   88380
gtggtgtgtg tgtgtgtgtg tgtgtgtgtg tgtgtgtgtg tgtgtctgtg tgtgaatgct   88440
attgaaggaa acccggtagg agaaatatcc acaattcagt taagatcaaa catgttacaa   88500
ttttctggga agtgccaagt tttacaacac ctaaactata tcctcttcct ctctgaaacc   88560
ccaaacatcc caaagtctcc ttcaagccag acatcctctt ggtctactgt gcatggtgtc   88620
tgcacggtcc tcaagtttgc ctcagggaaa gtgcctgttg ccatcagaaa gaaagaatgc   88680
agcaggtact gatttatctc aggcaaagga gctcttgtgg tgggtttcaa caagatatga   88740
aaattgtagg ttcttgaaca ctccttttct tcttccttaa aatggatgtc tttagctaca   88800
ttctactctc ttctctgtct tttatgacat aatcagtcat tcactcaaca agggaacatc   88860
taatattcac ctaacatccc atttgcctgt cacatatgga ctttagcctc cagtcgggcc   88920
aatgacacta ttgatctcct aattccaatc tagactcttt gggtattttt ttctcttttc   88980
cattccttat tttctttaga ggcatttttag ataactcatt taaaattat tagtaaataa    89040 atcattattt gcaatcagca tagacaaggc cttgggtgag tctaagtgga tatctggaga   89100
gatctaaacc cgctgctgga aaagtgagtg ggaaagcccc attgatatgt gacccaacta   89160
aaccaacgtt tcatcaaaag cagtgtcttc agggactgct ttaggatttc agggaaagaa    89220
aaatggaggc aaatctgaaa gtggatgttt tctatggagg atccttgata gaaaagtttt   89280
```

```
cacccagcct tgagtgaata tgcagagcgt aaacacatgt ttgtgcagtg aggaaatgct   89340
gtctatgttt cctaaaatgg aagttcttgt ttattgcttc tttagctgca cggagacata   89400
aaagatgcaa aactggggag aagggagaga taaaactaag acaaaactgg aggagggtgc   89460
aatgatgttg taatttaaca tgcaaaatac tcacttgggt attttttaaa ttgttacatt   89520
gtgacattgg agggttcata aatggaattc catccaaact aattctaatg cctatctttt   89580 cttttagca gactatagaa taaagttaaa tcaaagaaca tgaggtccca ttcttaccaa   89640
attcaaatat acttttatc acctggtgtt taaatcatta atacaaaagc tttcagtctc    89700
ctccaaattt ctattctagt aaagtacttt cataatttta tattggaaat gtactaatcc   89760
agataactag tatgaaatca agttataata ctattttgca tgtttctaaa atgtttacat   89820
ttaaaaatag agaagtaagc cttagggaga aaacttcagc tttcccaaga atattaaaat   89880
gttaacaaat tatttcattt tgagctaaaa tcagataata atgagaacaa atttcaccat   89940
cgcacattct acagggatct ttgcatttta tactttttt tttgttttgc tttataagag     90000
gggattttgg tatattgaat atcatactgg aaatttacct ggacggaaac gatagagtca    90060
acttagactt taatcacaga atgataacat cttccaagga gaaggagctt ttgaggtcat    90120
ttcaccaaaa ctctttcacc atacagtatt ttcccgttca ttaaccttt ggcactctaa     90180 gcagagatga agtatcctcc cctgagttcc tagaagttga atttaatcac catttttacga   90240 gtctgccctc cccagtagat ggtaaaccct ttgaagaccc agagcatttt tgagataaaa    90300
gaatgaatca tatacttcag tacatggaac aaatgaataa acctgtagtg cctggccacc    90360 cagcttttt tttgaacctg accgataaag acgtttacag cttttaatt tcattatcag      90420 agaaagggtt ggcaatattt acctgagcac tctctacaaa cagagatgaa gaaatttgga    90480
atgtttcctt tctctcctaa tacatagctt tggaagtctt agaaaacatg ttggtatgtt    90540
ccttctaggt agtctttgc aagcatcctc ttcagtgtca agcatctatt ctcatgcatc     90600
acattacagg ttatgaatat acccagagtt tatgtgagat ctttttttgt caaatgcatt    90660 aaaccttgg cttatatata ttgagctgga agccacaagt ttttgtaata tttttaaaagt   90720 aatatatttt ataatatgcc ttagaaatta aaaagaaaat agaatacctc cacttcctat    90780
gacaaaatgt cagcatatac agcaaggcaa agccatttgt tgctgaagct cagttttttcc  90840 caccggatgc tgaatgcaca acaatcacca gccaagccag gagtctgttt actgcacgtt    90900
tccctgaaat gccaagcccc tgaggtgtta caaggaggga aggcagcata catgtgtgat    90960
agaatggcca ataaactaat tggtttatag ttttgagaaa gcagctggtt gcctgttttt    91020
aaatgcagtg gtctataatt tgatagaatg cagaaggaat catttccaag aaattaatta    91080
aagttcatag gttggaaaat aatggagctc atcattaggg aaagcttatt ctaagactta    91140
ggataaaatg agcttcctct tgcatttcat tcaacttaag gttttgtagt tacttgtcat    91200
catcaaaaat atcatcagag tcatcgccat catcattatc taaatttgag tagctatgag    91260
aaggtattgt gaggtcctag ctttagagga atcaatttct ttgagatttg atattgttat    91320
tttaagactg cagagcatag gttagaatct gtgttttaaa aactttgaca ggccacgtca    91380
taggtagtaa agttttctct tggcatgagt tttgagttga cttgtgttat ggttgaattg    91440
tgtctctcaa aaaaattgtt tatgtcttaa ctcctggtgc ctaggaattt caccttatt    91500 gaaaatagga tttctgcaaa tgtaatcaag gtaagatgag ttcatactgt gttagggaag   91560
atcctaaacc caatataatt ggtgttcttg taagaagaga cacaacaaca aagacagaaa   91620
```

```
cagggagaac accatgtgag gatggaagca aacgttgaag tgattcatcc ctaagccagg    91680
gagcactgtt ggaaaccacc aggaaccaag aacaactcaa tccaagacag aagcatgaaa    91740
tggattttct ttaagagcct ctagaaggaa tcatcttaat tttggactct gccccagaac    91800
agtgagacaa tgcgttcttg tttcaagtca ccaagtttgt ggtaattagt tacaaagccc    91860
cagaaatgaa tgcagtctgg attaggtata ttctgcgtac atatgctgcc taagaatgcc    91920
agaagccaga agaggtgatg tctgcatttt tggttcctaa aatcctctct cagtacccac    91980
tgctctgtcc agggcaaagc tcccctgaca cattttagc ctttaggcta tgtcctatct    92040 ccctgctca ccagagaagt aggtcttgga ttccagtctc tcagggctgg catttccaa    92100 gtgaaagaca ctgcctttgt gtaaatcctt ccccttgag tgtaggcagg acattggatt    92160
tgtttgtgtc tcatggaata tggtagagat aatggaacac cacttccatg attatgttac    92220
ataagcatat aaattgtgtc ttactagtat acccttttg ttgcattctt ggtttccatg    92280
ctttgatgaa agagcagcca tattaaacag gtgcatatgg caagaagctc agagctgcct    92340
ctgaaacaac agccagcaag gaacagaggc tttcagtcca gcagtccaca gggcattgaa    92400
tcctgccaac aaccacataa gtttggaagc gaaccttcct cagttattca gctttaaaat    92460
gagaccccag ctcaggccaa caccttcatc agtgagagac ttcaaagcag tggaccctgc    92520
taaggttgtg cctggattcc tgatatgcag aaactcataa aataaataca ttacttgaaa    92580
ctgttaagtt ttggttattt gttacatagc agtcaataac taatgtggca taatatgcaa    92640
aacatggatt tcagctgagc acagtaatcc cagctccttg agaggctgag gtgggaggat    92700
tgcttgaggt caggaggtcg aggctgcagt gagctatgat agcaccattg caatcatagc    92760
tcatggcagc tatgagcctg ggagacagag caagaccttg tttctaaaaa aagacatgga    92820
tttcaaattt ggccagattg taacccaact tctacataga tattatgtct ccattggagg    92880
gatatatatt ttgagacttt gcaatcctta attacttagg aacaattagt tagcaagtga    92940
aagaaattca ggttgaattc acttaaggga aagaagaga ttttcgggtt ccatttacta    93000
gcggtgcatt tagtttcgaa aatggtgtcc tcaggtctaa tcattgctgt taggaatctg    93060
gcactttggc gccatgtttc ttcttttggct ttcttagaga ggcttgtccg tgtgtggtgg    93120
taggcagtca acagcatttc ctagtatgtc atccttttct cagagaagca cattggccta    93180
gcaactatgc gtactggcct aattttagtt gcatgccaac caatgtctat atccagtgga    93240
aagagatact tgaattgata tggactgctt gggttatgta tactcttcag aaatgagaag    93300
agattgggta agtccagtag gcttagggta gatggaagta agattgctcc ccagaggaaa    93360
attgaatgct aggtaagcaa aactcattga tgtccattgt tgcttatatt acaaatagta    93420
ccaaacaaga aagaatggca tggctgcttc atggaagagg atgaacttt ggggcaaaac    93480 cttacctagg atatttcctt ttttcagcta aaaagaggaa cttggacatt cagaaatgag    93540
aaaacttgta tatcagttgc tgttgttgtt ggtttgtaaa cagctgtagc tcttagtgac    93600
atagagagat aaagtgacag gaacagatga ggatatttct attaggatgt tatccaggca    93660
gttctatgtt gggagtcacc ctcctgggac actcctgggt ctggaagctg tcagctggtg    93720
gcaaatcaga gatagtctga gatttaatgc cagatgggaa acgtgacctc aaatgaatga    93780
ggctgtttag gagtgggcgc aacatgctgt gcttgccatc tcttttaaga gttctaactg    93840
aaaggttagg tttactgaag gataagccaa tttggggagc tgatctggtg aacatgaatt    93900
tggccaaact tcagcctaag cgtttagcag ggtgaaagtt tgggaagagt ttcgttgtag    93960
aacattaggc aaatggctga caaaagagct tccagttctc tcacaaggaa ttcttcaaaa    94020
```

```
agcaaaggag gtccttctca gtcagcctgc tctttctgct cagtagactt ctttgtgaga   94080
ctatgctgtg agtgagttct caggctggtg atataacctg gtcttcaatt cttgtgcagc   94140
tctgtaagtc cacgtaggca ccactaaata tccttacgac attaagtgtc attggattgt   94200
ttgctaacat ttgcttccat atgggcccca ggcattagca acatgtagt ttattcattt    94260 atttattcac tcagtgaata tttattgaac ttattctaat tgtcaggcca ctttgctaaa   94320
tgttgttcca tcactttcct tgcagaacat acagggaaa atgcacaact aactggaatc    94380
atcatttagt gtaatccatg caatgatgca acaagttggg gagatgtgag aacatctggg   94440
agaagcatgt gtcccagact gagagggtga aaatgcacta aggagaaatt tgaagaatca   94500
gtaactgacc aaattgctgg gaggagagtc atttcagaca gacagaggag cacgttcaag   94560
gctgaagtcc acagcctgac attaatatcg attctcttag ctaagttttg ttaaagaaac   94620
caaatgacag tgaatttgaa gtcctgcact cagccaaccg tatgaagtgt agtcactgta   94680
tggtcagtta attacagggc agcatccttc agtcatcagt cgagctagag agaatattga   94740
cagatgtgct cttatgaaag ctgagaagct caaccaggac aagtatttag ctaaaagggg   94800
gtctgacctc cttttagaga tgggaagcaa gggtggacag cataacctgt agactaaatc   94860
tatcacactg ctgtttttgt gaagggttta atggaacaca aataagccct tttatttatg   94920
tattgtctat gtctgctttc acactacaaa gacgaagttg agtagttca aaagagacca    94980 tatggcctgc aaagtctaca atatgtacta tcttacccct tattttaaaa agttttctga   95040
cccctgatgt aaaggaccaa cttcatgaag tcgcatgtgg atttttctagt taccatatag   95100 acatgaatgg aagagtacag aagttccatg tcagacagca attgttttca aacttgctat   95160
gaattttttc caaatgcaga ttcctgggct ccatccaggc ttccagtgac tcaaaatctg   95220
ggtatagatt ccaacaattt gccttttagt gaccttagag gtgatattga tggcaaaaat   95280
tttatatatg tacatattca tgaaacagaa aattggacgt gaaatatttt taatccacat   95340
ataaacagat actcctttct gtcattaaaa accaattagg aaaaaatgat aaaagcctga   95400
ttttaaaacc atggtccata tggcttatgc aagataattt tctgaagtga ccttcaagat   95460
gaaatagttg caaagtatat ctgtgttcag ttaaattagg aggtgtgtgt gcaacaagga   95520
attattagcc gtagatcttt aaaatcaaat caatgtaaac aaaacactgt cagcccagtg   95580
gccaaagaac acaatcaatc aaaatatgaa taaaatataca caattataca ctactactac   95640
tagatgatga tgatgatggt gatgatgatg gttatgatgg tgatgatgag gatggtgatg   95700
gtgatagtga tgatggtgat aatgatgatg gtggttatcg tgatgacgat ggtgatgatg   95760
gtgatggtga tggttatgat gatgatagca atgaagataa caattattgt gatgataatt   95820 tatgggcgata ataatgattg tggtgatggt ctgtttctat gcgtcaatct cagttgctcc   95880
cccagactcc atacaaacag aaccaccttta gagatgtttc aaacttacca tgttcgaaac   95940
tcagctgctg cttttgacac aatgaatgcc ctcctgtctc catttttacc atcttaggag   96000
aactcacacc atcccctcat cactcagtga gccaagtgtg ctagctgctg atccacatgt   96060
ctgaatggcc gccttgagga attgacatta ccttggggac ctacaggag caatgatgct    96120 ggactggggc aaggatgaat aaaggaggga taagtccaag ttgttggggg aagacagggc   96180
agccaactct atctggagct ctcagatggg tttagcggtt gtggagatat ttccaatggc   96240
attttgaaga cgtggaagaa tgttattagg catagcagag attcttaact aagagcaatt   96300
ttggccccac tgtaagggac attttgacaat gtctagagat attgttggtt gtcacagctg   96360
```

```
gggaggtgct actgacatgg agtaggtggt gaccagagat gctgctgaac atggtaaaat    96420
gcagaagaac gactcacaca gcagagaatt atctagtcca aaatatcagt agttctgata    96480
ttgagaaact tggctctgta ttgtgcatgt gtaatcgttt tttacttact gattctagat    96540
tcagctggca aggggtgtc agcaatgtct ggagatattt tggattatcc catctgggca     96600
gtgtgtgctc ctgacatcta gaaggcagag gatgctgcta acatcctac aatgcacagt     96660 acagccctca caacaaacat aatcatccag cccccaaatg cccacagtgc tgatgttgtg    96720
aaaccctgct ctaagtcaaa gcattgtctt actcaatttt taattcctag tgtatatcag    96780
tggttctcaa ctttggggag gggacaggtt tgcttccagt gtacatttgg caatgtggga    96840 agacatttt gtttgttgtg agtatggagt gtgttactgg gaatggaggc aagggatgcc     96900
actagacatc ttaacagtgc ataggacagc ctccacacct cagaatgatc tggcccctaa    96960
tgtgaacagt actgaggtag agaaaacatg aggtagactg tagaagccta tagaagaaga    97020
gaatctgaga aaattgttgt gcttggggaa cactgaagaa tgtggagcaa ttgaacaaat    97080
gcttgtgcag acagattggc accaaattgc aatggagcac caatgggaca gtgaaaaggg    97140
acaagtccta caatgcacag ttcttgacca tccccaaagt gctccaaagc tacagaagtt    97200
ggtgtgcatg tattatctca ttgatcctat ttgggaatta tcatgttgac agctggagtc    97260
ccatgaagga acattttaa gcagcaaagt gacaagctct gatttgcctt ttgagattaa     97320
tgactcagag actgccagtt atttgttaac ttgcttgatt cagcctaagc agacatctag    97380
agggtgtaat ttgatttatt ctgcagaggg gtgattggcc cctacattat cttggcacac    97440
tgcctgaatt tctgaacacc aaagactat ttatttagtg tatggccatc tcatttccaa     97500
gagtcaccaa agaagtgaga atggattaga tagggaacaa gctgaccatt ggattagttt    97560
atcagatgat tagcatgcca tgctaattta tcaagacatg gaacatttaa agaaggggag    97620
agtaacatat acagggaaga taggagatct ttgtcccaat tatttctttt tttttaatgc    97680
atgaatagtc ttttggtaaa tatagtttat gtttgtttct gctttctaag ttaggctgca    97740
aaatattatt tatcggtggt attctttgaa attgattggc atggcaagac tgtaaaagag    97800
tatccatagg tgtatttaaa aataaaagat cgtcttttca tctttgcaga aaaacatgta    97860
tttactattg cttggaatag aaagcagaat tttgctgtag ccattaggaa gtgacaaaca    97920
ctacgccata attatagtga gaagaaagca tcaaaagaa atgttttggt tttttttata    97980
tacagttggc acaaaaatgt ccacatatat gaatactcta aagaatgcac cataaaaaga    98040
accttccacc actattaaca ggattaatcc gtgctcatta ccatgggatt ggggatacat    98100
ttttacatgt tcttgattag attcaagagc caaagaataa ggcctaattg atgaaagtgg    98160
gctctaattt tgtgctttta aaataatggc ctctggccaa atatgggcaa agaaacagc     98220 acttgatttg ttactttaca tttgtttctt gcatcctgct cgaaaataga gatgatttac    98280
agttttaata tattttcat gcacaattaa catcattgtt gccagtttta tagaagaggc     98340
aggaaagtgg gccttctatg atttattgtg agtgcatgaa acagagtaa tgctactagc     98400 aacagagttt tagtaggaaa aagttaaagc acacagtctt aaaaaggaaa ggttggtgtc    98460
aaaattatgt ttgctttagg taagctttat acctccatgg atggcttttt ttatagtaac    98520
aacaacagta actgtattta cattggggcc ttttctctgt ttcagaggct ttcatgtgga    98580
gtgccaaaat ggtaaaatat ataacattgt tatatgaagg agtgagggaa aatccaatca    98640
agattggcat tttttaaaaa agaaaaggag catgggggaat attttaaaga tttgggccaa    98700
agcctcgtgg ctgatgcctg taatcccagt gttttgagag gctgaggaag gagaatcact    98760
```

```
tgatccagga gtttgagacc agcctgggca acatagcgag acctccacct ctataaaaaa   98820
gactaaaaag ttagctgagt gtgatggcac gtacctgtag tctcagttac taggaaggct   98880
gaggtgggag gatagcttga gcccaggagg gccaggcttc agtgagctgt aatcacatca   98940
ctgcactcca gcctgggcaa cagagcaaga cgctgtgtct caaagaaaaa aaaaaaaaaa   99000
agatttggta tctttctttc ccccacagtt tgcatataca ttgaaaactg tgcatttaag   99060
ccaaaatagt tttttttttt aaacatttca ctataaaaaa ggagtctggc tttcacatgg   99120
gtacatgatt ttgctttggc ttcttcaatt cccacctgcc ctgttgtgag acccatgaag   99180
taagcaaagc attcttttttg ccacggaaat gaaactccta aacatattgt ttattgtcac   99240
ataatggaaa ggagaaacgt ttcaaaaata aggatacatg aagcccttat tgaaaagcaa   99300
tcatacattg gtgaatttaa tgttttggag caaaaactgt tatgttggat acctattagt   99360 cttttagct agtgaaatat gtacaaggca aaatcaagca tcaatagaag ggtctaacta   99420
agcttgtttc tcatatggtt tctctgccag ctcacacctc aagggtgcct cctgcctgca   99480
atgtgtactc tctggtccac acactgattt cccctttcct gtttcatggg gtgacttgct   99540
gaccttctct gtgcatggct agtagtactc tattgactgg caaggttgt gtcttccact   99600 tgggtcttcc aagctgctga agaaagcaac acagaaagta tagctgacaa taattatctg   99660
tcaaatgtat gtgaatcaca gtgtggatgg tcgacctgtt gtttcttttt tctctttgaa   99720
aggaagattt cagttttctc tgcagccatg gtactttata aattatttcc tcttccatct   99780
cttaaaagtc actgttattt accacccat tagctgtgga tggggtgaaa tgcccactca   99840
tgcagcacag gaggatacac agattgtcac acatctttttc aggagaccac acagcagtgg   99900
gtagtgtagt attaaataaa tgcctgaaat atgagctggg aatgcattgc acttcaagga   99960
attttatcca taggatgtaa ctgggaaagt gcagaagaat gcatatatat atagttgttc   100020
attgttacat gttttatgat agcaaaaaaa aattaaaaaa tattcaactt tcatttaga   100080 cacggatttg caggtttgct acatgggaat actgtgtgat gctgaagttt ggggtataga   100140
tcccattacc caggtagcga acatggtacc caacaggtag ttttcaacc cacatccccc   100200 tgtcttcctc cccttctagt agtccctagt gtggagtgtt cccatattta tgtccatgtg   100260
tactcagtgt ttagccccca cttataagcg agaacatgtg atattttgtt ttgttttcta   100320
ttcctccatt aagtaaccaa aattttaac aatgtagaat ccattacata attagagata   100380
caatacaagc attgaatacc agctgttaaa atggcattac aggataatat ttagtgatat   100440
ggaggaatat tcagagtgta ttatatacaa acattttcat catatcgttt tttactagag   100500
tggactgtca ttttcttgtg ggctcccttg tattatttac tctattgcat ctcagttttg   100560
ttgcatatta tgtaaaatag aagataatga tagcttggcg cattctctgc tgagactatt   100620
tacagtggtg taaaaagatg ttgccagggg tgtgtgcctc agtctgtccc agccttcgta   100680 gggcccatg tttcaactcc ctaatgaccc attgaagaca cacgggcaca caggggagaa   100740
tgctctggtt taaacagtca accataagcc agacacagtg gtgcaacctg tgttgcacct   100800
tgtggtagcc tcttgctacc caagaggctg agacagagga tctcttgagg tcaggagttc   100860
aagaccagcc tgggcaacat agcaaaactc ccattctaaa aaattaaagc aaactcaacc   100920
attttgagtt ttacatgttg taaatatctt ctcccactgg cacccaccca tcattcctgg   100980
ttttgattga aacaaaacca ttagtttaa tgtagcaaaa tgccatcaac atattttct   101040 ttctaacggt ttctcctacg tagtgcctgt taaagaaatc ctgttctacc ccaacatcac   101100
```

```
aaaaacattt tcctataagt atcagaattt cattgttcat acagacagtt tttaatccat    101160
gcagagttta ttttatata tgaaatgagg tgggaatctc atgttatttt tttccccaat    101220
aggggaacat tgctttgaca catgaaggaa gcaatgtatt ctttttttc ttttgagaca    101280
gagtcttgct ctgtagccca ggctggagtg caatggtgca gcctcagctc actgcaacct    101340
ctccctctca ggttcaagcg attctcctcc ctcagcctcc caagtagctg ggattacagg    101400
cacacgccac cacgcccagc taattttgt aattttagta gagatggggt ttcaccatgt    101460
tggccaggct ggcctcgaac tgctgacctt gtgatccacc ctcggcctcc caaagtactg    101520
ggattacagg catgaaccac tgtgcccagc tacaatgtat tctttcccaa tgatttgtgg    101580
tgtcagccag gaccttgata gggataaatg gcatgcaact tgagaaatgt aattaagatg    101640
gggacaggat agtggagtcc ttatgtgaag ttgctgatgc ccgctgaggt tgaactggac    101700
ctacctacca gggagggaac tggaggtcat atatacaggc cttactcgcc ttctgccctc    101760
cggattacct gctagtgtct tccttggctg aaacccagga gcagccagaa ggcaagagtg    101820
aacctgttta tttaccttcc acaccagaga ggagtggaga tgaggaaaag tcttgaaggg    101880
gacagactcc tcccccaca aaatagtaca agcttttaaa attcatcata tatacatcag    101940
ccaatccaag ggctttatat ttggtcttgt tgatttcctg atccattcct gcaagattaa    102000
agtatgactc aaatagtaca aatgcccata tattttcat cttcaacatt ctcgttgctt    102060
tttgtagaat ttattctttc atatacaata tggaatcaat gtatcaaaat ctgcaacatt    102120
cttctgtctt tgctgggaat tgtatttatt gaaatgttgg tttgaggaaa aataaacatc    102180
ttccaagctc atgttatctc atttgtaaac tggcatagtt cattacttgt tgagatctaa    102240
tcatagcttt attaaagact ttgagcatta tgtgttaatt gattattatt attattttgc    102300
aaatgatatc ttcaattaca ttttctactc ctggtataaa agaatgtcga tctttttat    102360
acattgatta tatgttcagc catctttttt gattccctat tatttctagt agcttttctg    102420
ttaaattaca tggtttccat aaaaatggtg acattatgta caaataatga ccattttctc    102480
tctttccttt caatacttgt aattttcatt cctttataa cttgtaccat tgtatggccc    102540
actgacgtcc agtgcgagga tgaatactgt tggtacaaac ttttgttccc attcatgatt    102600
ttacaggaaa tgagtctaac atctttttg taaatgcagc gttgaggaga gattttaaag    102660
catgcagtca ttatcagata atatgaatta cttgcaattc ccagttttt ctaagttttt    102720
aaaaaatgtt ttcttttgtt cataaatgtt gattatgacc aaataatcaa ctggcatttc    102780
tacagctggt tatatgattc ttctcttata attaatgtgc tctgaaaatt aatatatttt    102840
taaatatata ttcaatttcg ggaataacac attttaatc ttaaaagaaa catttttaaa    102900
atggccatta ttctattata gtggaatata ttgtatatga aaaatagcta ctattctact    102960
aagtttggtt tgtaaatatt ccacttaggt tgtctacatc taccttcata aatgaatttg    103020
atttataatt ttctgatgtt atacactcta tacttttgat atgaatgtta aactgtccat    103080
acaaaaggat ttgggtagct ttctttaatt gtatattttc tgaagaaaac ttaaataagt    103140
agaattacta aaattttgt gaaattatc ttgggtggtg agtttttatg tgggagattt    103200
ttagtgattc tttcattact acttatagct tttagtttat tcatttcttt gcgtaaagtt    103260
gctttgtttg ttttttcct caaatatttc aatttctttt tttaatacca gggcttatac    103320
tattaaaata gtattttgta tttttataa ctttgtttat tgttatttt aaaaatgatt    103380
ttcctcttta aagactattt gttctcatta tttgttgtat attatttgtt gtatattgtt    103440
gtatattatt tgtttcatta tttgttgtat atgttactct tccttggtca gtcttgccag    103500
```

```
aagtttgttt atattattaa gcttttcgat aaactagctt tcattttggt aattagctca 103560
actgttttt ctctgtttcg ctaatttctg ctcttacctt gatcatttcc tattttcaga 103620
tttatttgga tttattctgt tttctcttct tcctgtttct tgacttgcct ccatggctcg 103680
tttatttcca attcttcttg ttaccttgta aagatatttg aagttttaat tatccctttt 103740
aagcacttct tcagtcccat ctgacaaatt ttcacatgtg acatttgaac tatcactgga 103800
ctctgactgt tttgtgttta tacggtagca taaaggcaca tgcacacata tacatacaca 103860
catagatgtg tgtgtgtata tgtttagtgt tctatcatta ttttgaatgc ttttactat 103920
tgatttctaa ttctgttgac cgatagaata tagtgctgaa tgctgctgtt tctttaaagt 103980
actctttatg aaaggcagat tttgtaaacg ttcggtgtgt gcttgaaagc tatggacaca 104040
tttacacata catagacata ttcacaaata caaatacaga tatacgtgta tatgtgagaa 104100
tgtgtgtttt gaggagcata ggtttccata gatacccacc agatcacatg tatgggttac 104160
ttcagtcttc tatatcttat ttgttttggt gggtggggct agggacagag tctcgctctg 104220
ttgctcaggc tggagtgcag tggcctgatc tcggctcact gcaacctcgg cattctggct 104280
tcaagtggtt ctcctgcctc agccttccaa gtagctggga tcacaggtgc acaccaccac 104340
gcccagctaa cttttgtatt tttagtagag acgcggtttc actttgttgg ccaggctggt 104400
ctccaactcc tggcctcaag tgatccacca gcctcggcct cccaaagtgc tgggattaca 104460
ggcgtgggcc actgcaactg gcctatatcc tcaattacat tttatttcct aagtttatca 104520
ctccaagaat gttgtgtttt attctactgt aacattttat cttttcttat ctgtccttta 104580
tcttatatat ttaatgtata tggatatact atgttatata tatgtagtat gtatatataa 104640
aatgtactta tatacctttt acatgttttg aagctgtatt attaggatgt tacatgaaag 104700
tgtcagttac accttttaa tcttccattc cttttctagt atttattatc cattttgac 104760
atttacaatt tttgtttgat actaaatttg cttcctgtga tattttttca tttataattt 104820
gttttatatt taaaatttt agtgtcttca ttttcaagtt tatgtatcca tttatttaa 104880
atatatcttt tcaacaatat gttgctaaaa gtattttaat caatatttta tctttattct 104940
aattttattt ctgcagttat cattattata gatttcactt ctgacatttt atttatatt 105000
ttatatttat caatcatgct ttttaaattt tacctttttt ttttttttgct ttacctgact 105060
tccattatat aattttaaaa gtttcttta ctgaccttat tattatattt ttctttcttc 105120
tgttttttt tccttatagt tgggattcat caaatttccc tcttcccatt ttatgctgca 105180
cttatatttt aatgaagatg tatctagtct tattagctat caaacatttc agtatccata 105240
attttcctca aaacaagata ttgatttagc attttctcta ctcttcggca tctctctctc 105300
tcaatcaccc cacactgtgt tagattctaa gagaatctgg gctctagatc atgttaaaaa 105360
tttgatttta gatcattgtt tcttcggaat aattttttgt cgttacctgt attatgttgc 105420
tgtgttctgg gttcctctcc ttgcagaaat atattgtgtc aagatttctg tgatgtaagt 105480
ggatttggat ttaagctatc atttaaatga cagtttcact ggacataaaa tccaggctga 105540
tttctttcc cttgtacttg ctgggggtga gaagccactg cattttgtat cctacgttgc 105600
tttgcaatta gcctggtttt cattcctttg cacatcgcct gcttttctc cttggaaaaa 105660
ttagacatat tttgtttaca tttgaggtac tcaaaaattg gaatttgttt ttgctttgtt 105720
ctgttttaaa tcaacgtatt atttactttg tgagtacttt cacttttaag ccttttttt 105780
tctttcattc tgggaaattc tcagcctttc tgtctaatgt agttcttcct agtctttttc 105840
```

```
tctttgttct ctttctgggt catttttttt tataggactg gtaacacttc tatttccatc   105900
ttccatactt tagcatttgg aggatgtttt tccaccattt ttcatcccag atccattttg   105960
ggaaaatgta tctctgtctt ttggctccta tgtgcattgt ttgtgggtat ccttccattt   106020
cagtctgttc tttgtgctct ccagttcaac aatttcattt cttctccccg gtatctcgtg   106080
tgacttcctt tgaaaccctt tgttccaact ttatatcgct atcattgtct ctctgtccat   106140
tggagggatc tgcttctttt gaatcccagt ttgtttactt gggtcatttt attattatta   106200
tttttaaat aggatgttcc ttttctttta agtgctttgc ttttgactg gctcttaaaa     106260
atttcttggg agttctttta ttttcttgag gccggtagag gtcttggaag gtaccaagtg   106320
tccaatgggc aatcaaaagc ccacctctct gcctggcgcg gtggctcaca cctgtaatcc   106380
cagcactttg ggaggccgag gcaggtggat catctgaaga gttcaagacc agcctgacca   106440
atatggtgaa accccatctc tactaaaaat acaaaaatta cctgggcatg gaggcatgtg   106500
cctgtagtcc cagctacttg ggaagctgag gcaggagaat cacttgaacc cgggaggcag   106560
aggttgcagt gagcagagat tgtgccactg cactccagcc taggtgacag agtgtgactg   106620
catctcaaga aaaaaataaa aaacaaaaaa taaaggccca cctctcgatt tcatgcctct   106680
gggtaaattg gagggaaaag agggtccctc tgtgaagagc ccttggaact cgagttctaa   106740
tttctaaacc aagaacttta tattctttcc tccctcccta tcacttccat ccactggctg   106800
gctcttatct gaaaactgtc gtgtgcagtt ataaatactc aacacttagg gaaggagaag   106860
gaattctgag agatttcgcc agcctgattc ttttcattgc cataaaattc cactgcttta   106920
ccagaaatcc ttggaatgtg gctttcctag ctttgcactg tgaccttctt cattcggaat   106980
aacgaagatg agaaaagcat tgatccgccc agacagtgag gagcgaagag caatacctag   107040
gtggaaagct ctatctcccc tgactgtcct gtgaaatgca cctgagtctc agaggactcc   107100
actgccatct gtctgtccag gaatttccca ttttgtatgg cgacttcaaa gtaggtaaat   107160
actttgatta aaggaataga gaacagaatt tgggtagctt gttcaaaaga tggcatgaa    107220
aattctgtga ctggagtagt tgtgaagcat cactcttccc gtaagaataa aggaggcatt   107280
tgccagatgt ctgaaaacac acagacacac acacaaagga attacttctg gctgcaagaa   107340
tattctctct cagcatcttc ctgcatctcc atgggcaaac agacccacaa cagcctggga   107400
ttttttaatt gccaacagtt ttcattgcat gagagcctga catgtctgtt gcatgatagg   107460
gtgtgttttt attttggct tcctattggt ttcaacatat ccctccttcc atgtcataat    107520
gacaattaca aagacctgag ttgaacctag aacgcttttt ttttgtcaga cacaacaatg   107580
cagtggatgt tagtcatagg gtaattcaaa cagagataat tttgtatatt ctagaatatt   107640
atgttttcaa acgtaggttt tgatgtacca taagatttct tctgccattg aggcgatata   107700
tatgtgtgtg tgtgtgtgtg tgtgtgtgtg tgtatgtata tatatgtgtg tatttttaaat  107760
ttaaattaga tatttttag aggccttagc ccttaagcag aattccctcc taatttaatg    107820
attttggacg aagctcattg tgaatcattt aaaaacacat tcatgcttct tcaaacagag   107880
gtaacaaagg atacagcacc ttgacttgtt gactaagtgc tgtcatggta gatgttattt   107940
agcatagaag atgcctgcag ggtcagttct actctctaaa gtttcttgag gctgtgttaa   108000
atgaaatcaa acacctgtgg attttttatt cttgttcacg ctttttatac ctctcctttc   108060
ttctcccctgg gcaacctgct ttcacactag tgcctacctc tgttttccct tcagaatgtg  108120
atctatgcta cacaatctga ttaacaagct caacagagtt ctactggaca tagaataaag   108180
aaaccagtat agttttctct ctagggacaa ggcagtgagg aagccagttt gaatacaggt   108240
```

-continued

```
tcttgctctt gtaagcattg acattcagca ggttccttac tttctgaaca ctgcagttat 108300
atgatgggca gacagggact aagaataaca cctacctcaa cggggctgtt gtgaggatta 108360
ctgagataat ttatgtaaat ccctagcaca atgcctgact catgcgagat ctttaattca 108420
tggtagcagt tactaatttc atttatcata atgagctgcc tgagctacca aggagctctg 108480
ccactcccag tactgttcta cagttcttta attcaacaaa gaattttttc tttagttcca 108540
aataagtgcc aggcatcagg ctaggtgctg ggtgtatgat gatgatcaaa acagtgttcg 108600
tatggggta gtcatcattt tgtcgatggg ccattttttta tgatgtccct cttcattata 108660
ggtcttgatt cttgcctctg ttttgtatac atatgtgttg cggcaggggc ttgctataaa 108720
aatcagaatt gcccaggctg agcgcagtgg tgcaatcatg gctcattgca gcttcgggct 108780
tcagtgatcc tcccacctca gccttcttag tagctgggat tacaggcaca ctccaccaca 108840
cctgcctctg ttttgtgtag ctgtgattac gtagcaattt tctgaatcag tgacaagatg 108900
caatgcatat ttttttcagt aggttaatta atttatctaa tctacatttg gagctatttt 108960
ttggagtgtt agtcatcata ataaatatgg tggcactgtc aatagtaata taaatataat 109020
ggtaccttaa ttccataata caaagatcac gtcttcatga ctgatgggcc atttcaaacc 109080
cataggtaca tttgctcgct ctgtaaagta tacaaaagta agaattctgg acatctttaa 109140
aagttgtaaa ttttttacatg aaaacttaca ttcacaccat cttttgaata ttgaaaagat 109200
ttgggaacat ggggcctata tgtgactgtg gatgaggtgt ggctgttccc tttagacaca 109260
gcactcactt tgccatagtc acactcccca ccgctcccta ttgtgtctcc aacccccagg 109320
ctgttgtctg tttcttttcc aacgttatta cccactcata gatggtcaac cttatgatca 109380
ttgttacttt cttttcctca gaatctttct agtatttgtg attttttttca tgtggttatt 109440
ttgagctttt tgcattaaga atttgggatc acatactcaa aagtttagta tttaccagtt 109500
tgtattattg agcacttcag aaatttattt ctgttgctgt tatcaactca taaaatatct 109560
gtttaattat ccaactaaag actagatagg atagtgattc ctatttttctc caagctcata 109620
tctgtgaact ccttgattgc ccaacatagg cattcaatca ttcattcaac aaatacccat 109680
tgaggaccta ctatgatctg ggcacttttc taggtgctga taattgtagt gaaatagtag 109740
accacagtgg acagtgtttc tttatggaat ttaagtgaat aaggaagtta ttttggagta 109800
tttcagatcg tgattcctgc tacgaagaaa ataattcag aataaagtag ataaggaata 109860
ataggaatgg acccacacag ttattatttt tattgctgtg gtcatactga tatctgaagc 109920
aagtaagaga agagtttcct atgaggatgg aatagcatgt gcaaagaccc tggagttgta 109980
gaatccttga tgcgtccaag gaatatggag aagaccagtt gggctagagt tgacaaaatg 110040
agggtgaagt ggggggtataa gaatagagag gtgctggaca gtaggccgtt gagagggctt 110100
tagcttttcc gtgatgaata ttggaaccca caatgtaatt ttgagcatga aaatgagagc 110160
cttgatttac attttttatca gatcaccctg agttctggtt ggagaatgag ctctaaggat 110220
ctgtgggtat atttagggag atacttaggt ggcctttgca ataatacgct caagggagga 110280
tgctggcttc accagagagc tgatagataa gccatggcca gattctggga atatttttaaa 110340
ggaagatcca acaaatcgat tattcctaga atgcagaata aatgagaaag agacaactta 110400
tggccaaccc caattccttt ggccgccgta actggaagaa ttgcgttgcc atgtgctgac 110460
aacagggaga ttgtgagagg agcactttag ggtgagggaa ttaggagact gcttttgttt 110520
aagttaagaa caaccaagga gagatagatg tcttagagac agctgggtac agtagtgtgg 110580
```

```
acatgaagag agaggtctac gctggagata caaggtcagg agacatgagc atgtagatga  110640
tatttacagt tgtgagactg aatcgcattt ccaacacaat gaatgtagat agagaggaga  110700
agtaagtgta ctagaagaaa aagaaggatg aagaggagga gagagagaag acagtgagga  110760
agaggaaaga agcagcgtgc atgtgtgcac ttgtatgaga aagagagaga gagagggaga  110820
aagtggaaga tatagataga aggagagaga gagagactgg gggaagaatt acatccaccc  110880
aaaacccaaa ttttaatgac ttacaatatg aaagcttcat ttttttttc tcttatgttg    110940
cacctcactg atggactatc atcagcccca cttctcttcc aagtctttat tccagaatcc  111000
aggctggagg ccatgcctga actgaggaaa tggtgttcat gtacaacagt tctttcagct  111060
tctgctcaga tgtggcattg cacatccact catatgcgat tgtccaaagc attttctat   111120
tctctgggag atacttcaag gggcacaaca gtggctgggg attgagggg ctgtgaatag   111180
actttcagga aaaaggatca gctgtgctaa atgctgctga tgagtgcagt aacacaagga  111240
tgagtaactt gagtagcttg tagagaggta taggccattt gtttcatgcc caggaacaag  111300
gcaggaccag gaatcctggt tgagatgctg cagtttgggc tagttggagg tggggcaag   111360
tttttctctc actgctggga cttactcagg ttaacagatg ggacgttgtg gaggagctgg  111420
agacggagga gaaagtgtag aagagttaac taggagatgg attgagagtg tttgatgtga  111480
gaggcagtag agcatgcatt gaacctaggc tgtatggttg gagggttttt ttccagccat  111540
gtcctgtctg ctcaggttca gaggaggtag gaggtagatt gaaccagcca caggtgatgc  111600
tccatgagta aagaagggtt gagagtcagg aattgaggag tccaaggcat taactgaaaa  111660
gatggttcat ggaatttaac aaagatgcgg acaaatatga ggagaggagg cagtcaaggg  111720
agagagaaag agtagggttg ggatacaggg aatgaaagtg agctccttaa gatgaatggc  111780
taatcccaca aaactggcca attcccataa ggtgaacggc taatcccatt agtgcattgt  111840
tgacatgaaa atgtcctcac caaataatga agaaaaattt gattttctta tgtggaaaaa  111900
gcaggaccaa aagcaatcaa ccaaaatcgt atctactacc tggcagtcca ttagaacaca  111960
ctaaacacac acataaagag aaaaatgaag tatgttaatt gtgaaacttg tatctccaaa  112020
aactggaaag cttcttggca cttaaaagca cttcttggca cttgggatta cttgcctgta  112080
atcccagcac tttgggaggc tgagacgggc ggatcacttg aggtcaggag ttccagacca  112140
gcctggccaa catggtgaaa ccctgtctct agtgaaaata taaaaattag ccgggcatgg  112200
tggcgcatgc ctatagttcc agctactcgg gaggctgagg cagaagaatc acttgaacct  112260
gggaggcggg ggctgaggta gaagaatcac ttgaacctgg gaggcggggg ctgaggccga  112320
agaatcactt gaacctggga ggcgggggct gaggcagaag aatcacttga acctggggagg 112380
cggggggctgc agtgaactga aatcgtgcca ttgcactcca gcctgggcga cagagtgaga  112440
cgctgtctca aaaaaaaaaa aaaaaaaaa aaaaaaaaa aaaaaaaaa agaaagaaag     112500
gttcaatacc tacttgttga atgaaagtgg acgtgtgaat tcaaagtttc cgctctttca  112560
cagtgttttt ttttttttt tttttttttt ttgacagagt ctcggtctgt cgcccaggct   112620
ggagtgcagt ggcacaatct tggctcactg caaactctgc ctcccgggtt cacgccattc  112680
tcctgcctta gcctcccgag tagctgggac tgcaggcgcc caccaccacg cctggctaat  112740
ttttgtatt ttgagtagag acggggtttc accgtgttag ccaggatggt ctccatctcc   112800
tgacctcctg atgcacccac cttggcctcc caaagtgctg ggattacaga catgagccac  112860
cgcgcccagc ctcattcagt tctttattac atttgtaaag gtaactctaa ctccgtgaga  112920
gcactttctc gctcacctct taattcttga gcaaacagag aagctgtgca tgataaagct  112980
```

```
ggagaattgg gtggtgtctt cctattaagc ttacaggaaa gcactgggca tttggaacag  113040
atgttgcatc ttgagagcca cagagtcagg tgtgcacgtt aaaacgatgc ttctaattgt  113100
tgcatagaga cagaagacaa tcacaaagat tctgccttga cctccttacc tctccagttc  113160
taaaaacatt tctcccacta cagaaagcat ccatctatgt gttttttgcc tccacgtggt  113220
cctattcctg aaatgctcct tccaagtctg tacttttcca agagctacta tttctggatc  113280
ttttgcagtt gcttcagcaa gaatcagttc tggcttcctt ggttctacca tgccaacttt  113340
accttctcgt ccctcagtgg gatgctaggg cttgggttaa ttcatctctc tccttcaagg  113400
cgacatgaag cccctgagaa caggggcata ttttgtccca gccattacct acaatgatac  113460
aggagtcctg taatattcgt tagagaaatg tgtccactga acatgaattt cctatcctgt  113520
tccttctaaa aaggatgcat gagttatcct atattcccaa ggcacaacat gactttgttc  113580
tgatatgtgc caccgtgatc ctgtagaatt tgttttgttt ccagtcccta agaataaatg  113640
tctcttaaag tattgtagtc attcactcta catttttatg agttattact ggcccaccta  113700
caaccatatt tcctccgaaa ttcatccatc ctcctggaat tacctgattc tgaattatta  113760
agtggttctc ttggccattt gctcaaaaaa agagcacact tattccaaca cacaggcatt  113820
gtttctaaat tattattgtt ttttcttcct agaaaccatt tagagatgaa gatccacttt  113880
agaacatgaa cccatttagt ttagactata acaattgaag atatggtgac tactgtttat  113940
ttctgttagg gatatatttt ttgtagattt cacaaaagac agaacctgct gtgtgacagc  114000
ttatctgcag gacaccgatg gtttgtagga cgatggtgag gctttgtgac aaggcagaaa  114060
tgtggaaggc tggcaagatt gtttactgag cttcccctaa ggatggaata attcaccaat  114120
cccacaactc ctccacccte agtcactacc aatagctgtg cctcagtgtt ttctttttaa  114180
tgattgtatg tattaagaaa aaaatcctca tatgtagtgt ttagtttatc tgattttcgt  114240
tactaaaata ataaaggaga aaagtaaata attcatataa aagtaaactt tcttattcca  114300
agcaggtgta tgtgtgcatg tttgtgtgtg tgtgtgtgtg tgtgtgtgtg tgtgtgtgtg  114360
tttgccactt tgatggaaag aggctgactt tgcagagact attttttgtt aagaactttc  114420
cattaaatta gagctttaag ttataacact gattgcatag gccagggaaa atggtaggat  114480
gtggcttaaa aggcaatctc acaagaagta tgactttat cttatattat aaacaacagc  114540
acaaccttgg aatttgtccc aataaattcc ataagtataa aataaactaa ataagtaaag  114600
tgactaatat cctactaagt cttttccttc acacatgctt ttttgcctaa agccatttaa  114660
agtctctgag gatttaaatc tatgattctt tcatggagta gaagaaaccc agagaatata  114720
gaaatttaga aaaactttaa gacttattgg tttaacagaa gtaggccggg tgcggtggct  114780
catgcctcta atcccagcac tttgggatgc tgagctgggt ggatcacttg aggtaggagt  114840
tcaataccag cttggccaac atggtgaaac cccctctcta ctaaaaatac aaaaattagc  114900
cgggcgtagt ggtgcacacc tgtagttaca gctacttggg aagctgaggc aagagaatca  114960
cttgaaccca ggagacagag gctgcagtga gctgagattg cgccactgca cttccagcct  115020
gggtgacagg gcaagactcc atctcaaaaa caacagcaac aaacaaaaca aaacaaaaaa  115080
cccagaggta gatctaattc tgcagactgc aatcactcag ttatggatgg ataagtcagt  115140
ccttaagtcc atctgctatt tgtgtatcgt gcattttttt ttttttttga aacaagcacg  115200
ttcccacctg gattgaatgt taatattcac tgaaagccag ggcattgcaa cgagcccttta  115260
ggatgttata attctgggcc attttacag ttcaggattt cagatttatt gcaatgttgt  115320
```

```
aagtttttag tttcttgtct ttctctaaca tctagtaagt tccaaaactt aaagaactac   115380
aggttttctt gataaatacc tgtgtcacta cttttttattt ttagattttt ctttttttact   115440 acatgatctg agttaaaagt taaatatata tgaattattg ttttgaaaaa tattacctat   115500
aatagttttt taaaagaaac tttaattta gatttgtgct aaattggcga agattgtgta   115560
gagttttcct tatacccac cctcaaattc cactactaga aacaccttac atcattattg   115620
tacatttgac actattaatg agccaatatg tgtgcaattt tttactaaag cccacccatt   115680
cttctgattt cgttggtatt ttccttctgt cttttttctt tcctcaaatc ctatccagga   115740
tcccacatta catttagccg tcatgtctcc ttgagctcct cttgactgtg acagttttc   115800 ttcttttgtc tttcatgacc ttaacagttt tgaggagggc tggtcacggg attggtacct   115860
tgtttggttt gtctgatgtt tttctcatgg ttatactggg gggctatgga ttgtgcagag   115920
gaagaccaga ggtgaagtgc cactttcatt acattgtatc aagggcacat actagcacca   115980
tgacattgca gttgatacta accttgatcc catggatgag gtgatgttgg ccagatatct   116040
ccagtatcac gttcgtcctc ctgcacacac actttctata ctgtaccctg tggaaagagg   116100
tcactacgtg cagcctacac ttaagaaagc aggaggccgg gtgtggtggc tcacacctgt   116160
aatcccagct actccagagg ctgaggcagg agaatcactt gaacccggga aaggaaatt   116220 gcagtgagcc gagatcgcgc cattgcactc cagcctgggt gatagagcga gactccatct   116280 caaaaaaca aaaataaatt aaaaaaaaaa aaaaagaaa gcggggacta taatcccctc   116340
cttgagggca gagtatctac agaaattatt tgaagttatt ttgcatgaga gatgtgccta   116400
ttctcgccta ctcattttatt tattccctca tttacatata tcagtatgga ctcatggata   116460
tttattttat actttgggtt gtaatctaat gtgatgttgt ttatctgcat agattttgtg   116520
tttacgtaac ttttttttcaa attcctgagg gatagctttt tagaaaatcc ctgttttac   116580 tttagatcca aggattacgt ctgcaggtgt gttacaaggg tatcttgtgt gttgctgagg   116640
ttcaggcttc cgttgatccc gtcactaggt tattctgtgc ccagataatg agcacaggaa   116700
gttttttagt ccttgtcccc cctctgcaac agattgtagg aaataatctg agactgatca   116760
tttttaattt tcaagcactg aacatgcagt tattttatct agaaggtaga ccagcaaaac   116820
aaaattatat ttgacatttt agcatataag tattttctag ttaactttga catacaagaa   116880
gccaggttat gaatgtattt gttcatgact ctagcttgtt tggttaaaat tattctcctg   116940
ccaaccaaat gctttttttgc taccctgaat atttaaaaaa ttttacaat atttcatctt   117000 taagagctat aaatgtatgt tttaatatcc cagggtaaga tataggata ttttttagtc   117060 tgtcgaggct gctataacaa aataccttag actgggtaat ttataaacaa tagacattta   117120
ttgttattat tatcattaag acagggtctc tttctgttgc tcaggctgga gtgcagtggc   117180
ttgatcatgg ttcactgtag ccttgacttc ctgggctcaa ctgatcctcc cacctcagcc   117240
tcctgagtag ctgggaccat acgtgtgtgc caccatccct ggctaatttt tatttttta   117300 attttagta gcgatgagga ctcactacgt tgaccagggt ggttttgaac tcctggcctt   117360
aaacatttct cctgccttga cctcctaaag tgttgggatt acaggtatga gccactttgc   117420
ccagctaaca acacacattt atttctcatg gtcctgggaa gtccaggatc aaggtgctag   117480
cagattcagt gtctagtgag ggcccattcc cccaaatggc atcttcttga tttatcctca   117540
catgttggaa gggacaaggt ggaagggcct gcagcctctt ttataaggac actcatccca   117600
ttcatgaggg tagagttatc atgttgtgta ttggatttca gcatatgaat tttggggaga   117660
cactaccatt cagactatat aacaagatac attaggtttg gggtgttctg cacttgagtg   117720
```

```
aatctatgta agcccttca catatttta ctttcactga aataaaacta aataaggaaa  117780
ccaatgctat cctatatctt aaaatgagaa tggtttgtaa cagctcattg ccttgcatca  117840
tggtctttta gggttagggt tcgggttagg gttaggatta gcttcgcttt gctgggcaga  117900
gtaggtattt ccgcctcgaa ccacctctaa gggcttcagc tttcagtaac gcacctgtca  117960
cttctaatgc aaaaccttga gtcctctgtc tgtgtgcaga ttcaggaaca ggtttgaggt  118020
ctaagaattt tcttattatt gccttccatt tcaatttcta gttcctccaa agtccttcac  118080
aatgatgacc gagaggagac actcaaaaat ttgttagcca gagtctcaaa gtacatagaa  118140
gctgtttctc ttgggtggat attacaagtg cctctacagg caactgcatt tctttctctt  118200
tccaggattt ttgcttattg tccagatatg ctcctcctag tgagagggac acttctgatt  118260
tttcctgcct ccatggaaca ggggcttcag agaagaaact ctctacagcc ccttcgttcc  118320
attaataatt tataattaaa tgcatttcca gcatgaaggc tgcctaggag tagagaagca  118380
tattagaaga accaatctgc tgcgtatctg cttatagggt ttgagcccag tcaaggaggg  118440
atgcacagaa actcaggatt ctgacagccc agcccccttg caatgggag ggtcgccaaa  118500
tttcttctt gcaaggggta cttactgtct gtgagtggga gcctcttgtg gataaggagt  118560
gagggcagag agggaacagc agagccctgg gaagttcttt ccacttgact ctgagcgtct  118620
agacagcagc ctgcccccac cccctagatt ggctttgtac ctgtgagcaa agttctgac   118680
tgtgccatac atctctggaa tacatttagt tgctaatgga gatattacta taattccaca  118740
tatgttttta gtctctcctt ggggctgtgc ccttctgtgt ggcttggcag aagagaaagg  118800
agagaaagat tatacatggc agccttgctt tggagggagt gaaacctgtg attttccttt  118860
tctgtgtcag gaaagcgttt ttctgctgct tgactagcca cctcccaggc acattaacca  118920
gtcaggtgat gctgacattt gtacccccta atctggctta tttctgaaac cctcccttg   118980
agccctaact gctataatta ggagactgga tcctaacagg tttggaaaaa ggtttgcaat  119040
ctcaaaataa agtagtgatt tgaaagaga aatgtatagt agagttagct atggggtttg   119100
cacattctac atttatgttt gtttgttttt atttttcgc tcagactgct cacagatgca   119160
gtgagcacac ccaaatgcat gtgatcaatg catgtctgac ttctgcagct atggaaggtc  119220
tgggtttgta agatcactgc tgtagaccct tgtttgacct ttttggattg ctggatcaga  119280
aagtgagaga ttgcgaaagt tttcttaaaa gaacaagtca gtgaatcaat tcattaattc  119340
ttttgttcat taggattagt taatatactg ctacagtaaa acctttgtt attgtctgta   119400
ataataaaag ttggattatg gcatggctaa ccccaatctc catacaatct gctcatagtt  119460
ttgacctcat tctaatataa ccctgtattt cacgtgattg aatgttttgc accatattta  119520
taatattaca tccaggtatt acttggtttc tgaaggttta taaaattgta aatgcagtac  119580
atagggtatt agagattttg ttgttttatt tttttagaga ctgggtcttg ctctatcaac  119640
ccaggctgga gtgcagtggt gcaatcatag ctcactgtaa ccttgaactc ctgggctcaa  119700
acgaccctcc accctcagcc tctggagtag cttgtattat aggtgcatgc caccatatcc  119760
ggctaattt ttattttgat ttttgtagcg atagcatctc agtgtattgc ccagattggt   119820
ctcaaaatcc tagcctcaag caatcttcct gcattggcct tccaaagtgc tgggattaca  119880
ggtgccagcc actgtgcttg gccattacct agagttttg ttagagataa tgaaataaga   119940
atgagattaa aatgaggtta gtctcatgct gctaaaaaca gtgatatgct taggagcagc  120000
tgcaggaaca tctgatccaa tcttggaggc agcctggagg gcttcccagg ggaagcacaa  120060
```

```
tgtagtccaa aacctgagag atgagcaggg attgactaac taaagagcag acctacacac   120120
caaattctgc catcagttcc ttgcatggca tggaaaattg atttctacaa ctacgcagta   120180
tttttcttcc tttttttttg aaacagattc tcgctttgtc acccaggctg gagtgcagta   120240
gagcgatttt ggctcactgc agcctcgacc tcctgggctc aagtgatcct cccacctgag   120300
cttccctagt agagtagctg gtactacata tgcacaccac catgcccagc caattttta    120360
tttatttatt tatttatttt tgtagaaaca gggttttgcc atgttggcca ggctgctctt   120420
gaactcctga gctcaagtga tcagcccacc tcggcctcct aaagtgctgg gattacaggc   120480
atgagccacc attttattt ggtatgtgtg cattcatagt tattctacaa aaataatat     120540
ttaataataa ttcacagtat cctgcagatt ccaaaataaa gtaagcttaa gttctgttgg   120600
aaaatgaatt tctgtgagaa ggctttggtg ctttgacttg aagctgacat caacattagt   120660
gttgggcatt tggctacaca cctgtcacat tcaaaagcca attcactttg agtctttatt   120720
ttgttggcag taagggctgc acatttcgat ccactgtgta ttttcctagc ccagattcca   120780
ctcaaagcag aggtttagag aaaacccttg tttattgcaa atattatgcc aaaaatagg    120840
atgaggaacc agcactgtgt tgtgggaagg aacgagaaat aatcactatt tacaatagcc   120900
gagttgtgga atcaacctaa gtgtccatca acagtgcatt ggataaagaa aatgtagtac   120960
atctacaaca cagaatacta ggcagccata aaatagaatg gaatcatgtc ctttgcagca   121020
acatgaatgt ggctggaggc cattatccta ggtgaaataa ctcaaaaaca taaatcaaa    121080
tatagcatgt tgtcacttat aactgggagc taaacaatgg gtacacatgg atataaagat   121140
ggaaacaatc aacactgggg actcaaacaa gggaaaggct gggaggggt gagggttgaa    121200
aaattaaccct atgggtacaa tgttcactct ttgtgtgatt ggaaccctag aagtccatat  121260
gtcaccagtg tgcaatatac ccatgtaaga aacctgcaca tgcacccctg aatccaaatt   121320
aaaatttaaa aacaaacaaa aacacaaaaa agtgtattgg ccacagagga gtgactgctg   121380
cttgacccag tgaggttgtc tgaaaaccct tatgttatgt gtctccagac cacctttacc   121440
cggtgaaaat ggaggaccca tattcacacc atctttcacc tcttattagt ttactgggg    121500
taacctctcc aggctgcttg gggagtgcta agtaggtttt agtgtgcatc cactgtgagg   121560
catcagagaa acttcaggaa atcaagaaaa aggcaagttt gcaggtatga agtgaggctg   121620
cacctgcgtg aagctggctg aagtctaggc agagcagatc accacaagag cggctggaat   121680
aagccatgtg gccgaatggc atccagcaca acgatcaagt gaaacagagc tcctccagct   121740
gtggtagaac tagggccaaa gtatgtgaaa gtgttcaaag attcttcgca ttgaattcaa   121800
gctcatcatt gtccacaaat caatgagacc atgtctatat tggtaaagaa agaataaagc   121860
ataaattcat atttcaattt ttaggttatc tgaataaatg aatttcaaga gtgcttaagg   121920
tttttgctag atgtttgcag gttttttgcct ggagaggcac aggcagttct tgtcctatc   121980
attctagcct tccacttgta gggattccct ggaaagttga cataaccgct gattcctagt   122040
tctgttttgt gggaagtatc aagattaaga gaccctctgg gtgaacaaga tgtctttcaa   122100
tagatgaatg ggtaaataaa ctatggtgta ttcagacaat ggaatattat tccatgctat   122160
aaagaaatga gctattaagc catgaaaaga catggaggaa aattaaatgc atattactaa   122220
gtgaaagaag ctgatgggaa aaggctacat acagtatgat tccaactata ggacattctg   122280
gaaaaagcag aactggggga caataaaaaa tccatcattg tcagagtttc ggttggggat   122340
ggggaaagaa aagataaata ggtggatcat agaggatttt tatggcaggg aagatattct   122400
gtgttatact gtaatggtgg atgcaaggag gttctttttg tctaattaac tgttcacatt   122460
```

```
catcataatt gattccatac agtatgcatg gattttcagg gtccaagtgt taaccaactt 122520
cagtggactt aaaccactct gtaaatgggg tgctctttag tgtttgtttt gtttactgtt 122580
ctaggactgg ttaatagaaa tcagaggaca tacagatcca gagtcccta tctacaattt 122640
gaaagtcaaa aacagttcaa aactttacag tgatatcaaa actcatttgg gggcaaaacc 122700
tgatctgaca gatgactatt tgtgttcttt cttttccacc tcagggtgga catttagata 122760
ttttcctgca ggaatattaa tgagtttgat ttgggagtga tgttccatat tcctctgagg 122820
gtgctgcata aaacagatgt aaaaaaatta aaaagttctg agtcccctc ctcttgtcca 122880
caaaagcata ctcattccca agggtttcag atccccattg gtggatctgt gatatcaaag 122940
gtctcattga taatgttggt ggtcagtgga aaatagttgt gtggagagag atgtgttagt 123000
ctggacctca tgcaatgact gcagaaataa ttttatgatt tccaaagaac aacagacaat 123060
ctaaccacct cccttacctt taaagactga catctgtgtt gtgttcatgg atgattatgc 123120
aaatcaagaa aagtggcttc catcaaaata atgtcatttc tttttggaga aaagagcctg 123180
ggactgagtt gtgttatgtg tgcagtttgc cagctaaact cctggcttaa tgattgggat 123240
gggtttccaa gggctggttc tgagactcag tggcagttag ttaggtggta atttccccat 123300
taacattaat gagaaatgaa ataagttact taagaaaacg tgctagacga tagtctctaa 123360
gtactgaaaa gtaaatgaac ccacctacgt ttgttcacat aaaatttctt agtatatttt 123420
aaatttgcta atctaatgta cttttttttt tgcttgtgct ttaactttgt taaattatgt 123480
cacgtaaaac atttattcc atattctaaa ttacataaat gtgtcacaca caatgtcatg 123540
aatcaagttt gtctaaagag gagataggcc aaggcaggtg gatcacttga ggtcgggagt 123600
tcaagaccag cctggccaac atggtgaaac cccatctcta ctaaaaatac aaaagttagt 123660
ggggcatggt ggtgcacacc tataatccca gctactcagg aggctgaggc aggagaatgg 123720
cttgaccctg aaaggtggaa gttgcagtga gtcaaaatca tgccactgca ttccagcctg 123780
ggagacggag tgggactcca tctcaaaaaa aaaaaaggag ataatacact ttcacgtttg 123840
taaaataatg ttgattaaat ggtctaatgt gattttatct tgctaatcca gttaccgtcc 123900
cagtatctga attatgataa cagtttacgc agcatagttt tctaacagtt ttggttccat 123960
ctctgctatt aaattcaggc cactggatct gtttggttca acttggatta gggtgtgagg 124020
ttctgttttc ctacctctaa ctccatatac attgtccgtg ctcctgacct tccatgcagg 124080
aggcttgcag gtatctcctt aatctgtctg tcatctgttt cttctgcca tctcagggac 124140
tcctgatctt tccagactgc ccatcctctc ctgtcccttt gactcttcct ttttgttca 124200
ctttctgtaa ctccagtctg atcatctaaa tagtctgagg ggaagatgag gtactgaagg 124260
cactcttgtg agaatatttc tcaggttcct aggtccaagt ttccgttgca tcttggtttc 124320
tatttcagtc tgagcagaga gagagagaga gagagcaaaa aagatcttca ggataaaagt 124380
gagagagaga gaagatggag aaataaatat aaatgaacaa ctgataaatg ccttgagcta 124440
taactctgcc aaatgaacac agaaactcat gtgcagttag atattatcca cctgagaatg 124500
tagttgataa catatttcat cataaataat atcgtctaaa gcccttactt gggaagatta 124560
tgaagcaagc caaatcttat gcagtatgtc cttctgttct cttgacaagc ataagtttct 124620
atttctgtat tgctagaaat ttttagtcac atgcaattcc aacagtgctt taagctggtt 124680
attactaagt agaaggtaaa tgtttgatga tggaagaatt tgcggtggag gtgaaattta 124740
ggataaatat tagcaacttt gaaaagtaag gtgtagatct gtgcggtacc agaaaacatt 124800
```

```
taacagattc agaagttagt ttatgtgtac ctatatgtgc acacacatac acacacaatg   124860
catgcacact tatgcaaatc acacacacat gcctcacgca caagtgcaac actcaggtgc   124920
acccaattgc acatacgtat tctattacta ttctttgcaa tgctttgaat gctcatcatg   124980
taccacaaag ttatggtcta attcataata ccataaggtg cgtgtgcttt agagatactg   125040
tgtatttcct ttcaacatcg aactagtgac tattaatgtt ttaaaatcaa atttgataac   125100
attctgaaat aaaatactga tgtattaagt accaatgcgt tgacatcagg tttcataggt   125160
gttgaactgt agcgaggaaa acagttatca ggtgtcctac tgtaactcta cccagcagga   125220
aagctctatg taatgatggt agaatatcca aatgatggtg tccacatctg cacaggtacg   125280
atttgagatt cactgactta tttaggagga ttcagtaaaa tttcgcagat gttgttatgt   125340
agtaatattt ggctcattca tattctgcac tcctagacat tgcagaaaga catgcaactg   125400
tgatttccat ctcatccctt tcaccctatt ttgaaacatt tagttatgtc tactagttac   125460
cctaagttgt attttttacc ctctaaaaag gaacaagaga agttggaatc catcccagct   125520
ttccttccag aaaatggagg ggaggaacaa ttggaatgga gaggaactcc agggagaaaa   125580
agacaaaagg cacatgagtg agtttgtcta ggctgggaga gtgggcgatc acatgagatt   125640
tgtgaactaa ttttgttctc cttctgtttc cactgataag cactttatga gtgccaccag   125700
tgtaagtaaa tattaaacct catctcaatt agtatctact cttttccaaa tatatgctta   125760
tgtcagaaaa tgagcagtag aaagcaacca caggatacca cctgcacacc cacgggctga   125820
gcattgcata ctttcaagga gtgctgttgt gttttcaaac ttagtaattt cccaaaacag   125880
agaattcaca gcttccctaa tcaccttcct cagaaccctg aatcttgtta attgagtcat   125940
ttttctgatg atcatgtact catacaattg actaaatgtc tcactatgcc ttcctgataa   126000
gtagtgtctc tacatgtgaa gtatctattt aatctatcta cccctctctc tctatctaat   126060
ctgttgattt cttatctatc taatttatat ctatcatctc tatgtatcta tgtatgtatg   126120
tatgcatata tgtatgtatc tatatatata tcgatctatc ttatctatat gtatctatca   126180
tctctatgca tctatgtatc tatctgtcta tgtatgtatg tatgtatgta tgtatgtata   126240
tatctatcaa tcctctctct ctctcttagt tcagcaaatt acttacaggt ttttgttatg   126300
taactgagca aaattatata cacacacata agaaggctgg aagttcaaga tcaaagtgct   126360
tacagattca gtgtctggtg gggacccact tcctgattca tagacagcgc cttctcactg   126420
tgtcctcaca tagtggaaag ggcaagggag ctctgtggga tcccttttat aagggcactg   126480
atcccattca tgaaactcca ctgtcatgac ctcattacct ccaaaaggcg cccacctcct   126540
aatactgtcc cgttggggat taagatttat atatttttc tttttaattt ctaattttg    126600 tgggtacatg gtaggtatat atatttatgg agtacatgag atattttggt gtagacatgc   126660
aatgcataat aatcatatca tagaaaatgg ggtgtccatc tcctcaagca tttatctttt   126720
gtgttacaaa caatcaaatt atattatttt agttattttta aaatgtacaa ttaggccagg   126780
cacggtggct cacgcctgta atcccatcac tttgggaggc tgaggcaggc ggatcacgag   126840
gtcgggagat tgagccagcc tggctaaca cagtgaaatc ccatctctac taaaaataca    126900
aaaaaattag ctaggtgtgg tggcgggcac ctgtagtccc agctactcag gaggctgagg   126960
caggagaatg gcgtgaacct gggaagcaga ggttgcagtg agccgagatc atgccactgc   127020
actccagcct gggcgacaga gcgagactca gtctcaaaaa aaaaaaagt acaattaaat     127080 tactattgac tatagtattg actatagtca ccctgttgtg ctagcaaata ctaggtctta   127140
tttattcttt ctgactataa ttttttgtacc cattaaccac cccacttccc cacatcccac   127200
```

```
ccccactacc ctttccagtg cctgataacc cttttttgac tctctatgca catgagttca  127260
atcttttga ttttagctc ccacaaataa gtgagaacat atgataacag tctttctgtc    127320
cctggcttat ttcacttaac ataatgatct ccagttttat ctatgttgta aatgacagga  127380
tctgattctt ttttatagct gaacaatact ccattgtgta tatgtaccac attttccttt  127440
atccattcac ctgttgatgg acagttagtt tgcttccaaa tcttggctat tgtgaacaaa  127500
gctgcaacaa acatgggggt gtggatatct ctttgatata ctgatttcct ttctttgggg  127560
gtttggatat aaacatatga attttgagag gacagaactt tcagactata gcatactgta  127620
ccatctatct atctgtccat ccatctgttt atctgtctcc cattcctgaa tattgcatgg  127680
catattttgt taattatttc caatgtcata ttgagttta aagtaagatt acatttctga   127740
gaggcctcac gtgggggcat cctgaaaagt acattctctt tatagtttaa atgttttggt  127800
ttttttcttt atttttttca tatttaatta tatttctttc aagtgactcc tttgggagac   127860
atgattttcc tacctcctgg gactgccaca attccctgc ctcttggaat gcaatcgatc    127920
tctagtctgc ctcaagtata aagatgatat tcatgttgat gacattgaga aggatgagga  127980
gaaaggagtt gatcagagat ctatattcat ggtatatatg tttatcgtat atatatttat  128040
ctgcttatcg tcttcagaat ataaactcca agactgtggg tctttgtttt cttcagtact   128100
accttgcaga gtctaggcct atttattcaa agcttaatat ttgtgaagtg catgaatgaa   128160
taaatgaatt ctaatgttat cactgccgtt ggtatggtat ctgtttctct atctgtattg   128220
tcctctctac ttttcattat ttgtttaatt cccactcatt gagacagatt gcagaagatt   128280
cctttgccaa ctacttctgg gtagagataa atttccctcc acggagctcc cactggactc   128340
tacctgcagc tatatgttat cttgtattt ccaacactca gctgtaccac ataagacttg    128400
attgagtgaa gaccctgact tagctttgca taaaaccaaa gtaaatgctt tccacacata   128460
gccattcaca gacattttca cattttatac agcaactgat gaactaggct agtgttggga   128520
acaggccccc taaaatctgg ccataaactt gcccccaaac tggccaaaac aaaatctctg   128580
cagcactgtg acatgttcat gatggccatg accccatgc tggaaggctg tgggtttacc    128640
agaatgaggg caaggaacac ctggcccacc cagggcggaa aaccgcttaa aggtgttctt   128700
aaaccacaaa caatagcatg agcgatctgt gccttaagga catgctcctg ctgcagataa   128760
ctagccagag cccatccctt tatttcagcc catccctttg tttcccataa agaatacttt   128820
tagttatcta taatctataa aaacaatgct tatcactggc ttgctgttaa caaatatgtg   128880
ggtgaactgt ttgaggctct cacctctgaa ggctgtgaga ccctgatt cccactccac     128940
acctctatat ttctgtgtgt ctttaattcc tctagcgctg ctgggttagg gtctcccgga   129000
ccgagctggt cttggcaggc tataaagaca ttttctactg gcttaacaga gaagaaaaac   129060
aaagcttagg gagactgatt atgcagaatt taatttgcaa caagcaaaga caagtctatt  129120
gacttcaaat ggacatcatc acattgtcat ctgataattt ttccagcatc ctttgcctcc  129180
tctgtgttaa attataaatt aatgctgatt tatacagttc agttcagctt cacaaatatt  129240
taatgagcac ttgctgtgta ccaggtatta ttatataagt agttctttat ggtgtaagaa  129300
tggatagtag atacttttt atccattcaa ctttaaaagg ttgatgccta gtcatagata    129360
ccaggaaaca cttaagtgaa tgaggacaag ttttctgctg tcaaagagag agatcagaca  129420
ccaactagag tccaagaaag aacaaagtaa ttttgatcaa caaaactcat agaagaaaat  129480
aagcattctt tgttgttaca tatacttcag agccatttta gtgctcaaag tttgatagaa  129540
```

```
attgatacac aggacttgct gctctgaatt ggctatccca gaatattcta cgagctacaa    129600
ccagacctga cattaacctg tagttacttg tggtttattc atctatccat ctaaatgtta    129660
tgagcatctc ctatgtactc ttcatggtac tagactttag acattgaata cggagcaaaa    129720
aagacatagt ttcttattta atgtggctta tactctgatg tagcatttct tcaccagggg    129780
taattttgcc tcaggggaca tttggcgatg tctaaggaca gtgtaggttg tcatgactga    129840
gatttgttgc tgatgtctag tgggaagagg ccagacaccc ttcacaataa agaattatct    129900
gaccaaaaaa ggtcagcagt gccaaggttg agaaactctt ccagcagttg aagaaaaata    129960
atcatcagat cacccacaag tataattaca aactgaaata catgttagat gctggtagag    130020
ctggtttcca aagtttctga tccagttgtg aggatacata ttgatattga aacgggcgg     130080 ttgaaggggc agtagtaagt tattagggta agaaggtctt ggtgagcaga gggactttca    130140
tgcgaagact ccagggctcg aaggagccca gtgcagtcag gatctgaagt gacaggtgtg    130200
gcttgagaac agcggcaatg gggagttagg caggagggga agctggaaat gcaggcaggg    130260
gtagacaata aaagtacgca ggccgtttat attatacaat cctgtagact tctttcttct    130320
ttcattcttg atacttttct ataataacat tcaagcattg gatcagcacc ctttgttgtc    130380
ttctgtcatg tagcccaaag gtttaccttg agacacaaa ggcaactaag acaatggttt     130440
ctgcactagg gagatcatat tctcactcag aagacatttg cagggtgtga ttagtgagtc    130500
tcacatacat gtcaatttct tcctaagacc ttgtgctttt ctagttttta ttttttatt     130560 attatttta tttatgtatt ttatttgaga gagcctcgct ctgccaccca cactggagtg     130620
cagtggtgtg atcatagata gctcactgca gcctccaact cctgggctca agcaatcctc    130680
ttccctcagc ctcccaagta gctagaacta caaacatcca caaccacacc cagcttattt    130740
tattttttgt agaggcaagg ctgtctctac aaattccgtt gcccaggctg gtctcaaatg    130800
cctgggctca agcgatcctc cggcctgggc ctaccaaagt gctgggattc caggtgcgag    130860
ccatcgcgcc ccaccctcta gtttttaatt ggtttatttt cttctcatat ttcagttgag    130920
cattattcat ttattgctgt tgaggtttta cttttttttt tcttcccaaa ggtagattgt    130980
agacagctca cctttgttac caatttgaaa tgctagatgt taattcttaa tgttgtagct    131040
gtaaagggcc atgatttgag gacgtgttat ttttttaagc ctgagtttgg attggtctga    131100
gttgaatgca gttgctaagc catcgaatga gggagtgtcc ctgaactaat gagtgacatg    131160
gaccttttct tataggtgag agtccatttg tgataaaggc attgttttag gatacataag    131220
ggtcatggtg tatattctta gcaagtgtta tgaatacatt cgatctattt cttttgaatt    131280
ttagtgtttc tctactctcc atcttactaa accaggtgtc ccagatttcg ggttcagcac    131340
atttgtgtct gggttcacat agagggacta actaggtgga gtttagggta agggggtatt    131400
cagagtcctg ccctcctgca accacagcaa cacccccaag tctctctcat tagattgtat    131460
ttgttctcct acttatgttc tttggcctct gctataaaca ttttcaaaaa agtatccaat    131520
gaaaacaatg ttgtcaatga ctgtctttag taagtctgta gtcagattca tatctttaaa    131580
atatgtacac tgtgtgaata tttcaaagta tgtatcatga aaacaaataa ggaaaaaaaa    131640
aaaaaagcca agaaagctga gatggctcta ttaatatcag gcaaagatac cttcaagata    131700
aggattattt ccaaaataaa agagagacat ttcataatga tacaaggaag aattcaccta    131760
agagaactaa taatgttaat ttgtgtacac ctaataagag agctgttaat tatacaatta    131820
gcaataaatg caaagaaaga ctcatcaata atgacagttg gagatgttaa gatgttacca    131880
caatagatga aagatgaaga tagaaaacac acacacacac acacacacac acacacgata    131940
```

```
tgaaaattt  caacagcacc  atcaatgtcc  ttggcaactt  cgtacttcga  gtccaacctc  132000
ccttcacaat  ctaatacaga  aacaaacaac  ccatgatttt  tctgcatttc  gtggttaggt  132060
tccctgtggc  tcaaggcctc  tggcgcaaat  gatgttgtct  tttagatttt  catgctaaga  132120
agatactcat  gttcgtatgt  gtgtgctttt  tcctctatag  catccttaat  gttggcctcc  132180
agatgagagt  ctctgacaat  ggggctttaa  catcaaacag  ccaaagtctc  tcagcgagtt  132240
aacctctttg  gccttaaatt  tctcacataa  tgacatacaa  cagtccgctc  ttcttcaagt  132300
ggcctttgag  gagtctaggg  acacttgtga  attcacttcc  acaactcagc  tgcattgcga  132360
attcaattat  tgtgctggga  gatgttgtac  cattattttt  ttttaaaggt  gcatattcta  132420
aaggttaatc  ttgaggctat  cacattaagg  gttaacattt  tatcgggggc  attatagagt  132480
gcattttga   tggctgtgat  ttcagataac  aagcttgttg  tttctatttt  tcagctctag  132540
cttggcctct  aatctgtagg  gaaggctggt  tcctaaatgc  aggaaatgag  gctcaataga  132600
acatgaaaag  ccagtgttaa  tacaccattc  aatctcaaga  aagagtggga  ggaagaatga  132660
cagagctgtt  ttttgacaga  tgagtggtta  ggcatccccc  tagctctcca  agtcaccact  132720
aggatgaact  ttcaggatgc  agtgtcctgt  ggaatttggc  tctgaaacat  aacttcttca  132780
taaggcagat  attgtaacgc  agttctggat  tttgtaccta  cagacagctc  tgtgttatgg  132840
taactgtttt  ctgttggcac  aacaaacaat  tagttagctt  catgctgtag  aatatttcca  132900
gatgccctga  tactccaaac  cattggtcat  tgcagcctcc  atattcagat  gtagcggcta  132960
taaacaggtg  atgcatgcat  cctggccagg  gaccattttg  atttttccac  ctttttcttt  133020
cccaaattca  gggtttgtcc  acattagcac  tattaaaact  tttggggcgc  ttcctgtgcg  133080
ttgtaagatg  tttagcagca  ctcctggcgt  ctacccactc  caagtcttta  acacctaacg  133140
cccatcctta  attgtgacaa  ccaaaactac  ctgcaggcat  tgccaagtgg  ctcctgaggg  133200
ggcagcattg  tcttcattga  gcaccagtat  ggtaatccta  gcctaatcta  ttgtgttacc  133260
ttattgttcc  ttaacatata  tggggtagaa  tcagaattac  aggaacgtga  atttctttca  133320
acaattattt  ctttacaatt  atgtaataaa  atcataaaag  gtaaaactgt  atctttttag  133380
aagccaagaa  gcaacagttt  atgaaacaaa  acctctttta  gtatttcata  ttaatcaata  133440
gatattgtgg  aaaggctagt  tcttctttaa  ggtaacagtt  gcttaagagt  tgaagtgcag  133500
cttatgagtt  ttacaagccc  tgatttatgc  acagcttgag  gcattgttgt  tttgcaacta  133560
ttgttttcca  gcagcactgc  tattttataa  aagcatgtat  cagcaatagt  atagaattgc  133620
atatatgctt  cagagtcaat  gcaatcatta  aatagcatgc  aatctgagta  gagtctaccc  133680
aaagctggaa  ttcagagcgc  atatttatgc  acttagcaac  attgccataa  ttacacacac  133740
acacacacac  acacacacac  acacacacac  acacacacac  gcacgcacgt  acttaaagcc  133800
ttagccattt  aaaaatagaa  ttcaacaact  aaggctcgta  cacatggaac  tcttttcata  133860
gcaggatttc  caatgtgcaa  atttgataaa  attactcttt  taaaaaaaa   aattgctgca  133920
acgttttca   ttaacaccat  aaacatttac  acatgattca  ccccaaattg  caccctagat  133980
gtatttaccc  tgacttggca  atttcatact  tcatgtctct  acttcccttc  atgcttcaat  134040
acagaaacag  acaaccgatg  acttttctgt  atttctgtgg  ctcaagtcct  ctggccaacc  134100
tgataaatgg  cttaggctat  tcgataacct  gcagcagatc  ctctgagatc  ttctttagaa  134160
atttcctcca  agatcctaac  tacattcatt  tgtagaaata  tttgagatgc  aatgcatacc  134220
ctgtctagta  tcccccacc   ccataacaga  aatgtgaagt  agggtgatct  gtcatctttg  134280
```

```
tgcaggtcat tgccagctct agcaccagaa tctcctcacc tggggaatat ctcagtccca    134340
ggccaactgg gacttggata ctctaattct aggtgtggtt gaagcatcgg tgggttccta    134400
taacactggc acagggaaaa acattaacag tgggacagaa tagagagtcc agaagccaga    134460
agtgcatatg aatagagaag ctggtcccag ctgggaccag cttttttaacc ttgccaaatc   134520
ttgctattgc atctttagct tttcttcttt ccttttttata ccttcttcct tctactttct   134580
gtttagtttc ttctgttttt ctccactaat ttcttaagtg ggatgattca ctcattactt    134640
tttgcccttg tgtttgttac tgatgtcagt atttatggct ttaaattttc tctactgcta    134700
attttcctgc ctcctgtaaa ttctaaaaca cagtatttca gtatttgtct attaagtgtt    134760
aagtgagatt tgtgtgacgt tctaataaac agttaatttt taagtgtttt gtgtgtattt    134820
tctaatgatg agatacaaaa ttatgtaatt gtctatcaaa tcatcggtta actgtttatg    134880
gcatctgttt ttcctatttt ttgatctatt aaaattgaaa ataggtttct ttgtatcttc    134940
cattaatgaa tgaatttata aattcttcct ataatactac tgatttgggg ttttttaaag   135000
aacgtatgtg gcataaaata tataacaagt tatctccttg aagaatgaaa tattttacta   135060
tgtaatattc ttgctatctc ttaaaatgct ttctgtttta caatagatat ccaatattag   135120
tagaaatatg cttgtttctt ttttacttttt gggttggcta ttgctgagaa tatattttttt 135180
atattttcac ctttagtaat ttcagatatt atggttgtat catttcatat gacagatatc    135240
tataattcct ttttttcaat gtgacagttt cagtctagta attgcataac ttatgctatt   135300
tatgagtttg aagatatttg atataattca acgtatttta atctttcgga tttccttttt   135360
tatgcattcc ttttaataaa tgagtttgtt cttttttctgt attttcttct taatttgcca   135420
tttacttgat ttctactttt caagaaaagc ttgcagttgt aaaactcaca tttaagtcat   135480
taaagtctaa aattaagcaa gaccttagct ccattctaga aaataccaat cacctgtctc   135540
cctagttaca ggctattatt atgtatcatg aatatttgtt ataaactctt tcagttttttg  135600
tttgattgaa taccttttgtt ccctgctcat tcctgaaaga taattttgct tattatgcaa  135660
atccaggtgg accattattt cacatttcac tgtcttctgg ctatacagat gtcagttggt    135720
tttgagttaa actttatgca caggttgtct ttggcaaggg ctaaaattta agatctcctg    135780
tttattttttg gcattcatca gtttcatgtc aatattgatt ttttttttgc tttatccatt   135840
cttttctatgg tttctgtgcc tttggattca tatatttaat cattatttga agatcttagg   135900
gatcacctttt caaatactga cacttctcca ttcttcctgt tttctcaaat tttgatttga   135960
tatatgagat tctcattttt gcacccatgt ctccctaaatt gacttttata ttattagttt   136020
ctgtcttctg tttttttgtaa gatttttccca gacatatctt ttttttattgt cttttcttct 136080
gtgtctaatc tctttagcta atccattaat ttctatttat ttcaacaaat acagttttta   136140
tttatttcat ttctatgtgg tcattttttca aatcttcctt gtcctttcca gtaatttcct   136200
gtttttttgtt tattgtttcc tgtttcaaac tttatttttt aaatagctat tttaatacca   136260
caagttttgt gtgcagcacc tataatacct cagtgttcat gggcttagtg atctttgact   136320
gtgaactcat gtttgtttga tcttaatctg tgggaattttt ctggcctatg ctggcattct   136380
ttccccaggc aggtaggttc gctttccttc tgatagaagc tagagtgtaa gacttgagcc   136440
cttttcaaggg tccaaattct ccaccttact ggaagccaag cttgggtttc tggccccagc  136500
cccttgtctt acacatctgg ctgcccttcc agctacctgc tcccttttgtc tgaggtcagt   136560
gctactatgg tgtgttaca taagggcaga cttcccttag gtccagtttt cccttttgctc   136620
aggacaccca aatattcttt tgcttacact gttggaggag ctttatgtgg gaaagcttaa   136680
```

```
ttttggatat ttctcttact tccttgtgcc cagaagttca ctagcaagtg catcttatca   136740
ggaggtaatt gttttgttca gggaaggtct cccagagtga tgtgttacct gctgatgata   136800
ggagtggaag cttttccttt gagaaggttt caccaatgga aaaacaggaa ggaatgaggg   136860
agggagggag ggaggaaggg gggaagaaag aaggaagaa aggaaggaag agagagaagg    136920
aaggagtaaa aaaagaaagg gaggaaggga gagaggaag gagtgaaaaa agaacaaagg    136980
aagaaaggaa ggaaggaagt aaagaaggag aggaggaaga agtactgagg aacatcttac   137040
tcaatggtga gacccagttc gtacatgttc ttatcctatg agctaatttt ttctcttttg   137100
tttttcttaa gagaattggc tgtctcttac tctgtaatac agatctgtga gaaaatagct   137160
tttataaaaa gagattttgt agtattacac acttggcagg aatatagttg tctgttgtaa   137220
taatgaatac taatctagaa taggaggctg agaagaaaaa tataattaaa atggtaatgg   137280 ctttttttt atgtgaatga aactcatcca gtattggttt tgaaagatat ctaagttcta    137340
ggagcagact gtagcagaat ctcctttaat actctaagga aaggacgctt ttagaaagta   137400
ggcattgcct ccttatgtga aaactgcatt cctttcatga gggttccatt ttctggaaca   137460
caggatgtaa gacaggagac ataagaaggg atcttgtagc agtgcagatg aatcaagtca   137520
ctgcactttc ttatttgatc ttattttaaa aagatgcttc cagggaagca ggaccttgga   137580
acccacaaag tctggagcaa gtcattgacc tcgcaaggta ttcacgtcct cacagtaaaa   137640
tggagaataa aattgctagt ttttaaggat actcttagga ataaataact tgttatagca   137700
catatcagac catcagtcat gccagcctgt tttcctttct ctcttactct ctccctctgt   137760
tcattttctc catcttctct ccaactattc ctccctctct accactgttg ctccctccct   137820
ccctccctcc cttccttcct tccatttttt ccttccttcc tttctacatc cctccttccc   137880
ctctctttct tttcctttgc ttccttttct tttcttcct ctctcttttt cctacaaaac    137940
agtatttgtc aactttggca ctcatgacat gtggagctga tcaccccgtc tttgttgtag   138000
gaggtgtcct atgcattgta ggaggtttag tttagcagca tgcctgggct ctgcccagta   138060
gatgacagtg gcaccactac cacaagttat gaaaaccaaa aatatctcca gacattgtca   138120
aatattgcct ctgaggcgaa accaccctg gttgtgaacc accactcaaa aatacacttc    138180
atatcaataa aaatcctgct ttatatatat atgttttttg ctcagttcag ggttattaag   138240
attgtaagac actagtgttt ttacaagatt tctagggatg ttctttgatt gagtcttaaa   138300
atcttactgt tgatgaaaaa ttgaaattat gttgttattt ttatattcct tcatatagca   138360
gcataaaact tggtattta tgggaatgag tatgcatctt gttctgattc tatggtctac    138420
ttttatgtgt ctcaaaatga gattcagatc aaagaaaatt aaaacgagag caaaagtgaa   138480
tattaaggta aaggtatagc attctgatta tctgctgctt gtccatctca ggtatgcaat   138540
actgacactg tgccactagt agcttcttga cattcttaag atgaaaatag tttagttttt   138600
atctaaatat attaatagag aatatacaat atatatttat tcatatatta atactggaac   138660
aatagagtaa ggttaaacac tcaaaattta gctcaaccct gagattatta tgaagtactt   138720
acaaaaataa aaactaaaaa gacattagta gcgtacttcc cagcttcatc tctgcaggag   138780
gtgttacctt agctcagggc ttggagaata ggacatgtgt ttacgtgatt gactcttgtt   138840
gggattgttc tcagagctct cctgaccttg gtccacacac ttgggagcac atgattccta   138900
atactgataa ccacagtctc atgaattttt ctcattttgc agaggaggga attgaggcac   138960
tagatggtaa tatcttttc atttcacata gttgctggtg gctaagggaa gctggtgctc    139020
```

```
agcttgtccc aggccatatc taagacattt gtctggcccc ttgctttcct tcctttcatg    139080
catacagcaa gcatatccaa cttttctatg ctggtctatt tctagaaggt gttatttgac    139140
atggcatcac ctcctttgta gccctctgac tatgagaatg atagaatgac ctctctttta    139200
aacctatctc cttatccgcc ccaacacata cccctttggg gtggggtcat aaggggtat     139260 cccttctcca cactaacttt accgacttct ctcttcattg tctctctgca gcagataatg    139320
taagcaagaa aaagattaag ttaattacat gcacctcaag tttcagtagg aatatcccac    139380
aattcctctg tctcttaatt taactgttat ttattgaaca cctgctgtgt tcttgggaaa    139440
attccaggtg ctggatggaa ttagtttatg atgatagcta agacttgcag agacattaat    139500
gtgctgttct tcttcttctt cagaaagtat agccatgtac aaactactaa agggcgatat    139560
caaatgttgg ggagataaat atcaaaatac agagcttcca tacctgtagt tttggttagt    139620
ttaataggcg ttaacattta ctcattttca gctacctaca tttattgagc agtgcctata    139680
ccactcattg taatttaatt gcataataaa ttacactgta tttgctgttt atagaaattt    139740
agaaatttag tttaacgata tgtttataat tttcttacta ctatggataa tacatttaat    139800
gactataatt aaattcttgc aaaattttg aattgttttt agtaaatttgc caatgattt     139860 cccaggtatt aatttaatat attgaaattt tgtctttata gcatagaggt ttttatttc     139920 attcatttat ttaacaggca tttatcattc atctgcttta tgcaaggaaa aaatggtca    139980 agacaaggat gccaagtctt taacctcagg gaacttacag tttatgtaca gggacacata    140040
cttatcaaat aaacagagaa aggaatgtat attcatatga actcggcatc atatattctt    140100
ctttatgtta tcattaataa catccaaatg tcaacaacac atctattgtt actttggtta    140160 aaagctaca cagacagtag tagatatggt acttggatga agaaagctga agtttattat     140220 tttctcttc tagtttaat ccctaagggt cattgataaa agacttacac aaacccccct      140280
ttagtaacct aataatgtat aataatcctg ttcttaaaat ggtgatagag atttgcttgg    140340
tttctactac ataacaccat aataccatat taagacttga atctctttat atcatggaac    140400
aactcaggta gtgttacaaa ctgctgttac tgaataaatg cggagaagaa caagctctcc    140460
agagcagtgc catgcctgtg tctgatgttt cccaggatag aaaactgcgc agatgttgat    140520
ggtttgtttc aggtgctttg acagcctgat catgggctct agccgtggac catgaaaaat    140580
ggcttctgca ggggcttaag aaagacaatg aagagcttcg catttctct tggcatttcc     140640 tgctattgtt taaaaggtca catatgcaat ttaaaatgtt ccatgcatgg agcatgacaa    140700
atgccacgta gaaaatgaaa ctgctttcgt tgacattttt ggccaatttc caaagggtac    140760
cattttccgc cttttccctt ttgtggattt gcaaatttg gcttgtgcaa aatgcgtgcc     140820
ccacggtgca ctctaggttg ggaagtgcca catgttaggt agaaaatcgt gtgtagatga    140880
gaatggcaca ttcagaataa aagtgagaaa ttaaatgaca tcaaaaaaat agagaaaaat    140940
agagaaaaac ttgtaaatga gtccatcaga actatcagaa gctcaaaaag aaagaaaggc    141000
ttagaactca tcaataacaa tgtccagtct cattcatatg taaagaaagt gaaatcaact    141060
ttattttagt taatttttact ttattttatt ttattatcct tttacctagc tgaatggcaa    141120
aactcagttc agttatcttt gggcatggaa aaatgagcac tctcacagtt tgctagttgg    141180
aggaagaatt gaagtagagt tttagaagac attgggtatt atacaacaaa atttagaaag    141240
agacccactt tactcctctg gaagcatttt tgcttccagg aatctatctt acagatatat    141300
acacaaagat atatgtacat aggtgatcat tgcaactgaa atttttctca tcaggaagat    141360
gagtgaatta ttttaagcac ttagaatatt aaaactatct ttcccttgaa attgaagagg    141420
```

```
cagagcaaaa tgtgaggaca cagagtaata ttcacataaa ctccttaaac ctatgtatgc   141480
acgtatagat acttgtatat atacatagat atgaatgcac aatagtatcc atacacatat   141540
gtgtacatat gtgtgcatgt gggtgaatgc ttatgtgtag atttgtatac aaatgtgtgt   141600
atgttgctgt attaaaaaaa gtcaaaaaat aaacaaatta ttaacaatgt ttgcctctta   141660
gaaggtgact atggtacggt gcccttagag agaggctttg attggcagag aaaatgaaaa   141720
accataactg cacctatatt taagatttta aaaaattctt tgtagtgagt ttgagtaact   141780
tttaaaagta cattgacatt tcatttatgc agatcttcta ggtgtgtata aaaagccatg   141840
agaaaaagat gatttcatgt gatagagaaa actagcacag gttagaattt ggactcagct   141900
gatgagacag tatctgccca aaccaattta atcaaagctt tgttgcatga gccgggtgtg   141960
gtgagtcaca cctgtgactg cagcgctttg ggagaccgag gagtgaggat cacttgaggc   142020
caggagttca agaccaggct gggcaacata atgagatccc ttctctacaa aaagtttaaa   142080
aaatctagcc aggcgtggtg actcaggcct gtggtctcag ctactcagaa gactgaggtg   142140
ggagggttgc atgagcccat gagtttgagg ctgcagtgag ctatgatcac accactacac   142200
tccagcctgg gggacagaac aagacccccgt ccttaaaaaa atttgtttta aacacttcat   142260
tgtgtggaag aaagctgtat atttaaacaa atataaccaa acccgtaata ctggggagaa   142320
agattgatgg attgttgaaa ggattatacc cgttaggcca atttttgagat gtaggcaagg   142380 aatctcagaa gttccaaaaa gttctgctgt ggttcagtgt tacagggaaa tctactcaag   142440
ggaataatat atggcttgca atcattttgc ttttttgtta catttcctat tattcattgc   142500
ttcattgggc ttgagagaag ccccacagag gaataagaaa taccctacat cattcacatc   142560
ttcttggctt ttgaaaatta aattttatat acttaaaagc agccatgaca catgaaaaca   142620
ttttctttct tcctcaaacc atctttacct agcctcaccc aaaccaaact ttaatttta   142680 cattaatttt tcttttccaa agctatgcag ctgacactca tctgctcact tggcataatt   142740
catttggtat ccagtaagtt taagaaattc tgtctgggct tcatgcaatc ataacctaca   142800
tccaaatagc aacacttata ataacagtaa taatagtatt ttttagtgtt cacatggatt   142860
ttctccctta attttcatga catctcaaca aaatagacaa aatacatggg cttctcctca   142920
gccctgagct ttgcctatcg ttaacccctt gaagaaaaat ggcgctgagc tatcagtcag   142980
tcattccctg gcagaaaggg aacagaatca gtatagatgg ctttctgaag acattgactt   143040
gatttctgtc accaacaatg gcatattcag gctgtgctcc atgccaggtg ccgtgtgggc   143100
atggagtcca ccacaccagg ggaattctca gaagcagtat tgaaaacaca taggaaagca   143160
ttacttaagc ctgtataaac ataagctctg tccagacatg gaatacagtg ggagttcttc   143220
ctaggataat cccaaaaact aatacatcag aaagcttacc tataacatga gaattcaagg   143280
caaaggcatt tttggtatgt aagtaaaata ttaggttgaa tccatctctt aatgcggatg   143340
ttgaagaatt aatgttatat ccatgaagcc agtgttgact ggaaggactc aaaaaaatct   143400
gaagaatata aattccttga ccttctttat tgaagacttc agctccatta cacgaccacc   143460
tcacagtcct cattcggttg ccttttgcct gtttctgact tactgaagga caatggtgtg   143520
gagctacgat ttatcaccca gaaatgatt actaaagtcc gtattctact ctgaatactg   143580
aaaactctga agtaatgacc ctaacctaaa cctcctcttc ttctggctat cacttcttcc   143640
ttcccacttt gatcactctt ccatgaatcc tggcaaacct cctagtactg agtatccttc   143700
cagccaccaa acgtctgaca tagatcgctg gatctgactt taattctctc actaagaccc   143760
```

```
tcaatttcct cctctgcttg tggtgggctc accctgttgt ttctcagcta agggtgcatc    143820
cagatatcaa tttcttgtgt cccatagcac tgctagcatt aagtgaatta ctgcatggtt    143880
tggtctcatt agtgtgtggt ttccagaaac acttgagatc ttactgttgg cttgtaatct    143940
gtcttagtcc attttgtgct gctataacag aatacctgaa actgggttgt aaaacatata    144000
aatttatttc tcctagttcc agaggctggc aagtccaaga tcaaggcacc atgatctggc    144060
aagaccttct tgaacatcat caaatggcag aagggcaaag agcttaagag agtgaaccca    144120
ctcctgcaag ccctttttat aattacactc atctgttcat gagggcagag cctttgttac    144180
ctaaacacct gccattgtcc cctctcctgc aacactgtct tactagggtt taataatatt    144240
catgtcaacg catgaattcg gggaacacat tcacaccata ggacaaccca tttacactct    144300
ctcctcatcg gggtcaaagg gcatcaattt aaggtttttt gaccttttt gttttcatta     144360 tatctcattt ttatactaac agattcattt gttcgtataa ctctcctgtc ttccagaatc    144420
tgggacagtt ttccacctcc caagtgggat ctaggagtta accccacca tcaacccaag     144480 tactcctcct gtgtccaatg ccagtcagc ctcaatcctg tcttctcttg agttatgaca     144540 tattttctc cttccattaa tagtgaccat tactgtaata ggaatttata gttctttgtc     144600
ctccagttct ccaaaactgg ttctctatcc tttcaatttt atgctaacaa atctcattaa    144660
agtatgacca gtgatttcta cattgccaaa acccagtggt gtcttttag tgatgatcct     144720 atatcaattt gatgggcact ttatcacttg cagaattctt attcctttc attttatcac     144780 tatgttctgg ttttattcta caattgtgag aagctcttct gtattttctt ctcttattat    144840
tcttaaatgt tgacttttcc taggatttgt tcttgacttc attctgtata ttgtatgtct    144900
aggtaattca ttgcatcttc ttatcttcaa ctatctgcct ctatgtggat gattctcaag    144960
tctttatttc cagctcaggc cactagcttc agttacagtg tttgtaattt tagcccctat    145020
tagaaatctc tagttgagtg tcacatagac actccaaaca caacacattc aaatattaag    145080
agatgctctt cctctaaaac ctattcctct ctgcaccctc ctgttagtta aaggtgcccc    145140 ataccagt gtgtccaaga tacaaactct gttggatttt acttctcttt tctcagcact     145200
tatgtaaatg gatgtctact tctcattct gccctgcaga acattcctag ctatgtgctg     145260
tcttcctgtg gcccactgtg acagcttcct tatctcagtt tagattgtta tgcagtccat    145320
tactcttctg cctcctacct tcaagctact attggagtca tcttcctgat tctcacatct    145380
gatggctttc agtggctaag tgatgcattc caatctttct tagttcattt tatgctgcta    145440
caacaaaaca cctgaaactg ggttataaaa aatagaaatg tatttctcat agttctagag    145500
gctgggaagt ccaggatcaa ggcaccatca tctggcaaga ccattttgca catcatcaaa    145560
tggcacaggg gcaaagagct caagagagtg aacccactcc tgcaagccgt taaaacgca     145620 tcatgggccg ggcgcggtgg ctcacgcctg taatcccagc actttgggag gctgaggcag    145680
gcggatcatg aggtcaggag atcaagacca tcctggctaa cacggtgaaa ccccgtctct    145740
actaaaaata caaaaaatta gccgggcgag gtggcgggca cctgtagtcc cagctactcg    145800
ggaggctgag gcaggagaat ggcgtgaacc ccagggggcg gagcctgcag tgagccgaga    145860
ttgcgccacc gcactccagc ctgggcgaca gcgagactcc gtctcaaaaa aaaaaaaaa    145920 aaaaagaaa aaacgcatc atggcaaaat ctctttttt accacctggg aaaacctaag      145980
acccttggga cagcacagaa gactcctaa tctgcccatg tgtccctttc cagtgttagc     146040
ttcttttact ttttcttgta cacctcgtgc ccttgcccct tggaacaaac agctcacagt    146100
tccctcagca cacccaccct tctacctgcc cgggagctgc cttccgataa gttgtatctc    146160
```

```
gatgacttcc tccccactct ccatctggga agatcccagt cattcatttg ttaaggccca    146220
gtgaaaaaga ttttatttat tttccttcat ataatatttt tatgtataca tatatatgca    146280
tatgtatgct atctatctat tagatacatc ttgttttggc ttattttat tttttatgtt     146340 ttgagacaga gtctcagtct gtcacccagg ctggattgca gtggcatgat cacagctcac    146400
tgcaacctcg acctcctggg ctcaagcaat cctcccacct cagcctcccg agtatctggg    146460
actacaggtg cataccacca tgcccagcta attttgtat tttttttttt gtggagacac     146520
agtcccacta tattgcccag gctgttttg aattcctggg ctcaagcaat ccacctgcgt     146580
cagccttcta tagtgctggg attgcatgcc tgtgccctg tgtctgacgt tatccttgtt     146640
attttaatgc ctacctcatt tgtcttttc aaataataat caacaaatga tttctggatt     146700
gataaatgca tgaatgaaat gatagtttgc caaaatacag aatattaaaa ccataggta     146760 accttgagac aatttaggta aaaataggg gattatttta tattagaaga ttattcaatg     146820
tattattaaa atgtttgttt attgcatgtg ttttaagtgt tgagaattta acagagaacg    146880
agacatgaat ggtctaagtg tttatgcatc ataataaagt tgaagaaatg tagggttccc    146940
atggtgtttc ttttcaaact ttgataataa cacttcttta ttgatcgcaa ctgtacattg    147000
gcagcaccgc ctccagactg gaaaataaga tcgatttctc ctttgtgttt cttttataac    147060
cttgcaattt tattcctctt gggcttactg ttatgagttt ggtttctagt ttctagagca    147120
tgagttctaa gaagtggaaa tcaagatgga aggaagttac tatagtgaga gggtgtcatg    147180
ccctgcaggc taggtatctt agagtctgac tgcaactccc ttgacacagg cagttctttt    147240
tcttgcctgc agccctttcc aaacaaatat caccagcctc atattcccct cccctttata    147300
gatggagccc ctttgtcaag caggccagtt tactgggaaa aggcccttct cagacatgct    147360
ttctcatcct gatgctttgc ctttaccagg agtgaggcca gaaccttcag catgcattta    147420
tatcaaaaaa gagagatgtg ctgttttcat ttaaattccg catttccact gggcatagtg    147480
gctcatgcct gtaatcccag cactttggga ggctagggca ggaaaatcgc ttgagaccag    147540
gagatcatga ccagcccagg caacataatg agacccgtc tctacaattt ttttgagaa      147600 agggtctcag tctgtcaccc aggctggatt gcagtggcat gtccacagct ccctgcagcc    147660
tcaacctcct aggctcaagc aatcctccca cctcagcctc tggagtagct tggaccacag    147720
gtgtgcacca ccatgcctgg ataattttg tttttggta gagacagggt tttgccatgt      147780
tggtcaggtt ggtcttgaac tcctgacctc aggtgatctg cctgccttgg cctcccaaag    147840
tgctgggatt acaggtgcga atcactgcgc tcagcctcta tatttttt ttttaatta       147900 gtgtgctagt agtctcagct acttagaagg ctgaagcaga aggattgcct gagcccagga    147960
gtttgaggat acaatgagcc atgatcacat tccaccctgg gtgacatagt gagacgctgt    148020
ctctattaaa aaataaaata aacaaattat aaattttcac atagtcgtaa acctctgaag    148080
atgtggatac ttcatttgtc acatttaggt ctttaataca ctaataccttt ctctggaa     148140 acagtgtttc tcagtctctc ccgtattgat aatgtttcca ctttgccctt gaagattttg    148200
tgggttatgg ggaaacagtt tatgggtgt cttcagcag aaccacaacc ctttttagga      148260
agaagctaat tatggtgtga aagggacagg tgctcttatt aggtagtgat agtaagagtt    148320
aaaacccagt tctcttgagc tgttacttgg attcttcaac tgagggtgat tttgcatctt    148380
tggcactaga tgtcattcaa ctgacagtca tggactccca ggggaccccc aaactctatg    148440
tcacctttat gagtaggcga gaatggattt ttcttggaga ggagtgtctc ctcaaagaag    148500
```

```
tctgtgacct agaagaaaag atgaaaaatc tctgctttgg attcggaatg tcaggactgt 148560
tcacttggaa cttaaggaga gtttcttcct agtatatacg agactgaacc ttatgggtt  148620
gccattttct tagacccaaa gctttcaaat acagtcattt tcatatgact tctacttaga 148680
caataagatc atcatgtatt ccttttttcc tctttcagca tctggcattt ttctcctctt 148740
gggcttgttg ttctggtttt ttttttttt  ctggtttcta gaccataagc attcatgcat 148800
tcacattatg ttgcctccta agttgtaagc tctccaaaga gagggaatat agctgcttta 148860
tgtcttcacc caactttgag tagagatgat ggcaggaaac agagagcatt tcacagaga  148920
agatggagtc catttgagtc aggggatctt gtttgaaatc ttacctgtgt gatctggggt 148980
gaattaatac agctgtctgg aaaatttaga acagagacct cagaggattg cagtaaggag 149040
tcctagaagt taggatctcc tcagtaaata taaatactta ttctcttggg taatgaagct 149100
gacccacagg atgatgccaa ttatttcctt ggtattataa gcacataaac aatagttcac 149160
atttattgag tgcttactat gtgtaagata caattatgtg ctttgggata tgggttcaca 149220
catgaaacaa gtgtttattt agtgcctact ctgtgcccaa cactggagat gcagctgtca 149280
tgagcactaa caccatccca atatcatggt gctcatgtac ccatgtggga aaaagtaaag 149340
acaggctcaa gcatataaaa tagggaaggt ggtcttagga taattcaagc tggattggga 149400
tcagtagtga ttgaagggct agattaaatg aggagtttag gacatgcatc tctgcaagat 149460
ggcatttgag caagaaacat aggcaagact tatctacttt aattttcaca gtagggtcat 149520
gagattacac tgtttattaa ctctgttaca gagatgtgga aactgagatt aggatgattg 149580
aataacagcc agattagtaa tagggctggt agtctttaat gcaagtctca tgggctatgc 149640
tgcacacagt cttaacaact tgccaccttc cgtggtataa gagaggaacc aacccaattc 149700
ccgttgcctg ccttccctgc tatattagtc tattcttaca ctgctataaa aaatacctga 149760
gactgggtaa tttataaagg aagaggttta attgactcac agttccgcat agctgggaag 149820
gcctcaggaa atttacaatc atggcaaaag gtgaaaggga aggaaagcac cttcttcaca 149880
gggcagcagg aaggagagaa gtgctgagca aggaggaaga accccatata aaaccatcag 149940
atctcatgag aactcactcg ctatcatgag aacatcgtgg gggaactgtc ctcatgatct 150000
aatcaccccc catgaggtcc ctcccccaac acgtggggat tacaatttgg attacaattc 150060
aagatgagat ttgggtggag acacagagcc agaccatatc acttgccatc taattacctt 150120
gatcaactac cctgcaacca ttccttagtg agtaatagg  ccacactcag gaatggtttt 150180
aatagaattt aaaagttatc agtattgtag tttaattgta atttaaaaa  tggtgaacct 150240
cacatcagtg gctaggatca gcacatgata tgctgcatct tggggtcaat aattgccgca 150300
agcacattat tagagttgct gttaatagtc atggaaacca ccctgtacct tcttccccca 150360
gtgcaaccaa cctggcagtg attgacctac tcggtagcga gttgctagac atcaggagaa 150420
gtcagaagta agtggaagaa ggccaggtgt ctagaagacc cccccactac ccatagcagt 150480
agcaacacat atgcatagga ataggttaaa tgagtcttca ctcattgatc cattcattca 150540
tctttcatcc atgaattaac tattcatgac ccattgttgt tgactctgaa gatacgatag 150600
caaacaggat gcacaaattg tcctgctgtt actttagtta tggggacaga agataaagca 150660
gtgatcaaat gcatgaagga cagaattgct gatggtgatc atagctttga gggaaatgaa 150720
gcaacgataa catctaatgt gggttatgag gatctttgag atggagtggc cagggcatgt 150780
ctttatgagg gtgaggaatt taagcatccc agacacaagt tctgactcaa acatcagcct 150840
tttaattatg tgaaagggtc tcgcaaaatt taataaactt agtggtagga gttcaggtaa 150900
```

-continued

```
cactacaaga aaccaagctt tctttgtgaa tggtgaggtt agaaggggtt tgttgctgaa   150960
aatcccattt gcaggttcta aggctgggga tgaagtagaa ggaacaatct cttgtcattt   151020
gccaatcaaa gaacaatccc tgtatctggc aaaagagaca tacctttcta tgaatcctgg   151080
ttttggtcat aagccaaact tctatattag ttttcccttt ttggttgagt tagtgaacaa   151140
ttggatgatt agctaaatgt tgctgaaata ggaggaaggc agattaaaaa tacagaaagt   151200
aactcttatt taatgatttg aaaaaatgag gttaatccga caaaatttta aggaaaagtg   151260
agataatttt ggtgtataaa actatgaaat tttaggctgg gcatggtggc tgacacctgt   151320
agtcatagca ctttgggaag ctgaggcagg aggattgctt gacccagga gttcgagacc    151380
agcctgggca acatagtgaa accccgtctc tacaaaaatt acagaaatta gctaggcatc   151440
ctggtgtgtg cctatggtcc cagctatgag ggaggctgag gcaaggagaa ttgcttgaac   151500
ctgagagttc aaggcctcgg tgcactctgt cctggcttgt agagtgagac cctgtcacac   151560
acacacacac accacacaca cacacagaca cacacacaca cacacacaca caaaataaaa   151620
ttttggaatg taataacatt gatgctgaag tgaattgtgg aaaaatatca tataaaatat   151680
attttaatca catagtataa atttctctct gtgcattagt taccaaaatt tgaacataaa   151740
cattttcaaa tacacacttg tgcaaatgtc agggatagca ggtggtatat cacttttat    151800
atttaaaatg catgtaggaa tgaaaggaaa aaggtaaaaa tatgttaagt gtagaattct   151860
aatgaaagaa catattggaa ctatgaaaac attatggagg actttgttca tttatggtct   151920
gagcacagat gatgctaaac atggtccttc aactttagct ggcagccatt tgaaatgaac   151980
acactaaaca ccatgagaag caactgcatg aaaagcaaag agagttatcc aagtgaactt   152040
catatctcat catttgcctg tgtttatgta atagtaaaga cccaaggaat tggtctaatt   152100
aattggtatt ttattttagt gatgaaataa tgagtgcggt tgagcatgcc agatgtattc   152160
atctgataca ttcttccagt cacatggtag gctgcattag gtgataatgc ttcaccctgc   152220
attcatttat aagttagtga agggaagtcc acaactctgg tctcagagca tttatcccat   152280
tgttgatcag ctaagctgtt gctcttactt agctgctaag gaatgaagct aattggacca   152340
ttccagcatg taaaatatgt aaaatatgtc ctttcatgga actctgaaac aaacaatgag   152400
aacaaccaga aaaattgcca gagtcataca aaagctgtct atttctaaat gatcattcct   152460
caagctcttg tcatctactg ggagcccta gatggatgta tagttgttgc tgttgtggct    152520
gattttgata ggactaacat aggaccagtg tatggagctg tttattaaga tgcttttgtt   152580
gctgagtatt tacattttgg gtgttctcgg ataacatacg ttaattccta ctgcagtatt   152640
taataaagtg taactagtgc ctgtctcacc tgtctgaaga cattcaaata tggagcgttt   152700
gtttctttct ctagtgcaga tactaaatat catattgtaa ttagagctat acagagattt   152760
agcatatagg actggcaagt cttggaggcc aatttttatg atgtgggaag agggggcgt    152820
gatttagagt ggacaaataa agtgtgggaa aattttgtgt ttctggcttg agtgaccagc   152880
tcttacctct cctccccata ttctcttcct tgcctcagtg caaattcaca ctgtcttcat   152940
tttgtatgat caccctctgt cttagtccat ttagttttgc aattaaggaa tctctgagac   153000
tgggtgacat atagaggaaa gagatttatt tggctatgat tctgcaggct gtacatgaat   153060
cacggcatca ggatctgctt ctggtgaggg tgtcaggaag cttccactca tggtggaagg   153120
tgaagaagag ctggtgtatg caaagatcac gtggcaagag aagaagcaag agaatggggg   153180
gaaggaggtg ctaggctctt ttaaacagtc agctcttggg ggaatgaaca gagcaagaat   153240
```

```
tcagtcatta ctgcaaggct ggcaccaagc tgctcatgag ggatccacct ccatgactca   153300
aacacctccc actaggcttc atctccaaca ttgggaatca aatgtcagct tgatacttgg   153360
agaggacaaa catccaaact atagcactct gtctccttag gtgcacctTT cttcttcagt   153420
gactaatcta gagttctctt tggaaaatgc aaatgtagtt atgtttcttt tttgctttta   153480
tgccttactg gttccctgtt ctttatagca tcaggttgca tcttcatcaa ctggggaacc   153540
agttgatgaa gagaagatca gcatcctgaa gtatcttgta acttcttgaa gtatcttgaa   153600
gtatcttcaa gattcagaat gcatgttacc ttctctgcaa agtgctcttt gcaccttgtc   153660
cagtgtagct gtgttaactc cagtgcacct tcctgatgat cttcctaagg ctcttacctt   153720
cttgtcatta gtcgtttctg tgaccatctt gcctatagga atgtgggcta ctgtgggcaa   153780
gtacaatgcc tggcatgcag caggcttTcc agaaatgctt gtttggcttc tagagttctc   153840
tttgctgtta ccacatccat ccctttatca tccttttttc cctagtcatc tttcctctgt   153900
acctttgccg ttggttcttt ctccatgaat caatataaat aatacaagct tgtgcatag   153960 cagaccttca ctcttgtctc atgatttcat ttctttcttc ggcatactga aaggcaagta   154020
cctttctctc tctgactctc aatttactca tctgtataat tttgatggtt ctttcaattg   154080
tctgctattg ctgatgatgg cacgaactca gatatgcaaa gtatcagact ttcactcttg   154140
tctcatgatt tcattgcttt cttctgcata cttaaaggcc attaccttcc tctctatgac   154200
tctcaagttc ctcatctgta taattttgat agttgtttct actgcctgcc attgctacga   154260
caatggcaca aactcagata tgcaaagtac ctctgggtta aatgtgaaca aaaccttcaa   154320
cctgctgcaa gataatctga cctctgcttg actgtctagc tctgttttcc tggcagttgg   154380
atgaagaaca tggcaacaat attcttggcc acattgctta caatacaaac gatcccctat   154440
ttgtaaatag catcatgacc aggagaaacc ataaagacct gaaagaacct agtggtaata   154500
ccaccccacc tcaggcttcc cggagggcaa gttttggagt cactttgcag ctgctctgtt   154560
cactctagga accatggaaa ctctgctcat ggagtattta cagggaatat tggctgctgt   154620
gaaggctggg acttcaatgc caaggaatac ccaattcccg tggatatgga ccttgtaggg   154680
atctttgcat ctcagctgtc ctttgtggag cagatggttc ccatatgcct gctgcagcct   154740
tcctgatgag ctgagcttct tgtctgtatt gttttgagtc ggttggcacc atggtaactt   154800
tgggggggtc ttgtgattct gcatgtttaa tggaacctga aagacccctt actgggcatt   154860
aaagaacaaa gacaaatgtc cctgtgacag aatactggct caacaattgg ttttctctct   154920
gatgcctctt ccctgcttgg aaagcccttt tcttttatcc ttcataatca cttcttacat   154980
ctggcacagc cttcagcttt gcattattcc ttcattatct tttctcatcc cacattaaaa   155040
aaaattcttt aaattgtggc caaatgaaca tgacataaaa tgtaccattt tcacatgtgc   155100
agttcaagag tattaagtac attcacattg ttgtgcaaac atgctttttt tcactctgtg   155160
ccctcatttt gctctttcct ggtttccaat gcagtatctt atatatgatc taataaatgt   155220
gtcctgggca tctcagtctt gtatattttg gtcctctgtt atatcaggta cacccttaagg   155280 atagacattg tgccctacta atcttcctcc ttcatcacat gaaatattgt gcttgcatag   155340
tacattttct tcactcccct ccctgttatt ttttatgtat atcatgacac ttatttgcca   155400
aggatggctt tggccctcta tgcaaaatgt caccaatggg aacaatgcta aagtctgcat   155460
aaatcttaag tttaattcta atttTaaata tttgaatata gtgctagtgt tgtcattcta   155520
taggattcat taattcatcc catcaacaaa cacttattga gttccaaatt tgttcaaaac   155580
atggccgtat gtgctgctgt agaaaaaatg taaaaagtca gtttctagtg taagggaaat   155640
```

```
aaaatatgga tatcattaag tcctggagaa ggcaggggt gactgatttc aggcttgtac    155700
catagggatt cccaggagga ataagtaggt tgcagcattt aagaagggat catgaaagac    155760
atgccacttt aactagttcc aaatggaatt ttggaagcag agccattgga tgttatagct    155820
gaagtaatat tttaagcaag gtgtcagaac aggattgagg cataatttca gaagaacatg    155880
aagtccttgt ttactaatgc agaatatgtt ttatgatagg ctggaaagtg aatctgtgac    155940
tagatttggg agtgattcag tgtacaatga atatggcagt aaagagcttg gacttaattc    156000
gggctgctgg tctggtcagc ccttgtgttt ggagagatga gtaacatttg caaggtgga    156060 gagaaggaat tggagattct agttaggtgc tttgggcata tgttcagtga gggatgaggc    156120
attaatgttc atcaaggcag cattcacaag ggctatggcg gcactgaatg ggagagcaga    156180
cagacacagg tgtcatccca gaggtggact ccgtatggca cagcggcaag ggagtgtgaa    156240
gggttatgac agatgctgag taggtgctag caacatattt tttaaaatag tggcaaaatg    156300
tatgtaagat ctataatttt tgcatgtaca gtttagggat attaacaata ttcacactgt    156360
tgtgcaaaca tgcttttttc actctgtcct cattttactc tttcctcatt tacagtgcag    156420
tatcttatat atgatctaat aactgtcccc taagcatctc agtcttgtat attttggccc    156480
actgttctat cacgtacact ttgagggggc attttcagat aattccaggt aaaacgtaaa    156540
cctcacgatg gcagctaaga aaacagggc gttctctgca ttggttagtt gcagggctat    156600
tagtcaaaat tccaaatctc atatgcagaa ggccaggatc tgcagtctta agtagttcag    156660
tttgtttcac ggaggtaaat aaaagaaaaa aggcatgctg aagatacata tccctggcct    156720
ctagataatc agacagtaag atctctccca cacaccagag aaatctattt ccagctttct    156780
gttgcagtcc atgaaaatga cagaaaatac atgccctgct tggaccacag cctagctcat    156840
gggaaaaaaa aggaaaataa aaaagaaccc gagcttgctg tggatggttc ctatggagtg    156900
tttttggcac tgtcagagtg cacactctga caggctgggc atggtggctg acacctgtag    156960
tcgtagcact ccatggcact gaatttacgg tggaaggatc acattggcaa gtcaaatcct    157020
tgggctacag gaaagactcc catgtgctgc tttttatgctc cccagcagcc aggctgtcgt    157080
tcacaaagca ctctccaagc atcttcattt aatgttgttg ggcacaaggc cctggtgacc    157140
ccgttaaaat ttaaatcttg ctcatacaaa gtgagggcag gttttcagtt gacatttgga    157200
ggtttctcca gccatgttag aaacaaaatg catttaagtg atgagccctt gatacataag    157260
aaggtgtaga gccagctgga tttctccggg accatgaggg gatccatctg attagggctt    157320
ctgaagccga aggaaactac agagagatgt aacttggctg actctcagtt cattatttc    157380 tcttggtaag agcacttctc atattggaca atctttctt cactgattta gatattattt    157440
tagatgcacc ttttctttt gttatggaag ctttattta aaataaagtt aacctaaaat    157500
gggcgtatta ctctccccc gcccaccgc taatgattta gaacatgaaa ataatccaca    157560
agaccatggg tgctgtcttc agctacaatt actactttct taattgtcat ggaaacatga    157620
tttattattg gatggttttt tactgtctta tgcaaagatt tcatatgagc cgcaatacac    157680 actgttcat atgggtaagt ctcaatatta tctgacaaag agagcttctc tgcccaagtt    157740
tatgaaaagt acatttttt ttaagtcact gtcttgccca ggctgcagtg cagtggtacc    157800
atcatagctc actgcagcct caacctcctg ggctcaagca gtccgctcac ctcagcttcc    157860
ttagtagcta ggtgttttgg tttggctttt tatccccact tgaatatcat cttgaattgt    157920
aatccccaga tgttgaggga ggaatctggc gggagatgat tggatcatgg gggtggtctc    157980
```

```
ccttattctg ttctaatgat agtgagtgag ttctcacgag atctgatggt tttaaaagtg 158040
tctggcaggt tcctccttcg cacattcttc tctctcttcc caccatgtga aaaaggtcct 158100
tgcttccatc ccgccacctt ctgccatgct tgtaagtttc ctgaggcccc ccatgccatg 158160
cggaggtcaa ttaaacctct ttccttctta aattacccag tctcgggtat ttatttatag 158220
aagtgtgaaa acaaactagg acactaggac tacaggcaca tgccatcacg gccagctagt 158280
ttatgtttat ttttttaattt ttgtagagat ggggtctcac tatgttgctc aggctagtct 158340
caaacttttg gccttgagca gtcttttccac ctagacctcc caaagtgttg ggattacagg 158400
catgatccac tgcacctggc tgaaaagttt ctattgaatg gaaagaacaa tgctgtgaaa 158460
atatatttta ttaatgttca ggaaattgtg gaacttgaaa aactctagct ttttagcagt 158520
tttaatggct actatgtgct tctaaaattt gtacctgctt ttttgaagtg ttatatgcat 158580
ttttgtttgt tgatggtggt gatgttttttg ccgttgatct cacctgctaa cgtggaaaca 158640
tttcaagaag tggaaaaatg tcttatttta gtacatacta tggtgtcagc tacattaaaa 158700
aaaaaagcct taagaatgt agcttgaatt gagggttgct atgactttttt gttgtagtag 158760 atttatgaat tgtgtatcat catttttcctt cagtggaaaa ttcagtaact agtatgttac 158820
tggttcctgg attccaaggg aggagaacat gaaacattgc aatggaatta aactccaatg 158880
agcttgaccc agctacgatg ttgaagtgag ggaatacata aagacttggg tgtatgtgtg 158940
tgatctgttg gtattaaagt gccaggatta caacattcta tgaaaatggc taatcatatt 159000
caatatttat ttgagacgct taagatgcat ggtttgggtg gaactagggt taggggctg 159060 ctgttttgaa cagccaaact agaattctgc tcaattatct cacacaggca cacttctgag 159120
gcatttttta catgatgcct caagaaagct ttgctccatt ttgtatttca gcatgaatac 159180 aaattttttga aatttccaca gtaaagtgtt tagacttacc aaaaggtagg ccttgttata 159240
ataacaccag taggaccgat gtagtcattt ctaaaatgat tcaagcactt tatgtttctg 159300
gatgagctat tagatcttac cttatgtgtc tggataagct attagatcat tacatatttt 159360
aaagtgaatt tttgaaattg ttggttcatt gtttaaatttt tcaatttttgt ttctgttgca 159420 ttaatctctg agatttgaaa atgagaaaag aaaaaagatg gatacacatt aatgctttta 159480
taccttcctt tgtaacagca attgattgtg cacttgcttt tggctgtagt tagtcctttt 159540
cttaaattag tttctggtat ggatgtctac tttatttaa tttttttttt tttttgagac 159600
ggagtcttgc tctgtcaccc tggctagagt gcagtggcgc gatctcggct cactgcaagc 159660
tccacccccg aggttcaagc aattctcctg cctcagccag ctgagtagct gggactacag 159720
gcacctgcca ccacgccagg ctaacttttg tattttагt aaagacgggg tttcactgtg 159780
ttagccagga tggtctcaat ctcctgacct cttgatccac ccgcctcagt ctcccaaagt 159840
gctgggatta caggcgtgag ccaccgtacc cggccccact tttatttaat ttttattcaa 159900
ttttacattt tatatgcctt gttacttcat ttcttagcac cagaactaca agtttaattc 159960
ttcagacatc ttctctagca cctcataagg tattctttgt tacttggtga tagagaacta 160020
tgtaatttga ttttcttctt ttgcaatgga gtgttcaaat acgtcgttgc ttttaggtga 160080
gggatgtgat taattagaaa aatgagtgga tcttagctca atgaaattta atcagcagaa 160140
tggaattttc cattcagagc aaatgagttc ctaggactgg acacacctag atctgctgac 160200
ccaaaaccct ttatagattt catttctgaa tgagctatta gatcattgta tattttcagg 160260
tgaattttta caattgttga ttcatcgttt aattttагt tttattttct gttgcattaa 160320
tctctgagat ttgacatata gaagaaactc tcatgccagc cccaaacgct ttccctatct 160380
```

```
cctcctccca tgccttcctg gagtggaggg aacgtcaggc ataagcagag cccaggagac   160440
actcatagac attctgagaa agcttttctc tgtagaaggg accaacacat cttgcaccct   160500
ctccctctct tgcccctgc ctgcatgtgg gtgcaggtgc ttttgtcagg accccactgc   160560
ttatctcagg tcaggagctg gcaaacctat gaacaagatg gaaacccaac tgctgaccag   160620
ggtggtgttc tgacaggaga gaagacttga gcccttatag acactgttga atcactaagc   160680
tgtaaacaat tttctttggt cttcttgtct ggtaaaatca attctctttc atcctttta    160740 aagacctcag tttgggcttt agaatccata ctggcaaatg cttcctcact aatattgtga   160800
gatttaatta gagatagcat tttatgtgct caccttaaaac tatacggtag acacaaagga  160860
gtctgggtct cagatcccaa cacgtggatt atagagaagg cagaatgcta taatgccttg   160920
agggtgagcc atccattatt tggggatttg aaaaaggaca atttctgttt tatgtttctg   160980
tcctcctaaa tggagttgag agacagcttc ttttctcctt agcatttggg caagaacaga   161040
atccagtaaa accactgagg aaggtcatca ttgcagcgtt tatttaacat gagtaattct   161100
agcatgagct ggcatgccat ttacatccat ctgttttaag tgtttgcaag cagaatggta   161160
ataagaaact ggggtaagtg ttaaaaataa ttatatggaa tatagattgc cccagatgca   161220
ctatctaatg ctgatgggaa aggagagagc aggggtacc tggaacctgg acttctcctt    161280
ggaaacatgc catgaccggg tatgttactg gattgcatag gtgcagaaca tggaacattg   161340
cagtggaatt gaactccaat gagctcagcc caactacgat attggagtga ggaatgcatg   161400
aagacaaaac ctttattata agtctgtgtg tgtgtgtgtg tgatctgttg ggattaaagt   161460
gccaggatta cagcattcta tgaaaatggt agtggagaaa aggaaggta gaggaaaaga   161520 gaaaaaccaa agcaagagga aaaccactgg aagaaaagaa gatgggaagg agaaagggca   161580
tctctgaaga atgtaaggag tacaagatcc cttacaggca gtgaacacat aagaaggcat   161640
cattcaccag aaagtcatac cagtttatgt attaaaactg ggaatggcaa tgataggcat   161700
tagttagaga ttatgcttta aattgtatgc atttgcatat ttttatatgt tttatttaat   161760
tttgttttgg gggggggact gtatctcact ctgttgccca ggctgatgtg cagtggtaca   161820
atcctagttt actgcaacct tgaactcctg gcttaagtg accctctcac ctcagcctcc    161880
caagtagctg ggactacagg catgtgctac tatgtccaac taattttgtt attttttgt    161940 agagacaggg tctcaatgta ttgcccaggc tggtctggaa ctcctgggct caagtgatcc   162000
tcctgccttg gcctcccaaa gtgctgggat tacaggcgtg agccactgtg accagccctt   162060
ttgcatattt attgttttg tttgtttgtt tgttttttga gacagagtct cactctgtca    162120
cccaggctgg agtgcaatga cgcgatcttg gctcactgca acctctgcct gctgcgttca   162180
cgcgattctc ctgcctcagc ctcccaagta gctgggatta caggtgccca ccaccaaacc   162240
cggctaattt tttgtatttt tagtagagac aggatttcac tatgttgggc agactggtct   162300
cgaactcctg acctcatgat ccgcctgcct catcctccca aagggctggg attacaggtg   162360
tgagccactg tgaccagccc atttgcacat ttagtgttta ttttcttaat cagtatcgaa   162420
actgtgaaag ggaatgttaa aacggtggag ccaggtgaaa aagaaaatcc aagagtcaga   162480
agagagcatc caaagaagaa ggcagaggca ataacaagta gactctgaga ctgaaattaa   162540
actgtatggc tagaagatgg gctagcatag gacaagatga ggtaacatgc taacatggaa   162600
gattgagaag aattgcaaat gagaaatcac ggataaaaca ctgaccgcct aataggataa   162660
aagcagagga tgttcataag cagctgtcat caccaaggaa gaggaaaaca tgggaaaggt   162720
```

```
tttgccctct gagcagaaca atcctgcatg tcaaggggga gcctcatata ccatgtaacc   162780
tcatgttaaa ccataaatac ttaccaatac ctcttacagt gtgacaggac acaaactatt   162840
aaacctgatg cagataatgc cttttaaaat gagtattata tttgattatt atttctaata   162900
atgttataac tatgtttaaa ccatccactt tattccctag atgaaatata attgaattaa   162960
atgttaaaca tatttgacat gcatttctcg gggcttttga tttaacattt taaaatatgc   163020
aatttagcta ttttaaaaaa cagtcttaaa aaataacata gtatatcaag ataggcagaa   163080
ggaaaattta ggcaccaaat aatagagtac atgtttccta ttatgtgttt tggttgggag   163140
atgatctttg gaaagtgctg attctgtttt tgtttccata aaacaaaatt tccagagatt   163200
atatattgga ttctgcttga aagagttcag tagacattgc acttctatca cactgatagc   163260
ccaggaggaa ttttaactat gtaattattt aaccgcaaaa ttttccacct tctccccttg   163320
aacatttggc ggataaatta tgataaaagc agtcatgata tgcagttcgg tttcatagtt   163380
tcctttctct tccttttttgc tatatttcct aaagttctat tatggagaga taccagtttt   163440
aaatgtcaag caatgttaac atctttgcat ctttatcttt tcctatccac tcttctctct   163500
tttcttttct tttttttttt aagggccaga gagtgacact tagccaatac ttaaccagta   163560
ctctctttct gtttgtttgt gggaatttta tatctatttt ttcttttttca attttttattt   163620 taggttcaga gggtacatgt gcaggtttgt tacatgggta aattgggtgt cgctgggggtt   163680 tggtgtacag atgattttgt cacgcaggta gtgagcatag tacctgatag gtagttttttt   163740 gaccctcagc cttttcccac ccaccacttt gaagtagacc cttgtgttta ttgttcccct   163800
ttttgggccc gtgcgtcctc aatgtttaga tcccacttgt aagtgagaat atgcagtact   163860
tgcttttctg tttctgcatt agttctctta agataatggc ctccagctgc actcttgttg   163920
cttcaaagaa catgattttg ttcttttttat ggctatatag tattccatga tgtatattac   163980
accacatttt ctttatccag ttcaccgttg atggccatct aggtggattc catgtctttg   164040
ctgttgtgaa tagtgctgtg ctgaacatgc aggtgcatgt gtctgtttgg tagaatgatt   164100
tatattcctt tggatagata tccagtaatg agaatgctgg gtcgaatggt agcgacttgt   164160
ctcttaatag ttttttacttt gcctcgatct cctgattctc tccctttttt tcctggccat   164220
tcccgctgca cttgcctcat ttgctattga tgacatgctt gtccctgct tccatagatg   164280 tgtccacaaa tgcatgtgca cacgtgcttc agctaaagat tcctcagcta aagattctcc   164340
ctctccatca gggtttctct ctttagctca cctgcccttc tctacatggt tttaaagtga   164400
gatgattgta aatgtgtttt tcacaatgga aattctccca gcgggcgggg aggaaaaaag   164460
acatcttgaa atattttctg agaactatga ggaccggcag agtttgacat gttttttgagg   164520 cgataaagtc atgtgtccat ctgtgaaaga caggcattgg cttttatccac atccacacag   164580 ccttcccgc tgtgtggctt cattattgat ttgctgtcat gtagagtcga taatgagaaa   164640
acctaggtag ccttgaaccc aacttttgcaa gaaccttta ggactctggg acttctaacc   164700
ctctaggaag gtggagttaa ggggatatag gcacagaatg gggcagaagg gaaagacatt   164760
aagagacagc ctttagcaga ccagagaata catgccgttt atcaaattgt tagatgtctg   164820
tgcaccagga atgttgattc aattatggta tctaaaaata ggacagaaat aaggaggaaa   164880
taaaaggaaa tgaaatagca gtttacctct ggcaaaaaca aagagcccaa tcagaaaaac   164940
tagacaaagc cacctgtagg actggaagaa accatgtgag ttaggtatca ctaaccttgg   165000
aaggacaagg acttcctagt attttgtat tttgtgaagc actttctctg catttcttaa   165060
atttgtcctt aagtgattat ctctcaacca accccaaaat ttgactcttc aaatcattta   165120
```

```
ttctctaaga ttttaagca ttcaactgta atggcttatg tatcagcata gtcttatata  165180
attctaaaac aacattcata gcatggtatc ttgtaatatt tgactttcac tattaattct  165240
ttcagttatt atttgagtgc ctgtcacatg ccaggtattg ttctaagctt cagggatgca  165300
tccatgtaca aaataaataa aatttcctcc cttgtgccac tgatattcta taggtggatg  165360
gaaaacaaac ttaagagtta ataaattag gttttattta aagacagggt cttgccctgt  165420
cattcaggct gggtgcagtg tttaatcata gctaccgta ctctccaact cccgggctca  165480
agcagtactc tcacatcagc ctcccaagta cctaggacta caggtgttgc caccatgccc  165540
agctatttat tttctgtatg ttttctttt tgtagagatt gggtcttgct atgttgccca  165600
agctggtctg aactcctag gttcaagcaa ccctccctcc ttggccccct aaattactag  165660
gatcacagac atgagccacc atacgtggcc aaagttttgt attattttat aaggtgatga  165720
gtgctgtgaa gaaaactaga agaggataag tggaattaga attgctaggg aagttgcagt  165780
attttaagta gggtggtcaa tgacaacctc aatgaaaagg ggatgtggga gtagagaatt  165840
gaaatagcta agggaaaaag ccatgatgat atatgagaag gatgttccag gcagagggaa  165900
cagccagtgc caaggctctg gggtaggaac atccctgttc tgtttagggc agagcagtgt  165960
attagtctgt tctcaagctg ccaataaaga tatgctcaag acttgggaat ttataaagga  166020
aagagtttta gtggactcac agttccacat ggttggggag gccttacaat catagcagag  166080
ggcaaggagg agcaaagtca tgtcttacat ggatggcagc aggcaagaga gagcgtgtgc  166140
agtccctta caaaaccatc aggttttgtg atacttactc actatcacca gaacagcatg  166200
ggaaagacac accccatga ttcagttacc tcccatcagg tccctcccac gattatgaga  166260
gctacaattt aagatgagat ttgggtgggg acacagccaa accatatcaa gcagtaagat  166320
ccacatttct agagtatcag agtatgccat cagaatggca ggtatcagag tagggtggtg  166380
ctatcgagaa ctttgtaatt ctgagaacca gggagaacaa atggaaggat ttcaacagat  166440
aattcatgtg tcaaggtgtg ttttaaagga gcactttgct tagctgaggc ttgtctgtag  166500
gggcaaaggt ggaatgtggg agaccagtta gaaggctgat gtaagagtca agataagaac  166560
ctacagctgg gaggtgagaa gtggttggag tttttatac atttgaagta agatttgcta  166620
gttatatgga tgtggagtgt gggagatcga aggaagtcca gagttttgg cctaaacact  166680
ggaaaaggta gaggtggtca caggtgacat tggaggatgg gctagtagag acattcttaa  166740
gttatcatca aagtttaaat gtttgagttt gaaatgtcta tgagacatca aacggaagat  166800
atcccataag gagatggatg tcagagtctg aagttcaagg cagaaatctg tgctgaagag  166860
aaaaaatgtc agcctagata gtgtcgatgg tatctaaagc tatgaggcgg aataaaatta  166920
tcaagagagt tctgtggaca gagaagagaa aggaccaagg ctggagcttg ccaacaattt  166980
gagattggta ataatacgag gaacctggaa aggaaatgaa cataattgtc cagggtgtaa  167040
aagaaagtct ggtaatgtgg aagtgaaggg gggaaaaagg catttcaatg acagagaggt  167100
agtcaactgg gtgtaattca aataggtcat aaaatgcaca tctgctgcta tggtttccac  167160
tacagatgca aggaaaaagt gtcctcgtcc ttttgtctgt ctgattgtgg cagttgagat  167220
tgaatagagg tagacagagg ggaaaaaaga atgaggaaaa ttgagaacat agcaatgcaa  167280
atgtcatttt tgacctttag tagaaaagta ataattttgg tggagtgttg ggggtaaaag  167340
ccccaattgg ggcaggtttc agagagaata agagcaataa aattggaatc aatatcaata  167400
aatattttca aggatatttt cagaaaagga acaatataga cacactttt tttttaagat  167460
```

```
gagaaaattg ttttattgct tttaagatgg aaaatctaac cacatttctg tgtgctgtag   167520
ggttgatcta gaggcgtggt gttatcaatc agtacagtgt atagtgtgct acattaacaa   167580
atatccctaa aatggcagcg acatccacag ccactaaagt tgatttctcg ctcatgttca   167640
aagttcgcta agggttgact gtggctgttt tctgtgtatt cttaattctg ggacccgggc   167700
tgatggagaa gactcattta ttcttattat tactaattat ttttgttatt ttagcaaagg   167760
gggaaaatgg gcagaaccac attatagctc ttaaggtttt cgcttggaag tagccccact   167820
aatttctgtt catgtttcat ctgccaaagc aagtcaatta gctataactg aagtcatgga   167880
agtgagtcag tgaaattctt tcgagttagg gacaggaaaa gtcttgcaag tgtgtatttg   167940
tccccttgag aggtgtggac agtttttttac acaataatac aacatacaag aggaagacaa   168000
ttctgaggat atagcaagag caaggtgttc tattgttggg ttgtcaagag ttgatggagt   168060
ttgatgggtg agagtcagcc ttatattggg ttcctatcat tattctctta tgaaaagagg   168120
aggcacaaaa gatggggcca ttattgtcac atgggtaaat gggttagtgg tggtttgtgc   168180
atgttttctt gagatagaat ttcttcagtg tagtaagaag ccaggtcata ttctaacagt   168240
gaagatggag cacgagggat tggggattag aagaggaaga agaaggtgct atttagcaga   168300
gcctttaagg gaattcatca gagaaattta gtatgatata caggcatctc gattaaccta   168360
ctggaggttt gtgttcatga atttaatgtg agataagtca gcatgattaa atatcttctt   168420
tcatctgtgc tgatcagtaa aggtgaggcg gatgcatgct gggtggggag gtggatttca   168480
ccagggttgg agttttgcca aggaagaatc aagaattaag gctggattag aattgagggt   168540
gtctaaagga tcgtggatct gctatgactc cacaactcta agaaaagaag attcggtacc   168600
accatcctca ttatggaaat aacaaacgaa tgaaacaaaa ccatttgtca ctttctacaa   168660
gattcagagg gcttgtatgt ctatgatctc aggcctcaaa aagagtaaat cagttacctt   168720
tttcccacat aactctgtgt gtgtgttagt acaatttgt atgtttgccc tagaatgtga    168780
accatgaatt tgtgaaatga aagcagtgaa taggaaaaaa ggtaaagata cagttttgta   168840
ttatctgtag caaaaatatt accacagcta tgtaatccac aaaaatggaa gaaatttatt   168900
aggtatttaa ttttttatcca agagtagtaa aatgaaggca gctatataat tatgtaggtg   168960
actgttaaaa tattagactt tttgttgaaa ttttttggct cagaaaacag gtttcatgcc   169020
atgctgaaaa attacttagt ttgatgaaaa agtaaacaag acatgacagt gaaatcatac   169080
agtgttgaaa caggaaatag ctaaaatgta ttttttctcag taaataagtg gctggcataa   169140
gttgtcctca ttttggggtc aagatcttat tttggtgtct cagctgaaga tgacctcttc   169200
acaatccatt aggtattgtg acactgatta attattatca agcagaaagt atttttttgga   169260 agtactttgc actaggcagg taaggcagtc gctaccacag gggcacaggt ttcgaagcag   169320
ttcaggagga gccaacgtct tgctgagaaa cccaaggcag acagcaatta gaggataaga   169380
taatgtataa ttaactgcca ccgtgtgtgg ggtagacaat tagagaacaa ggcaacacag   169440
atgttgtaag gtgctgatta tgggttttaa caataatgaa aaatgaaga caacatcatc    169500 agcgtgggct gacgctgtca ggggtggtgt gttttctcat gtgctgttac cctctaatca   169560
gtgttgagtt ggatagtatt cccaggaatg gctgtttggc ttcgcttctc ttaccagaga   169620
attgctctgc cttataaatg tagagactga catgtagaca cacttggatc atgaatttcc   169680
attctactct acaagaagta cagctgcaaa gaaaatcaaa tcatgttcag tacctttctg   169740
gaattttccc aagtactcag tagtcattct agctcacatc ttaactctgc tagggttcaa   169800
taagtatacc aaatgcatat ttttttttag ctaattccaa aatctaattc actttgatca   169860
```

```
atagtcatct cctatgaatt ccttgtgttt tcttcactat aaaatatttt tgtgattcat  169920
ctttcagtag acgaaaggtg aggtactttg agattatatt tctactaaat catgaatgat  169980
tcattatttt actgaaagta aacacatcca tcatattaaa tccatatcat gttctgttgt  170040
atattgtcac ttaagtgttt ttattatttt taaacaggtt gtataattgc atagagcttc  170100
aggctatcta catagacaaa atatctgaat aaaagtacaa cgatcatatt ttatcttgtc  170160
agtttaaatt atgtttaatg attttaattc cagggaaaac tctaatgtac caagttacca  170220
actgaaatgt gcccagtatc aatcctttat ttttaaatat aacattgtaa gttgttaagt  170280
aagttgttaa ctcttatccc taaaaagaca taatgttccc ttttcttatc atatgctaaa  170340
ataaaatttt ctaacaatga atgtgccatt tttataagcc agcaaactat gcaagtaagg  170400
atctcaatag aagatttaaa caaaataatt attttgctcc atattctgtt gcttttgttt  170460
tttgatgaga taattaattt tcatggaatt ttaaatgatc aatttgtagt aaattttggg  170520
aaatatgtcc attatttaat cacagattta gtatcttaaa cacattgaca acgtcaaact  170580
tgtctgcagc aaatggttac tgttaaaaat ttgccatagg ggtgagaact gcaatttata  170640
ctatttctaa gctatcaatg cttcaattat tacatgtgtt tatatatata tgtgtgtatg  170700
aacatgtgtg tgtgtgtgtg catgtataca caaattttaa agtaatggct tactgaaagg  170760 ccttttttc tcttcatatg actaagatat ctgaaattct gcccaaaatt gctaagatta  170820 tataccctc tgaaaaattg caatgtgttt atgacgtatt tttatgatat ttcagtaccg  170880
gatatgttca ttaccccatg tatgaagtct tatcttgtga tgatgagttg atcagaccta  170940
ttacattgag aatattttta ggtataaact ttatatagtc tctgatggtg agtgtgtagg  171000
taaattgctt tgggctcacc tgattgtatt ttcattgttg ttgactttca ttatttcact  171060
aatttgggag caagggcttc ttttttatgg tctatttcta gatcatcttc ccttagatta  171120
catcatgtaa tgaactggca gaagatatta agtagatctt attcaaacaa gaactttgaa  171180
cctaaatgga gatttatcaa gctaaattag cctaattgtc tgtaacaatg accacagcat  171240
attaataaaa cctgtgaccc ttacatatat acatgtgcat tttaatgttc ttccactatg  171300
aaaggcattt tgtgatttaa tctgcttgat gaacgattaa tatgatattc actaattttt  171360
actcatctta ttcttaattc atctaattta tctaattctt agtaatctaa atgattcaag  171420
cctcttacag atttttatct ctacccagtt tttcatccag ctgtccgtgt ggtcatctct  171480
gccttggtgt gcttgagaat tatttctgat tctatgacac caatgcactt tgcagtctt  171540 gaacttgaat tggcagaatc aagcttcctc tagacaaatc actgaatctc ttttctcacg  171600
ttaaggtttg taggaaccct attctcaaag ctgccaaaac actactgctt agtctatgca  171660
aatcaacaac tacaaatgca cgtcactcaa tcaacattat gaaactcctt tttggaatga  171720
ttgatgatca caaaatgtga tcttgtgaca atatgatata ttcatttaag ccacattgag  171780
gtttcaaatt ggcaccattg acaacgtacc tctttcatgc taagtgtaat aatttgttgc  171840
ctctcatttt cctatgctgc ttcacttcat taaatctgaa taattaaaaa ttttcgtagc  171900
atcgccaaag tcacttccca ggagctaggg aatgtgtcga tctgtacact gatccagttc  171960
ctgctgacgt ttgcttggat gcagaggcca tccatcgctt tccattgatt tttgtcaatt  172020
gatgcttttc ttccttcttt cctggtgact taggaaatgt tctgaaactg tgcattcaag  172080
tcaacacatg ttagattcat aactaggatt caccttcaca gtggactggt cccaatttgc  172140
tgtattttta ttcagcctgt caactcacac tatctgacta aagacgctaa atgcagtgtt  172200
```

```
ggccagtccc ctgtcatctc tttctaattg tttggtctca aagcaatggt gcatgttaca 172260
catatccatt taactgtcca attaacgcat gtttctagac aattctgata gaaagggtct 172320
cttttcttcc ttcagcccaa acaaagcaaa acaaaacaaa agggcactta cacgatgttg 172380
atctatgttt tatctttttt tttttttgag atggaatctc cctctatcac cctggctgga 172440
gtgcagtggc gcgatcccg ctccctacaa cctccgcctc ccaggttcaa acagttctcc 172500
tgcctcagcc ttccgagtag ctgggactac aggcatgcac caccacccc ggctaagttt 172560
tgtatttta atagagatgg ggttttgcca tgttggccag gctggtctca aactcctgac 172620
ctcaagtgat ccacacacct tggcctccca aaatgctggg attacaggtg tgagccacca 172680
cccctggcct gttttgttt tatcttaaat ctcttaggct gagactcata tggtcccact 172740
tacccatctt tttacagcat gaaattgtcc agttaaaatt acagctcttt attaatggcc 172800
ttaagactct tcattttgaa tggataaaat agtaataggc tgtgagcacc aacagtatta 172860
atgtatcatt catgcatgat atagtagtgt tgacatcttt cttttccttt tctgttttta 172920
aatgaagttc aggaaaccaa tatgaaaggt aagaaattgc caacatcttg gactatcaaa 172980
tcatggcaga caatgaatta aagaattcaa caaatctttg gcagcatcag tttcaaaggt 173040
atttagatac aaccaccgtg taattctaca caatttaatt aaatcattta tcaaatcctc 173100
tacaacttga ataatttaac tgatatcaga ataatccatt tttcagataa ttatttttat 173160
atttaatgtg ttaaatataa aaatatgaca cttctcttgc ataatttgca gaatgttatt 173220
tatttcatta ttttattatt attttaaaa tttcaacttt tatttgatac atgtacagat 173280
ttattaaatg gaaatattgc ctgatgctgg ggtttgcagg aaggatcctg tcacccaggt 173340
agtgagcata acatccaata ggtagttttg taagcccccc cacaaccagc accctatagt 173400
agttctcagt gtcttgctct tttgcccagg tgcaatcaaa gctcaccaca gcctccaact 173460
cctggactca agtgatcctc ctgcctcagc ttcctgagta aataggacta cagatgccac 173520
catgccaac taattttta attttactt tgtagagatg gagtattgct atgttgacta 173580
ggatgatcat ccactcctgg cctcaaatga tcctcccggc taggccttcc aatgtgccag 173640
gattagaagt gtgagccacc tcgcccagcc ccaatgcttg atctttaaga gcttcaggca 173700
gttgaagggt tttgtctgcc tgccacagcc ttccatcttt ttgagatgtg tttacctgag 173760
acagctaagt aggtgacaac ctgaactacg gttgctggca attggaaaac agaagattgc 173820
tctgttgatc cattgggaga agtacagtag tctgtagagg aacagaatcc cagggttttt 173880
ttctggcatg gaatcactct agagagccac attaaaaatt taattcctgc tgagcacagt 173940
ggcttacgcc tgtaatccca gcactttggg aggccgagga gggcggatca tgaggtcagg 174000
agttcgagac tagcctgacc aacatggtga acgctgtct ctactaaaaa tacaaaaatt 174060
agctgggtgt ggtggcgtgc acctgtaatc ccagctactc gggaggctga ggcaggagaa 174120
ttgcttgaac ccgggagatg gaggttgcag tgagccaagt ttacaccatt gcactccacc 174180
ttgggcaaaa caagcaaaaa actccatctc aaaaaaaaat taattcccct ttgactgttg 174240
attttattta tttattatta tttttttaga tacagggtct tgctctgtct ttcagattgg 174300
agtggtatga tcatagctca ctgcaacctt gaaatcctga ggtcaagtga tcctcccacc 174360
tcagcttccc aagtagcttg gttgacaggc atgcaccact acacctagct aattttttcta 174420
tttttatttt tgtagaaaca gggtctcgct ctgctgccca gtctggtctt gaactcctgg 174480
cctcatacga tcctcccacc tagttcttcc gaagtgctgg gtttataggt gtgatagtgc 174540
cgagccattt ggctgctgtt tttacattta taccattatc ttcatcctaa ataggaattc 174600
```

```
tgatagtatt gttggcagaa tagggtcaac tggaacacac attttttgttc tctaggtaaa    174660 gatgatgaaa cttaaaatgt agctaatgtt attcctgcaa tgaatatgtc aatttctaat    174720
ctggggacaa aaataaataa aaaaaaagtt gcacgtatta aacaccttct tgactaagtg    174780
gcagctgtaa tgatttcact tggggatagc cattgcttct taactcatgc taacagtgca    174840
ttaaagctat tgattttttag tggctgctgt gctttcgtga ttgtagatca tttctctctt    174900
tggaaactct atttgatgac aaagctggct ctgttgcaga gtaatgataa aagaaaggac    174960
ctaccagaat ttcaagtgaa atgtataaca tatgtgataa tgcatggtga ctgcaatgat    175020
tatttcccga tgttgctgtt taatagccat gaaagcatcc tactgaaata gagtatttct    175080
gctttgaatg gcttagttag ctcaaaaatt ttgaaagctt tctcagtaaa gcatggtgcc    175140
aggcactgaa agattccttt tggaggagcc agagtcaatt tggatgatgt ttataaaatg    175200
ctgctggaaa attgggtggt gttttctaaa tgatcttcct agtaatgatt tatgctgtaa    175260
atcagaaagg ttgccatctc tctggatgga aatgcatagt catatgcccg taaatgcagg    175320
gatttgacct cctataaaaa agctctctct tcccctcat ttatgtgatg attgtatacc    175380
atctgagcgc tgagaaaccc attggccatc ttccacttgt gtgtggctgg aggtgcttgc    175440
tgcagctctg tgatgccctg agccagcatg ctcgtggagt tccagtctgc tgcatgaaca    175500
agtggagaaa catgatcttc ctaaactgct cacaagctgc taaatgagtg atttgtgttc    175560
cctttgaatt catgctgtaa atggaaatgc ttgctccttc ccgggttatt actctgtgta    175620
cacgccattt gaggatgcag ataattgttg catcttcact gaagcatccc atcttagtcc    175680
agatttccgt tttcacagac caaaagggca aagtcagact tggcagacag cgcagcttca    175740
gtctcatggg gggatttctt tgtctcatca gcctcagtca tgggcttttcc agccattata    175800 atttcacatg taatatggtg ggtgtccatc tgagcaagtg tggtgcctca gtagggttgg    175860
aggaggcact tggagctgat gtagagaaag gagagtgaat taaagtggaa aggaggcaaa    175920
ttaaaagaag cgaggaaaca ttcttttttca caccagagaa acgttttcaa aacaccaggg    175980
aagcctcaga accaatccag gtactgcttt tatttctgaa ctctgttata atttgtgatg    176040
tcagaagctt ctatggaatc tactgatatg tgcagaaata atgtgctgct gtgcccattc    176100
tgtgttatac atttagaagc agttgcggta tcatgggata cataatattc tttaatccca    176160 atagggggctt caattctaaa tataacaaaa acagttggga aaggcacaca tacacaggtt    176220
ggcctgtaga gatggaggtg gccaatttgg tgtgttttga acagacgggg atgctctctg    176280
cgtactgccc ccacaccaca ggacagctga caggcagccc aaatgcccgt gcagactgct    176340
gaactccaga tggcttgctg gtgctggctg gcacgccttc aagtcctgcc tttcttgggt    176400
ccctaacaga attcacatta cctgaaattt cagggaattt gtggggctgg ctaaacagat    176460
tccttacata actggtgatg tgcggtcaga aagagaatag atgagtaaga ttgcattggc    176520
tgcctgtgtg tattagttttt cttttgctgc atattgaatt actgcaaact cagtggctta    176580
aaatcacaca catttattat gtcacaattt ctgtggtcag gcgtctgggc atgtctgagc    176640
tggatttcct cctcagtgcc acacagagat gctatcaagg tgtcggctgg gcagcatgac    176700
tctcgggagg ctcatggtcc ttttccaagg tcactcaggg attggcagaa tctggtttat    176760
tttggttgta ggattgaggt cccctctttc ttggtggatg tcagcagggg tcgatgtcag    176820
ctcctagagg tcccccaggc agcttcttgc catgaagcca tctcagggac tgtctcccaa    176880
tacggcgaca cgtatcttca agtccagcag gagaatctct tacttccagt cggctaataa    176940
```

```
aataatctta gataacataa cctaatcaag gcaatggcat cccatcctat ttcctaggta   177000
atgtaataca ctcaagggat gacttctatc aacctcatag gtccggctca aattcaactt   177060
cctgggatta cgggagggca tggcttatta ggtccttctg agtcataaat gctctaatgt   177120
ataaacttcc tagggtttct ataatatatt aacactgggt ggtaaatggt gtaaactggg   177180
tgacttacaa caacagaaat atattctctc ccggttctgg aggccagaag accaaaatca   177240
aggtgttggc atggttggtt tcttctggag cctccgaggg agaatttgtt ccttgtctct   177300
ctcctacttt ctgggggggct gccggttaac ttttggcttt tcttggaagc gtcacttcaa   177360
tgtctgtctt catctttaca aggccttctt ctctccatat gtttctggat cctctcctct   177420
tcttaaaagg atactagtca ttgggtctag ggaccactgc aaatctgtga tgattttatc   177480
tccaaagaaa ttacgtgatc acatctgcaa agaccctgca gtagtacctt tttatccatg   177540
gttttgcttt ccagggtttc agttccctgt gatcatttaa tctctaggct tagtcagtta   177600
actcttgaga tattaagagt taatctcttg ctgtgtataa tttataaatt aaactttatc   177660
atagacatta atacatagga gacaacatag tatctataca atttgatact agctgcagtt   177720
tcaggccttg aaacatatcc tcatagataa ggatgtgggg tgttatatat ttccacatag   177780
gaacacattc tgagattctg gtggatgtga attttttggga cattattcaa cacagtacac   177840
cccgtcaagc tttgcccatg acctgacact gcccaatcct ctggtctcat cttgtgggga   177900
ctctccttca ccttttctgg aatatttcct tacaacttcc tttctaactc cttaactcct   177960
aattcagatc atcttgggct aggagtaata ttcagtactc aatcattaga gaagatgggg   178020
tcaccaggag ataaataggt aagcagatag gtaggttgat agatatagat agttagatag   178080
atagatagat agatagatag atagatggac agacagacag acatgggtga atagatgatg   178140
gagatggata gatagaaagg tagatagatg atatatgtgt aagaatagat agataaatag   178200
atagatatga ataggtggat agatgataga tcgatggata gatacatgga tagagatgat   178260
agatataggt agatagagat ggatagataa atgatagaaa ggcagataga tacatagatg   178320
catagacaga tatggataca tggatagatg atagatagag atgggtagac aggtagatat   178380
atggtagata taaagatgtt agagatggat agatgataga gatggataga taggtaggta   178440
aataagtaga tataaatta gatagagatg aatagacagg tagataggta aatagacaga   178500
caggtaggta ggtagaggac agagatggat agatagacag gtagatgata gatggtagag   178560
atggatagat agacctctta atccctatgt atcaatccat ctctatagct atctgtaatc   178620
acacatgtat atgtctacat gctcattaat aacattttca cagcaggaat tcagtgattt   178680
agtgattatt gaattaattg ttgcataagg ctccctgagg gcaacactgg gtcttcttgt   178740
tcactatcct cagtgctatc attttacagt gggaggaagc ttaccttcct accaaaagca   178800
ttctgtggct ctgaagtggg agaaagatag attctctgcc acctttccca aaccagggat   178860
cctggttcca acatcaggat ttacctggcg ctgaaaggat tcattccatt gcattaattg   178920
tattcatgca catgagtatt ttctgagcat ctctgaggaa ggcaacagtt tctatggtga   178980
acggtgtgga gagcacagtc actcctcatt acagcactgg aagtaatcac aatgatgata   179040 acatacccctg cattctatcc agagccattt ttaagattta aaaaatttac ttggcattat   179100
tttcttcatt tgagtagctc tttaaggtat tttgtgaccg ccccccccc ccattttatt   179160 tttccttttg tagagaaggc ataatttac tttcaccctc ttaagagttt tttctgatgg   179220
tcctgagaat taaatggaca aaggacagat cagcaggaga aaaacataca aacccatgta   179280
atttaaggtt tctgtgacat gagaaaaccc tcagatggaa acgaagactc aaagaagtgg   179340
```

```
cgacacttca gtgcttttag agaaggttga acaaagacag acgatgatgg aaaagtagct  179400
aacctatgtg gaggctaaag aaatatgtgg tttattttaa catggtcttt tagtacacaa  179460
ttctcttatt tcagcctccc cttctcaatg acaagaatgc ttttccttc tggtataggg    179520 agggcacagt ccatacagga gtttcatctc ttgctttcag aaaggaaaac aggatcgag   179580 cagctttctt gtacctgctg tttttttcct cccctcccct cccctcccct cccctccct   179640 cccctccct cccctttcct ggcctggagc ttaaatgacc atacaccaac atagcatttc  179700
tggggtggca gattctgcca gccttcact ttacatcctc ctgttatcat ctgaatttt   179760 gaattatcac tcacaacttt tgtacatggt ttcttaatat tttacaaata tctatatgca   179820
aaaataatgt tcatttggca tacccttatt cttttttaaa attttatttt attttatttt   179880
attttaagtt ctgggatcca tgtgcaggac atgcaggtgt gttgcatagg taaacgtgtg   179940
ccatgggggt ttgctgcccc taccaatcca tcacctaggt attaagcccc gcatccatta   180000
gctatttatg ctaatgctct cccttccccc cgccctccct gacagaccct agtgtgtgtt  180060
gtttccctcc ctgtgtccat gtgttccaat tgttcagctc ccacttatac gtgagaacat   180120
gtggtgtttg gttctctgtt cctgcattag tttgctgagg ataatggctt ccacctccat    180180
ccatgtctct gcaaaggaca tgatcttgtt ctgttttatg gctgcatagt attccatggt   180240
gtatatgtac cacatttgct ttatccagtc aatcattgat gggcatttgg gttgattcca   180300 tgtcttttgcg attgtgaata cgctgcaat gaacatacac ttgcatgtcc acattgagaa   180360
accatctcac gcaagtcaga atggcgatta ttagaaaact catattcttt aataacatct   180420
ttgaaatgat gattcttcag tcttgaatca tcagtgcttc caggccatac cttccccatt   180480
cttaacttga atcctgactt cattcttgag cttgttggag ttgccctgag cttgattct   180540 tagagtgaat tatcctgtga ttttactct atgcctaagt tagatggact ttcttagcat    180600
gctaatctct aaaatacct tttcaaagga gagattggga aaggttttgt accaaaacat   180660
ggtagatctt gttccattat caactgcgtc tcgtgtcaga gagttctaag gtgagtgaaa   180720
ttgtgcgtgt ttgtagcgtg gtcataaaga catttcacag agtggatcgc aaacaaacca   180780
acagagcaca gagggcttga gagcaatggc agctggtgga agcacaggac agggcacagc   180840
gggaatttca tgggaccacg aaccaagaac agaacccatg accaggctgt ttttccttcc   180900
aggggcccag gctttctcag ctcagccttc acttgcatgc tgctttgagc atgtttggct  180960
tctttgagaa aatgagccac ccaagaggcc tacatccaag tcacctgcac tcagatccca  181020
gccaggagta tggagggccc atgtggggtg gagtggtgca cgtcctcacc accttagaca  181080
cagggaccac ctacctcatt ttagatggag tgggcagata atctgcacac atacctccaa   181140
aggtgtcctc tattgtagag acacctttg ttttctccc tcaatcctgg acattttgtt    181200
tgtttttctt tatttcacta atttacaat aaactgccag gatatgtctc catgtctagc    181260 tcttttgtg aattattctg gaaataacag cctctgcaag gctgctaaag tgacaaaggt    181320 attttcaat cgcgtctgat tcctttcaga tatttccatc ttcctactcc atcatccatc   181380 tcttttaaa aattttgttt tgttttgag acaaggcctt gctctgtcac ccagattgga    181440
gtgcagtagc atgatcgtag ctcgctgcag ccttggtccc gggcttaggt gatcctccca   181500
cctcagcgcc cccaagtagc tgggactgca ggtgcacacc ccacgaccag ctaattttg    181560 tgttgttagt agatactggg ttttaccatg ttgcccaggc tggtctcgaa ctccggggct   181620
caagtgatcc gcctgcctca gccttcatgt tttctttacc agttggttcc ctctcttcc    181680
```

-continued

```
cacacttgct aagaccacta ctggttcact gtcacgatgt cacttacttt tttgactacc   181740
ttcagtgatc tttcttttct gatttatgta tatatttcct gagtaatgtc attctttatt   181800
aaaaatgtat atgtatatat gtgtacacaa agtatacat  atatgtgtat atatcctaaa   181860
tgattctatt atttattgaa ataaataatg tatgtataat tatatattta tatataagt    181920 aagcattagt atataatgta tattatggat acattatata tacattttat acacaattag   181980
gttctgtgta tactatatat gtatgtatac agacatgtgt atatatatat gtgtttataa   182040
tatatacaaa tgattgtaac agtgtgtgta tatatgtgtt tatgtgtata tatagtatat   182100
atataacatt aatgtgataa aagtgtatgt gcatatatgt gtatttgtgt ttttgtacat   182160
actcatgacc acatttaaag aataccattg taaaagctga ccatataatc gtctatgcgc   182220
atatatatat gcagcaaaaa tgccatcatc ttcattaata aatgccttct ttattaataa   182280
atatacattg gttcacaata tcaacctcag cattatatac atttcaacaa acatgctcat   182340
tgttttaagc atacattatt aattcatatt tattttgttt taagttgaga ttgttataac   182400
tccctctttt ttcaaatttt tagctaatgg tacttttaa  aaagaatgac tttattgtat   182460
tcaaattatc actagtggga taaataatgt aatgatggga aaaagcttcc tttgttccag   182520
ctataattat ctgtagttgt ttatttgttt tattcaactt aacattcatg ttttattcaa   182580
atcatcaata tataatgatt ttgttctgtt accaaagatc ttattgggaa ttctaaagta   182640
ataaattatt ttgaagaggt atcgatacta ttacactctt gatttatacc tggatcaatg   182700
aatgttttta aatatgtaag cgttcttta  tgtttcttgt tattttatat atttatgta    182760 acatgtgctg tacacttctt agagttattg ctagaacatt tatcatgaat gtgcaaagaa   182820 tttttttcaaa tatatttatg tgcatatata tgacaaatca ttttgtgtta attttataca   182880
attctaaata ataagtgact cattctaaat tatttagctg attctctaga ttctcttttct  182940 cttgttggat agtcatatgc aggagtgact ttattttgtc tccttctttc tgatatttc    183000 agttctcaat acttttttaat aaaaacatat aggcttcgag tctgtagaag tatcttgaaa   183060
tatgatggtg atgatgaaca tcattgccct gtttatactt ttagtgaaaa ttcacttagt    183120 gcaacattttc ttttcctatt tgttgataag attaaaaagg atttcctgcc aaaataaata   183180
ttccatgtac tctactttt  aaattaaata cattaatagt accagatact atttgccatc   183240
tttcaaatag ctttttttctc ctttgatctt tccctcagct atcacctgac ttctttcctt   183300
caactgtgaa tgagacaaag caaaacaccc tacttcttcc cattgaacca tcttactgta   183360
tttgtagagt caacctaatt ccttattagg tcactgcata gtttttttt  aatttaatat   183420 tttacgctat ttattataat gatcattgga ggaataatca gaacgtgtta agattcttta   183480
caagtaactt ttcattttta gtgttcttgg cctttgaact gcgttttgga tgaagaactt   183540
ttaggatttt ctgtgcttgg gggtgctaaa ggtgtttaca cctgagtgaa tgcccagaat   183600
ttgatcatat agatttttct attgacagtc tcaccttctt atggttattc tcttgtaaat   183660
tatctttacc tcaagaccaa gatttgcaaa tatattgatt ttcagtagat gcagtgttca   183720
catagtatct cctgaaacaa tcactttttg cagtgtcttt tgtatatcac tggttgcgtc    183780
cctttactca gatctaaggt acatctgttt ctgtattttt ccttatgagt ggtctggatt   183840
ttaattcttt caatacactt tatattttat tggagtatgc tttgccaacg catccttttt   183900
atctcagact gttcttatgt ctctgtaata aagaaactgc atcttatttt actccatgaa   183960
aaatcacaaa tgattcccta agtgttcctt tagagtgttc ctgagaggac tgtggttgtc    184020
ttttattcta cattgtgtgt ctttttttaag actttattag cgcagtttta ggttcacaac   184080
```

```
aaaatagagg ggaacgtaca gagagttctc atatatcccc tgcccccata catggacggt    184140
cttccctatt ttccacatca cccaccagag gggtgtgttt gttacaatcc atgaacttac    184200
actgacatct tcatcaccca aagtccgtcc tttacagtag gctacagtct tggtggtggt    184260
gtacattctg tgggttcaga caaatccgta ataacataaa tccaccatta cagtatcaca    184320
cagtatagtt ctgcaaccct aaaaatcttc cataaaaaaa cctccacaat tttagcagtt    184380
tgtaacaaca aaggcttatt tccttttttct gaagttcatg tcggttgtgg gtggacttgc   184440
ttgttactta ggtagactga tattagaagg tgggaaaaga ataataccct tccaggaaag    184500
gataggaact attttgaacc aataatacag ctcactacac aaaatgagtg aacacagtca    184560
cactgaaaga gagatgagtg acatatgctt aagttatgct tatgttgaca aggtctcact    184620
cacctaaact ggagtgcagt gccacaatta tagctcactg cagcctgcaa tccctggact    184680
caagcagtcc tcccacctca gcctcctgag cagctgggac tacaggcaca cacctgtgtg    184740
attttgttat ttatttattt atttatttat ttattttttaa tagaaacagg ttctcattat    184800
gttcctagac tggtctcaaa cttcagcgtt caagcagtcc tcttgccttg gcctctcaga    184860
gtgctggaat tacaggcatg agccactgcg cccagcctcc tttagtgttt aactgaacag    184920
aataaagaac ctcttcatta tggtgaattg gctaagttca aaagagtagc aaaagccttc    184980
gtgggcagta ataattactc tatcttccaa atacttgagt gaccttatgc ttcttaaaat    185040
atatatttta gggctcttaa ttgaaatcaa ttgcctttat agcctctatt acagcatact    185100
cagaaattga gagcgggat gattttgtat aaatctagac taattttgtt tttctggaat    185160
gactagaacc atttaccatg tcaggtacac acacaagaaa cgctaagggc gagttgtgaa    185220
tgatttgact aggaacaata gttgggctgc ttttagatgt ctccttttgc tacatagaca    185280
gcaaaaggag aattccaccaa aggtgccagc ccttcagaat ccttgtccca caccaccaaa    185340
aagtcctgtg acagaaattc cacctattaa tcagctgctg tgtcctgact acggagaaaa    185400
gtatgatgca acagaacgca aacttttcca caatctcata acaaggaaaa aatatatgta    185460
tgtataatat gtgtacatat ataagaaaat gtatattaca tatatagtaa atacatacaa    185520
atacacgtat gtgtgtatgt atatatacac acatattttg ttttgttagg tatttttttat   185580 gactattttat ttaaaaaagt cacattgaaa ataaaattga cttttatttg ccctaagtta   185640
cctcttgaaa tattgtgtta aaacctaat aacttctgac aggtatatat ataccctag     185700 aggttaatat atatacgtgt gtttgtgtgt gtgtgtgtgt gtgtgtgtat gcgcgtgcat    185760
agaagttatt aggttttgtt tgtttgatgg tttttgttgtt gttttttgag atggaatctc    185820
actctgtcgt gcaggctaga gtgcagtggc gtgatcttgg ctcactgcag cctccgcctc    185880
ctggattcta gtgattcttg tgcctcagtc tcccaagtag ctgtgattac aggcatgtga    185940
caccatgtct ggctattttt tgtattttta gtaaagatgg gatttcacca tgttggccag    186000
acttgtcttg aactcctggc ctcaggtgat ctgcctgccc tggcctccca aagtgccagg    186060
attacaggcg tgagccactg cgccaggcat tattaggttt ctagtacaac atttcaagag    186120
ttatatgtat agatatgtgt acgtgtgtgt gtatatatat atatatatat atatatatat    186180
atatatatat atatataaaa cctctatggg tatgttaggt ttttaataca acatttcaac    186240
aagcatctta ggacaaatga aagtcaatta tgttctcaac atgacttttc ttaataaaca    186300
tacatttaaa aataccctagc aaaatacatt atttagtacc tatttttaaa cacactgtgg    186360
tttaatctca agctcataga ttcttcgaga taatattgtc tatcagctga aaattctaaa    186420
```

```
aaaaaaatgg gaaaggctca tgtaaatata ataggatttg tatttcattt ctgaggacag    186480
aaacatttca atagtaaaat ttgcaacaaa aagtgcttat ggaaagttag acaatgctct    186540
aggactctaa tagtaagcac aggaatatgt cagagaccca taaaatcttt agatttattt    186600
tgattcctac ctgtaaaagt gtgaaatcaa ttattgctaa atccagcaaa acagcaaagg    186660
aaaattacta ttcacctttt tctctcagtc tgtcttccaa agctactaag agaaaaacaa    186720
gaaaaataca gaaaatccta cttccattat acaatgaag cattttgag ctagtagaaa    186780 attagaatta gaccttgctt ttactggcat cacaaaagca tttcatcctg tttttgaaa    186840 tgacaaatgg cagaattctt atatacaata tgctaaccaa aatcatgtta ttgccacgtc    186900
atgaattata atttaatttc tactctcaaa gttaaataag aagatacaat attgcatttc    186960
cctgcttgaa gaggagaatt agttacactt gttacgtaaa ggctgtattc atcactggtt    187020
gtcatagctg ttatgactgt gactcttata atagaggtgg gcttgcagcc aaaaatatat    187080
gattcatcca aaagatattt accatgtaac ttatattata tgtgctgaat attttggtag    187140
tcattgcaaa ttaaggaata tggtgttgaa aaatcacagg taacaccttt ttcttgttgc    187200
taacaatcta acagggagac cttatttaac aagatatcat attacacatt acaattcatc    187260
ttgtgaagaa aaatgccaac tacagtgaat aattgaggaa cccaagttca tttacgaatg    187320
gaaggttggg atgaacaggg aatgcctttc tgaggaaatg gaatttaagc tgatcagtaa    187380
aaatgaatct tccaggagca tatgggcttt gcagatggga gaaacagcag agaatgccca    187440
aaagttctaa aggaaacctg atgatgaaat gagttaagcc atgttcctgg tagtgtatca    187500
gttagctttt gctacataag gaaccatctc aaagccgagc atctcaaacc acctttattt    187560
agctaagcat ctcaaacaac ctctatttag gttatgattc ttggctggac atctgggctg    187620
tgctcagctg ggaggctctt cagtctagag tcagcttcca ggtctgttgg gtgctcattg    187680
gccaagcact atcttaacag ggtgcttgac agtgctccat gtggaatatc atcctctaac    187740
aggctagtat agactcttca tggaagcttg tcagggttgc atgtaggtgt gttcaagtcc    187800
tcttataatg aaagctaaga ataaggacag tgtgtcaccc cccacatccg gaatgtccaa    187860
ataagcaaat ccagaaagac acagatgaat gggtagtttc caggggctga gagtgaccac    187920
taaatggtac catattttt tgggggggat catgaaaatg ttctgccatt agatattgtc    187980
aattattgca cagatccatg aatatattaa aaaccattgg attgcatact ttgacacggt    188040
gatgtgtatg gtatattaat tatatctcaa ttaagcaatt atatctgtct atcatttatc    188100
tgtaaaccag ataaaataag acaggctagg tatatagaaa aatagaacag aacaaggtag    188160
gcagaaacag aatctagcag atataaaact tggcatgtaa gtaaagagct gtaataccta    188220
tgtagctgaa aatggaactg ttctctaagg aaataattaa aataatctct atgctctagc    188280
atccagataa ataaattcca ggtgagttat gacccagatg tgaaataaaa ccttaaaact    188340
gttaggagaa tatgtaagca aataaaatgt ctttatgttt ctggattaag taatccttt    188400 tttttaaaaa aagcagaaat tatagagaaa atagtgataa attataatac ttatgcattt    188460
taaagcatta gtttagataa ttaaaaatca ataaaatggt taaagacaac agactagata    188520
tcaccaatgc tcaactgtgt aaacttgggc aaattattta atatctgtat acctaatttt    188580
cctcagctat aaaatgatat tagttacaca tctcataagg tatttatgaa gattgcatat    188640
tcggagctgg acacagtggc tcacacctgt aatacagcac tttgggaggc tgaggtggga    188700
gacttgcttt aggccaagag ttcaagacta gcctgcacaa catagtgaga ctttatctct    188760
acaagaaata gaacaaaatt aaccaggtgt ggtggtgcac acctgtagtc ccagctactc    188820
```

```
gggaggctga ggtcgaagaa tcactggagc ccttgagttg gaggctgcgg taagctacag   188880
ttgtgtgact gcactccagc ctgtgtgaca gagcaagact ttgtctctaa aaacaaaca   188940 aacaaaatgc atattcaaca tgcataaagc ccttagaacc atacgcagca ctgctatgca   189000
ctgttaaatg tttgctttta catgctcaaa agaggccag catccatgaa tataaagatt   189060
tcctacaaat caataacaga cattcagcca gtcaaaaatt ggattgctat tcaagatggg   189120
aatttagaat gggaatatag aaatgcatct gtactagttt taaggaacat gcaaattgaa   189180
atataaactg ttaatatttt atactcatca aagtggcaaa tgtattgtct gataatgtca   189240
agtgttggca acagggtaag ggccaggaaa ttttcttacc tgctagtggg tgtatagcat   189300
aatacaactt gtttggaaag aaatatgcca gtatctactg aagataaaat tagtattacc   189360
ctatgtatca gttagctact gctgcataac aaaggactct aaaagtcaat gccttaagac   189420
aataagcgcc tattactgct tatgagcctc tgcatcttgt tagctggaaa tttattttgg   189480
tcttggctgg gctcattcat gtgtatgcat tgttgatttg gagtgagttc tcttaggtaa   189540 ttggggggttg ctggaggtaa ttttgcctag gttagggcca atgggttctt ctctatgaga   189600
tcttttgttg tgcaacctgc tagtctgatt tttcacagga cagtggcaga atttcaagag   189660
agtaagaata ggtacagggg atttgagtcc cagtcttgga aacagcacat cattatattt   189720
tttcttttga aaaatgcaa tcttaaagcc actcaagatt caaggggtga agtacagac   189780 tctctatgta tgaggaatag taaattcatg gggaggattg tagaactggg aacctttgc   189840 ctgtcagtgg actacaccct gtaattcaac aattgtctat ctagtagtta tgtgccctgg   189900
aactggggtc ttcaaactgg cagatgtctt ttcaaaattt ttcaaagtat gactctgctg   189960 atgatttta agaaactaat tttcaggtac tcagccccca gatgttctcc tttctaagcc   190020
ttcctggtca ccaaaagctt cttcccacat cacaaaagga tgaccttcag taggcatgac   190080
actttgttac caacctttc tgccagggtt tataatacaa gaaatatctt tttgaatgct   190140
gctttctgga aagccccttt gctgaaggct ccataaaata agcctcctat cttatacata   190200
tttccattaa gagtgaagtt tggtcctgtt caggtgttct gatttcagaa aaagaaaaaa   190260
gaagccatag gtcagctatg gcagttcttt caaatgcaga aactgaactt ttctgttgct   190320
aaccaatttt tcaaggtgca tatacattgg gtgaagccca tcggtaaatg atccaatccg   190380
aaaatcatct gaaggtcatc tttcaaattc attgtggtag tgttattcaa gtggaggctc   190440
aaatatattt caagtgtatg catggaatat tttccccagc tagagtctgt tctccaggtg   190500
tatggaggaa agaggagttg tccaggttgt gtacctgttc ttctcatctt tctgggcta   190560 ttcatgtcct ttctgtgccc tcagcctcca acccatgctt ctgctcagag cagcctgttt   190620
tctttgctcc cataaatgta ttcctggccc cagatcttct gtgcatattt agaagcccta   190680
acccacttcc tcaccagcca cccctctatc cccagactct cctaccagga acagcagagg   190740
atcctaaatt catgcatgca tttttcctgcc ccgttggaat gatctgtgtg catgtctgtc   190800
tctgatgttc atctccttct tcagtgtggg tgtgtcatta cctcttttag ccaggactgc   190860
atggcattac ctgtcttagt cgggactgca tgttaaaagg gtcaacacat atttgtagaa   190920
ggaattggct tctgagtgaa tgaacccatg tgtcatgggc agtctgtgag gacataccag   190980
tcacttcctt gctgccgaga gctggggata ttgcattgga ttagaagatt aagcccatat   191040
tactctatgg ccaagtgaca aaataatcaa tcacatccac atctgtgata gccaggaaaa   191100
catttctttc cgtgcccctc ccccaccccc cgccgtatgc aactttccct gtgtggaaat   191160
```

```
aatgtactta gcttaaaaag tctctttctc tacttaacaa gactaagttg aaaattaacc   191220
ttgcccactt aaaagaaaac gaatatgcag taaactatga actactaata cagttcaata   191280
tgatatctca tgcagaacaa taatgctgaa ggttcttttt ggttctatta tttccttata   191340
ttcttgctta gataagatca catttgtatc tattgacttt ctatgatgat ttagatacat   191400
aagtggcaat aattaatata tattaaaaat acagatttaa attgtttttc tgacttgtaa   191460
tgttaacagc agtatatgtg actgtgaggt tttcctttga tgttaatttt cactttgaca   191520
atagtcttcg ttttccaatt ttttttaatt tttttatttt tatttttatt ttttttgtg    191580 ataaggtctg gctgtttcac ccaggctgga gtgcagcagg gcgatctcag ctcactgcaa   191640
cctccacctc ccaggctcaa gtgatcctgc cacctcagtc tcccgaatag ctgggactac   191700
aggcatgcac caccatgtct ggctaatttt ttgtaatttt catacagaag aggtttcacc   191760
atgttggtca gtctgttcca gaactcctga cctccgccca cctcgacgtc ccaaagtgtt   191820
gggattacag gcatgagcca ccgcgcccat atcattttcc aaattcttta caaagttttt   191880
ctcttacatt cataacataa agtgctattt taaatagact aacttttgaa ataacatag    191940 ataaagcact aaatggggac atcagaggaa caggctaaaa aaaagctgga atattcttca   192000
ggattaggga cattgagatt ttatttataa aatgatattt aaattttaat aatagaattg   192060
ttgtactttt gcttggagta tttaaatctt ctctttaata tttaaagcca gttctgcaca   192120
gaggttttac ggagatgcta attgttgtat gaaaaggaat attattctgg aattttgagg   192180
aagggtagac atagagaaga taaaggaaac tcacagccta cctaggtttt atttgggctg   192240
tgtgtgtgtg tgtgtgtgtg tgtgtgtgtg tgcgccagcc acaagctggg tttattcttg   192300
aataaactgt agacaaattg ttttcctga atcttctaaa acctgcattt acatagtcca    192360
tggttgtgtc taaactagat actcaagaga acttggtttg ttttaaaggc atttaattag   192420
ttatatttac atggacaaat agagcagcag tttattaaaa aagaatgaaa ggataaacaa   192480
attaaatata cgtagaacag gaaagacagc atctaattat gtttctgggt caggctctga   192540
tatacaagat taatttaaaa ttgggatttg gcaagtaatt tctatcgaaa tctcagcagg   192600 agttttatt gcaactaaca agctgatttg gaaagtttca tggaaaggca aaggatctag    192660
agcaatcaaa aagaccttgg aaaaggggaa gaaagttgga gggcttccat ttctctattt   192720
taaaaggtac tataaagata tagtaatcaa gatagcaggc aactcacatg ggtataaatt   192780
tagaccaatg aaatataatt aattacagtt ggcccttgaa caacgtgaag gttagaaccc   192840
ctgcacagtc gaaaattcac ttaaaacttt ttaccccccc aacacttaac aaccaatagt   192900
ctactgttga ctggaagcct taccaataac ataaacagct aattatcaca tcttttgtat   192960
gttatatata caatgcactg tattctcaca ataaactaag ttagagaaaa gaaaatacca   193020
ttaagaaaat cataaggaag agaacatata tttaccactc attaaataga agtggatctt   193080
cttaaagatc ttcatcctca tcttcaggtt gaataggctg aggaggacga gggagaggag   193140
aggttggtct tgcagtctca ggggtggcag aggcagaaga aaatccacat ataagtggat   193200
ctgcacagtt cagaactgtg ttgttcaagc gtcaattata agggtttaga aataaatcct   193260
tcaatttgta gtcaatagat ttttaacaat ggtgccaaaa caattaaagg aggcaaggat   193320
agtcttttca ataaatggtg ctgagacaat tggatattca tatgtaaaaa gatcaatttc   193380
aactcttacc tcttattgta cccaaaaatt aactcgaacg acaggtggca atataagaat   193440
taaagctctt aaacttttag gaaacttcag caacacagga gaaggtcttc agggccatgg   193500
attgggaaag atttcataaa tatgacctca aaagtacaat ccttaaaaga attgatcaag   193560
```

```
tgaaactcat caaaattaaa aacttttaca cttcaaaagg cactattgag aacataaagt   193620
gctatttgtt gagaaaacca aaagacaagc cataaactgg gagaggagat ttgccaacca   193680
tattcccaat aaaagacttt tatttagaaa atatgtaaac aaaccactta ctattcaata   193740
ataagaagga aagaaattat tttttaatgg gcaaaaataa attaatagac atttctgcaa   193800
agacagtgta catgagaaga tatttaatat cattagttac taaacattag ctaaatgcaa   193860
atgaaaacta caatgaggcc aggtgcagtg gctcatgctt gtaatcccag cactttagga   193920
ggccaagatg agtggatcgc ttgaggcagg agttcaagac caacctggcc aacagggcaa   193980
gacccatgtc tactaaaaat acaaaaatta acaggaata gtggtgcatg cctgtagtcc   194040
cagccacttg agaggctgag gcacgagaat tgcttaaacc caggaggtgg aggttgtcgt   194100
gagccgagat cgtaccactg cactctagcc tgggcaacag agcaagactt tgaaaaaaaa   194160
aaaaaaaaaa cctatgatga gacaccattt cacatccatt agtatggtta taacaaaaaa   194220
ggatattagc aagtgttggc taggtattag agaaatagag ccctttata ccaccgttgg    194280 tgagaatgcc aggtattgca gctgatttgg aaaatagtct gtcagtttat taaaacatta   194340
agcataaatt tgccttatga aacagcaatt tcacccctag gtatctatgc aatagagatg   194400
aaaacatata tccatgcaaa aaatagtaca caaatgttca tagcagcttt attaataata   194460
atcaacaagt agaaataaac caaatgtcac tcaacaaata aatggattta aaagatgtgg   194520
tatacccata caatggaaaa taatttagcc ataaaaagga atgaagtatt gatgcatgct   194580
acagtatgaa aggacattga aaacatatgc taagtaaaag aaaccagaca caaaataccg   194640
catattatat gagttcattt atatgaaatg cctagagaag gcaaatctta taaagacaga   194700
aagtggatca gcaaggctat cacacccacg caccacccag gtctggtttt aaaaggtatt   194760
aagcccccat gaaatggaca ttacttgact tttgtttgat atatgaaaac agcattatca   194820
agtcttggtt tcaaaatatg tttaagctct tctgagttat gtagaacaga ggagtgtttt   194880
ccattcacaa gtgttggaga tgacagtatt ttcccttttgc cttaatccgc ttatcctaga   194940
accctatagg aaggcaaaga ctgtcttgat tgattgacgc agttaaagtt attgatagtg   195000
ggatatgcac atatgggctg catctgtcta tgagaaggaa gcaatggagc caattaatta   195060
attcaagcaa aattaaatgt tcacaccttt taaatgtgga aactataaaa accaaaatgg   195120
tgctctgtgc actaagagca taagctagtt ttttgctatc cttaagggcc tcttcctgca   195180
ttttgcctat attaaaattc ctatgcagat cttattgagg tgatcaaggt agatgacttc   195240
gatttttatt ttcttcaaca aattcacgta ccaataactt tcaaatgata tttagtaact   195300
attttaaaca cagaggacat gatcttcaaa cgatatttaa tagctatttt acacacagag   195360
ggcataactt tcaaatgata tttaataact attttaaaca cataggacat ggtctataat   195420
gttttgtcct gacttaaata tttattgcat gtagtagatt ttaatagaag aaaacaagag   195480
tgaatagtgg gtagtgcttc tctaaacaca gagtagaggt aaatcttagt gatttaaatt   195540
agtcacaatt ctgactttt gagattgcat gtttataagt ttttaatgca tgaaattaat    195600
gtcaattata taatattttg aataaagtcc ttccatgttt actgtgtttt tgcttgcctt   195660
atgaaaattt ctaaccataa tgtgtcagta acatttcaaa aatttattta aattacaaca   195720
tgttaacatc agaggaccat tgaatacgcc ataagcattt cttaaagaa tgtgggaaat    195780 gtcttttcta ataattaat ttttctttt tttaaaacaa ctcacgttag catttttttt     195840
tttgcagtag catcatttta acccccaact gcatattcac aggatatcta atattttttg   195900
```

```
caagtaacat tttgaatttg ttcttcttga catctttatg tttatatgca ttttgcattt   195960
ccctatctca tttttttgaa atccaaatgt aacaaatttc aacttttgt gttacattct    196020
tttctttttt tctttttctg ggtagcatct ctctcttttc tgaattttt gaaaacctgt    196080
tgttttgaa ttctctttt tcccttatt ttccttctca atatgacccc aggagccaac     196140
acaaagaaaa acgcagatga tataacgagt aatgaccgtg gtgaagacga aggtattttt   196200
tgttttca aagctcaacc ccagtgcatg atttatatc tatctatct ctttttttt       196260
tttcatttca atctgttttt tctccccta tttaaaacta gtacactttg gtgtgcttcc    196320
ttaattattt tcttcttgta tagaaaccac tgtcatttt taatcccagt taccatgtac    196380
aggaaacaaa tcactgtgag aagtataaac attgttcta aacatgaaaa gagtaatgaa    196440
ctactgttta cagagaagcc cttttttttt tttttttggc ttggtcgcaa gaagagaaaa   196500
tggaatttta aaacatgcat gtatagtcta ttttctccct tccaaatgtt attttgtaag   196560
ttaatatact actttggagc tttggtcttc ttaattattt ttatgaacta caaaactgta   196620
cagcaccta gaagaattt ttttggggg ggggggctg aaatatcagt tttttttc         196680
ttcacaaaca tattgattcc aacatagatt tctgataatc tgctcacagt gaagtacacc   196740
aaaaagtgtt ttaatgagat gctgttgtta acgagccctg atgcattcag gactgccttt   196800
tacagcattt aaggggggt ggggaagata agagtatctc agaactgaaa aggacaaaa     196860
agctagctat gttcatcttt cttttcacac cacggctttt ttgaaaacgt ttttctcctt   196920
aaaatgtttt gttgctgtga agttcttct taaggctacc aaattgctca acacattgtc    196980
taccagaagt gaaaggattt ttttttaaaa gatggtaggt ctgaggtact catgcagaca   197040
actcgcatgc tgttttctg ccctttctgc acaagaaatg atttttttt tttttaaga     197100
ggagaagcaa caaaaaagt actcaagcaa gcccttcttc attggtaagg ctctatagga    197160
ttagctaaaa gcacattttt cccatctggg tagcaaaatg catggaactc cattaaggtc   197220
ctggctggac ctttgggtct ctgtctgaaa ggcaatttaa agcccaaaag tgagtcctga   197280
attatccttg ctggtcaagc ccaacgtcca tgacagggtc ttttgaccaa ttcttgtagt   197340
tgctccctc cttgcttatc ttcataaatc aactgttctc caagaaaaga atcttgcca    197400
acacccttgc tgtgcccagt cttcccttaa cattttgagt attgttactt ttactgagct   197460
catagagctg tcactgtctc aagtagctct ctgagagatc tccattctga tggccatagg   197520
agatcaaaat ctacacctgc ttcaggtagc cccttctttg ataagggctt ctgaatgcct   197580
gacatttat cagtattgag caaatacata aaaatgaaat aaacttttgt ctcatatctt   197640
atactgctct aatttgtatc ctgtttggcc ttctctttt aatacatttc ctctcgataa    197700
ttagaatctg ttttcacagt gttcccagtg aatctttatt accattaaaa tgccatctaa   197760
ttttcatttc atattgttaa gttatgattt tttgactttg cattaatata acagctggtt   197820
attacttcca caagttcaag agagtcttgt tctatatttt atgaaaggta agagatgtta   197880
atctcacata ttttccaagg gagcacttta aagcagccct tcaaaatctc tacttactct   197940
ttttccaca atttactagg caaccgctgg taatggtaaa agaaatgagg ccaaaaacag    198000
caaattagga accagaaaga agcagtggat catgagaaaa gccatttctt attcatatag   198060
cagaagacat ttcccgtagt gtatgatgaa taaatgatta atagaagatt tttacttcat   198120
atttgaattt tatatgagaa aacaaaagac acttttctgc cgtggattaa atatctgcaa   198180
ataaatactt gggtaacttg acactctttt gtgtgctttg ctgtgaccaa tgggtatgtc   198240
gtgtcttctg tatgcaccca gtaaaattgt gatcataatt cattcaaatt ggagccacca   198300
```

```
tccaaacgat ggtaattcat atcctcagaa ttcctttgtg gtatttcaaa agtgtccctg   198360
tggattatga ggaaaaaaaa actttattga tgaagaaatt gaaataaat atgcataaat    198420 acttgagttt tcttttagtt acaaagatat ttaaattgta cacacacaca cacacacaca   198480
cacacacata tctgtatcca gaatatttta tacgtgaggt cagtcttcca aagattaaat   198540
gcagccctaa tggctgatta atgttataaa acaggtcttt ttcacaaagc aggccctaca   198600
gatggtctcc aactttctat catcacagat cattgttttt acatcattgt taatttaaat   198660
aataaagtaa attaccaaga ggaatcattg gttgcaagtc acaatgggag tttatattcc   198720
ctgtgaaaat ataaagcatt taaatagttt ggattctttt gccatttttt attacatctc   198780 ttttatttt gtcacctaag tatgttagta tgttactgta atcactggaa caaagacatt    198840
tgcttggaca tcttttcttt tttttcccta tttctgttca gttaataatt tttaactgtt   198900
gattttgctt tcttgtcatt atctgtccct tattgatagt ttatagcttc actactactt   198960
ttatgttttt attgttaaat tgaagatgaa tctgtacact cacctgcgaa ttaagatgca   199020
actatattaa aattaattat aattttgaag ttgattttat acttaattag aagataaaat   199080
atatttcatc aagggtccca tgtgtttatt caatttaaat cacattttag ggtttgagca   199140
aaatttagga aatgtgtact ttacctaaaa ccatttcttt tagtgcttta gatatatata   199200
gaagcttaga tgagcagagt acgctaaatg tctgtatgct tcttaaaata ccatttccat   199260
aaatagaaaa cgtaatagca ttgatcattt tccttagaca ctcttatcaa gggtcatatc   199320
atccataaaa ataaatgtgc ttaattcaag tcaaaatagg gaaatcagtg aatctccttt   199380
tttcttaatt tagcattggt gagtcagtgt gattctttat tgtgtttcct tacttggctt   199440 tttttttccag atattcatga tcagaacagt aagaagcccg tcatggtcta tatccatggg  199500
ggatcttaca tggagggcac cggcaacatg attgacggca gcattttggc aagctacgga   199560
aacgtcatcg tgatcaccat taactaccgt ctgggaatac taggtaagtg atttcatcat   199620
gtgaatgact gagcaagagg aaacatgaaa agtccacttc tcgttttgac ggggctcgtg   199680
gatttgaatc ctgttattcc agttcctggt taattccact tcacggtatt tactttatgt   199740
gattggatat gttattcct tttactacct ttgtgcaaca tggtcatgaa tcccttctca    199800
aaccaatgca gacttaaga tcttaaagat gaaatgaaat tttatttata gcatgtttct    199860
cccttggagt tcaatgaatg tatgtttgtc tacatagacc tgtacaatga acacatattt   199920
ggtgatatta tagttgggaa tggccataga tcttagcttt cttttctgat tgtgtcattg   199980
tatgaatcag tatattgtgt ggaggaaaag attttatcca attctctaac tgattatgtt   200040
gagcctttgg aagatctgtt gttttggttc cattgcattt gcatgcaggg aaacttagct   200100
gttagttgac ttttgtccat tgatgatcta cgattaaagg ctaaatacat ggaaattcaa   200160
gtttagttcc tccttgtttt gatgtttcat ttcttttctt tctttctttt ttttttttt    200220 ctttgagatg gaatctcact ctgtcgccca ggctggagtg cagtggtgcg atcttggctc   200280
actacaacct ctgcctcccg ggttcaagtg attcttctgc ctcagcctcc caagtagctg   200340
ggactacagg cgcatgccac cacactcagc taattttgt gttttaata gagacagggt    200400 ttcaccatat tgaccaggct ggtctcgaac tcctgacctc gtgatccgcc tgcctcggcc   200460
ttccaaagtg ctgggattac aggtgtgagc cactacgccc ggccatcatt catcttcttc   200520
taattgtagg ttgaaaaatt atacatcttc agagtcagat ttcagtacct tctgagatgg   200580
cctttcctgg tgttggttag tttgtgaata atattcctaa gacctatgta aaaacatttg   200640
```

```
ttttccaggc aaaaatgcat taaaatggta tagaagataa agtttttaac aagttagcca 200700
tgagagagat gtgtatattg gttccagtgt gattatgata caatatgaaa tacaaaacaa 200760
aatgaaggcc aggtgtggtg gctctcgcct ataatcccag cactttggga ggcccaggca 200820
ggcagatcac ttgaggtcag gaattagaaa acagcctgac caaagtggtg aaaccctgtc 200880
tctactaaaa atacaaaaat taactgggcc tgatggcagg cgcctgtaat cccagctact 200940
caggaggctg aggcgggaga atctctggaa cccagtaggt cgaggttgca atgagcagag 201000
atagcgccat tgcactccag cctgggtgac cgagtgagac ttttctcaaa aaaaaaaaa 201060
taataataat actagtaata aattaattaa aataaaaagc aaaataagat ggactaaagg 201120
aggtctgtca aacaagaaat atgactgaaa atgttttctt caaatatggc caagaatatt 201180
ttcttttcaa tcagatgact tcatttcatt ttgagtgggt tttttttttt cctatgtgaa 201240
aacattaacc tgtaagaagc cctaaaaggt ggtgaattgc tgagaaaccc taagaggtgt 201300
tgtaagaaac cctaagagaa atgcatttct tactttgaaa tgcaaatcag tcacaggtgt 201360
tgctaaagtt gtatcttttg aaacattgat aaagaactca aaattccagg ttggtttctg 201420
cattaaagaa aataaacacc accaaaaaac cttttagtgt caaaaaactt attatgtcgt 201480
tggctttatt tcctatattt tttgtagttt tctgtgagcc acatcttggc ggaataatgt 201540
ctctgaactt ttgcatagca gtaattgcac gcttcactga atagttttca gaggcgctgg 201600
atagttgctt tggctactag tgttggaaac aggaaattgt gcttcttgat gttttacaaa 201660
aggttcattc tgacaaagag gtggaaggag gaaagtatgt gtgagggcat gcacaggcc 201720
ctcttcaaag ggagcagtgt gtgcactgcc tgtagcacgg ccacacgaaa gaaagcttgg 201780
gcatgctttt ctgagggaag cagtgggcat caagaaaatt cttgctttgc tggaaccaca 201840
caatattctg ttgcatgcgt gatgaattga tgtgtctgat aagatagagt ttcaaaataa 201900
attgatctcc ttttccccct aaagctcagt tgtatcaagc aactctacac tatgattttt 201960
tttttatcag ttttgtccct tcgtgaatca attgcacatc ttgcaaatta gcctggaaag 202020
tatacacact ttttttagag gaaaaaaaaa ctaattgaaa aattgttaag tctactttt 202080
gttatggaga gttttttaaaa gtcataagat aacagagagc tgtaaaattg gtggggaaga 202140
aataaaagaa gcgatttagc atctctatgc cggtctattt acattcctcc aatgagctag 202200
tgtggaacag ccaagcacac tacagacccc ctttcatttg atggaatgaa atgtgccaag 202260
tttgccgatt ttacaggacg atagagactt taaaatgtga ctgcgttggt ttttatcatg 202320
gatcttgcat ttactattgt cctcttgaaa acagctaggc ggcatttact ttttgcttgc 202380
aggaaactcc tattatcggt cttgaaaaaa tgttttaaaa cctttggcat ccagatattt 202440
aaaaagatga tcaaataaaa tacacagcag gcactgcaat gatcatttca gtgagtgcat 202500
ttcatacaag tagatacaat tttaggcaaa aagttgaaat attctttgag ttcttttct 202560
tccagtaaaa gtcataaatg cataaatgtt atcttcctac ctgaggaatg gaaaatatt 202620
gttttaagat tttttttttt taatggagta acaaatgcta ttctctgtta cccaaaagag 202680
aggattaaaa agatgaaaca tgcccataat ggaagcggaa tgctggcatt ggaaagaatg 202740
tagatcgcag ccagagacag acaggagcta acaactttcc tctacctctg ccttgagaaa 202800
gtcagctagc gtttcctcag actctttcct tagatgtaga aggcagtggt ctctcccttg 202860
caaggttgtt gtacagtata aaagttccat ggttcaaaat accacacttt acctcattaa 202920
tatataatct gcttgtcaat aaaaaaataa ctttttctt ttcttttttt ttttttga 202980
gatggagtct cgcttttatt gcccaggctg gagggcagtg gcatgatctc ggctcactgc 203040
```

```
aacctctgcc tcccgggtcc aagcgcttct cctgcctcag cctccgcagt agctgggatt 203100
acaggcgcct gccaccacgc cccgctaatt tttgtatttt tagtagagac ggggttttgc 203160
cattttggcc aggctggtct caaactcctg acctcaggag atccacctgc cttggcctcc 203220
caaagtgctg ggattatcag catgagctac tgtgcctggc caaaaaataa ccttttaaaa 203280
aagatttaat ggactcatgt agatgaagtt tcataggctc tcagcagcaa ccattatacc 203340
cagtcacact acaatttcta gtgttattaa taccattatg cattgtatta atactactgt 203400
ttatccacag taagaattgt agctgaccca acctgtaatg ctaactaat atctatcaaa 203460 tattggcatc cagactgaac catgttaatt taaaataaca ttacaagaca cttgtagaca 203520
ttaaataaat cagaagatca tcatgtttgc tattttttaa aaaataatca gaactgtgct 203580
acacaatctt gctagccatt ggccatataa tttatgatcc aatccaggac atgtttgaga 203640
gttgctcatg tgctatgaat aaactgggat tgtcccaggc aaattgagat gtatcattat 203700
agctataaag taattattta tatctacatg aagtgtcttc tgattgaatt ggtgttcagt 203760
ttgtttttaa agaagctgca cttctataaa cagatttcct atgtgttctg ctatacaccc 203820
ttgtcactag gaaggtgtat atgttaccag aaagggatcc taatccagac cctaagagag 203880
ggttcttgat tctcgtgcaa gaaggaattg gaggcaaatc cgtaaagtga agtaagttt 203940 attaggaaag taaggaata aagaatgact gctccataag cagagcagcc cgagggctgc 204000
tagttggcta tttttatgat tatttcttga ttatatgcta agcaagggt tggttattca 204060 tgagatttcc gggaagggg tggcaattat tggaactaag ggttcctccc cttttagac 204120 catatagggt aacttcctga cattgtcatg gcatttgtaa gctgtcatgg tgcttgtgga 204180
agggtctttt agcatgctaa tgcattgtaa ttagtgtata attagcgtat aatgagtagt 204240
gaggatgacc agacatcact ctagttgcca tcttggtttt ggtgggtttc ggctgttttt 204300
ttttactgca tcctttatc agcaaggtct ttgtggcctg tatcttgtgc tgacctcctg 204360
tctcatcctg tggctaagaa tgcctaactt cttgggaatg cagcccagta ggtcccagcc 204420
ttacgttacc cagcccttat tcaagatgga ggtgctctgg ttcaaacgtc tctgacatat 204480
atattcaaga atttggaaaa cctcaagttc accaatgcct ctcagattag tcattgccag 204540
ggtgtgtggt gttcctatct gctcagaagc cagaagccag caaaatcctt gctgagctgt 204600
acgtgccagg gcatttgcct ggtctcacct acccacttga gtacctatgc cctatcaccc 204660
attcacctca caacatccat acgtatcatt taccctaag aagattagac attaatccag 204720
gtaataaact ttcagaacaa tcacctccag acagaaactg cagaggataa tctgataat 204780 ctgaatccct gtaaggccat tactgaatca ataaatactc ttttctccat cttagttcct 204840
tactttagta taacttgagt tctccccaat ctgttttttt tttgttgttg ttgttcatga 204900
tagtccaaag accttcgatg taaaagagaa tgcatcttgc tcatgctttt tgatggaaat 204960
acctggaact tatttattcc ttccccttc cagttgtctc caagtgcaag tctgtctgta 205020
cctgcagtgg atttcatcta cctccattta aatatgtatt tccgtttagc tcacatggta 205080
ctatcacctt tttggtgatc ctatgacttc atgcttcatg tatgctgaaa ttaattgttg 205140
cttcaaaaga gtcccaacta tgtaacatca actcattgtg tgcctctatg tggctggcag 205200
atattacttc atttaatctt cgtaaactcc cttggaagag ttaaccttat gtcctaccta 205260
tgaggagatg aatgctttga ggtaatggga tttactcatg gcatcacacc ttctagcagt 205320
cagagcaggg actgaaaccc gggtgtaact gaagccagag ctctgactta ccactcagaa 205380
```

```
ctcatccaca gccttcttaa ttaatgtcaa gtatgaatta gtaaaccatg gaatgagtga    205440
agaaattgag tatcacttta gcatcagatg tagctttat cattatgcaa aaagttctt     205500 actgctgatc aagatacaca attgtgataa gatgcttaca gtgtattttt aagttcctca    205560
aagtgggtcc ttgaaggctg attcatttcc attcaatcga tactggtttg ctttggttca    205620
cggtgatggt ggcattaacc acaacaatgg catttgtcac atcaaagctc ttcggtgcag    205680
tagaactagt gttcatcag gaaatttggt gtcctacccc cagttcccat gtcattgctg     205740
gcttgctgtg tcgtgtgcat aaattgagtc aaatgatcat ttcggtgcat ttcttacaat    205800
ctttcacata ttatagctat cctgaaaatt ttcatctgag ggtagattgc gtcatggtct    205860
tctgaagttg tctttctctt taagaccatt cattgaataa acctattaga cgctttggag    205920
tcataattga atataagaca gaaatggttt gatataaaag caaccaacat gcatagcaga    205980
aacagcattt gtagtcataa tttgggtgac ttaacccata tgcacgtgct cagcctaata    206040
atgtggtcac tttccctgtt ctggtgtccc ttgtagggtt ttcctctgaa attgagggag    206100
ggtgggctga gctctgaagc attcttgcaa catcggccag agtggtctca cctttatgct    206160
tttgtgatat gtgtgagcca tgtaatattc cactcaacaa agaagcctg gaaatcatta     206220 gaagagagga ccaatacgtt cttcccaaga gttacagcct caattccatg ggtgtgcatt    206280
tatgtgacat gcatctgaca ttagtgggag ttcaatgggt cactataatt cctgaagc     206340 acacctgctg aaaaatgtca agctatctta taaatgacct gtatgttctt ctcccctttg    206400
gaagttagag gagttgctct attttggta catttgctat tttatttctt ttttctaac     206460 aatatttctt ttcttaatg ctttatgaag gattttattt gaaatgataa atggaacaca     206520
tcttatgtat caagtcaaaa gttcataagc gtatatatta aaaagaaag catcatttcc     206580 ttttcgaga atcaacacac cttgatgcca gtctcctggt ttcattagaa tccctctctt    206640
ctcttcctct aaccaaaatg tctcagattc ccccgatttg atttctgtaa atggcctact    206700
ttgactggaa gaattgcctc tctctgtcta aaacaggacc caggcgttac taaaacaaaa   206760
cactgcaaaa agttaaatga ggagaaagga aagttaagca ttgtacttag tgagaaatac    206820
ataaacaaaa gtagagacgt aaaagaagca tgagagaagg gtgagaaagt gaaatcctga    206880
gacaagatga atggtgtgtg agcactcaaa cccaggaagt agcaaaaggt ggaaggaaga    206940
atgggagcct ttagaataag attctttgtg ggctgggtgg cagatgttat cggtaaagcc    207000
agcctgggga gttggcaggg gtccatgcag tagataacac agcaatagag tgaacacatt    207060
gcagaagata gggcaacctc taatccagaa attatcagat aaagaaaaac caagacactt    207120
tgcaaaacaa aaaaaaaaac aaacaaaaaa acacaacaca atgtcttgtt tttcatcatc    207180
atcttcttta taatgaggtt tccatgcatt gaatacacac ttggaaacac tgtaatccca    207240
tggttgttgt ggctgcagat tgataggtgt ggacaggtct ttggtggggc aaacaaaacc    207300
aggatcatgt ttttgctct cagaatgatc gtttgcttgg acttttcctct tctgcctcct    207360 agtggctcaa aatgcccact gcattcattg gatttattca ggatgtgaag aaggtcaggg    207420
gaaattaagg atgagtgctt tgtcattagg acctgagagg caaatggagc agagatgggg    207480
acgactgcag tgggataagg actctctcac caggaaggtg ccattgatgt aatagttgat    207540
gggaacagca gagcaaagag gctccctcgt cctcagctga ctcaacaaca agcgagacat    207600
cagatggaac ggtatttatt gggcaaggaa aatcagggga aggctaggtg cagtggctct    207660
cacctgtaat cccagcactg tgggaggcca aggtgggagg attccttgag gccaggagtt    207720
ccagatcagc ctggacaacc tagtgagacc ctgtctcaga aagaaagaaa gaaagagaga    207780
```

```
gggagagggg gagagagaga gagagggagg gagggaggga gggagggagg gagggagaga 207840
gagagagaga gagagagaga gagagagaga gagagagaga aaagaaggaa ggaaaaagaa 207900
aaaattagcc agatgtggtg atgtatgcct ggtgtctcag ctacttgaaa agctgaggca 207960
ggaggattgc ttgagcctag gagttcgagg ctgcagtgtg ctgtgattgc actccagtct 208020
cagcaacaga gtgaaatcct gtctcaaatt tttaaaaaag actcaaaaga aaatcaaggg 208080
agggagtgga gacaaggtag aaaagaattt tttttatttt gtgcttttt ccctaatgta 208140 ttcatttaat catcaaataa aaattgaata tattgatcat gtacaaagtg atgttttgaa 208200
atatgtatcc attgagaaat ggctaaatcg agctaattca caagtgcatt acttcaaatg 208260 cttattttc tggtgcaaac acttaaaatc tactttctta gagatgttca atattcaat 208320 tccttgtgat tcaactttgt ttgccatatt gaacagatct tttgaacttt ttcctgccaa 208380
ctgaaacttt gtaacctttg gccaacatct cccgtttcct ctccacctcc agcttcaagt 208440
tctgtaagag aacattctac tctctgcttc tgtaagcttg actttttttt agattccaca 208500
tataagtaag aacatgtgat atttgtcttt ctgtgtctgg cttgtatcac ttaacataat 208560
gtcctctggt tcatccatgt agtcccaaat gacacaactt cttccttttt ttttgaggta 208620
gaataatagt cccttgtgtg tataaacccc attttcttta ttcattcatc taatgatgga 208680
cattcaggtt gattccatat ttcagctgtt gtgattagtg ctgcaatgaa catgggagtg 208740
cagatttctc ttcaaagact tctttttcc aatcccaaat acacaaaatt atcatctggc 208800
atctgtcatg ctatggagac tctccttgat ctatttataa acgattcagg atttctttaa 208860
agaagctgaa atttttatttt tacatgcata accatattta gaaatcaaaa tattcaaaca 208920
gaaatcacag aagaatctat tccatcaata tataattccc agttaattga ttatataatg 208980
tcatttaagc atgagttagt agtcacagag aatatgcctt aaaaatgttc tgtctttgaa 209040
agttttacat tcaaaacagt ctcttaagat tattaattct aaaagacacc atcccttct 209100 ctcttcagcc tgttttcttc attttgcttc tcatccagta tgtgaaaggt tgatgatttt 209160
tagttgatga ggttgacgtg ccctctttct ccttggggac agaaggacat aagttgtgct 209220
ttaaatgaaa ataagagtat gatgagtatc ccaagggatg atggaaagtt ccagggagaa 209280
gcattgaaat tgagagccaa attcaagtac attggaatta gggttctggt gataattctg 209340
tcagtatcta catatattca aggaaattag tcctttcgag taggataatg gaaaaatctc 209400
taaaaggcaa tctgagcggg atgtttaaag actacgtgat tattatgcag tgcatgcctg 209460
taccaaaaca tctcaagtac cccacaaatg tatacactta ctatgtaccc ataaagttta 209520
aaaaaatgta agactactac acatattctg gcctgcagct ttttttcccc tgacatttgc 209580
ctacccgcct gtaatagcac aggcaattct acaagaagca tgaatatgca catatgtaca 209640
tgcatgacag cagtgataca aagacagatg tgttgtgttc tagtataatt gtcttatttt 209700
tgtccattcc aacgttaata agtcattagc tttatggaaa tgaaccctag gggatgaaac 209760
atacaggtgc aaagtaaatt tcctagggac taaattataa ccaaattatg gcaggtacac 209820
cctgcattta gcgatataaa tatatgtttc aaataaaatt gtaacatatt gattggcacg 209880
tccagccata ttcttaagat actttatcct tggactaaaa ataataataa tcgctttttt 209940
gaatgaagtg tttaattttc agtgtaaaaa gtcaggaata ttttagaatg ctcaacgcaa 210000
cattgcttca atgagctagg gccttttatga agataagtca ctagaaagtc tgtgttgatt 210060
cggttaatta tttgagattg tatgcactga ttttcactgt gttaagtata gtggcattta 210120
```

```
ttagaggctc agatgttata gagagaaggc tgtgtccagt tatagggctg tagtcataaa  210180
cagatgggta aaatcaacac atcattgtaa atcataaaca ggcaggtatg ataaacacat  210240
aatgataagc atttcagcac tgggtgcagt gttgcatgcc tgtagtctca gctactcgcg  210300
aggctgacga tctttggagc ttaggagttc aagagcagcc tgggcaacat agtgagaacc  210360
catctttaaa cattaaaaag aacaacaaaa aaacatcatt tcagtgtaga caggcataac  210420
atgatctcac agagaaacac tacgatttgt acacaagaaa actaagcttt gcactggtgt  210480
tgggagaaca ttttggaatg ataaactatt tcctgtttgt tttaagaaat atttggtaag  210540
gtttaaagta gtgtctgcct ctttactaaa atattccagt atctgtttag atgtcccagt  210600
tggtcttaga tacttggtgg taaacatata tatacacata tatagcgcat atatgtgtat  210660
atatgtgggt gtgggtgcat atgggtgtgt ataatctatg tgtgtataca tacatatatg  210720
tgtacataca tacatatgtg tgtatacata tacatgtatc agttgtttgc ccttgtgatg  210780
cacacacaga tctatatgtg tgtatatata tgtgtctata tatgtataca tgctaatgtg  210840
tatgtataca tatataaaat atgttccttg attcacagtg ggattatatc ccaataaacc  210900
cgttgtaaat gtaagatgtc attagttgaa aatgcatcaa tacatctaac ctaccaaaca  210960
tcatagctta gcttggctga cattgaacat acttataaca cttacattag cctacagttg  211020
ggtgacatca tctaacacaa atcctatttt ataaataaag tgttgaatgt ttcatgtaca  211080
ctgcagagta gcagttgttt gcccttgtga ttgtgtggct gactgggagc tacagaccgc  211140
tgcctggcat ccaaagagac tatggtactg catattgcta gcttgggaat atatcaaaat  211200
tcaaaatatg atttctactg actgaatatc atttttgtat catcttaaga tcaaaaatca  211260
taaatcaaac cattgtaagt ccgggaatgt ctgtgtaata atttggctat agtcttaaac  211320
aggtgggtag aataaacaca ttattataaa tccatcctgt gcttttgaac acatggaggc  211380
taccccacca aaatgcctgt gttcaatata ttgcgaacct ctaggtatct ttttccttca  211440
ttgctgttta atttttcctt ctaagcatga acttacaaga ttacttagga atagcattca  211500
tccttcttca ttcctctttg tttaaaacat gcttagcatt tctcatcttg aaagaaatga  211560
gtagcttttct tcttttcaat catatttcat cagaactatt ctcttgaggg ccacagaaat  211620
gtcataagca ttttctctgg cacttctgat acttttaatg gcttttgata catcttcatg  211680
tttcttaatc ttccttgtgat ccttaccatg taagtgaccc gttgagctta tctccaactc  211740
ctatttttca ttgtctcctt cctttatttg aaacaactta catccagcgt gcacgtttga  211800
agtgtgcaat tcaatggcct ttagtatatg cacaacattg tgacaccagc aacaccatct  211860
aatttttgaa cattgacgtc attccaaaga gaaatcccat acctcttctc tcccaggtcc  211920
ccaggagata ggcttccact aactatctac ctgtctatat agatttgcct tttgggggca  211980
tttcatgtaa attaaatcat ataatacatg ctttttttgtg tgtctgactt cattcccta   212040
atgttttga ggctcatcca tgttgtagca tgcatctcta ctcttttatt ttttatggtt   212100
cggtaatatt tcatttttatg gatataccac actttgttta tccatccatc tgttgctaga  212160
cattgggatc atttccagtt tctggctgtt ctcaataatt gtgccatgaa cgttcatgtg  212220
caagttttg tatggacata tatttcattt ttccttgattg gggatatagg agccgaatcg   212280
ataggtcata tcatgaactc tgtgtttaaa tatttgagaa tctttcaaat tattttccaa   212340
aataggtgta ccattttaca ttttcaccat caatgcacaa aagttttaac ttctccacat  212400
cctcactcac acttgttctc atctgtcttt ttaattatag ccatcctaat gggtgtaaag  212460
tgatatcatg tttgggggtt tatttttgaa tatttacatc attccaaaaa gaagtcccgt  212520
```

```
atctcttctc tcctacatcc ccaaaaagta ggcaagaggt aatctactca agaaatgata  212580
ccagcttaaa ccagggcagt accagtgaga atgcaaagaa aataaaaaag aagaggttgt  212640
tctgcgtgtc ttacagatgc aacaggattt gctgatggat tggatgcaag gtggcagaga  212700
atgagaatgc attttcctg atgactaatg atgttgaaca cctattcatg tgcttattgg   212760
acatgtgtgt aaatcctttg gaaaaatatc tattcagatc ctttgcctat tttaattgga  212820
ttatcttttc attactgagg tttaggaggg gtacttttaa gtagtataat gtggatacat  212880
gttccttacc acatgtggga ttcacaaaca ctcccattct gtgtcttcca cctccacttt  212940
cttgatggca cattcttatt actcatgttt ctgaaaacat aatcttcagc ctcattgacc  213000
aatgactctg aatattgact catatatgtt taagcaggct tgtccactta ctatatctca  213060
caagtcccat ggttatcgtg acagtccact gctatcccgt cccttgtggc tgtctcatca  213120
ttgtatggag acaatataag gatgccggga cagataaagg gtattaggat agagtgccat  213180
caatgtgtct gtgaagaagg gttcgtttca atcagttcac catgactggg gatttgattc  213240
tgtcaattgc tgactcagga atgtaaatgc tgagtaaggc aggacttgat cagtctattg  213300
ggggaaggca tcattgacca aagtgcagtg caaatttatt cattgactat gaggcatata  213360
actctttata actgtcaata gaaaatggac aaggcatccc tccgttcctt acaaggtttt  213420
gtaatgagcc ctggatttaa aaaaatacta gtaataataa gagaaagaga gggagacaga  213480
gagagagaga gtgagataga gtttctagtt taagtgaagt taaaatgttt tttctatata  213540
tacaaaacta gctttgccaa ggaagatgta gtagtggttt tcattcattc attcttcttt  213600
cattcaagaa acagatattg acaacctgct gtttgacaca tggtataaca acttccattg  213660
aaaatggagt agcaaacaaa acagagaaaa aatccccaat cctacagcat ttctatccag  213720
taggggaaaa aacaacgaca gacaagtatc gtaaaataca cagtagaata tgatatcaca  213780
agtgctatgg agaaatattt agtagagaag ggtgctaaat tagaaatttt gtgccaaaat  213840
tttgactaag gtggttatgg aaagtttcac agataaggca aaactgatgt gagggagtga  213900
tccatacagt tacctggagg aacagcatct tgggctaagg aaagatccag tgcaaaggcc  213960
ctgtggccac agagtccctg agaatatcag tgcagctgga aagtagtggt gaagggggata 214020 gtagcacctg atttcagaga tgtcagcatg agccacattt tatatgcctt taaaggacta  214080
gtgtattgtt cttagtgaga aaggaaatgg ctgtctatgt aaaggggcat taggttagaa  214140
ggttgttgca taatccaccc aagaaataaa aggcatttcg atcagaattt agctcttcta  214200
ctccatgaaa ctacttatca gttccattaa tgccttccac tctgcactct cagggttcga  214260
ttttctggaa aattttgaat tttgattttg attttccaga acatttagag ttctcgatga  214320
ctctctcctt cacgaaaaac attccttact tggtatctat atttgtttct ttcctattgc  214380
tgctaaaaca aggtatcaca acttgttata actctaatgt taactctagg gaattaaaag  214440
caatgcagat ttattatctc acagttctgg gtgctaaaag tcccaaatgt gttcacattc  214500
aaagagagaa tccatttcct tggtttgtct gtttgtcttc ttttgaagac tggctacata  214560
tcttagatct cattctctgt ttctaacctt ccattttaaa aaacaaacaa acaaaaaaca  214620
ttatgattac ctagattcat ccagatgaac cgggttaagt tctcatctta agatcctcac  214680
tttttttttt ttttctctct ctgagatgga gtcttgctct gttgccaggc tggagtgcaa  214740
tggcgcgatc tcagctcact gcaacctccc cctcccgggt tcaagtgatt cccttgcctc  214800
agcctcccga gtagctggga ctacaggccc gcaccaccat gcctggctaa ttttttttgta 214860
```

```
ttttactaga gacgggtttt caccatgttg gccaggatgg tgttgatctc ctgacctcgt 214920
gatccgctct ccttggcctc ttaaagtgct gggattacag gcgtgagtca ccgtgcctgg 214980
ccaggatgtt cacttttaa aattgattta ttcttatttt attttagaga tgaggttttg 215040
ctctctcaga taggttggag tgcagtgtca taatcatagc tcactgaagt cccagcctct 215100
tgggtcaatt gatcctccta tctcaccctc ctgagaagct gggactacag acatgcacca 215160
ccacgcccag ctaagtttta tatttgttta cagaggggt ttcaccatgt tgcccaggct 215220
ggtcgtgaac ccctaggctc aagtgatcca ccggcctcag cctcccaaaa tgctgggatt 215280
ataggtgtgc ttcctgacac cagtttctga ggtccttgac ggctgtggtc atagctcata 215340
ctacctctct ctccctagtg tctaccggac aataagcagt ttctgaatga ttagccgttg 215400
cagggttttt gactccaaat tgcaaaatgc aagctaatta aaaaaggagt gaatctattt 215460
actcattttt ttttttttt agtttgagtg aactgattct caaaatcagt gaatgcccag 215520
tttcatgtaa accgtgttta tttccactgt ttacactcag cagctgtttc tttttcacaa 215580
acactggaga ttccatgttc cccgaaatat ctatgtatac ctgtatcata attcattaca 215640
cataggttag ctggaatgga gatattttat atttgtggca tgcatttgat cttgaattga 215700
aacctgtagt ttagaaaaat ctacatatct ttatattttt aacagatttt gagaattata 215760
aaagcaaaac agtagagctc tacggtagaa tttttttttc tttaggtctt tccatgggta 215820
ttttaaatgt ctcattatga aaagaccata aaccatggtt ttctaagagt tctgctgaat 215880
tttgcaattg gctggcacat tttctaaatg atcctgtaat ctccatgtat tagttttcta 215940
gagcggccat aacaaatgac cacaaatgtg atggctttaa aagagagaaa tttactcttt 216000
ctcatagttt gggaaaccag atgttcaaaa taaacgtgtt ggcagggctg cctttccctg 216060
ggtggttcca gaaaagatc cttccttgcc ttttcagctc tggtggcctc ggtgtttgtc 216120
tctatcttcc caaggctgtc ttccctctat tgtatgtgtc gtctcctttt cttataaaga 216180
taccagtcat tggatttagg gttatacccct caattcagga taattttatc tgcagatcct 216240
taactaatta tatctgcaaa gaccctattt tcaaataggg tcacattctg agtttccagg 216300
tggacatgta tttttggagg atattacgca acccactcca cccaacacat cattattgca 216360
atatatatgt atgaatatag gtgtttcaga tatttacact acacatgtgt gtacaaccaa 216420
tgtattcagg atgccacctg gctttctcct tactaggcca cactctggca agaagatcta 216480
aggacaatct gggattcttc atctccttct tgcatcctct ttgcttccaa ataatgtagt 216540
catgcagtat ctgaaagttt atttcctgag ccttttaaaac ttctccatca gtttgacaag 216600
gagtaaaagc gttttccccc gttggccaca aaacttgtgc ttttgctcca gcaatacgca 216660
aagctatatt tcacacttcc ttcttaaatt acaggctata aatataaagc aaaacctttt 216720
accttggata ttctttctgt ctttttccctc tgtgattaaa tctgattaca aatgctcatt 216780
aatgctctgc cttggaattg caatttgggc atgtgccatg tgaaaatgga ggttcctaaa 216840
aattaaaatc aaagattaat gcaggtttta aaaagggtc ttattcaaat atatctcaag 216900
ttttaaaacg actcatggac ttttaatgaa atcaatggcc ttgtaatgcc tcattttttt 216960
tttcaaactc aactgtttca tagccttctc tttagaacat atctgattta ccagaaccca 217020
agatttgtga gatggtgtta tttttatct ttactttttc ctcacccac ggtaccatga 217080
agagatcgtg taacatcctt tcctggtttt aaagacaggt gagtaacgat tacataacgt 217140
tcaaacaagt caggtgttct ccagaagatg gtgttaatgg tgtctgattc acagatgctg 217200
ccttgacccc tggcggtggt aggacctata ttctggtgaa agccaatttt aggccatgga 217260
```

```
ttataggacc tagatggaga aaaacgatac ctaaacctca tgagatctta attcactgat  217320
cggtggagag atatttttct ttcagatggt atcatcttat tgcatctcca gcagagtgtt  217380
tggccggtga aaataaaaat ggccattata aagaagttct ttagacttttt aaaaatttta  217440
ctaggatcat gccagaaatt cctgctgtag aagtagatat gtatgtgtgt atacatatat  217500
atatatatat atatatttct gaatttgaga tgttgggtat tggtagagat tcattcattt  217560
gaatggaaat acgcttgctt tacttttggc cagcatgaat gctctcattt gccacaggtt  217620
ggcaagctta ttggtttaaa tataaaggat cttgtgggta agactaacag caggttttca  217680
tagtgccaac atttctttct tttttattat catatttagg aaagtctctt gactctgaga  217740
tactttatat tgtgaaataa tagttctggt gcaagtatag attaatagat tattaaacac  217800
tttaagatat ggatggaaga gtacaactag gatattatta atgagtccca tttactattc  217860
tttaatttgc agtggaattt tcatttaact tttgaatata ccaatgatag gaagttagta  217920
gtgtttgcct gtaatttatc ctgagctcat ttatttgaag ttcaaatttg aaagcttcct  217980
tttgttgttt ggtaaataga gattattgtg attcaaaatg agtaatccct aaattgatgt  218040
agaaaagat atttgaggct gggcacagtg actcacgcct gttatcccag cacgttggga  218100
ggctatggga ggtggatcac ttgaccagga gtttgagacc agcctggcca acatggcaat  218160
accccgtctc tactatgaat acaaaaatta gctgggcatg gtctcacaaa catgtaatcc  218220
cagctacttg ggaggctgag acccaagaat cgctggagcc tgggaggcgg aggttgtaat  218280
gagctgagat tgtaccactg cactccaccc tgggcgacag agcaagactt cgtctaaaat  218340
aataataata ataataataa taataataaa ataaaagaa ctttgagata ttcatattgt  218400
ccaaaaagta taattcaaat acttaatgca gaaggcagta ggatcactaa actcagagct  218460
cattcatcaa ttataacaga tggaagggtc tttgttagag tcctggaggc tgattgagca  218520
ttttaaatgg caggttcata ggggagatcc aggaggtcta aaggtgaggg tctacaagca  218580
ggaagcaccc ccactcccac ccccaaattc atgacaacaa cactaactag gcagcaaagg  218640
gatatttcct gatgtcagca gtcagcagaa tggtactgaa ggttgctaga taaatgcaag  218700
ttttgtagtc actcacctgc aagttatagg caagatattt atctgtactc ctacaggaaa  218760
ttagcccctaa ttgactgctc ttaatcagaa caagacattc taacctctta ttcatggtta  218820
gcagtatatc ccacttgctt cactttgtga ttctccatca cattggaata actggacgtg  218880
ggatacattt ggaattgagt ctcaaattca aatcgccata gaacctgaaa agaaaatgta  218940
agaagagaca aaacagaaga aaaatgcagg atagagagtt atgatttaga tgtgttcatt  219000
ctgtgaacag agagcagatt ctcttggatc tggctgaaac aggggccccc tgtgttgtga  219060
aagtggtgta tgtcttcata cgtgttccca cgggcctgga caaccaacca catttgaaaa  219120
atgaagaaat gaaagcttgt ggtcagggtc acaaaacttg acagtggcag aagtggatcc  219180
aatttccagt caaatctatg actcgttcca tcttggccac aattatactg caactcaatt  219240
gcttttcttc cagtcagtac ccacccaccg aaatgtcagc tcttcaaggg cattaattgt  219300
tgtttgtttc attcattgtt gagtcttagg agcctgggac agtacattga aaatctcaat  219360
tgttgacatt ctcaataata cacaagaaat catgttttca gatcatggaa atcatatcca  219420
ttaggatggc tgttaataaa gtaaacgtaa aataagaagt tgtaatggag atgtggagaa  219480
actggaactc tttcacattg ctggtgggaa tgtaagatgg tacagtcatt gtggaaaact  219540
ctttggctgt tcctcaaaaa agtaaacatg gaactaccat atgtgatcca acaattctac  219600
```

-continued

```
ctccgggtat atactccaat tctacctctg ggtatatact caaaagaatt gaaagcagga   219660
attccaggag atatttgtat acgcagtcct taaccatgtt attcacaata gctaaaaact   219720
gaacttttga actagccaac tatccattga tggatgaatg gataaacaag tgatatatat   219780
gtatatattt atgcgtgtac acacacacac acacactgct gaaatggaat attattcagc   219840
ccttaaaaga aaggaaattc tgatacatgc tacaacataa ataaaccttg aggacatcat   219900
tctaagagaa ataagctaca tgctagtcac aaaaggacaa aagctgtatg attttaccaa   219960
tatgaggtac gtagagttgt caaattcaca gaggcaaaaa gttgaatggt gtttgtgtgc   220020
ggctgagagg cggagagaat ggaaaattat ttcctaatgg atagagtttc agtttggaaa   220080
ggtacaaaat gttctgaaga tagatggtgg ggacagttgg acaataatgt gactgttctt   220140
aaggccactc aattatacac caaaaaatag tttaaatgat caatttcata ttctctatat   220200
cacagtaaaa taaacatta tggtatctgt gatttaattg actatttgta atcatcacca   220260
tgttagagca tgttcagtat ctcatatcct gcaatattgg aatggacatg gtaattttg    220320
agtggtagaa ataaagtaa cttttaaaaa cccatctcta tgtattcaca taatcttaca    220380
tttcatataa gtgaaatcat acactctata tctcatttct ttctcctaat aaaatgttta   220440
caaggtttac aaggttcatc cacattgtag catgtatcaa tcagtaccgc atgctggttt   220500
atggctggat actattccat tgtatgatag accgcattct gttatgttta tctattttc    220560
atttgatgga tatttggatt caattcatag agacagaaag tagattagtg gttgctggtg   220620
cttggaagag gactataggg aattagcgtg tcatggttac agagtttcag tttgcgaaca   220680
tgaaaaattt ctagagatag attcacaaaa atgcaaatat actaaatgac attgaacaga   220740
acagtacact ttaaaatggt tcactttatg ttacgtgaat ttcctcttaa atagaagaaa   220800
aataaagtct gaagttgtca tatccttcac tgggatgctc tctttaaaag tgtagaaagg   220860
tcctgaaagg agcatataaa caaactaaac aacaatcaaa caaaacatgt catcgtaccc   220920
cacagcatcc tgacatggaa gactaaaaac tgtcccaggg ctctcttctt ccttatctgt   220980
tactttcagg ggcattttag cttaggattt aatttgacta ttgacaaccc cagtgtctcc   221040
atttgatctc agagcaaact tgaattgata attaaatttc catgcttttg accagggaaa   221100
gactttagga aatgtctttg aaactgtgaa cttgcagaaa ggagaaaatt ttatatgtat   221160
ctagcttcta tccattccat ttgtcatatg gtcagaactt acatgatgca agcaggccat   221220
ttacagggcc ctgggctgac agctacatgc tatattttgt atttgcttcc actattttgt   221280
tagcaaatgt atgtacttac taacaaaata cgtgttttaa gaaataaaat tattttaaga   221340
acaaaataat acaatgtttt aagaaaacct gcttttattt gctttttatt ttttatttaa   221400
aaatgtttat aaatttatgg gtgttacaaa ttcagttttg ttatatgggt atattctag    221460
tggtgatgtc ggggctttta gtgtactcat cacccgaata gtggaacctt tatccagtag   221520
gtagtatttc atccttcatg ccccttcctc ctccttccac ctcctgacac tttatagtct   221580
ccagtgtcta ttattctacc ctgtatgtta atgtgcacct gttgtttagc tcccacttat   221640
aagtaaaaac atgcagtgtt ggactttctg agttatttca cttaggataa tggcctccac   221700
ccagtttcat acatgttgct gcaaaagaca taatttcatt ctttttatg actactactg    221760
agttgtattc catggatata taaccatgg tatatataaa catttatata tccagtcatc    221820
tgttgatgga cacttaagtt gatttcatga ctttgctgtt gtgaatagtg tagtgataaa   221880
catatgagtg gaggtgtctt tttgatagaa ccatttcttt tcctttgagt agaaaccccac  221940
aagtgggatt gctgggccaa atgatacttc tatcttaagt catttgggaa atctccatac   222000
```

```
tatttttccat agaggttgta ttaatttacc ttcccaccaa cagtgtataa ctgtacccct 222060
ttctcagcat ctttgccaac atgtgctgct ttttgacgtt tttcaaaatg tcattcattt 222120
tcatttttat tataattact taaaaatgat gacttttaac agagaaggga aaaataaagt 222180
tggtaatctt ttgtagtgcc atataatttc tagttacaag accacagata agtcccatgc 222240
tgaagagagg tgggtaaaat agctcgtttg aaatgaagca catttgggaa gataaaattg 222300
tttttaggat gataacgatg tttgatgtct aactttggtc tagttttttct aatgttaagt 222360 gtattcttaa catctgccca aattattcac tctttaaacc acatgccaaa acattactta 222420
catttacttg gtttataata aaatttggga ctattagtgg atgatattta ctgcaagaat 222480
tgttaatctg gcgtttggat ctagtattta gattacttta tattttcagc tgcatatgca 222540
actattagat atctgcccac acttttttcct tcccactgtg gaaatacac actgtattaa 222600 ggtgacaggt tttcctattt tcaccccttta gacttgagtt attttctcat cattattaac 222660
tcatagaacc tgtgctttgt tcctggcttc agcttgagca ctgtgcaaaa atttatctta 222720
taagatttgg tcaaaactgt tggctgtgta ggcacttccc ctagtagaaa cttcccctttt 222780 cccctctgag ggttcactga aaatcaact taaaaggca gattaattga agaaaaggca 222840
tgcaaatttc ctttaatgtg gatagcttgg caggaaggat taggagactg attacccaat 222900
atcttaatgg agtagatatg cttatatact ctacttccta gaggaaaggg aggtgaggac 222960
tcctggatga tacttagggg gatagtaaat gattttttagg ggaattaagt gggcttgaag 223020
aacatacagt ggcttagaac aaagtctgtt gggcttgcag agcagacagt ggtttgtcac 223080
aaaagtctgt ccaggtgtgt tgacagactt cattctttct tcctgcgata tgagtccagt 223140
tactagaatc tcggggaagg gaccagaggt cattgttttc ttctttgatg ggtccagact 223200
ttaggcagat aaacaacttc agaaacaac ttcctcctgt gctttggggg tcacagaggg 223260
ttgagagaca agagggagtg ggagaagatg agagagacgt tgaggcttct tcttcagttc 223320
agcacatcaa agtgccatat tttgctgtat gggtttatga gtcccaacaa ctgggtagtg 223380
aagacaaccc agggctgtgt gttgatggtt ccgctgcaga cagtcaaggc tcacttctct 223440
gggaggaagc taaatgccac tcagagacac atccccatct cagatgtctt tgttatattg 223500
atgacagttg gcacccagat ggcatgtatc ccttgtggtt tcaaccattg gttgacatga 223560
ccttaaaggc ccaaggtatg tattcgttgg tccattttttt ggaggaatgc catttttactt 223620 ccacaatgca gcatagctgt taaccattca tcatgccagt aagagaatcc ccgggatctg 223680
cattgggaca gaatccccat tcactgcctt gtctcacttt tgtagtttgt tttgttttgt 223740
ttgaatttgt tttagtttttt aacaaataat ctgaaggtaa aatacaattg aaagaagcac 223800
ttatcttatg atatcaggat aagtaaacta gtgcagtttc agaaacatct aaccaagtgt 223860
tgttttcttg ctggattgca atattgatag gcacatggga taatatctca tgtaaattct 223920
gaaacatcta attgcatctt gatccttcat cttgaccctc ttctcagtgg gctgcattta 223980
tccctaaaca gcaacattct gtcaattctt aggaacgtga aacgttacag tctgcagagc 224040
aaattaccag caggagaaaa tattactgaa tattcaaaag catgccttttt gtgtgaatga 224100 tcttgaagcc ccagggaatg ggggaaacag ggttgggagt acataagcca agaaccttat 224160
ttgatccagc agtttccggc ttctaaaacc ctacccatgc agttccaaga agaaaataac 224220
aaattggcat cacttaatgt ttagtgatag aagaagaaaa gcatgccttt gttcatttttc 224280 tactcttctc atttcctgct tcaccattcc tatcaaatga aacatttcgt tttcatttcc 224340
```

```
tctctataac ttgtactatt tctgtgaata gatgatgtgc ttaacatatt gatgtttgtg   224400
agtaaagata ctcttgctat catcaaaaga aatagtatcc atttgagaag catctagtat   224460
atgaggaaaa gttttgtttt cattttttccc ttatgttgtt tttatatttt taaatgtagt   224520
tgtaaaatga cagaacatgg gatcacaaag aaacacaaaa ttcgtaatta ataaatgtga   224580
ttttgtattt attttaggta tgcaaggggc acgtttgtgt gggagttcaa aagcatttaa   224640
atattttaaa tctcctttca ttcatttaat aagtgtcttt tgaggtcaga tgtaaacaga   224700
caacttgtta cacatgtttc ttgttttttag ggaacttcca ccccaacatg ggaaataaac   224760
agagacccta ctagttcttt aacagtttct taatgaaaca ggatatttcc ctgaccccctt   224820 cacaggtggg aactggagtg cactggtgct ggaactagcc ggctgcttcc aggccagcgg   224880
gggtgaaccc tgctcactcg ctgctctacc ccttgtggga ggggaagcac aggtgagcag   224940
gtacaggagc cagggcgaac aattttgggc accagcaaga atgaactcca taccagcccc   225000
acggcagcat ctagtagagg gtagcccgca acccctgaag acccagagga agtgttacac   225060
tgcctgtttg gctttgccat ccgcagagac cgtaagtgtt aacagctcag tggagggtca   225120
atgtgacagc cttttgcacc cacactcatg gcacgcaagt ttttgtcctg aggtgggaaa   225180
ttaaagaaaa ataaaatcaa aaagaaagag aaataagttt tcctgtatta ggctgacttt   225240
tcccagaggc agcaacaggc acagcccaga cccaggaaaa gtcttgataa tattatctaa   225300
tgtgctctgg agactctccc agcactccct caacataggg agaaggaaaa caaattttcg   225360
tttgttttat ggaatgagtt tatagattcc tgttctctgt aactaatgac ttcaagtatt   225420
ctgttttatc taaaaagtac aacgaaggtc atgagaagcc tgattaggcc tgaactcag    225480 ctgcttgggc accatagtga aggttatgaa ataaaccagt gcaaggcact ttagagcaaa   225540
acctaggtaa cagacatctg gattgcttgg caatggtcat atgcggtcct gagtttgtcc   225600
tgcctctgta tccctgcttt cacgccactg taagcttact tcaagctagc ccaccccctt   225660
ttgttaagtg tgtatgaaag acaagtgctg tcttttgttcc gggcccagtc gttgacgtt    225720 gagtctgctg ggtctgagtg cactcaataa taaagatatc ctcctgtata caccccgagg   225780
tctctctctg gtcctcctga tcccgcaaca gactgacgtc caggagcaat caggtcacac   225840
gaacaaattg aagatggtaa atgcaggga ttttttattg ctggttgaaa gtagctctca    225900
gcaggaaggg gaactgaaaa cgggatggag caggaagata atcttcccca ggagtcccgt   225960
catccccggc cagaatcttc tccaaagcta tgccatcaag ctgtccctct gaagtcaagc   226020
cacttctctc tgatgtccaa ctataatttc cgatgtccag ctgcttctcc cctttccaag   226080
ctatgcctgg agtttttatg ggcacaggat gtggtgcagg gcaggccatg ggtggttttg   226140
gaaaaggcag cagtcgagtg ggaaaacagg aatgtaaatt ctcactttgg gccctggttg   226200 cttttttggct tgagggtggg gcacttaccg ggaacccgct ctcttctgcc cagaatttcc   226260
ctgccttctg tccctatcgg ttttgtattt attttaggta tgcaagaggc acgtttgtgt   226320
ggaagttcaa aaacgtttaa ttatttaaaa tctccttta ttaatttaat gaatgtcttt    226380
tgagctcaga tgtaaacagg caagtacagc ttatagctgc agtgaatgct gagaatgaag   226440
tactcaaaca attccagctg aacggggcgg ggaacagctc ttctgagaga gtgctgcccc   226500
aagatccatc cacctgaata tttattgaga gagcttgttt aaactacagt tcagatgaac   226560
aaaagacatc caccaggtgg ctctttgcgg ttgggtcatg aggcacatat gaccttgtaa   226620
aaaacactca aaccacattc ttaggagct gtgttcagca ctccttatca cacatactac    226680
tccctgtcct gttttcaggg acaaggagtt ctagtctcat gcacaaacaa catgcacaca   226740
```

```
gtgcctcagt attttttccat gcctcgacct cacgtgtctt ctacattagc ttgaatatgt   226800
tgccatgcac cccccacagg aagtcattac acatgtttcc tgattttagg ggagcttcta   226860
ccctaacatg ggaattaaag agagatccta ctagttcttt caagtgtctt aggtaaccaa   226920
ttagatatat tctacacccc ttagtggcaa gtgctcatgt tgtcaaattt gcatttgttt   226980
tcaaatgaga ttaaaacaca acaacaacaa tgtttaaatg tttctactat tagaaaataa   227040
aatcaatgta ttctatcttg gattttttcct ttatttcttt atagagttct ggtttgcaac   227100
aaagttttat cagtagctta tttaccttcc caagagctcg ggcaggattt gatggtgaat   227160
gtacatttag tggtttccat atttaaaaaa aaaaaaaaat gactctgaat aagctcccag   227220
gctctcagtt tcttctagtt ctttctgaaa tggtccacaa catgattgtt ttgaaattga   227280
aaaattaaat gcttttattt caaaccccac cgatctaaaa ccagtaggtg tacctttcat   227340
gagcacactt cattctgcag gtgaaaaatt ttcttccaac aattgtctat gatagtgatt   227400
tataagtcag caatttgctc taagaatgt gtctctttct aagcatcaca agaagtaatt   227460
taaattatgc tgtttcttag taagcatgtt gattgaacct cacatatttc cactgattct   227520
acactaaaca cagactctct tttagttgta ctccatttga cttggtttat acagttcaca   227580
tagtcacttt tgtatgtcta aacttgcctg accattttac tagatggcat ggtgatatgg   227640
tttggctttg tcctcaccca aatgtcatct tgaactgtag ttcccataat ccccatgtgt   227700
catgggaggg agccagtggg aagtaattga atcctgtggt ggttaccctc atgatgttct   227760
catgatagtg agttctcatg agatcagagg attgtgtaag gggcttttcc tccttttgct   227820
cagcacttct ccttgctacc accatgtgat gaaggacata tttgcttccc cttccgccat   227880
gattgtaagt ttcctgagga ctccccagcc atgctgaact gtgagtcaaa ctttttttcct   227940
ttatacatta cccactctcg ggtatgtctt taatagcagc atgataatgg aaattgctac   228000
tgagagtggg gtgctgctgt gaagataccc aaaaatgtgg aagtgacttt ggaactgggt   228060
aacaggcaga aattggaaca gtttgaaggg ctcagaagac agggagatgt gggaaagttt   228120
ggaactttct agagacttgt tgaatggcct tgaccaaaat gctgatagtg atatggacaa   228180
tgaagtccag gctgaggtgg tctcagattg atatgggtaa cttgttagga actagaataa   228240
aggtgactct tgctatgttt taccaaagag actggaggca tttttgcctgg cgttgttgtt   228300
ccatgatttt ttttttttatg ttcaacagga cgatggcaca acctagctgc aaggcacaga   228360
ccaactccca gcattgccag ggcttagggt acattaccag gtcagctgct gaccagcagg   228420
ggctgctttt ctcttttgtg agtaactgag aattaaataa actaagtaac atgcctcaaa   228480
tcctgcagag ggttggagat aatactggag tctcaacata gactatatgg gaaagtctag   228540
cccattaatc tccaggcttt ttttctaagaa accaaacgcc aatatttttat ttgttgcaga   228600
aaagggacat cctgtggtca acacaatctt cagtgggagt taattttaat caggttcttt   228660
agaattcagg aaagctggaa aaaagaggag ttgtgtaact cacatactgg gaggcatctt   228720
ctgtggccag tcagcagata ccatctccat tggagagatg caggcatctt aaggatggga   228780
gaattccatt tatagcctag gacttttgtc catgggcctg gcttggatag ggatggccca   228840
tattaatgtc tttgactctt ggttttattg ttacattctg tatggctgat tcagatttgt   228900
ccacactgat atatttgttc tctgattctg atcattgtgg ccatctttttc ctagaacaaa   228960
gggcttaggt taattttttgc ggagtaatga cattttctgt ggcagccaaa ctccgtagaa   229020
caatattgct cctacttctt gttttcttcc aatggtaatt gaacgtgcaa gccacattca   229080
```

```
ggagtagggt ctgaaattcc ccaagagcta gccagcgata atagtgcaaa tctaatacat    229140
gcccttgaaa caccaaggga taaactcatg tgcatttgtt cttttggggt ttgaagaacc    229200
agatgacatg caaaagaaaa atattgacaa aagatatctc atcgtttact ttcaattatt    229260
gagtttgatt ttcatgcatt caaccttagt ttttttaaga ggtaagtgat tctagtttgt    229320
gagagccaga agcatgcaca aataaacctt atttaacaaa ttaatctcat attttcttgg    229380
ttctgatgat tgcatactgc ttattttaaa aaggttgtga gcaagccaaa gttatcatac    229440
ttatttttaa agtgacagca tggctgagct ttcaaaatat gtttaaagat tctaagagaa    229500
acaggttaga aaacaagatg attgacagct ttttgggtta ttagatacag aaaattatac    229560
ttagatttat ttaggttgaa aattaatcct acagcattta aaccagctgg gagagcttgt    229620
gcatgcacaa gagtgttcaa gctgcaactt aaggccattg gcaacagta gaaagaaaaa     229680 aatggttatt tcttctcttt cagaaccaac tgtgactgat taaccacaaa agatcagtgg    229740
gggtattcag gcctaggtcg tcttggtggc aactggggtt ttagtttgct tcaggctca    229800 ttgctggaaa aggctgttca gaagcttcct ctacaacaag ggagatgaca gtgcgtgagt    229860
acaaagcaga gaggtgcagt gctttctaca gcaccgagtg ggcaaattgt gcagatttt    229920 cagtagaatc tacttaacac caatccatgc atttgcattt tattaaaatg aaactgtgat    229980
catttcaact gcacattgca gacatgccct ataaaatgtt tgaagtcctg ttttggacaa    230040
aagttttgaa aacatgcacc ccgtatcaat ttctctactt atattttgta tttaatttgt    230100
ctaaagaatg ccacatttc aaagcaagca ggccaagaga atgatctttt tttcctcttt    230160 ttttttcccca gtgtttaaaa tgcaactgcc atggggctgt gccatttag ctgttggaaa     230220 aaataatcta ctatgccttg gttgtatgtc tgagtcatca gagcttctgg gaatgattct    230280
ttggcacatt ctaccaacaa tttaacatga cacaaaatca ttttcatatc ttgtgatagt    230340
gtcagccaag tgtttcatac acatggtgct aggtgctgaa aaaggtgtct gaataaaatt    230400
gttttcttaa aggaaccata ggggacatga taaaaagatg cacaattata tatctttttt    230460
tttttttttt ttgagaagga gtttccctct tgtcgcctag gttggagtgc aatggtgcaa    230520
tcttggctca ctgcaacctc tgcctcccag gttcaagtga ttctcctgcc tcagcctccc    230580
gagtagctgg gattacagga gcctgccacc acacccagct aattttgta ttttttagtag     230640 agacgaggtt tcaccatgtt ggcctggctg gtcttgaact cctgacttca ggtgatccac    230700
ccgcctcggc ctcccaaagt gttgggatta caggtgtgag ccactgcgcc cggcctaaag    230760
atgcacaatt acatttcata aattgagaga gtttcctaaa caagagagag catacctgga    230820
aatatcagag aaaaatacaa agggcttaaa gatgttgtat taagcaaagt tagactaagg    230880
cagcttggat gtgcatctcc tccactttat gtttatacct aagtagagat taaaagcaga    230940
ggaatttcaa tttccacatg acttgtatat gagcaacaga tgggagttct aactactgac    231000
cacattggca catcacacaa tgttttcttt caggtttctc tacctatggc aaaaccagtg    231060
ctgtattaga gcctcgtgag ctgtgtgttg ttgattaatt gacttaacct ctctgggcct    231120 cattttctc acctttaaaa taaatgagtc ttatggtgtt ttgaggatca aaagagttac     231180
tgtacaaaca gtgctagtaa gagtccctgc cacatggaaa ggctattata tatatata     231240 tatacgtgtg tatatatata tatatgtg tatatatata tgtgtatata tatatacaca     231300
cacacacaca cacacatgta attttatata ttaaatgtgt ataatttata aattttgta     231360 ttataaatgt aaatctgtga tatatattaa aactatgaaa tacagatcat gtaatatata    231420
ctacctattg tttttttttt aatttgtaac catatttga aaattttatt ttgcttatag     231480
```

```
gtcttgaaag tcattcccca atcaaccttt attaaaatcc ctttgattca ttggagaata   231540
tcaatacata tgaggtatta atatatataa catatgtaac tcttctgagt ttataaatgt   231600
atgtataaaa cataaaaatt actaactctt catatatatg tttgtatcta tataataattt  231660 atatatatag atatatatac atatttgtat tacatatgaa taatcatcac agtgtgtctg   231720
catttgttaa tctaacctcc tccaacccca cccccaaaaa agcagaaact aaaaatagag   231780
gaattttaag ttccacatga tttatatagg agcaacaaat ggaactacta acttccgacc   231840
gcattagcta atcatacaat ttttttcttt cgtgcttttg ttgtaaatat gattttatt    231900 taagagggta ttattgatta tctacgcaag aattagccat gttctccata cttctacttc   231960 agtttttaa aaaaggatga ggatagaccg ggcataagtg gctcatgcct gtaatcccag    232020
cactttggga ggccgaggcc ggcggatcac ttgagggaag gagtacaagt ggcctggcca   232080
acatggtgaa accccatctc tactaaaagt acaaaagtta gctgggcatg gtggcgcatc   232140
cctgtaatcc cagctacttg ggaggctgag gcaggagaat ctcctgaacc cgggaggcag   232200
aggttgcagt gagccaagat cacgccactg tactccagcc tgggtgacag agcaagactc   232260
tgtctcaaaa aaaaaaaaaa aggtgaaaag ggtgaggatt gttatttctg tgggcaggcc   232320
cacacagcat cagattcctc agaaactgca ccggtaaatg ggaaagtctt tgagtccctc   232380
tgacagagct tcaaggggct ggctgttcat tatcccacag cctcctttgc tctgtgtaag   232440
tggaggctct gtgcctctgt tatcttgcag tccctaggtg accccggcag ggagaaaaat   232500
cagtggaatc aaactcggta gcacagaaaa acgccccaaa ggcaaggatg agaggaaagt   232560
tgtgatccca catatcaaag tcggactctt atctagatgg gcacacctga gccacaggct   232620
ggcaggctga gattctgcaa aggctctgga ccccagataa gcttgactga ttgcattgtg   232680
atctcttctt ttcatcaggg gaggcgctgc tttgaatgac taagctggat ctgactttcc   232740
agggaatcct ttcagggact gtgaccatcc agctatcttt ggatggcttt gatgccctaa   232800 ttattttca cttggttgag gatacttta ggtatctgtt catgtgtcat cttgtacaga     232860
aatgtgtgtt ctgggcttat aaaaaaagtt taattgtaag acaaagggct ctaggtttca   232920
tatttattca cagtctgatg aatggcactt atggatacgt acgtgtatac agtaagtgct   232980
cactgaattt ctcttgagtg ataaactggg atacaaaatg tcagaaaaga aagagtgagg   233040
atgggcactg gatccagatg tcagtgaact ctgagggtct cttgctggtt aaaagaacag   233100 ggtacttta ttttcattct aaaccctgcc tgacccttgc ccttatatca gtgaatcacc    233160
atctcgatgg cccctcaaac atggcatctt tgaagtagag cctcattgag aaggactcct   233220
tagaagtctg tcatggctac taaaattcat atctgtgctt tgtgcctgag cactagtaca   233280
tgtgtcagct gtttcttaag cctacattga accattaggt aaagcccagt gtgctcccag   233340
ttcctaaaat ctggtcaagt cttgatgttg gtcaacatct tgcctggccc cagtcagatg   233400
tctccagcta tctgtaacag gactcagtgt cttgtttaca aaatgcatta gtcatatggc   233460
ttcgttgctg gctttgctgt ataggtcagg aataagtcag aaataaccaa aatgctccaa   233520
atcaagttct agctgttttg ataccaacat cttccatcaa cttcgcttct ccctgactca   233580
tctgtctgtc tgttcctgtg ctcttcgcac acagaggcaa ttttgtgtat aaagctcccc   233640
aagggaagaa gaggacagtg ccttcatggg aaactccttt ctcttaaata ggatttgcat   233700
acttaaccag agcatttgct tcagttaacc aagtgagagg tggagaaatt cttgcaaaac   233760
tatagctaca ttgagaggga ttattaaaag tattgactca ttcattagag gagctgttac   233820
```

```
aaagattgta gcaaccaaag caaaataaaa aatattgcca aaagtattct caaacgtatt   233880
ttaaaatgtc caaatattg ggcaagacta acatcaaaga aggtatatgt tttgacattg    233940
atttactaac tacttatcag tgtaagtaaa tacaccttca agcacttatt taggattaag   234000
gtagtcaagt tatatgagtt gtatgagtat gtgcaggcca caagggttgc aaaacatagt   234060
gaattcaata tccctctgcc atattgaata tccttctgcc gaacttctgc atcacagttg   234120
tggcctgcaa acaggtaaca gttgtctgcc aatcccttag ggatcactgc attctatagg   234180
gcttgaccag gaagtaagag gctcttccca ataagcgata tcgttatggt ccttgtggtt   234240
ctgctaagaa tctcagagaa gaaatgaaag atacatgaaa ttgtttgcat gctactagct   234300
ctagtgggta ggttggtagc gtagttcttc atggcaaaag acagaatata tccaaaattt   234360
tcaccatttt gcccctggtt tgagggatgc atattccttt agaccattat gttgaaaaga   234420
aagttaaaaa taacataaga agagacctcc taagttgttt aatccaagcc ctcaatctta   234480
gcaagtgcct ggtgtaaaat gtctcattag gtaattaccc atctcctgtc tacccactaa   234540
gaggttctag taaagtacat actggctgga ttcaataaag cacaaatagg cagcaaatgc   234600
ttcttacatc tcaatctaat cggtagcctt ctttatcctc acccttggct gactaacgtg   234660
cataaagcat aggaattctg gccactcaag gatcttaacc atccagttca gtctgttgca   234720
atttctcctc cattacaaat ttttttcact ttcctttcct gggaaagcca cagacaggac   234780
aaccattcag tgagaaagga gtgtgaagct gacgtctttc ctcactaaga ggagaggggc   234840
catgagagga aaaggcaact tcttgcgtgg ctggtggtag agttaaagtc tgatgctact   234900
gtcttctggg agcagcagct gtacacagtt gaacttact ttggaggcat atatgatttc    234960
cagggtttct gtggcaagtt ccacccactg cagttcattt gacttgggtt gaatctcttt   235020
cctccctcca tcacttcagc tgaacctctt ctgtgatcct cacctgttct ctagaggtga   235080
gaccagggca cagtcccttt ctagatgacc aaagagcact tctttctatg tggttcacat   235140
ttggctccat caccatcgta gctgacaggg ccaaccctcc ggcatcttca tccttcacca   235200
ctgtctttgc tgtgccccat aaggcctgaa caaggctgat gggccaagta tggtgtggcc   235260
agccccacag tctgttacta ggccttgctt tggtagacac acttcttgat ttagaaccat   235320
ggctctcagt catgggcagt tgtgccctgc ttggcaatgt aaggagacat ttccagttgt   235380
cagagtgagt ttgaagggtg ttaatgcact tagttggtgg agaccacggt tactgttcaa   235440
catcctacaa ttcgtaggac actcatccat aacaatgatc tgattccaaa tgtcattgat   235500
gctgacatta ataaaccctg ctctaagtta atgttttttt cttactcata tttaaaatgc   235560
ttcctctagc taaaccatta gcccccagtg aggtataagt tttcctctcc aagggacatt   235620
tgactatgca tgtacatact tcgggttgtt acagctggag attggtgatg cttctggcat   235680
ctaatggata taagtccaag atgttgctca atatactgca atgcagagga cagcccacga   235740
gaacaaggaa ttatcccatt cataatgcca ctagtattaa ggttgaaaaa ccttggttta   235800
gaatatgggg atacttattg gtgctcccta aggtgctatc tgaaagcagc tttgaagaca   235860
agcagaggct ttgaagacat actcacaggg tatgatatag tttggatatt tgtcttctcc   235920
aaatctcacg ttgaaaactg atccccagtg ttggaggtgt gacttggtgg gaggcatttg   235980
ggtcattggc cggatccctc atgaatgact tggtgcagtc ttccaggtga tgcctgagtt   236040
cttgctctat tatttctcag gagatcaggt tgttaaaaag agcctggcac cttcctctcc   236100
tctctctctt gcttcctctc tcaccatatg atctgcgcac acagcagctc cccttcctct   236160
tccaccataa gtggaagctc cctgaggcct caccagaagc agatgctggt accatgcttc   236220
```

```
ttgtacaccc cgaagaactg tgagccaaat aaacctcttt tcttttcttt tttattttc    236280 taattagaga caaggtcttg ctctgttaga ctggagtaca gtggtgcaat catagctcac    236340
tgcagcctca aactcctagg ctcaagccac cctcccacct caacctcccg agtagctagg    236400
actacaggtg catgcctcca tgcccagtta attaaaaaaa ttgtagggac agtcttgctg    236460
agtttcccag gctggtctca aactcctgac ctcaagcggt cctcctgctt cagcctccta    236520
aagtgctggg attacagatg tgagccacca tgcctggacc gtcttttctt tataaattgc    236580
tcagcttcag gtattccgtt atagcaatgc atatggagta agacattgta caagtcccac    236640
tttgggcacg tctagatctg tctgtgatcc tagacaagtt atgtaatctc tctttgtgtc    236700
taaacctgtt gtttgtttct gtcttttattc ctcattaggt ccaactctaa agatagtaaa    236760
attataggta taaatggagt taagagggggt gccttaccaa gagtaaaccc tccaggagtg    236820
ttattctgtc agtatgactt ggttttttagc tttgaaactt ttagcatgaa actaacatgg    236880
caggaaaagg cctaaattag aattcttcac acacaaaact ccttctatca ggaggcagcc    236940
catctgttgt caaataatcc tactcgtaga aatgtattaa attttttcttt tccttcccttt   237000 ttccccccttc attaaatgga attagattgt gacactatga ggaaattaaa gtgaaggtaa    237060
aataaaacaa acaggaagaa gtctgtcttc agattggata tgcaattatc ctgtctttac    237120
tgctgatttc aattataact cattggtgtt accagcccac gatagatgtc ccctgcctat    237180
gtggtgttta aatcaagtgt tggcatcatt cacacttgtt tactgttatt agcactgatg    237240
gatgtaatct tcatgtcttc ctctgaacac tgcatgctga gaaagggggcc ttatttcctc    237300 gtggattttc taggcaagag aatgtcaggc cctcacctgt cctatttcca tctcactcag    237360
cagaaaacac actggctcat ggaaactgca agcatcgttg tcagctgcac ctgcaggcac    237420
catggggttg caagtcagca tccccttttca gaaatgagga tggaattaga ggtggaaaga    237480
aaattctcca cagtcctctc acttctctgg gcttagacag ggaggtttct gctatgtttt    237540
cattgattat gctgtggggg gaagggagag gaggaatccc ctaagaagaa caatgtctca    237600
ttggatattg ttcctttggg ggaaaaaaaa aaaggaaagg aaatattttc attttttctt    237660 acttttcta ccctagaatc tcaatgccac cttcaaacat ttgaatctca cagggagaag    237720
gcggccacat atttcacccc caaatgctag gccatgtctt ctcatgtcag aaatgccta    237780 ttgtgcgtgt gtccttgttg caagccatct tagacttgtt gtttcaggga tagggaaacc    237840
attctgcaat ccaaataagg ttgcatttct tgcaattcaa aataaaaggt gtgcatgcac    237900
acacgcatgt gctggtatta ttgtacagct tgcgtggtgc aaggctgaag gctaagggac    237960
taatggaggc tgaaatttag ccctagatac actctgcaag ctgagtacct gtggggccgt    238020
attacctggc tagaggtgtg cctatttctc atgcatccag tatcaggtac tttttctgact    238080 tagagggtcc ctcaacccctc tcctccttcc cctccaccta tcgtacttag catactgtat    238140
atttgccctt agtctgtttc atccaacttg atcacttggt agcctgtctt tatccccact    238200
gtctaaatca gtatttggaa tgtagtaggg acacaaaaaa aattagttga ataaaggaat    238260
aaatgggtga aatagtgaat gcatgaaaaa ggaaaaaatg aatatttttgg ctgctgtgta    238320 ttcttgtatt gttgttatat ataattcttc tgcctgtctt tcttcataca tacctcatta    238380
ttagtataaa ctaccagcat tcgtgatatg caggtctttg cttttgcaga gagccatggg    238440
tttctctaaa aggcatcttg cagcctcccg cccagggtgt ctctgtgcag ctaacctggt    238500
tgctaatctc tgcaagctcg tacttttttct gcagcacgtg attctgttct catttactct    238560
```

```
tgtaatccett ctgtttecctt ctgaccagct tgagcttctg tatctagtgc cttgacgttc    238620
tctttctttc ttggtctttt taacattatt atgtcagtta taatgttttt cagttgcttt    238680
tagtattcag aaaattcttg aagccttctt attgcccact ggtattttgt cttcgccgct    238740
tgttgtttgg gtggatttag atatagcaga gagagagaga gagagagaga gagagagaga    238800
gagaggaaaa tagagacaga gatatgtaat ccccccaacc aaccccgtt atctgtgatt    238860 tccattaccc atggttaggt tagtacagta cagtgatatt ttgagagaga gaaagagaca    238920
tcacattcac gtaacgtttt attagagtat atattgttac agttgtattt tattttaatt    238980
gttgttaatc tcttactgtg cctaatttat aaaataaacg ttatcatggg catgcaggta    239040
taggaaaaaa cattgcatat atagagtttg gtactgtcca cagcttgagg catccaatgg    239100
gggtcttgga aagcatccct cactgccccct ggtaaggagg agctactcca gttttgagag    239160
gagaaactaa acagatatga aaaacataca agttgtaacc taataggaaa attttttaaag    239220 tgttattaaa aaccatatct tatatatctc atatattaaa ggacttcaca atggacttta    239280
ggaaattaag atggaagttg caatagcaaa agtttagcaa tgcgtattct tacatatgaa    239340
aatcaaaatt aacctagcag tgttctgagc aacttcactt taagaagtaa aactagtgaa    239400
atgataaagg tatatgggtg ctgactgtta cgtaattagg ctgatataat ttagcaagga    239460
tatcagaaat catataccca aaatgagctt tattatattc aaattagtca cttcagaggc    239520
agtacactaa ttacaataag gtaagactgc tggaaacttc tttatttctc ctcactttaa    239580
aacgtttcag agcccatagt aatttatttt taatatcttg ctgaggcaag tcttaatcct    239640
taaggaggca tttatatttg gatacagcca gggttctgtt gagtaaggtc agtgaccaca    239700
ttgtataaca caattttaat tcaaagacaa ggaacagcta taaataaagg tgagcttgtt    239760
tcaactaact ctttttattt tttttttta ttttttttat tttttttatt ttttgagac    239820 agagtctcgc tctgtcgccc aagctggagt gcagtggcat gatcacggct cactataacc    239880
tccacctcac aggttcaagc gattctcctg cctcaacctc ccaagtagcc agaaatacag    239940
gcacgtgcca ccacgcccag ctgatttttg tatttttttt agtagggacg gagtttcacc    240000
atgttagcca ggctggtctc gaactcttgg cttcaagtgt tctgcccgcc ttggcctccc    240060
aaagtgctgg gattacaggc gggagccaat gcgcccagcc tcaactaaac cttaaggcac    240120
attgaaaaga aaatcaaaat gcattgagct aaatgccagg catatgcctt tccaaatgga    240180
cttgccatga aggatgtcat tcctgtgcag ccaggtgttg tcttctatgt attttttagaa    240240 tgcccatcat atagtctcac ctttttaaagt ctgtttagtg gaatgttttc taactttccc    240300
atgtacctcc catgtcattt tttgccagtt ctgccttccc taataaccaa tgaaggtact    240360
tgcttcatgt taaattctag gtaatctggt ttctactgaa ttagaacatt cccacccgcc    240420
aatgtctttg aataattaaa ggttttataa tgtggtttcc atacaactaa ctgaatattt    240480
catgtggcta gataaatagg taaattgcag tacagtagca attggtgtag acacttagag    240540
ggtcctaata aattattgca cacgccaatg tgcaatcaga aagaataact gtagtgttaa    240600
gcctcagaca atgctataga cctgaggatg ggcctgtgat ggacggatca atggctcagt    240660
tcctattgga gtttcacatc taggaataag tgaattcacg actattcatc agctgctgct    240720
actgtacgga agtgtgtcca ttgagaagtt gcagaagggg ctgggagatt ggataaggct    240780
tttgcagtac ccctcctttt taaaaaagca gacagggtgt aactctattg caggctggag    240840
tgcagcgttg tgaccatggc tcaccgcagc ctccaactcc tgggctcaag tgatcctcct    240900
gcctcagcct cctgagtagc taggactaca actaggcacc accataccaa gctaattttt    240960
```

```
ttaaataaat tcactgagac agagtcttac tatgttgccc aggtgggtct caaactcctg 241020
gcctgaagca gtcctcccat ctcagcctcc cagagtgctg ggagaacagg cgtgagccac 241080
ggtgcccagc ctcaatacct tttaaattaa caggaagtgg aaaacagaaa ttctgcagca 241140 tgttttctc attagcatga atcactctct ggtgatgtgt tcatggtttc taatggtatt 241200
ttcaagatgg acaatataaa gacaaccatt agaaaccaca aataatagg ccatatgaaa 241260 caatataata gatgcatgag gttaactggt caacatttat gctgaactta gatttacact 241320
gattaaaaaa aataatccat ttgaagtgta acacacagaa accaaagttc tgtgtgttct 241380
gttatcttat attatcaatg ctccatgcaa tgtgaaagct taaggcaagt gtttctataa 241440
ccaacaccca tgtgaagaaa tatagtttcc atcttcaaag cagtgcatgc tcttttccca 241500
ttctatctcc ttatcctcct ccgtgataac cattattccc ttttactact catttccatg 241560 cttttctta tattttccca atgataaagg catccctgaa tcacataatt aaattttgct 241620
tgtttggaga ctctaaatga atgcaacttt ctattacttt ctggtgtgtt tttttcatgc 241680
ataatactgt tttataaatt tcatatgtgt tgctgtgtat acatccattc cactcatttt 241740
aattgttgta tagtgttcta aagtctgaac ataccacagt ccctatgtcc attttattcc 241800
taatagatat ggttattatt ttgagtttga ggttattata aattcgtgtt attaacattc 241860
tttttcaggc accctccttt ctcacaagca ttggttttct gagacatata ccattatgga 241920
attgctggtt caaatcttca actgtatagt ttatataagg atgaactgtt ttccagtaca 241980
gaaatgcctg ttttcaccag gagtgtgcaa tcttcaacat gtggcagtat aaaagttcta 242040
ttttattttt ctgatctagc gtgtgtacat ggaaacccat tgtgtgttca ctgtgtttac 242100
tctgaggttg agacatttcc atatatctct tggccattca tatgtcctgt ttggtgaagc 242160
gtctgttttt gatctgtttt tctactgggt tgtgtgtctt attgctgtat ttcgattaga 242220
gtgcttcact gattatatat gttgcaaata tcttctgatt ttccttccat gtttttaatg 242280
atttatttaa ataagctaaa gttcttaatg ttagtttata gactttacaa tattttcttt 242340
cagattagtg ctttggaatt tttgtttagg atatcttttc ctaccaagag atatgaagat 242400
ttccttttat tttatctgaa aaaagcttaa tattttatct ttcatattga aaccacacag 242460
ggaatatatt tattgcattc tgtaagaggt ctagtttatt tttccttaga atatcacaat 242520
acaatttatt ttaaacagtt tgatccatgt cactaaagtt caagtgatct ctttgtctac 242580
ctctgtgcca atcatcacat ttttatcttc atgatttat aataatccgc aatttatatt 242640
tttatacttt gtttatttct tgccaatatg cattgcatcc ctgagaaaag tgtttatttt 242700
gcgatggttg gtgcaatgtg ctatatgtct aatatctcaa actgttgaag tatgttgttc 242760
acatactcta tatagttttc caggtggtag tttacatatt ctttcagtaa ctaaaatagg 242820
tctattaaat tttcccacga tgtttatgga tgttttaaaa tcttttcgta tattttccca 242880
aaatttagtt tcttgcattt tatatgctta tgaattttag tggatacagt ctagaatttt 242940
tattgcattg tggcaaatta aggttcttct cattataaag tgatcctctg taagtctgtg 243000
gtgcttcatg ccttaatgtc tgtttagttt gacgttaaca ttacctttgt tttgttagta 243060
atccaattgt gtatagttcc catgtgttta cttcaggcct ttctgttgac tcaggttttg 243120
agtcttttct acatagcgtc tatttgggtc tcataatctt tgattttcaa ccgcagatcc 243180
actgatattt acttttattt ttgatatatt tgtgtttaag tcttctatcc taaattgtgc 243240
tactaatatc ccacttctac atcttgcttg aattgctttt taaaaaatca ttcaggccag 243300
```

```
gcacagtggc tcacacctgt aatcctagca ctttgggaga ccaaggcagg aggatcactt 243360
tagaatcctc caggagttca agaccagcct gaggaacata gcaagacctc atctctatga 243420
aacataaaaa aaaataaata aataaaaaaa ataaattagc caggtgtggt ggtgtgcacc 243480
tgtagtccta ggtactccag agataagagt tgacaggaga gtctgatccc atgagttcaa 243540
ggctgcagtg acctatgatg gcaccactgc actgcaacct ggatgacaga acaagatcct 243600
gtctcagaaa ataaagaaat aaaagacaaa taacattact ccatttcctt cactcccact 243660
tctccctcta cactagatgt taaaagactg tactagtttt agtaaataac cctagaaatt 243720
acaacacaga tccttaatat aatcactaat tttaattaat acattttcca cttctctgaa 243780
aatacccagt agtcagtgta ttttagctcc atgtttatga cctaacctac ttgctgttag 243840
tacctttcaa tgttttgtgt tttttaggaa tcttttttcag atatgattgc ttatcttatt 243900
atttcaatat taattttgat tttctgatga ttacactatt ttatttatgt ttcattactt 243960
tttgtacctc ctactttat ctgtgattat tgtcttaaaa gaatctatcg gtgatctaaa 244020
atatattttc agagctaaca agctgttgga aactctgttt gcatggctaa atgtgtcttt 244080
atgacatcct cttcttgaac aatattctca ttgaattta atttgcaatt acttctttca 244140
gccatctgag aaatcattct cctattctct ggattccatt attggtatgg agaatttagc 244200
tgtcagttta agtgttgctc ctttaaaaat aatatatttt ctgcagatag tttgtctata 244260
tcccccctgat acctttaaga tagttttct ttgagtttct gccgtttcac tgtgatacca 244320
ttaggggttt attaatctga ttggaattcc ttgatgacct tgaaatttgc aatcgtggtt 244380
tcttccattc tgaaaatagt cattacctct tcaaattttg gtgctgtttc tcttgttttc 244440
actctgtttg cacataattt agattttctc cctctggctc cttttttagt ctttttttt 244500
ttgtattttg tattaaattt tactttcaag cttcattctg gattactttt tctcaagacc 244560
tataatctat ttcattaatt ctcttttcta ctgtatctaa tgcatggtta aaccaatgca 244620
tcaaatcttt atgtttgata tatattttca ttacatttca aggattaatt ttagtttctt 244680
cttatagttt ccacattttc gaagttctca attttatatt ttctggaatg cattcttcct 244740
agttatttta aagtctgcat tttgtatttc tattttttc aatcacccctt ttgtttcttt 244800
ctctttttg ctttttggtt tcattgacta atatcttcat ggtctaagta ttataattat 244860
gcatatatta gatattctca tattgttttc cttattctctc actctctatt ttatatttt 244920
tgtatatgac agctccctgt gttgcccagg ctggagaggt tgtgctctgt gcccagtggc 244980
acaatcatag ctcactgtag cttcgatctc ttgggctcat gtgattctcc tgcctcagcc 245040
tcctgagtag ctgggactac agtcacatgc caccatgcct agctactatt ttatacttta 245100
aaattttttt agagactagg tcttgctttg ttgcccaggc tgttctctaa ttcctggcct 245160
caagcaatcc ttctaactca gtcttttgaa tagttgggat tacaggtgtg ggccactgca 245220
cccggttttcc cagctttttt cagatttcca cgatactctc tggatcgttt cttctcacct 245280
cttctcaagt ttgtccattt ttctcttcag ctttgtttaa tctgcccctta ggtggaccca 245340
ttcattttct cattttgttt atttctctga tctagaagtt tgatttgatt tttatttttt 245400
cattttaat acttcttat tccctgcaga tgttttccaa cttttttgttt tcaagctttt 245460
tgaacattct tcaaaaaatt ggttatcatg tatatatttt catggcatct taattccttt 245520
gggatttctg ctggctcttg ttggtgactt cttgtttctt tcttcatggg cttggtaatc 245580
attgtgaatt ggccattgta tttgcaaatg gattagtggc atctttctcc aaagcagata 245640
acccatgggt agcgaaattc taggttcttt catccatggg gccatgctct tccctgaatt 245700
```

```
gttcatagat gttatgaagg tagactgcaa gcacttgcaa gactgaattt agttttgttt   245760
catgtttgcc ttgagggtga aacccatgaa ggtaggaaaa tgttaaaggc aagtatatta   245820
gattgggacc ttcaggcgtg actagggtct gagagttgcc ccattacatg gtgatgctgc   245880
aagaactccc acagtttctt ccagattgga acagtgcact agggcaaagg ctgctttgtg   245940
tgctgggcat ctagctggat catcatttgg tcgtcagtgt gttttgtttt gtttctttgt   246000
tttttgtttg tttgtattgt gttttgagac agggtcttac tgtgtcatcc aggctggagt   246060
gcagtggcac gaacagggtt cactgcagcc tcgaactcct gggctgaaga cttcctccca   246120
cctcaccctc cccagtagct gggaccacgg gtgtgtgcca ctacgcctgg ccacttttta   246180 aaaaatttt tgtagagaca aggtttcacc atgttgccca ggctgtgata atcagttttg    246240
aagctgtaat cttaaatatg attttagcac taaaatgttt ttaagagact taaaaaaatc   246300
acacatatta caatccattt tcaataagaa ggttggtttg aataatctac tctgttactg   246360
ctagatgtag gcttctgatt tattctaata tattacagaa atgagtaggt ggaacatgag   246420
tttataaaga taatgcaaat atttattag cactgtattc tcttaagagc agttcagagt    246480
tcaaagaatt gtgactttat ttcacaggca ttaaaataaa ttaaatcagc aatctcattc   246540
ctaacaactc aaacttcaaa gaaatttcag acagttaatc atcacctgac accacagcct   246600
atgcaacttg ggtttaatta ggatttatgt tactggtagc attgtggttg aaaagatatt   246660
ttcattaaca tttctctctg aagcactgag tcatactctt gtttattcgc aagtttcttt   246720
acacttttca atcaatattt gagtgttcct tgggaaatgt atgtttggct attttggtgt   246780
ttttgagagt gtttgatctt tgaaaatgca tgattaaaag ccatttaga aataaacatg     246840 agtgttttaa atacaaatta ctaaagccac tgttttgttt caaatttagg gatttaattt   246900
ttttaatgaa aatgctcctg tttatatatg catgaggtta tgtaaggtca tcaacttaaa   246960
gattgatgat ggatttagtg ccagctgttg attagtatgt ctgcaatcaa tctacaacat   247020
agcaataacg ctagctacct tggagagtta ctggagaaaa taaataagac acaatgtatg   247080
taattggcct agcaaacttc tttgtatact ataattattc agtaaataat acccttgtga   247140
ttatttatct atcaatcagt cttagagcag tgaatttacc tttaaaatct agacacatta   247200
ggaaagaata atggtagatt ttaagacaaa attaaaattt cttggtgtac tcaaaaatat   247260
atattttctg ttaatgcaaa ttaggctttt atatttatta tttttaatat ttgactctgg   247320
aatgttttca aaatttagtt gagtagatct taatgcaagt ctacttttaa aaaatctcat   247380
tatctagtag gctttactag taattaattt gaatttggta gacatgaaac acaccaattt   247440
cttgtacaca atcataaatc ctgtatacta tgtatactct gtatgcctgt atcttggtga   247500
agtgggaatt aaactttatc aaatttccat tgaaaaactg aagagcaaac taagatgtaa   247560
tcagaatgtt aataaatatt gtagaaatgg aaaagtttca gaatgtttag atttctcaag   247620
gaaatctcaa agcatgacac ttttcattgg tctgtcatgg ataattaggt cttttgctat   247680
ttttatttat ttatttccaa tccgtcacaa acgtactttg gttgatgcat atatcaacta   247740
tagagtagta aatctgacaa agtctatgca ctgaaaacta tactctgtca ctgagggaca   247800
ctgatgaagg cttaagcaac tgggagacag actgtgttca caaacacaac accctcctga   247860
gaagatacaa tattgttaag atatttattt tgtacaaatt aatctacaga ctctttgcaa   247920
tcccaaataa aataacagta gacttttaga aaatacataa attaacaaga taaatttaaa   247980
attttaatga aaatacaaaa gatctacaat aaccaaaaca tttttgtagc agtagaacat   248040
```

```
acttggaggg ctcctgctac ctgagctcaa gacttagtat agagctatat taattgaaac 248100
agcgtattat tgacataaag atgtaaaacc tgatcaatat catagactag agacaccaca 248160
tagaactgta catatatgga caatgaattt tccaaggaga ttcaaaggta attctatgca 248220
ggaatgattt tttttcaag aaatggtgtt ggaaacatta agtatccata tacaaaagaa 248280
aagaaaaagt aaacaaaaag cttttgatcta taactcacaa tttgtacaaa aaacaactga 248340
aaagtgagtc aaatacctag atgtaaagct taaaattgta aaacttccag agaaaaaaaa 248400
aaaaaaagaa aattttgtg actttagatt ttggcaaata tttcttactt aaaacaagaa 248460
gcttgatttt taaaggaacc aattaataca ttggactaca tcaaaactta aaaaaatgct 248520
tatgctacat gaaagacatt gctaagggaa tgtaaagaga attcacaaac tgggaggtaa 248580
gataggcaaa ttaaatatcg gatgaaggta ttgtaccagt ataaatgtat gcatacatac 248640
atatatatga tgcagtttcc tataaatata tagtatatat ggtattagac atatatgtat 248700
agacacgtac tggtacaatt atatactata tacaatat tcatatatag tatatatgat 248760
acagtattgt atactatata taaaatatat catatattta ccatacagta tactacacat 248820
atgtatatat atgatatact gagtatcact attactaaaa attacagaat gtgaactatg 248880
aaaatgtaaa agcctattta aataaaataa atatttaaaa tactgtgttt tttatatata 248940
tagcacatgt agtatactaa attgtataca gtatagtata tatagtatac tgtatcatat 249000
atattgtcaa tatagtatat aatttacccc tgtgtgtgta tagatgtgtg tatatgtgtg 249060
tatatataca catatatatg tatgtgtgta tatatacaca tatatatgta tgtgtgtata 249120
tatacacata tatgtgtatg tgtgtatata tacacacata tatatattct aaaaggagaa 249180
ttaaaaagaa accaccccat aacaattgga cagaaaattg aacaggcagt tcacctagga 249240
aaacatacat atgaccaata gcccaatgaa aatgtgctca gcatcattag tcattggata 249300
aatgcacaaa tgaaaccaca gtgaaatacc actacacatc tgagaatggc tgaagccaca 249360
agactcgcta tgccagggct tggtgaggat ttggaggagc tagagtccac cccaagctgc 249420
tggtggggaa gtgatatgaa accaggactt ttgagaagag tttggcaatt ttttttgttgt 249480
taaacctaca agtaccatgt ggttcagcca tttaactcct aggtatttac acaagaaaaa 249540
gaggagcata tgtccatacc aagaccaaga acctgaatgt attcataggc tggaatgctt 249600
ctgagcagta aaaatgaatg aactgttggt gcatgctaca acctgcatga atattaaaat 249660
gattatgcca agcctaagag gccaagcaat gaagagaccg taattctgtt acttcgcttt 249720
taatattttg gaagctgtaa ttcataatgc ctgtctgtaa gcagataact gttttgcctga 249780
gatgaggagg aggagcaaga gatatagatt ataaagggat atgggtaaac tttggggtgt 249840
gatatatata tatgtacatg tatatatatg tgtgtgtgta tatgtgtata aaatacacat 249900
atatgtatat tttaaacaga gtctcactct atcacccagg gtgaagtgca gtggcacaac 249960
ctcggctcac tacaacctcc acctcctggg ttcaagcagt tctcctgcct cagcctcccc 250020
agtagctggg actacaggtg catgccacca cgccctgcta tgtgtgattg atatttctgt 250080
cacctggact gtggtgatgg cttcataact gtatacataa gtcaacattt attatactgt 250140
atactttatg tacagtttat acttttacaa ctataacttc agaaacccac taccctattt 250200
taaaaaagtt aataattact ctcagccact gtgagacctc actgtttcct tatgctcatt 250260
tttcccttta acaacaatgg ggaactagta ttttatcaga taaaaataat gtttgatagg 250320
attttgtgca aagtctgttt tgcctactaa ttctgcctta tggcatctca gacatgtaaa 250380
ttagacaaga gccttcagta tgtctgatct gttgtcacgt tattttccac tagtttgtgt 250440
```

```
gatttagatt attttaaaag agctgataaa ggaaaggaaa ggaagagaga gatagaagaa   250500
agaaaagaga gaagaaagag aaagaaagag aaggaagga aagaaagaaa gaaagaaaga   250560
aagaaagaaa gaaagaaaga aagaaagaaa gaaagaaaga aagaaagaaa aaaagagacg   250620
cctgtctttt taattccagt tggaagcagc tttagttata aaatttccac tctctagaat   250680
attcttgggg aaaaaatgaa gtgtcaatta aattgatttt tttaacttgc atcctatgtc   250740
tctgaacatg attcttttc aatcaggcat gtagttattg aggacccatt tatgagctgt   250800
gcatacatcc catccaattc catccaattc cgtccaatcc tgtccacaga catgttgaaa   250860
gcatgagctt cctgcaagag caatgcacca gccgttttcc tagagatggg tcttcaaaga   250920
gagggttctt tctcggagca cctgctcagg gaacaagact gactttaaac cagtgttagc   250980
aatatgcatg gtacactgaa ccatctgctg gaggacctcc ttgtgtccaa cacagtcctt   251040
ctgttgaatg tcatggaaaa gactgagggt tgaagcaaat cattttatgc agtgaggaga   251100
agaccgtgct catcttcag ttttgagcc acatctacct aatttatagt caggtttggt   251160
agcctcagca ctactgatat ttgctgcata aatctatgct ttgttggggt tgtcctgtgc   251220 atttaaggt attgaatagc atccccagtt cacacccacc agataccagt atataaatat   251280
ataccgtttt tgccaattaa aatgaataag aaaaaaatca ttgttacaga ttaataataa   251340
taataataat taataataag tggctggaca cagtggctca tgcctgtaat cctggcattt   251400
gggaaggcca aggcaggagg atcccatgag cctgggaatt tgaggccagt ctgggtaaca   251460
tagtgagacc ccatctctaa aaaaaaaatg aaaaattagc caggcatggt gatatgtgcc   251520
tgtagtccaa gctactcagg agactgaggc aataggatca cttgagccca ggtgtttgag   251580
gctccagtga gctagctatt gatggttcca ctgcactcca gcctaggcga cagagcaaga   251640
cctggtctct aaaaaataaa aataagtaaa taagctaaat gctcttgaac tgaaaaaag    251700 aatgtattct atgagagata cctgataatc acctactttg accatgtttt tatccttcaa   251760
ggatttcaaa ctgttacaac aaacttctaa acgtgtatct ctttagttca gcttccttac   251820
atgaatttaa tgctccagta tgtgagacca attattgatt taaaaaaggg tagatctgtt   251880
ttaaaattcc tttaccaata ttcctcatgc tcatgagaaa gatatgaggc agtgctgttg   251940
actgcatttg tatttagtta ataccacgag caagtgggaa aaattcagaa gtgacactga   252000
gttggtcatc tctcaattat catcatgaga agtacgcaca atgtgaacat tctgccatag   252060
ggcttgtctc tgtaaactgc tggtcaaggg gcatggacag attctactat ttttaaaaac   252120
atctttctga acagataacg gaggcttaat tgtagtgtaa acacactgat gtacaaatct   252180
cgaaaaacat aaaataaagt gtgttgagat tggaggtgct ctgttcaact ttcgagggat   252240
agaaaatatg cctatcagct gtaaaagcgg tgcatttatt ttcattttt gagaccaaca   252300 ctagagcaga aagacacatt aacaaaaggg taagagtctt cagagcagat tactcccact   252360
tgaaaaatga gttaagtgat ttcacagcgg gagagaggga tatttgcagc aagaagtttc   252420
attagtcact gaatgaggtt tctctgacat atattttcac agaatgagaa gcatgatctt   252480
tagaagcaag agccataacc tttctatatt tttcttctgt ttattcattt tgctggaaga   252540
ttcccttccc tagccttctg gaaatttcag ccttctagtc tgatttggtg accttttgttc  252600 actaggaaga acatagtccg tttctctttg ccaaaggta gttgcatgca tttgcaattt    252660
aaacaaggaa catccaaaaa aattagaatg tgtgtttgtt gaaatatttg tgattattaa   252720
agtcagagaa gatagctaaa acagaagatg cccatacttt gaaatcagat gattattaat   252780
```

```
agatgctgct tgtgttgac tggagtttaa ctgccagtcc tttcttttgc caagatattt  252840
tcccaaaaga aacatttcag ttgtaggctc aataaggaga ctggaatctg ctttgtgaat  252900
tggtggcaaa aggaaaaggt ggggaaggta ggagaagaaa agagagatgg agccttcagg  252960
taggagacta cttttttcttc ctttggtgtc tcatcttaat atttaaaaaa ttaaattgaa  253020
gactcagcta aggtatagaa aatatcaggc ttttttcttt tgacatataa ccaacattat  253080
ctcttgtcaa gcaatttatt tttttatttt attttttttaa ttttctaata agactaggtt  253140
tattcagtac cctagtaaaa gttttttatta taagtatcca acagtataaa aagtacaaaa  253200
cagacctgta gatttctaat atattaatac aaagtgctta tttttaaac tgctttttttt  253260 ttttttttt gaaacggagt cttgctttgt cgcccaggct ggagtgcagt ggcgccatct  253320
cagctcactg caacctccat ctcccgggtt caagcaattc tcctgcctca gcctcctgag  253380
tagctgggat tacaggcacc caccactatg cctggctaat ttttttgtat ttttagtaga  253440
gatgaggttt caccaagttg gccagcctgc tctcaaactc ctaaactcaa gtgatccacc  253500
cacctctgcc tcccaaagtg ctaggattac aggtacatgt caccacgccc agctaatttt  253560 tgtacttta gtagagacag ggttttacca tgttggccag gttggtctac atgatgactt  253620
cctaaacaag tgcataactt cgattctaca aaagatgaca gaattcatta gtactactcg  253680
tttgtcctca gttatacttt ctgcagtttc agttatctac ggtcaaccat ggtctgcaga  253740
aaattccaga aataaacaat gcatcagttt tacattgccc ttggttgtga gtagcatgat  253800
gaagtctcca gcagtcctgc tccctcccaa tccatcctgc ccaagaggtg aatcctccct  253860
ctgtctggca ttttcatgct gtagagactg cctgacccctt agtcacttag tagtctgctc  253920
agtgaccaga tcatctgtca tggtactgca gtgtttgttc tcaagtaacc cttatttcag  253980
ttaacaatgg ccccaaagtg caagagtagt gatgctggca tagtgttata attcttctat  254040
tgtattatta gctattattg ttaatttcct gtgactaatt gataaattaa gctttatcat  254100
aggcatctat gtataagaaa atgcacagca catataaggt tcagtactat ctgtgttttc  254160
aggtaaccac tacaggtctt ggtacgtgtc ccccgtgggt aacggaggac tcctattgtc  254220
tgtgttttat ttgaagggat tttgattcat ttgtgatctg tttcacgccc tcttcctttt  254280
ctcctctggc aaatttgagt tggcatgccc tccacttaat ctttttaaatg cttgatccat  254340 tctattctgc agaagaatgt taaattttc attatgtcag tcaatatgct tttgaaaaa  254400 gggacactcc tgtttgtgtt tcctcttttaa attcatggtt tagagttttc tcctcttcct  254460
ttcgcttgag cctccccaac tgcagtgtct cctcagtcct ctaactccat gactgtggat  254520
gaaactccat cttgttttc ttcaatgtgc tatttctcaa gtttacatct acaaatgtgc  254580
tgcaaatatc tggtactgaa tgatgtttca tttcagtgaa gcgtttgttt tgtttgttt  254640 tgaaagttaa ttgtgcatgt ggtttaaaaa atccaatata acaaaggca tacagggaca  254700 ccatttgacc atgccattcc caccccttc attcagttgt ttcagcgacc acctttcttt  254760
gttgtggctt gagaatcctt ccagagacgt gactaaacag ccatggaaat gccagtgcaa  254820
cagagcattc tttacatctt gctttttcca cttaataaca taactttgag gttgtcctat  254880
tttgacacat agacatccac ctcattcttc aggaagcctc tgtcacaggc acatatatg  254940 acctaccata attcattgat tggactgcca tggttggaca cgaagattgt tccaaatac  255000 ttgctaccat aaaccctagt gcagtgaaac ttccttcaca cacctttttt tttcttttt  255060 gagagggagt ctagctatgt caccccaggct ggagtgcagt ggcacgatct cggctcactg  255120
caagctccgc ctccctgggtt cacgccattc ccctgcctca gcctcccgag tagctgggac  255180
```

```
tacaggtgcc cgccaccaca cccggctaat tttttttgtat ttttagtaga gacggggttt    255240
cgccgtggta gccaggatgg tctccatctc ctgaccttgt gatctgcctg ccttggcctc    255300
ccaaagtgct gggattacag gcatgagccc ttcacacacc tttgagtggg ggtaggattc    255360
catatctatt ttaaatgtat atagatgtta ttgagtttta gaggactaaa caatttagct    255420
tccaagcata acctataaat gcatcttggc cactttcttg ccaacagagt gtgttataaa    255480
gcatgtcatt tttgtctgtc tcaggtcagt gaaactcctg taaaggacca gatagtaaat    255540
gtgagccaca tggtttctgt cctgactact caaatctgcc cttgcagtgt gagagcagca    255600
atagatgatt tgtccatgag tggtgtggct ctcttccaat aaatctgtat ttacaaaagg    255660
aggtcctggc caggtttgct tcctggatca tagtttgctg accCctggtc tatctaataa    255720
caacaataat aatctttagt ttgtttcttt tgtatgagtt aggctgttca tctgttttaaa    255780 aatctactta ggtattttt tcctgttaat tacatccgtt gctcattttg cataatgcag    255840
tttaactttc tcttgttggt ttattaaaag caatctatat atttgaaact taattacttt    255900
tatatattct gaaaaataat tgatctgtta gctgttgcaa cagttggctt tctgataaat    255960
ttctatttga catagaacca agtaaaaatt atgttacctt gggttgtaac agttactctt    256020
aaaaacattt agatctgcaa ggcacagtgt ctcatgcctg taatcccagc actcttgaag    256080
ctcctggctt caagagacat ccccgccccc accccgcccc cgcccccac cttgtcttcc    256140 caaagtgttg ggattatagt tgtaaaccag caggcctgac cttgtgtaga catggtaatt    256200
gacaagaatc ttgtagtcac attttcatag actatgcagt agatgcaata gactaacttc    256260
tgtatgaatc ttttttcattt tgtattaatt ataatcattt gccaagtttg cttcattcat    256320
ttgtttagta aaagagtatg tgtaaggaat ttggtaggca attttttagaa cttttagtga    256380 caactttgtt tttgattgtt tcttagtgaa agaaggatta caataagaac ttagccacaa    256440
aatacaagtt tccatgagtc actgcaaaat aacagggata gtttggaaag gcaaggagta    256500
accagaagct ttggggcata gttttccctta gttaaatcag tataataaat ggggtacaca    256560
ttgcaaatta tttattcata gtttggtagt ttgcattggt atgtcttaaa cctgaatact    256620
ttagagtgaa tgaagtaaat aggatgagat gatgggggaat gcacacacac ccacacacat    256680
gcacacacaa acacacatgc atgcatgcat acatacatgc acacacacat atacatatgt    256740
gtgtgtgcct gtgtgtgcac atgtgtgtgt atgtatgtta cgtttacatt atttctgcat    256800
attaaacact ttcccctttc gttagatatt ctttattgag aaaatgcact acactagatt    256860
accattactt aaaagttgct ctcgcagcac aaatcaattc attatctta aggataagcc    256920 catgtctgga ggtagggaaa tcatttttta aaaattaaag tttctgtctt gaaatattgt    256980
catccttcac tttttctatg cactaggatg ctctttgctt tcaggaaaac acgttatgac    257040
tcatttaata ctgttgtccc tcttatccag aacagaacat accgtggttg cctaacagga    257100
aggctgcata taaacccag ttttgtctag tatcattttc cccaagtcca ttatgtgtgt    257160
tattgtgcag tgcatgtcca aatgaggatt tgagcagtag agaagaaatt cattaaagaa    257220
atgtgtcatc tccttgcaaa aaggaaagta ttgttgagga aattgttact gataagacaa    257280
aagtggtgaa tgaacatcta ccatttgaag gcatttctct gaagtgaaaa ttaccttgaa    257340
ttgtcttggg atcagttgtg acttgatcct tctattagga gctgtttcaa actcagagaa    257400
ggggtgatga ttcacactga tgactgaagg tttcttggag ctggtgtgaa taagaaggga    257460
aaagtattgc aaatgcatca ttgtggcttt cactgagact cagtggacag aattcatcat    257520
```

```
gatcttcctg ggctccagaa acacaggctt gaaatttagt agccagtctg ccaagcatgg 257580
agttaggcac agatgggatc tgagttagag aactctcctg ggactggtac ccagggaggg 257640
taatgtaggg tgaaatgtca ttgttcaaca tgcttattat tcacctgaac atgggtgaca 257700
ttcctttcct gagaaactct ggtctgacaa atgggttctt acaattattt ctgaaaatag 257760
aaaatgtatt tccataatt attagttata tctatttatt atttctagtc atattattcc 257820
taataattga gctctatggc tattgggtga ggttcctcag ggaacagcgg attctctgtt 257880
actgaaggag tttaaacagt atctataccg agagtagtca agacatgcag agatgatttc 257940
catattataa gagaagttgg attgaattaa gtctgtgatt ccctgccatt ctgagatttt 258000
aaagtccag gcctttaatg taccaattcc ctgtcatcat tagtctaatt attggcaact 258060
acattgaatt atacagtata gtatcagttg atgaatatag tatcaattga ttggtacaac 258120
actgtatcag gttgaattta actgagttaa ggtatggccc taccttctaa gagcttacca 258180
gttgacaata aaagcacatg ggtaggcaag agacacccac attattagat ataactatgt 258240
tattcatgtt acctaaagtt ggagagtaag aagaatgaat ttcttgaggt agggatgaaa 258300
gtatatcccc attccaacag tttagatcca gagaagaaaa aatgtttcag agaggagata 258360
tgattttaaa aattgcttca gaggaaaaat tcagattggt aatggcagcc tagaaagatg 258420
ctaaatgagg aattctaagt caaaggcctt gcagaaagct aggaatgaac atgtcactgg 258480
ttctcatgga aaatgcttag agtcctgcag ggaataaatt cctttttttt tcttttctt 258540
ttattattat actttaagtt ctagggtaca tgtgcacaac gtgcaggttt gttacatatg 258600
tatacatgtg ccatgttggt gtgctgcacc cattaactcg tcatttacat taggttatct 258660
cctttttttt aaatcattat tactattgta tttatttatt tattttttat tatacttta 258720
tgttttaggg tacatgtgca caatgtgcag gttagttaca tatgtataca tgtgccattt 258780
tggtgtgctg cacccagtaa ctcgtcaatt aacattaggt atatctccaa atgctatccc 258840
tcccccctcc ccccacccca caacaggccc cggtgtgtga tgttcccatt cctgtgtcca 258900
tgtgttctca ctgttcaatt cccacctatg agtgagaaca tgcggtgttt ggttgttttt 258960
ccttgtgata gtttgctgag aatgatggtt tccagcttca tccatgtccc tacaaaggac 259020
acgaactcat cattttatg gctgcatagt attccatggt gtatatgtgc cacattttct 259080
taatccagtc tatcattgtt ggacatttgg gttggttcca agtctttgct attacgaata 259140
gtgacgcaat aaacatacgt gtgcatgtgt ctttatagca gcatgattta taatcctttg 259200
ggtatatgat cagtagtggg atggctgggt caaatggtat ttctagttct agatccctga 259260
gaaatcgcca cactgacttc cacaatggtt gaactagttt acagtcccgc caacagtgta 259320
aaagcattcc tatttctcca catcctctcc agcacccgtt gtttcctgac ttttaatga 259380
ttgccattct aactggtgtg acatggtatc tcattgtggt tttgatttgc atttctctgg 259440
tggccagtga tgatgagcat ttttcatgt gtcttttggc tgcataaatg tcttcttttg 259500
agaagtgtct gttcatatcc tttgcccact ttttgatggg gttgtttgt ttttcttgg 259560
aaatttgttg gagttaattg tagattctgg atgttagccc tttgtcagat gagtagattg 259620
caaaaatttt ctcccatttt gtaggttgcc tgttcactct gatggtagtt tcttttgctg 259680
tgcagaagct ctttagttta attagatccc atttgtcaat tttggctttt gttgccattg 259740
cttttggtgt tttagacatg aagtccttgc ccatgcctat gtcctgaatg gtattgccta 259800
ggttttcttc tagggttttt atggttttag gtctaacatt taagtcttta atccattttg 259860
aattaatttt tgtgtaaggt gtaaggaagt tgagactggt agaagactaa gcttcttcca 259920
```

```
gactttaatc attgttatct ggaaaggaat tgaaaatagt ttttttctga atcattgtaa   259980
tcatgtgaaa tcactaaatg tcagtgttga attgaccaca aggaccaagc taattatgga   260040
agaaataggt gggggagaca ttgaacacag caatccacag gagtttgagt aagtctggag   260100
tgttgaactg gtgaaagtcc tccctgcaac agctccatcg gggcaattct gttaagtcaa   260160
gactcaagca ctggacggtg aatggtccag aaaaactatg tcattaaaaa tgcacatttg   260220
tttaaaataa ctaactgctc tttcgtggat gattggtact aagattttat aaactgttta   260280
gggaccacca tgattcctca cacacattaa ttaattcatg agagttgatt ttcttttcaa   260340
acacattgat acattattag tagatagcac cccaacacac acacacacac acacacacac   260400
acacacacac acacacacac acacagagag agagagagag agagggtac ttacaatcaa    260460 agacagccat actagatcca attggtagca acaaagtgag aaaagtacca gaacacacag   260520
gcaaattgaa aatacacaaa gccacatcca cagcatgccc tttaatggag gaagtgggaa   260580
gaaggttcca ttttccactc tgctcatttt cttccccacc acccattaag agtgtcaatt   260640
ctcattcaca ttccttttag agaagaacga accatcgaaa agggagctga gagttgtaat   260700
aaaaatattg cattacggat ttctccagtt tcctttcagt atgaagtatt tgttacttca   260760
ttgaaaaaag tagaagtatt gatcagccgc ttagcttgtg gcttctgctc tcaaggagtc   260820
agcacatagt ctgatgtgga ggaaaatcta taaatggatt tctgcaatct gcaggtaagc   260880
atgggatgaa atgttccttg acatccaacc caggttagaa atcagttttc aagactctaa   260940
atttgaggac ccctaggagc tcaaatgata aagagaagaa ggtttatagt ccatgatggg   261000
ggagggactg cacactacct gcagggtgag cagaaaggat gcaggggctt ggtatcacag   261060
gaccagcatt gtaaatatta caggaagtaa cctttcctgt gtgtccttca tgtgcttttc   261120
tttgtgcata ttcttgaggc ttaaaggaaa gggagccagt ctgtgtccat acttctctcc   261180
cgtgcacatc atcccggcat ggcactgctg atgcaaatta aaaaaataac ctttgactag   261240
aagcattttc ccagctacca gtttccttct ccccagtgca agacaatgtg acagcaaagg   261300
ttcatgcaca gaagcagaaa ggtagtggaa tgactcagct tctaactaaa ttccttccac   261360
cttccttagc tttgtggtct caggatttta taagaggtct ctcatgtgct gctacagaac   261420
cagcaggaaa aatcagacag ggccaagaca gagagaaaag agacaccttt ctcctatatt   261480
gcccctacct agggctccta tccaaagcat gttctagttc ctagatggtt gattccaata   261540
aaataacata aaaataaact gtgcaataaa aatttaaagg gagttgcgct gaccatcatt   261600
tttgaaatat ttaaaaatga gtcctcagta aattttggtg tgaacattag tattttgtca   261660
tggatagagg cacaagaaag gagtaaatgt gagacctaca ttgcatccaa tgcctgcatc   261720
agtagaatct aatctcttcc ccccatgata aaatggcctc attctgtcaa ctacaggctt   261780
tgctagcttt ttctcagaca acagaccaaa tttatcccca gcctgataag gatctttatt   261840
gcatttgctc ccaccccacc tactgtattt agggtaatgg tgaaaatgt acattgatgc     261900 tgaattttat agaaatagta gaatggaaa tgatcttaca gagttgtcat ctactatctg     261960
gtgtaggttt ggttacaaag ctgtatttcc tcttccaagt tttaagtaat caagtttcaa   262020
aacaatcttt cctgacatcc agtttgtgtt aaagccaatt tcccaaatga ttttcatttg   262080
cattctggaa atgcagtgaa gccttgacat tttacaaaat gacctatctt ctactcaagt   262140
caatgaaact acagtaaaca ttttatgtgt agttgcaatg cttgtatctc cctcaagatt   262200
aaacacagaa aagcatcttt ggggaggata tttaaatacg atattaaagc ataacatg     262260
```

```
tgtctgtatt ttttcagttt taagtatact tactaataat aacaggcaaa gtggtacgag   262320
gtaaaacact acttttcatt gttcagttta cagtagtcat tgactattct acatatgcgc   262380
ttagcataat atttacagac tatgtaatac aaatcacact ctgtgaattc tcatgtcctg   262440
tgagacacag gaacagaaga gctttgtaaa aaaacagcaa agtacaactt gaaaagttaa   262500
gccatatgag taagaaatca aagtgatgaa tttactaagt gtttattaat atttaagcta   262560
agtttacaca tgactcaaca tcatattcat actcatagtc tgttactgta ctttgccaaa   262620
ctgtctgtac tattttgtga gaggatatta tctttaatat tgctctcact gcaatgaagc   262680
ataaataaag tatatgtcat gttctacctt tcaggagct ccaatgaaca catgctatgg    262740
tttttaatga ctgtaaagaa aatttcaaag ccatatctta tctgtttcta tggagaagtt   262800
gatcaatgat caataccatt tgcaaggacc ccgatgtgtg acttgtttct ctttatactg   262860
tgacatgttt ccctgaaggt ggaacgtcaa tgagacattc attttctact aaatgaaaat   262920
gatgttaaag ttgcagtcta gtgataaagt taccaagatc tgcttcttgg attttttatg   262980
gggtttgggc aacacataaa gaaactttcc tctcattcaa gttgaacata tccaaccact   263040
tatatatatg ttgcccagtg aggtcagtgt tacatgaagt tgtagaacat ttactttgaa   263100
atgaggtttt ctcatttaat aaaagtgtca ccttgtgtca gtggcttagc tagttccagc   263160
ttctatttta tctcttatcc aatgagaata tgcctatcac ataaggagtg tggctgggaa   263220
gaatggtggt ctgtccttat ctcctgggtt tctctggttt c agaacctgca cagcggacag  263280
ttccaaacac tgcattccac catcatttca tcagcattcc tcttggaata aatgtgtctt   263340
gacagtctct cttagaagtg ctttctctga agctactgag gaccatgcca tgtgtaggca   263400
taactgaagc gtgcacattc tatagagtgc ctcgaagatg tgcacattct atagagtgcc   263460
tccaaggttt tcaagaagaa tggagcccaa cttggccaca ttggttacac acttgtgcat   263520
ggtccattta ttgactatcc caccttccaa gtaatttacc tgcacccgac ttcttgtctc   263580
atgtggggcc tttagagtaa ctccaaataa gaccaggtgg atgtgcagat gaaacgtttg   263640
atgcttgcat gtgcttgcct gattatgact gttaatcacc aggtgtgtca aactactcta   263700
gatgctcatt gtgtgtgtat gacaggtttt ggtgctcttt ctgcttttga taagccattc   263760
aatttaatag ggtgttctct gaatgcccag ctttttcttta aacttagcat gtatattcac   263820
taccccacga tccacctaag acagttgcgt atcatttctt tatgcctgtt ccgtgttcta   263880
tgtatattag atgatttcat atagataagg agggaaagct catattttat acattttaac   263940
tattatgatg aaaaccttat ctagaagagg ttctcttctt tttgaagttg catagcatta   264000
gtaaagctat aggagctatc tcttgtatct gactagaaac gatacacatt taagataaaa   264060
agcatgggcc agtggtggc atatgcctgt aatcccagta cttttggagg ccaaggcagg    264120
aggatcattt gaggccagga gttcaagact agcttggacc acatagcaag ccctccctcc   264180
ccaccctgtc tctacaaaaa gtgaaaaaat tagccagtca tggtggcatg tgcctatagt   264240
cacagctgct cgagaggcta agttgggagg attgctggag tccaggagtt caaagatacg   264300
ctgagctatg atcatgccac tgcagttcag cctgggtgac agagtgagac catgtttcag   264360
aaaacaagtg agtaaaataa aataaaaagc aataacaaga ttgcattatg ctttgagggc   264420
attaattttc aaatttaact ttacttgcat ttttttcctg tcattctttc tgtgtcggct   264480
agttcttatt ttagttgtaa tcttttttta gaatacttat gaatagaata aataccactg   264540
tattcacata gtatatttac tattattttt gtctccttgc attgtatttt aattatctat   264600
gtcagacact ttcctcagtc aaatgtacta ctagccatct aaatggagaa tttatcttag   264660
```

```
gaggagaatt cttctcattt attttttgcat acccagcaaa ttattcggga gtgagtgcac 264720
tgtttcatcc tgttgatagt cttccctgaa catttataac ccacccctga ctggctccag 264780
tctttacacc ttcctcaaga cctaacttaa atacactgaa ctgcctgaag tcgtctttga 264840
attttacatc ctttctctta actctcatac actttgcatt gttttcccat acagggcat  264900
caagaaatag accatattat aatgaatgta caataaagta ctaagagtaa taaaagtaaa 264960
tatattccga agcaggaaag agcaaatgct tgggttttt atagaaggag agaaacgata 265020
atttgagaat gtttcatgga aactcttgca tttgagcaga actttacaaa ttaggcttag 265080
gcttcaatag ttaaaaatta gtgaagagaa catctctgca aagttgaatg ttctggtctc 265140
ctttctgttt gtttagtgag cagaattgat aatcgacatg caagtggctt ttaaactttt 265200
ccaaggacca gtcattgggg aattagtgtg gttcctctga acctttctag taatcccagg 265260
atttgagtat taagaacagt tagttgtgtt agccttaaga tgaaattctc ctaccttgtt 265320
gttttgaaga tgttacttag agggaaggag atgttttggt ctgttcgggc tgctaataca 265380
tcttttttctt ctcaaatttt actttaagca gtcaggagga accaagccat tccttcaaca 265440
cttttcttag aaatagcttc agctaaatct acttttatca ctcacacgat ctgccttcca 265500
caaattacta aaacatgaac acagttcagc caagttcttt gccactttgt agcaaagatc 265560
acctttcttt cattgtgcaa tggcatattt ctcattgcc tctgacagct cataaaaatg 265620
gagcttcctg tccatatttc tagtgtcatt ctgttcaaaa ttgcatagat tttccctaag 265680
atgattgagg ctttctgtac agctcttctc ttttttttc tgagccctcc cctcactaga 265740
atcaccttca aaggtctatt catggcaacg taggctgtgt ctagcataca cttcaaaact 265800
tttctggctt ctacttatta cccagttcca gagctgcttc tgcattttta ggtatttgtt 265860
atcttaacac cacactctca gtaccaattt ctgtcttagt ccactcagac tgctataaca 265920
aaataccata gtctgggggt gggggtgggg ggggtaata aacaacagac atttatttct 265980
cacagttctg gaggctggaa gcccaagatc aaggcagcag aagattcagt ctctgttgac 266040
aacccacttc ctggtccaca gacagtgact tctccctgtg tcctcacatg gaaaaggggt 266100
gagggagctc tttgagatct tttcttgaag gacactaacc tcattcacga gtactccatc 266160
ctcatgatct aacaacctct taaagatgcc acctcctaat accatctcct gggggaaggg 266220
agtttaggat ttcaaggttg aattttggga gaatgccaac attcagccca taaaggaga  266280
tagtataggga aaactacaga aatcaataaa ctcttctact gttttgatta aaatatagca 266340
agtgcatttt tggtgtacat attttacttt atctttgtta ttattcatct agaaaacaaa 266400
cgtacatagt gatagttaat tcttccatga ctttttttgca aaagtgttgg tatgcattgg 266460
ctataagtct cctctctgac ttcataagac cttggaaagc tgccaaatat ctcagaactt 266520
gttgtcttga gtcttaaagt gactaaaatg accttagctc tacctgcctt ataggatgct 266580
ctgcccaatg atgcatgcag tatgcatgtt ctttaacaga gtatgttttg agactgcagg 266640
tttaggcgtt attagaatcc atttgactcc atagcccttt ttatggaaac atacatacat 266700
acttaatgtc aaatagttta tatcttttta ctagctaata tggataagta ctgtctcttc 266760
ccatttgact gtgtgtaact gccttctctt agaactcaac acaaaatgag ctttatgatt 266820
cacatttaca gtaacatgga gacagaacca cctcattcaa aacaggaaaa agcaggtata 266880
agatgccatg aagggaaatg agactgaatg tgttcaattt ttctttgttt ggcttatcac 266940
atatcgtaga gagatgtcct cttacatgca gtagaaaataa gaacatcctt gaaaactcgg 267000
```

```
tttgagcagt tcaaaatcat atatttttta atgttgtatg agtttcaggt gataaatcct  267060
cttcaggata cctcaggggt tcgcaaaaat gtaaaaatat gtttaaagtt tgaaatgact  267120
cacattttt  agtatccacg gcaaagaact gcttttccaa ccttaatagg atttcaaatt  267180
gacattgaca ttttagtaaa tcagaattag cttttctttt ttaagctcct gtgtcttatg  267240
taaatggctg tgctgacttt tatggaattg aatattccag aaaatgtcat ggaacctaat  267300
ataaaacaag ttaacattct cattttcaga tcttaaaggg atatggtgtt aaaatatagc  267360
ttttgatacc catccaacct gtgcaaggtt ttctgtgtat atgcgaattt caaatttgag  267420
aacttagcat gtcgatgaag gcaaatctat atacctgttg aaaacaaaat tgaaattctg  267480
aaggaattat tgtaatttac ttaaataaga actgtaagaa gtcagactgt taatggagtg  267540
tcaatagatt tcttctgaga gcttcaaaat cttttcactg cctttattac aagtctacca  267600
aaatatctgt tagattctga aagccaatct ctcattacaa aaagcattat tcacaatttt  267660
aacttatttc cacaatgaac attctacaga attattgtat ctttgtttaa agataaaaaa  267720
ttctcccctcg ggaggctgag gcaggagaat ggcgtgaacc cgggaaggcg gagcttgcag  267780
tgagccgaga tcgcgccact gcactccagc ctgggcgaca gagggagact ccgtctcaaa  267840
taaataaata aataaataaa aataaaataa agtaaataaa taagtaaatg aataaataaa  267900
ttctccccc  gaggtctgaa atttattatt aatgtgaata ttttaagcat ttttagaaga  267960
aaataatttt gtaaaaaata ttgtaagtta tggaaaatat ggtggtgaag tataacattc  268020
acgaacttgc tagaaccttg ccctaaaaat gaactaatta ttggatcata tggcaaactg  268080
attaagaaga ataaggaact actttatatc atgaaaaaat acatgactat ccacctgcct  268140
tcctaaaact tcttcctctc atgtgccgct attttactta gagttttctt tcgggttaag  268200
gaacaatatc tttagaaggc tattcattaa agtactaatt agaaaggta  gttaattaag  268260
cttgtcacac acaatttata tattttctta tgatgtgtaa gagaaaacag cataaaaaag  268320
ataaattatt tattttcagt caaaataggg cactttttt  gctttcctgc agctcattat  268380
acctaaattc ctttgtgaaa gtatttaagt aagttctttg aaatattgct tttaaaatat  268440
gtttactctt taaagtttta aaaataagga aatgtataat atagtgaaat ttccccatca  268500
gtgtgttctg tgtattttct ccagctcttt cttgaattac aaacagcagt tctacaactt  268560
taccacccac acacacacat ttattcattt gcacatattt cttttttagtg tttttttttt  268620
tttgcaaaat tggcatcata ttaattatac tactctgcaa cttgctttat ttactgtttt  268680
taatatggaa attgactgaa gttaattttc aagcagttgt gtaatattga ttgaacttaa  268740
ttgatatact ataactgatt aaactacctc actgttattt ggaacactta tcgacaacac  268800
tgcagtgtaa aaccctcttt ctacttttgc agctttatga taattctata aataatcaga  268860
caccgattgt gatgcaatcg tatcacaaat tcaaagacac attataatgt cagtggaata  268920
agttagacat acagtgccaa ttaactcagg gttccagggg taattctttt cgtattgatg  268980
aaacgcaaat gcatcttact cattcagagt tgccagggcc ctggtgtaga aatctaaatc  269040
ataaccaaaa caaacagcat caccacgaag aaatcaacaa aaacaatttc atgagggttt  269100
tgagtatttg aataatattt cagtaattaa attttaaagc aagaactgac aggtttgccc  269160
acccccatcca tcctgtgatg tcaaatgcac ggtatgtatc tggctgacag ggaaattgag  269220
gtaggaaaat agaatagata atatgctatt atgtacctgc gcttcagttt gaggaggata  269280
aaattgtttt aaccttatgt ccacattcct ggagtggttt gctagacctg catcagaaaa  269340
tccacatctt agttcttcag ctgttcacat ctcaatccac acagccttttt gtcattagca  269400
```

```
tgccagaaat gcactacatt catgaaagga attactagtt acatcatggt gaatgttagc 269460
atgaactctc attggcccat aacattaaaa tattcaaaac atacaaattg gctaaaatcg 269520
tttagagaaa atgttcacaa tggcatgatg aaggtataaa atccagaaaa tgcctatgcc 269580
tttgacctgc tccagtgccc ataacttgaa gtctctttag tcctacgctc agccatggac 269640
taaggaaaat ttctcattac ctgatgctga ctgagaaaga taaagaaaca ccacttgttt 269700
tgtccttaaa gacttgagag gcaaagagct acatgatgaa agttgtacct ctcacaagtt 269760
tatggaagga gacatatgaa ctgttttctg tctgctgtgg aagtcagatg aatgactgcc 269820
tatatgtgta acacatttgg gcctgagaca cacatgatga ggggaggaat tacaaactat 269880
cactggtctc cttctttttc tgcgattact gttaccttac ctaacagtag gtaactgtaa 269940
tctaaaatga acctaaaaat tgtgcatgaa caaattagct caggtagctt gcaacattga 270000
ctttacagtt tgacctaggg gagccccacg ggctgaacct aatgaaactc agccaggtta 270060
tattaaaact gcgatagcct gtatctctac attttctgca acctggtttc tatataggga 270120
aatgctgctt gtgtttgctg taggcaaatc ttaaataaac catgactcag caagaagaag 270180
agaatgatgt gcagagatat tttagggaag ggataagatg gcagttttga atgggagccc 270240
acatggtaca agtactcata ttccattacc aacttcagga gctttttact ttggaaaacc 270300
atttttcacc ttatttcagt aatatgtcaa gcatttcagg tggtctgcaa aagccacata 270360
gctcagaggc ttagcaaacc tcctcagaca tcaggcagaa acactttcta aacccttaa 270420 tgagtgtcaa gcaggaaatt gtgagtatat agtattaagg agatggactt gctattctta 270480
aatttacaga aaaaaattct ggattttctt cctcagtctc cacttaatga cagattttt 270540 tttaacaaaa agatgcatga cagtacctat ttaaacttac tctgataaat ttgatgaaat 270600
attctttttt taatccagac atctctatga gtttcagaat tattaccctt gtcaaattca 270660
tctatgcttt ttttgtggaa atgttcaact tttgttctca ctgctccctg ccttccccca 270720
tcaacaaacc ctgaatatct gggaatttct caccagctat tatttaactc cattccacat 270780
gtccatcaga tgtcctacac aagattggtt aaatagaagt ttgttcgctg ggagaagatg 270840 acaactttt atattaaatg cataaaaatt ttctcaatac tgcagggtga taaagacaaa 270900
gaaaaggcca atttaaaagg aagtctttag aaaaaataca ataaagcaga aatgcttcac 270960
tttcctacac aatagggaaa aaatttaat gcttttgcaa aaattaaact ctaatgatgg 271020
aacaaagttt attttatact gggtaaattt atgttaggca tgaaactaca taaaaatatg 271080
tggacaacaa agagtgattc agggctgctt aatcgctgtt gctcttggtg tggttttag 271140 gggattgcat aattggtgag ttccttacac gttgatttct cagattcacc aggcaataca 271200
taccagctgt cttggtaaat gcatgaaatg ttgcaatctt tgcaagtcct gcaatttac 271260 ttcaccagta actttccctg gtcaactaac agtatctaga gatcaggcag agggtgacca 271320
atggctgctc tgacgtacac atggagatac tgaaagatgt ggagttaagg atatttgaat 271380
aaatatttca tataatgaca actgtctttg ttagcaagca gaaatatcca ctgtgatgca 271440
aaggcatatc cttatgtcat atatatttgc tgtgaaaggt actgattcgt gcttatgtga 271500
aaacctctta aatcccgaat ctggggtctc ctctccccgt ttttctgga actcagatgc 271560 taaagttgat acaggaggag tggactgtcc caaataaagc agtcgggaa aggaggatcc 271620 attgcaaata aagggtaaaa aaggtacata tgaaatagtat atctatttgc acgtaatgca 271680
ggttattctg gagggtatta aatatctatc agtaactatc atttgttaaa aaccagggat 271740
```

```
tcccaaggat gttagtggat gtatgagaaa gagtttctgg agatatatgt ttgggtgtcc   271800
actacgattg ttgcatttct tttcttcttt gtctctctct gtctctgact gtctctctct   271860
ctcagtttgc ttctctttcc ctttaaacac acacaaacac acacacacac acacacagac   271920
accacacaga atattcccaa cttcttaaca cacaacacca ataaaaaatg ccaataatca   271980
gattgtaaaa ctggcagttc ttttctttca atgtggcttt ctattctatt gtctctcaca   272040
tatcaaagaa acaagaggac aacagatcag gatacatttt gtcatgttta cattatgtag   272100
taacctgaaa caaatgccca gtgagtggag ggtttcttag cttctgtca gttttcaaat   272160 gttttccctc ctcctgcctc cctggctttg ggttggtgat gcacgtgctg gtgctcagag   272220
atgccgtgcg ccctgacaag agattttgaa ctggggcata gatgattgtc cccaaagtga   272280
tctgctcagt tcccataatt ctacacattt caggcaatgg aaacacaatg agagagatag   272340
tttgggtggt ttttggattg caaacttagg cagccacagt ttcaaccagc aatactgatt   272400
tttctcagcc tttccatttc tacccagtgc ataacttata taattttct tccaaaactt   272460 cacaattaaa ctattcctta ttttatgaag ttatcaatgt gtgtatgtct tagaatataa   272520
ttggtgtcat acaaaccagt ttatgcctct ttaactttag tgctatgatc ttaaaaattt   272580
tgactcccag gcaaatatag atataaatat aaatatacat gcattttttt cttgagagtc   272640
aaaattatat atttatatat atgtgtgtat attatatata tgtgtgtata tacacacata   272700
tagattaaat atatatattt catattatat attacagatt aaatatatat tatctatatt   272760
taatttcatt agtcatattg ttttctacag tttgatttcc agttttgcag gactttgtat   272820
tcatattcct gatatcagga aagggtgcat attgacacta cagctcaggt ggaatattta   272880
gaagacacat ggttgtaatt agttacttgc attttcctg aatgcttttt atggtgttga   272940
ctgtttaaga atatcttgca ttgctttcca aacaaatata ctacacaagc agcatttctt   273000
gaatctcgtt gatctgtgtg gtgtgttggt gtggtcttat acaggatttt gtctttttt   273060 ttttttagt gtggttgttt ctccttttt cctttaatct aacaaatatt gaagtacttt   273120 aaaatttta atactggttt ttatggagaa tgagagtttc ctatcatttt cctggggtaa   273180
tgtcatacaa tgcatttctg aaaaaaaaat acttcttaaa ttttgttaat gttctgatta   273240
tttttctgtc attattttgc cactttgtat tatgttacat tactattcca taacctcctt   273300
tgattccagc attgggaatt ggttttcatt tccatggact cattactgag gtccttgttt   273360
ctttcgagat attaaacctg accctgaatt ttttttcttc cctgtgagag tggaaattat   273420 aattctttc tactggttca ggaaaaaaag aaactttact ttctaaagaa tatatttctt   273480
tttatggtca gatacgtttt aaataaaacg aaagctttca atatctgtct gtaaaagagc   273540
agggtttgga attctcattg gtgatggata tgtttatttt cttacctgac acgtcagcta   273600
ctgcagctaa agccagtgaa ctatttctat atcacttact gatgaagaaa taagggctc   273660 tctcatgata ctaagtgtat tgctgttcca ccatccggat attttggct taaaccctga   273720 ggtgttacca gatggtaagg atttagaaa tgctaaaatg ataatagtag ggactacttt   273780
cgatattgtg aagtcagata tatcattgca agttttaaaa aaatggaata tttatattt   273840 ttaagtatct gatttacctt aataaacact ttcatcaatt tcaagagcat ctacatgcta   273900
cattctggtc ctgaattttc atggttaaaa taaagcccca cccagagact agctaataac   273960
tatggtgatc aacagtggac agaaattcag agatactagt tatggtaaca tcctttaatg   274020
ctggagcctt actgtcatag aaacatgtga atgtcaaact aaaagtttaa agccagata   274080 tttcaaaaga gtggggagtg ggagagtata aattaccccc aaggaccctg gaagtgctag   274140
```

```
attctgggca agatccagat atttgcaatt tgtttaactc ccagttgacc atctgagaaa  274200
tattgagcaa gagagacaga gagagagaga gagagagaga gagagagaca gagacagaga  274260
gagacagaga cagacagaga gacagagatt gccagggacc aagggatgat gctagtgaac  274320
catttagcta caaagtgtca atgtatgagg ctggcgtggt ggctcatccc tgtaatccca  274380
gcactttgg gaggtcgagg caggaggatt acttgagccc aggactttga gaccagcctg   274440
ggcaacatag tgagacctca tctcttaaaa aaaaaaaaa aaaaaaaaaa agttagccaa   274500
gcatgctggt gcctgcctgt agtcccagct acttgagagg ctgaggctgg aggatcattg  274560
agtcctgcag ttggaggctg aaatgagctg tgattgcacc actgcactcc agcctgggtg  274620
acagaacaag accctgtctc taaataaata ataagtact atgtatatgc tgactctcca   274680
gccttgccta gtccccagaa gccttgcaac cttccaaaac ttgattgttt ttctcctaaa  274740
tttctcagat aattgagggg aaaatagagc tcagaatttg acaacagctg tccacatctc  274800
ctggaatccc tggcagaatg ctggtgctgt ctcttctctg ggtttcacag ggcgggcata  274860
aattataact ttattaggtt gagcacatat ggcctttagc cccaggagac cctccatggg  274920
gctagtctgt tggcagaggc agcttctgca ctttcattca aattcacaat ccataaggaa  274980
aaagaggcct tcaaggctgc agcctgcctt gggcttccgt ggggcatctc ctatcattgc  275040
caataatgct gtggtgaaac ccaggccaaa tattccaaca tcttttttgct gcttgtatga  275100
acacgatgca tattgcagtt caaaactagg aaaaagaag agcatattac aggcgaacac    275160
gaatgcatca gaatatggta cctttaaatt aaaagagaag gctcttgatt ttgaattctc   275220
aagtgtttct cttcaaatac acacaatgat gtctttcact ttaattttaa ctattatgga   275280
tacataatag atgtatatat gtatggggca catgcagtgt tttcctacag gcatacaatg   275340
tgtaataatc aagttagggt aattggggca ttcatcacct caagtattta tcccttctct   275400
gtgttaagaa cattccaaat ccactcttta gttattttaa aatatacaac agattatttt   275460
tgactatagt cactctggtg tgctatcaaa tagtagattt ttttttcgag gcagggtctt   275520
gctttgttac ccaggctgga gtgcagtttt gtgatgatag ctcactgccg cctcaatctc   275580
ctgggctcaa gcaatcctcc cacctcagcc tcctgagtag ctgaggccac aggcacatgc   275640
taccacagct ggctaattat tattttttta attttgtgta gattaggtct cactgtgttg   275700
cccaggctgg tctcaaactc ccgagctcaa atgatccccc tgccttgtcc tcccacagtg   275760
caacgattac aggtgtgaac ctgtgcccgg ctgataggaa ttttgatgg agtttcccaa    275820
tatctgggct ttcaaagatt ttggatagtg aacgagatac tgcaaagatc tctctaaata   275880
tcaccagcct gaccagggac cttgtgttac ctatatgaat acactgaggt tgctgtctgt   275940
ttctctgtta atgtataagc agagaaagtt acattgatgc tcatcagatt ttcagtttaa   276000
tatcagagca ttgcaaatta aaatataagg tgcgggacat gtacaattt actgcggggc    276060
atgcaaaacc tgagggcccc caaagcagaa gaaggcattc ggcctctagt ctgcatttcc   276120
tccctcctga gttgccagcc agccagccag cctgtcttac agattccaga cttgccagct   276180
cccacattgc atgagccaat tccttaaaat agatcaattt aataaattta acctatattg   276240
gtgaacaaat ttagcagaga actttgatat acattagtac cacttattat ttttagaaaa   276300
attggaattc gaataactaa cactaaagtc taattcgtca tctggtgtgt atgttataaa   276360
tgcacaccca ctcaccgaga cctattcaca gccacagcct catataaaaa taggcaatag   276420
atacaggaaa tgagaagcag ccatagaggg tcttacgtaa gaaaccccat ccttctcaca   276480
```

```
cctactcaag aacgttgttc ccaacatcta catcttttgt agtttatatc cactgggcgc  276540
acctaacatc acatccacat tcttttgttt atcccgtttg gaaatacgtg cctgaccttc  276600
actttctctg cctgatgtgg ctgcatgttt ttgtttctct ggcaaccatc tcctcgtctt  276660
ccaagagtcc tcaccgatca catctcaact cctctccacc tatcctttct taaattcact  276720
ccaatcagta tatagcctca ccacttcacc agactcctct tgccaattat accattgcat  276780
cctaggcccc acaaaagtgg agttgctatt cctaatgttt ctaaaaaatg gccattctgc  276840
attttccctc gaatctccac tgcctctatt tttggaaaag agtttcatct ttgaaaaagc  276900
atttaagacc aactttttc ccactctgga gggaaatgaa atattgctga atgcagagga   276960
tatctccaag gcttcatact acttgctctg gcaatatttc cagatcctta tcctgcagca  277020
tttgcggtag ttgtcccct agaaatcata gttgaaacct actcctcaac tgtgtaggta   277080
tttggaagtg gggctttgga aggtatttgg agagtggagc ctcatgagtg gaattcctac  277140
cattataaaa gggaccccag agggcaccct cgtccctttt atcatgtgag gacacagcaa  277200
gaaggcgctg tctatgaccc agaaagtggg tcctcaccag ccactgaatc tgccatgcct  277260
tgatcttgga cttccggtct ccagaactgt gagcaatttt ttttacaagc cgtggggtct  277320
gcagtctttt gtttttagcag ccaaaagagg taagataggg catgttggga aggaatggag  277380
atgtccacaa acaccctgaa tcatatactg ctccccaacc ccccgtcctc ccagcagaga  277440
gagcaggaaa gagaaggctt acttcctcca ggttcgatgc tcttctacac acagttatga  277500
cagacagatt gccttatatt tttattcttt ttagttcatc tgaccaattg tcaaattgct  277560
caaatgtcag aaaaatggct caagggccg ctatggattt ctgcagtaga aaagaaaag    277620
acagaagact agatcccaat gtgttcctgg actggaagaa agttcttatt ttatggagcc  277680
ataaataaat atgacatttc ttgtgcctga gaatttgagg caggtagtac tcctgtgaag  277740
taagataatg tcttctgtaa aagaataaat tcattaaaaa ccatgggaat cattgtaagt  277800
ttcattgtca agaaagaaac agacatgatt ttggatgtag gtgaatgtta attattgaag  277860
atgattattg ttctcagaac aagtttattc tgattcgtag ccacagcagt tcaagagaaa  277920
agcaataaag gaaccacaac catatgaccc ttcttataat catgttgtgg tggggatgtt  277980
tcttctccgt cctacttcct gagaatgaca gaagggtttt gcaagagtga aggcagctgg  278040
gaatatattc cagccgcttc catagttcat gctgtggtaa ggagtttcaa ggtcacagtg  278100
aggcaaggag tttcaaggtc acagtgattg aacactagaa cttgtgcctc tgttctctgc  278160
tgaacgtctt ccatgactgc tacatcaggg cttggggttc ccactgacgt ggtgtttaag  278220
taacatttag agtccttatg gttatacact ttcatctcct tgtacagaaa gtttctggaa  278280
actgcccact attatatgac acatattaac ctgttgaatt tggttatttta tgtgaggaaa  278340
ccacagaaaa ccataacaaa tcaaaatacc taagagccac aaatttcctc cagtgcagcc  278400
acatcccata gacaggtaat gtgcactaca tgtgtaattt taagtttct agtagttgca   278460
ttcaagagtg cccgaagaaa ccattgatac caattttaaa aatacattta atgtatccca  278520
atatttataa agtactaagt cagcagacaa tagagacaaa atatagtttg catatttttt  278580
actacatatt tgatattcag agtacatttt acacttacaa cacatctcgg tttgaacaag  278640
ccacatttta tgtgctcaat agccacatgt ggttattggc tagcattttg gaaaacacag  278700
tgctagaaaa tgcattcttc ctgccatgat caaccattgt ctctcactta ctcctgggca  278760
actgtgttct aattgatttc cgggcattga ttattgcctt tcaggagaa caactgatca   278820
ccgtattata gtaggtcatt cctacacatg gccttcaggt cccaaacccg tctgatttgc  278880
```

```
taagccgttt ttccctcttg tcatgccatc ttcccttcat ttgctacatt ccaggttttc 278940
tagtctaatg cagtcactcc aggcactctg tacttgtact cagcatttac tgggtggtgt 279000
atatctgtcg taggctgttg gttgtaagtt tcatgacagc atacactatg cctcccuttt 279060
tccacatgca ccaatccatc aaacctcatt gaggacataa aacacagcat ataaagcact 279120
ccatcgattg aattgaatta atgtgtgaac aattgcacct gcaagtgtaa ctgagggctc 279180
acgtggttgt catgtatcat ttttaaaatg tttaaataat gcgagttttc atctatattc 279240
ttattacttc tgtagaaatt aatctataat atttcaacag taacatggtt gaaattgagg 279300
ccttatgtaa tgtttgaaca caatgataa cttgattctg aatcaacact gtatgtgcga 279360
tttgatgtct gatgtatgat ttggggcagt ttgagggtca gtcatttatt tgtactgagc 279420
ctctcaaatt ccctgtatgt gaagggaaca gttgagaata agtgtcttca gtggataaga 279480
cagtcgtctt tatccctgga aggcatcacc aactgatcac agcagtctgt ttttctgagt 279540
caagaggcaa cttcccctct atgtaggata ctactttag tgtagtgtgc tcttccatat 279600
ctattggaat cattacacct gatcaatcag gtttaagata aagggtgtga tagatagaaa 279660
tggatgcaga tgctcttgca aattgagttg aacccttgt ctttgcatct tgtgctggcc 279720
tcagtgactg tcttcttgaa tagaatgttc tgggagtaaa gcactgggac ttccagggct 279780
ggatcataag aagctattaa gcttccattt agggcacttg gagtactgac cctcaggca 279840 ttctctcttg gaaaccacat ctcatgttgc aaagtgttca gccccatgg agaggctatg 279900 catggtgctc cagtcagtag ctttagcttc actcccggtt gacaaccatt agtaccgcca 279960
tgtgagtcac ccattgtgga catcccagct gattgaggac tcctgtctct tcctatccct 280020
tagctgacta aggagatctc aagagagaac ttctcagcta agcccagtca gctcacagaa 280080
tcatgggaga tcctcataaa aggttgtttg aagccccaca ttatgggcat gtttgttaca 280140
caacattagc taaccagagc aggcactgaa actggaagtg aggttctgtt caacagaaa 280200 cctaaagtac atggtgttgg tgttggaccc tccatagggc aagactaaag gcttgaagaa 280260
caagggaaga aaattggagg ctggggaaat ggaatggaca aagagaactc tttgaatgac 280320
tcactcacag ccttacagga cgagaagtaa cttttagcac tgtgcaactg caagcaaact 280380
ggattttgtc ctttaaaata gaaagatggc atctcaaaga acacatttgt catgagtagt 280440
tcctaataag cataatactt aacataaagt tcactggcgt atgttattta taatcttact 280500
atagtataat ttccattgga tagcaaaagg tcaaggatat aattacagaa atatattctt 280560 ttaaatttc ttttggttac acttaaatgt aaattgtgaa caccattta tttctattg 280620 tatcccatga cttttctatt gtttgggtca tattaaatct attttacag tataaatttt 280680 gcagcatata ttcccacagg aaagaacaaa ttataaaaca cacagtttgt atatgtcttt 280740
cctttaaaag tgaaatttta actagttttt cttttttttc tgttactatg tctttccatt 280800
ctttggttca atacattccc acctactctt gaacgttttt tggaaagttg gcaatgaccc 280860
tttaaattct tttcagtctc tatctgccta acatatattt aggttccgta tatatttata 280920
tcatttccta cttaaataca catatttcca tttttgtgct catgctattc tgcaaatgcc 280980
tgcattttaa ggatgagaca tacatttaaa aagggcatct atgccttctt tcagaatttt 281040
ttttctaaat atctattact ttgatatttg aaattttgta cccacaaaca tacacataca 281100
cccatgtgtg cataatatac atctcacaga aatgccagcc atgtcgggaa aatgacagct 281160
ccatcagaaa tgtctttaca tccacgtaat atatcttatt tccttgtata aggcacagat 281220
```

```
cctctgttac caatatcaac ttatccccag gctctaaatc acttgaagct actttgatt   281280
ctctggagaa tttcagaata tattttttc ctcaaaattt catgaacttg tatgcatttt   281340
gtgcctcaga cttgaacgc cttggacaaa ttcctttatc cctgtgaatt tttaacgaat   281400
tctaaacaaa atacctgact ccactttccc cccaaatttc ctgaccttgc gtgcattttg   281460
aactgcagac ttgaaaacac ttgtgcaaac gttccttcat ccctatgaat ctttaatcct   281520
aaacaaaatg cctgtatcaa tgctggcaag gttgtggaga aaagggaatc cttatacact   281580
attggtggaa gtgtaaattg gttcagccat tgtggaaagc agtgtggcca ttccgtaaaa   281640
agctaaaagc agaactacca ttagacccag caatcccatc cattactggg tatatactca   281700
aaggattata agttgttcca tcataaagac acatgcgcac atatgttcat tgtagcacta   281760
ttcacaatag caaagacaca gagtcaactt aaatgtccct cagtggtaga ctggataaag   281820
aaaatgtggt acatatacag aatggaaaac tatgcagcca taaaaagag caagatcatg   281880
tcttttgcag gaacatgaat agagctggag gccattatgc ttaaccaact atgtcggtaa   281940
cagagaatca aatactgcat gttctcactt ataagtggga gctaaagatg agaacacatg   282000
atcacatagt agggaacaac agacactggg gcctgctgga gggtggaggg taggagaggg   282060
agaggatcag gaaaaataac tattgagtac ttggcttagt acctgggtca tgaaataatc   282120
tgtacaacaa accccatga cactagttta cctgcataac aaacctgcac atgcacccct   282180
gaacctaaaa taaagttttt aaagaatgcc agtatccact acatttatgg gcggtctttc   282240
tgagtttcac ctcagagaaa cactcctaaa attcaagtta tgactattta gactatttgt   282300
taatgatagc tctgtgtgtg tgtcttagcc ccctctctgt ttcctatgtg ttctacttga   282360
tttttaaata aactatagga gctccacata ctaatttgat tctctacata aaatggtgcc   282420
atattctctt atttttcctt taggatttgt acagagactg tacaaaatat ttttttgagtt  282480
gtgtaatggt atccaatatg gacaataaat gataagtaaa ttttggaaaa atcagttaaa   282540
agaagtgtaa tagatacata ggtgtcttaa ttgttttccg tcctcaagta tggacgtttt   282600
tgcaaagaca cgagcttttt acttcaggag acatttgtcg acgtctggaa aaatttttgg   282660
ttgccacagc tagatcatgg gggtgggtat cacttgcatc tagaggacag aggccaggga   282720
tgcttttaag ggacccacaa ggcacagaac agccccccat gacaaagagt ctttcatcta   282780
catgtgtcaa tatcgatgag attgagcaac ccaggtatag agtaatactg atgagcacaa   282840
agtatagctt gaagcctctt tttccatatg gctgtgatag attgttttaa atgatcattg   282900
gaagaaataa acccttggtt ctatggaagt catgaggaat attctgccca tgtgcttgtg   282960
aaacctcagc ttggagcaaa gaggcgaata tcatgcaagt ggcttcctag aatcatgggg   283020
ttttgtacag attatttcat catccaggta ttgagccaag tacgcattag ttattttttt   283080
gatcctctcc ctaccccac ccttcaccct caagtaggcc ccagtgtgtg ttgttcccct   283140
ctatgtgtgc atgtgttctc atactttagc ttccgtttat aagagaggac acgcagtatt   283200
tggttttctg agctggaggc cattatcctt agaatcttct atgttaaaaa caacagagca   283260
cctcctggct ttcctgggaa tccttgtttc ctgattccag acaagcgcca tggctgtgaa   283320
atcatgtatt tatgtgtatg ctgttggatt ttaatgtgaa atacctttc actgcgccaa   283380
gttcgcttcc aaatgtgatc ccgccaggct gaccaacaag gcattcagtc agcctacttt   283440
cttatgccgg gacctttcac aaaatgaatc atatgtcact tttctttca gaagcatatg   283500
ccattttatt ttattctggg agtttgaatc acaccatgca tctgtttag tgttgttttt   283560
agtaagttca ctatcagtgc ttcctgagca tggtttctcg tatgggtac tcactgacct   283620
```

```
gtcccatcca tctttcttc ctataaagcc tttactgcta tacttgtcta cttgcagaac  283680
ctccacactt tttatgagct cccatttttc tctcttcttg gtatttatca ttacttattg  283740
tgactcttgc atattggatg gtcaaaagag atccccagtg gttacactac aacaagataa  283800
atgtaggtat acttttctta attgttatta gtgttactta ttattttgtt ttattagaca  283860
ctactttcaa aggctttaca gcactgggta tgtgttctac cttttctt catttatcc    283920
tccacaacag ttctgtgatg aaagtactat tattaacttc atagtttaca cgacaaagca  283980
tggtttcata acttgtcagg atttcttagc cattatttga taaaattagg gatctaaatt  284040
ctgtcttcta gctccaaaca gatggttctt tccatgctat ttgctattat cttgtcaaaa  284100
gtaatgacaa aatagaactc aaatagtatt tttcttttgg ctgatttctt ctttcagacc  284160
agagaggttt ccaaggttaa agtagttcat taatttcaat ttcttcttct tttttttttt  284220
ttttttttt ttgagacaga gtcttctggt tcttttgccc aggttgaagc acagtgacac   284280
catcatagca cactgcagcc ttggcctcct aggctcaagc agtcctcctc tcttggcctc  284340
ccaaagtgct ggaatacagg ggtatgccac catgtcaggc tacttttat tttatttt    284400
ttaagagaca gtcttgatct gttgcccatg ctggtctcga actcctgggc ttgaacattc  284460
ctccctcctt gacttcccaa agtgctgaga ttacagacat gggccaccat gcctggcctt  284520
aatttgggta tcttctaatt gatgtggact cttatgccct attcatttgt gttttgaagt  284580
gaactgactc tgaatgtcag tgatagggca ctgcttagtg ttggggtgg ttaggaagat   284640
atgcaagttt cttagagaat aaagcagctt gctgttcaca gcagagggg tgtaactgtt   284700
tcaagaattt tagaatacta ctgtctgtga gttctgcaag aagttaggga agcctccac   284760
tcctggttag actggcagca acttttgca ttataacaca acagacattt catgtccaag   284820
ccaggtaatc tgagctaccc ttgttcattc cagatccagg gttggtgagg caaaagggt   284880
gtccccaaaa tagatgggtc tcttttattga acttctgggt tatctccatc atgtacagag  284940
atacagaatc atgcatttat aaactttatg gttgaagatg gcacccacag ttacagttc   285000
ctcccaaacc tccctggcct atctcagttc ttaaagatgt ctggggattc ccagttaggc  285060
atagagtaac aaggcagctc tatccttaaa tgatcatggc aagctgccat atggctggta  285120
ttcatcctca gttaatgtgg atattctagt aggagggcac agtgacatag gaagaaatgg  285180
tcactctgtg ttcaaattat tccttaact tagaaggcaa gttaccacc ctgtgggtac    285240
tgagcattgc agacttcatg taagcatatt tttgagcatt ttctacaaac cctcatttct  285300
ccaaatccca tcctttgcaa cctcaagttt atccagggga ttcacactgc ctgcatgtcc  285360
ttgtatgcgt ttcttattgt tcctgtaaca aattatccaa cctgtagtgg cttaaaacac  285420
acgcatttgt tatctcacca ttctgaagct ctgaagtgtg agtagctcgg atggtttctc  285480
ttcatcatca cccaagggtg atttctgtgt gttggcagaa aggctgtgtt tcttcctcca  285540
gactccaggg atgcatccac ttccaggaac atttggttg atggctacat ccagttccat   285600
ggggttgagg ttcctgcttc cttgcaggct attggctgag ggcaaatttt ggcttcttga  285660
gaaccgtagc attccttgac tcctggcctc cttcctcccc cttcaaagcc agcagtggca  285720
gcttctaatg cactgaatct ctccgacttc cttttctacc tcttgtctcc tttcccaagt  285780
tgcatggctt gtctggactg attgttccat taccattttc ctgcttctca gtatcatgga  285840
cccacttgga tattctagga taatcagctt atccttgacat cagctgccta gtaaccttaa  285900
ttatatctgc aaagacaatt cacaacagta cctagattca tgtttgattt aataaccagg  285960
```

```
ggaacgagaa tcttgggtgg atgactttat aattctgctt accacattcc tgtctataaa    286020
ctaatcttaa ggttggtgga caggcccctt acaactgact ttgagtaccc agaacactgg    286080
cttcctatct ttactcaacc agtgggctcc tccaggaaaa gcccaatcaa ggaagataac    286140
gccattattc tcatgctttt cctttcccct tccctcccct tctctcccct ccctcttct     286200
cccctttcct ttccttctct ttcattttga cacagagtct ttctctgtct cccaggcagg    286260
agtgcagtgg catgatctcg gcccaatgca acctctgcct cagcttcccg agtagctgag    286320
actacaggac catgccacca caccacctaa tttttctatt tttagtagag acgaggtttc    286380
gccatgttgg ccaggctggt ctaacctcag gtgatccacc tgcctcagcc tcccaaagtg    286440
ctgggattcc aggcatgaat caccatgccc agcatgtcat gcccttcga agtctgggta     286500
ataatcctca gatggtagtg cacatagtta tggagaatta gtgaaccact cctccctgat    286560
gtggctcgcc cccactgcaa ataatttgtc tatttttatt tttattttta tttatttatt    286620
cttttttgag acagggtctt actctgtcgc ccagtcttga atgcagtggt gcaatcatag    286680
cccactgcag cctctacctc ccaggctcac gtgatcctcc cacctcagcc tcccgagtag    286740
ctgggactac aggtgcatgt caccctcgcat gactaatttt taaatttttt gttgacgcag    286800
gatgttgtta tgctgcccag gctggtctta aacttttagg ctcaagcagt tctcccacct    286860
aagcctccca aagtgctgaa attaacaggt gtgagccacc cagcctggcc tatttgtcct    286920
ttttaattta aaagactcaa catgtagaaa ccatttacc ccttcacctt gtgcattaag      286980
agcttccttt ttcttaacat cctgctcctt gaaatcaacc cactctactt gtatggcagt    287040
tgttatttta atatttctaa ttaagataca gttttcattt taccttacag agacagtgag    287100
cgggtgctct tgaattccag tctggctttc tccattcctt tgggtaatca caggttaact    287160
tttttccttc atcagttttc agcagtcagt gaaaggtgca ttcattttca taaatcagcc    287220
atttggcaac atttgaatgt ttaatcagtt tgcgatcaca tcaaagaaca agggaagttc    287280
ttgggagatt tattacctcc tttggaatct gtgttcttag ctacaaaggt gcaatgactt    287340
tttctagttc tctgccccag atgtctgaac tgttaatatt tacagtgctc ctttcctgaa    287400
attcagagtc agcacctcat tttatcctat ttgtatccca acttacttta ttcaaagaga    287460
ttttacaacc tgagatagct ccgtaggaag agttcagttg tcagaagcaa tctgatccat    287520
ggaaattttc tggtgtttgt ttttccttga attaatttgc aggtttaaat tcttgcttag    287580
gccactctag gactttaat tgctatttct taggaaatat tccttagaac atgaagcagt      287640
ctgtctttca acacacacac acacacacac acacacacac acacacacac acacacacac    287700
accccctagc atacgatcca gaacaacgtt ttatcttttt tttttttttt tgtaggaggg    287760
agtgtctcac tctgtcaccc acgctggagt gcagtggtgc cctcatagct cactgcagcc    287820
tcgacctcct gaacccaagt gatcctccag cctcagcttc caagtagct gggactagag      287880
gcacacacca tcacacccag ctaatttaat tttgaaaaaa cttttttttt tgtgagaca      287940
aggtctccat gttgctttgg ttggtcttga attcctgggc tcaagtgatt cttctgcttc    288000
agcctcccaa agtgctgaga tttctggcgt gagccaccac acccagccct aacattttat    288060
tcttttactg actgtgagat tttcattgac ttacgctatg tcaggcagac ttttcaagcc    288120
ataacctggc tttggtgatt tattatttta gctcttcatg ttttaacagc ttctctgcta    288180
ccatgatagg ttataataag tgatagaaga aaggcatttt aaagtaattt atgaatgtgg    288240
atctcatttt gcttagctaa aaaaaaaaaa gttttttttt tttctagaga atagaaccaa    288300
acagtgttca ctgtatcaca tattcctttt agtgtattga gcattaatgg ggtattttg     288360
```

```
cagcatcaga tcttcacaag gctggggttc atcagcagca cagtagctat taggtgattt 288420
tactcaaggc agcaaaattc gtttcttata acacagtctc tattgaagac acactctaag 288480
gcagtttgcc tcatctattt agctttccaa aattctctct taaattgcag tttaatgaat 288540
agactaaaac acaattttta agaaaaatgt agttataaga tatgaagtgt cttttaaatc 288600
tgccagtggt ttaagggata gtatacattt aaaataaagt tataggcact gatttagtcc 288660
tggaaaataa tggctttatt tcaataagcc agtatcagaa attagttttt gttttctttt 288720 ttttttccg tgatgaaatg tggtttctag tactggataa gaaatgcatg agaaataatg 288780
tatcccagca tatttaatat gcaacagtgt gatctcagta gccttgcaga tggctgagct 288840
gaggcactaa aagtgatgag atgacatttt gtatttttcc acacgttctt gcccattctc 288900
aggtgagtct gggctctcat cagtatttaa atgctgtttt accttggcaa gacatttagg 288960
tccagaaaat agtttaaaaa attaacatct acgcagaaag aacctccagg tagttaaaaa 289020
tagggcaatt gcggataca ccacatcctg aagacttagt gttgctaagt aaaccacatt 289080
attttaggtg tttcttcctg acatttttat tttttttcttg tgttatttta attctggaac 289140
ataactggga actgagaata ctacatggga cccttatctc ttttctttgt tatgactgaa 289200
aatcataatt tgaaagatgc ttggaaaagg gaaagcttaa tatcttacac atatttttat 289260
aagacaaaaa tatggaaaga tatgaaccat aaaatcagtt tagaatggga agggttagta 289320
aaacattttt tttgagcaga aaaggaatca tggaatggac actttataat atagtaattc 289380
agccaattta tttgatggaa ttcaaatgtc atgtcctctt tgtagctaag agtgcacatt 289440
agcattaacc ctaaaccaga ccacttggag ccaaagagat gtgtatgtgt gtgtgtgcat 289500
ctgcttctgt gtgtgtgtgt ttgccccatc tgagtgattt gattttttcac catctctcta 289560 tttttccact tccaaaattt aagcatttag acatttatta tattaaatat gtttgcattc 289620
tccctccctc cacatgcagt gttttacaaa tttcctatca gactgttccc atcctgcaaa 289680
cccccagagc tctatggctg aggtactcct ctttctgttc ccttctccat gcagatggaa 289740
tgtctgctgg gaactatctt caatctatat gtttcccatt cgtagaggtg gctaaatctg 289800
tgacatgcat ccatcctcat ccaatagtgt ctccacatga gtgagctgga taatgcaaaa 289860
ccaagcttcg acatcagtgg tatgaagtac acacacacac acacacacac acacgcac 289920 acacacaaat acaaacacac ataatctctg tagctcagat tgggattgtc tagggttaat 289980
atcttttgtg ctaaaaatat ccctgtgcca cattgaagct tattataata attattaatt 290040
actgatatat ttcaactgtt atgtctccta aaaatatgca tagattatta agttttccct 290100
tctccttgtg ttttttctgat tatgattttc tatcataaag gtgaaagtga taagggtccc 290160
atgtagtgtt ctaactctaa acctaatact gaccctaaac agaattgaac gctttaaact 290220
aacccatggc ctttgaccat tgcttcttga ccgttgagtt aacccataac cctgaacaga 290280
gaatgagaaa ttgaacccaa atttgaaccc aaacccctaac tagtgactgg atatgaaacc 290340
taatcctacc caactttgaa aaagaactca attctaaact caaaagcaaa gccaaccgaa 290400
cacctaatct aactttaatg taaacctttg aacttaccct taactttgc cagtagccct 290460 tgactcttga cccctgatct gaacactgaa ggcatccccc aaattctccg acccatggcc 290520
tttgatccta atcttgactt ttgatcactg tccctaataa tgaatataat cccttgatca 290580
taacattgaa ctttgctcct accctgacat tcaattagtg atctaaccat accacaacct 290640
gaacttgaac ccaaatccta acatgaacct tcctccatac ctgaaagcta tcctaaccct 290700
```

```
tgacctttga tctttatttt tctccttgac tcctgactgt gagatcccag cctggactaa    290760
aatgtataca cacactcaaa atctttttg ttctgaatcg ttacccaaac ctgaacttga     290820
acccaaaccc tgaccctacc caattacaaa tctgaataca aaacctatcc ctattctaaa    290880
gttggggatt tgagtctctt agtcccgtag ggtagatgtg gtgtttgcag ccctgcagcc    290940
actatggaca ccacagactt ggacaaaatc tccaacgtat ttttgggaaa aaggatgca     291000 accattagag aacaagatgt tgaaactttc atccataatc tctgtttgta cagacttcag    291060
ggtgaaatac atgtggttgg aattgtgata tttccagcca caaaattgta ttatgttgag    291120
ataatgtggg tttccctatc cctgaaaatg tgttcatcca accaatagtt acttgtacca    291180
gcagtgcacc agggaccatt ttgggttcct ggaggcagcc gtaagcaaaa gcatcccaga    291240
tccctgcttc tggaatccct gactatggaa ttggcatcct cataatgaat gtaataaaga    291300
aataaggtaa ataaagaaat aatctagact caaatgtgaa ctttagtcgc tctggaagtc    291360
caaaccctgt ccaaacatgt ccgccgatta ctttcagagg atgggtgatg actcaggtta    291420
atatggttat ttttggagcc cgtcttacct attgtccttt atagatgatg tgttttccac    291480
ctcagatatc aacatgaaag actgggtcac ttctcaattc agaaatccac tcaaggttag    291540
gcactttggg aggtcgaagt gggaggatcg cttgagccca ggtgttcaag accagcctgg    291600
ccaaatggtt aaatcctgtc tctacaaaaa atagaaaaaa attagctggg tgtggtacca    291660
cctgcctgta gtcctggctg cttgggaggc tgaggctgga ggatacctga tcccaggagt    291720
ttgaggctgc agtgagctgt gatcatgcca ctacactcca gcctgggcaa cagagtgaga    291780
ccctgcttaa aaaaaaaatt cattcaacta tgtgtaagag agagagagag gtgtttatta    291840
gatttaactg aggatttggg gagaaacttg ggggcatttt atcctatggg ataagaggga    291900
aaaataaacc tttaaaatta aacatctcgc ccttttgctg actaccttt ggctatccta     291960 acatgaaata ttcttctgga tgctacaact ctcagctcca ctgatcggct agagcagatt    292020
caccatcact tcttgttttt ggatttcacc ctctgccact cgtgatttaa caaataattc    292080
tctgaaaggc agttctcttt tgaaaagag ttttgcttct ctgtgttaaa ataatgtgtg     292140
ctgctgttaa aatagttttg tatacacgag ggaactcctt tagaagcttt atcacgtctc    292200
ttagctgtgc gtgcaatttg agtaattact atgtaccaat tccagtaaca tagccaatac    292260
atcagaactc tcaggggacg tagctgggaa ctttcttgca aaacaactcc cacgtgttca    292320
ttcctgtctg gaaaccacca gtaaaattta atcagtaa taatttctcc aggcacagca      292380
actgagaatg gtagaacatt agttttaaaa accatttaa taaatgcct ttataaatat       292440 tgagacttaa ttatttagat taatttgttc cagttaatga aagatctctt agcacaagac    292500
tgggaaaaat tagaacacgt ataattttct tcattccaga taaacaatta ttttaatgtt    292560
tatctggtat ttgaccacaa acttaaattc ctgggtttcg taggattaga aattttaagg    292620
ttagtaatca ctcccgttgt taaactgctg gattttacct aaaattactg caaggatgta    292680 tcatttttt atacctcaag ctgttttgtg cagttctgct tccaacttcc atagacaatt     292740
ttaatcattt attttttgttt tttcttatca gataatgttt cataacatgg atgtgaagaa    292800
ttaaatgaac atccttctgt gcacaaatta agattagaac acgaagattt tgggattccc    292860
ctcagttcct tttataaatt gtatttcttt ggacctgtcc taaggataac cacttttgtg    292920
aatctgattc attatttcct tcttttatta agttttattt ctgcaaaatt gtcatgacca    292980
gcataaccca aagaatatat tgttcgctct gcttttgatc ttttataaat aggatcatcc    293040
tatgttcttc ttgacctggc atttcccttt tcattgaata gtatgttttt gattttaacc    293100
```

```
atgaagatgc ttggagctgt agtttatttg tgttcactga tatatggaac ctcacccgat   293160
ggttatacca caagatattt aactctttca gaagctggaa atttgaattg gccttatgta   293220
aagagttcag ctattaggat tctgtgcgtg tctcttgttg aaaaaaaatg cagaagtttc   293280
tccaactaga aatgtattta ctggaccata ttttatgtgc atatttggat atacactctc   293340
aggttaaaaa ctgtttaagt ggttggacag ttttattcac ccaagaacag tatcagagtt   293400
ccctgtcctc tctgcattca ctgcactgaa tccaaaattg aatagaaatg aaattagctg   293460
tctttgattt gttctctctt tagacaaaag gcttccaatg ttgtatcatt atgtataatg   293520
tttgaagtaa gatataaata aactaccatt ttcagataaa gaaatgttta tttctttcct   293580
taatttgata acatacaatc ataaattggt tcaaggcatt tttctttatc ttgtaagatt   293640
atccttgctt tgcatttaat tttttcatgt agcaaattaa ataacttaac tttcaaatgt   293700
taaacttagc ttgatattca gtatcttctt taatactgtt tttgtatttg ttgttagata   293760
ttaatcattt ttttctatct ctgtacaaaa caagatagac tataattttt ctttgttgag   293820
cttccctggt tttagcatcg actaatagta gctgtgtaga aagagtaaga gaacatttgt   293880
ttatgctttc tgggagagtt catataaaaa cacaaattat tcattcatta ataggtggta   293940
gacttgccat tcagtccacc ttggacagat tatttctttg ttgtacttaa aaccatcatt   294000
tatttcctcc ttgatttgtg gactacatta catattgact tcttgtatat atgaagaaaa   294060
acatgtttgt atgtctgcac atgtctgtta tcactctatt atgttccctt tctgcatttg   294120
tctgtctgct atatacattt tgctaaactg tcataacaaa ttatgagaaa tttagcagca   294180
taaacgaata gccatttatt acatcaggga tctgtaggtc agaaatcctg gtgcagtgga   294240
gcctagcttg gtcctcttct tagggtctcc catggctgaa atcaagagat tggcagggct   294300
gcattccttt ctgggtgctg tagggatgaa tatatcacaa catatagatt tttaaaatct   294360
aattatttgc actaacttct gattttacca cattagattc ataggtgaa ttcctgtcat   294420 attgatcatt cgagtcttat ggaagctttc tttctatctt acaacatcgt cagattgtta   294480
caggttttca tatgtattta ttcttatgct ttaaacaagg ggttttctct gttttatgta   294540
aagtttgacc taatattttc atcatatctg tgttatactt gagatgtata ttgtgaatat   294600
ataagcacac acaatgaact attcttcagc cttaaaaaag aaggaaataa gaaggaattc   294660
atgtaatttg tgacaagatg gatgtacctg gaggacatta tgttaagtga ataagccag   294720 gcacagaaag gtaaacactg catgatctca attatatgtg gaatctaaag aagtcaaact   294780
cagagaaaca gagagtagac tcatggttgt cagggactgg aagttgggtt catggggaa   294840 ttttggtcaa gaggcataga catctttctt cttcttataa tattatgttc ctatgttcta   294900 gttttgagc tattaggatt tccatatcag cattttaggt cttatttatg cttgcatttt   294960
ttatattctt gataatttta gtctttctat atcttttggg tttaaatttg tctcttgagt   295020
tggatgcatt cttcatctta ggttttgtta caaacatgag attgtctgga aatttttta   295080 aattcatgag tttaaaccat ttatgtttgt tgaacgttaa ttttaccgat gcttattctt   295140
gccatcttgt tttatatgtt caatttagtt acttcaggat aagcgtaact gtacattttg   295200
tttttgaaaa cataagtttc tacctgtcat ttaatagata tttaaataca tagttatttta  295260 aaactctgtt atctattttt tatccttact atggttaacc ataactgatc acagggaatg   295320
ctgtttattt ttcccagttg ttttttataaa tttaacaaca taatattggt ttataccaat   295380
tttgttcaat ttctatatga aaatcaaaaa tatatagaat acatcaagga attcattgac   295440
```

```
agatctggga atttctaaca agataaactt ttttcaaaca tgcatctttt ttagtcccac    295500
ccctagtgct atttaagtag atatttccaa gaatttaagt tctgggctat tatccatata    295560 tgattttgt  cttccttttt ctacccattt tagccaaata gaaattatag ttattggttg    295620
tgcttgcatt tcatatattt ttcagaattc ttaccaaatt agttatattc tttgataagt    295680
attttctcaa agataatttt cagtctttaa atctttgctt agcaaaatga ttgaatctct    295740
ttttgatctt tttttttaac ttggcctata gtattaaatt ttttttaaatt cagagttatt    295800 tttcttcaaa ctttcaaata tgactcctgt gtctgctaat gtcttgtgct atgactggga    295860
agtttgatgt caatctgatt cctattcatt catagctcac ccattttttct ctctgaaggc    295920 tattagaatt ttctgtttgt ctttgatgtt cttaaatttc ttagtaatat atctattcag    295980
ggcactcttt gagcccattc aaaataaggt ttttgttctt tttgtttgtt tcaagtgtat    296040
tttcattctt tcatcaactt agttcttcct ctgtattttt ttttctcttt ctgttacctg    296100
atcctggtat ctctaacaaa gtcatccatt tttccaagga tgcctttctc tcctttattc    296160
tttcctgatg ctttctggga atttcttcca tctgatcttc caatttggta attcattcta    296220
tgatttatct taactattag gttcttgttc atctttacta ttatttattc tatacctact    296280
atatttacca agttctcttt tacttcttat tataatctcc tatttgaaat atattcccctt    296340 aggtgatcga atatatttat tttgtctatt gtaatttctt cattgatctg ttccaatcat    296400
tatatttaac gtagaagaat tttttttttct gttgagagag agcgtttggt acctttgtaa    296460
atgttcaggt atatagctct ttgttaaaca tttagcctgt gttctcctta ggtgagtgga    296520
aactcatcca tcactctggt ttgtaattac gcatgtgatg ggacctaagg gcagacccaa    296580
gtctatgttt cttctatgag attaacattc aacaaacact tttagatcac tctggcgcac    296640
tgaagaagtt tgaaatttga gatttggctt taaactctct aaaggagcca gcattaggaa    296700
gaaacagcct ctttagcttc attcctgggg gtgtggaggg aaggggggtg aaacaggaaa    296760
agcccatagt ggccataagt gactggtggc cctgaaagtt tttaaccagc tcctcaacgc    296820
agctgagttt tccgtgggct tgccagagtc ccactacctg atggctgccc tcgagttcta    296880
agttgtatgg agaagagaag atgggaggga gattagacaa tgattaactc aaggcattct    296940
ttataagaga caagagtgaa cttaatactt tgttttttaaa ccagcatctt tctattacca    297000
cttccaccct ctgccagaag gtgcagccac tcccattcac catatataca tgattcatca    297060
gcttgtaatc tcctcgggat ggcttatagc ttactgattt catgttctat tattgctctt    297120
tccgcagatt gatgcctcgt cttatcctct gtagttttttc aaaagtagat ttctgtggag    297180
gaaggggcat tatgttctat tcaccatctc aaaagaagca taactctctt tcttggatat    297240
attactattt ttcccacgtt gtgtatgctt ctcattaaag gtaggattct aaaccatcca    297300
aatgaatctg tgccaccacc tgcccctgga ctttggactg aagaggattg agaaatggtg    297360
aaatacttaa ctatttgata gcttccttca ttcccacaga ccacatcaga tgtagttagc    297420
taatatacca attaacaaaa ttacccagga aatgcaacat atatacttat ttcattactt    297480
gtcaaaactt tctaaatggc tttcatctat ttctaaaaag aatcccaaat gttccaggaa    297540
caatttccta atgttctggt tttgaatatc acagctcatt tatcagcgta tatcatagct    297600
atgactatag acgccaaaat attaagtaat tcataatgac aatttggaca atgaagggta    297660
tattagaact tctttgagta tttttttattg caatatgaat ttttaaccaa agacttgtat    297720
gagctccaga gagcaaatcc actacatttc cccactctgc ctcccaaccc atcactatat    297780
agatccattg tggagctttt ttacttcttt gtggtgtatt aaaacaaagg atataatatc    297840
```

```
ccctgattat ggatgaaagt gatggaacat ttactgccat gagagtccct tatgataagt  297900
ggtagctgaa ctggaagttt aaagaactgt ggcagacagg atggggtaaa tcaataggat  297960
ccaggaccta ggaatgcatc aggaaagaca gcaacaggga aggatgagct agagcaattg  298020
aaagggtgat acatatattt ggagccaatt cttttatgc tatcatcaag ataaaaccag   298080
tattcctcac ctggtagata tttctctttg caaaggtgga tattccacag ttcacttcca  298140
cagacctcat gcaaatgtca gattcagcgg ggagagggag caccccagtt tctttggcag  298200
cacagaatat aatgcatcat gtttatttgc aagcctggag atattcttgc atacatattt  298260
tatctagcag atgacactgg atccaattaa ttggtggctt tgaaatatat ttattggaat  298320
tcattatttt gggttatagt tgtttctgtg atccatgcaa tctaccagga tactcttcat  298380
gcttttgcat ttaaaagaat gacaccaagg gcttgtgaaa ggcacattct ggggtccatc  298440
ccccacaatt tgtgttctgt tgctttaggg gagggtgtga ggatttgtgc atctacctgc  298500
tttccacaaa gtagggtccc tgctggtata agggcacacc gtttaagtgc tactgcacag  298560
aagcatcaga tgtcattaag attgtgtgtt atctacattt cttattgttg ctcaactgcc  298620
agttactctt ttcataaaat atgtatctgt cctatatagg gctaagaatt aatttatccc  298680
agtctataac tacagagaga agcctactta atgagcattc ttgatggggc ataccaccca  298740
taaatatggc accttagcat ttgaaaaaac agaagaagca ggaaagttct ctctgacctt  298800
ctccccatcc ttctccccta agccaggtc ataagaccct cctatgagag gtgactctct   298860
ataccaagag gaatagaaca ttcttatctc tgaggacaaa aggacacaga ggagaatctg  298920
aacacacagg ccttgctaag ttctccccag ttttttccca ttagataata aacattttta  298980
cttcaatcat acttttccaat gactgtccac tctttatcaa acctaagtat ctaagcacaa  299040
aaatccacag gtttccctgt ttcttttggg tcttcattgc cttatgaagg ctcctgtgtc  299100
atataaaact gttattaaat gaagtgcact ctttgcttaa tctgtctttt gtcatagggg  299160
cctcagccat gaaactaaga taggaagaaa agatatttct tttcccttat attattcaac  299220
aatattctag ttatacatgt aagcttaacc aaaagcttct agaatatcaa agtaataagt  299280
gtgaaatatg tgtgtgtgca cacatgtgtg catgcatata tatacacaca ctacattgta  299340
ggtgtgtata tatatgtata tacatataca catatatatt ttataagatg cgtatacaca  299400
tatacatttt tgtatgtgtg tgtgtgtgac agagtcttgc tctgttgtcc aggctggact  299460
gcagtggcgc tcactgcaac ctccacctcc tgggttcaag tgattctcct gtctcagcct  299520
ctggagtagc tgagattaca gccatgtgcc accatgcccg gctaattttt gtatttttctt  299580
ttagtagaga tggggtttca ccatgttggc caggctggtc tcgaactcct gacctcaggt  299640
gatcttccca cctcggcctc ccaaagtgct gggattacag aggtgagcca ccacgccaag  299700
ccggcacata atacatcttg taaaatatat ttagcaaagt ctatttaaaa ataattaata  299760
gtttattaaa tcttatgtag attttttttt caaaatgaac aagcttctgt ctttccaaca  299820
aagctttgga ataataatc attgcatttt cctctaacag gttaatcagc agatcaacta   299880
aaaccaaaat gagtctttct ctgggcacgg tggtgcatgt ctatagtccc agctactcag  299940
gagactgagg caggaggatc acttgagccc aggagttcaa ggaccagctt gggcaacata  300000
gcaagatacc atctctaaaa aaaactaaa aattaaaaaa aaaataagt ctttctataa    300060
ctgtatgaca gggctaaggt gatttttattt gacagaggaa ttaaatttca atgtaccaag  300120
ttctatccgt atgatatctt ttctgatggt tggaagggca ccaagggggct tccatgaagc  300180
```

```
tcagtgacag cattttcaca tggaagtcac tgcagcggaa agtagggtac acattcttgg   300240
taaataatat atgattgcac tattgatgaa tagcatttca aaagctctgc tatttattgt   300300
ctattgaaag ataaatgaat ccagcaagta aactgcctaa aatatttgta cactgttata   300360
aaatgtaaac acctctatca tactataaat ctccctcccc tccgctggaa aagacttcaa   300420
gctgagatca tcctcgtcct catcacatga ttgcttggaa tagagttgtc cctgaggcca   300480
cctgtcacct aagaggactt gtattcattt attcagtgtc catgtaatga agaataaga    300540
cagacatact gtgaatataa aacacagag ttcaaaagac tattctgatt gagcagaagg    300600
aagatactaa acaaatatta gatgaacaaa gcttgtgtgt atggctttgg aagataagcc   300660
taggatctta atcttgttta tataacacaa ctattaaacc ttcctgcgta aaatacattt   300720
taattgagac ttagcatgaa gatagaacac caagtctggg cattctgaaa agtttagacg   300780
cagaggaata actggcaggc agtgatttaa agtggataca gattttttgcc ctggagttgc   300840
agatgcgtgt aggaatgaaa aggaagtaat gggtgtgata accgatttaa acactaatca   300900
gtgagcccca aatattaacc atatactggg attctacaaa gagatgccat ggtaaaaata   300960
tgaattcaag tgttttaacc tgtatagctg gatacattct tgtgatatta acacgggaaa   301020
taagaaaaga gacgagtttg aatgagaaaa agatgtttag ctcaatatag cacacactga   301080
gctttaggct cgaataagac atctgagtgg tggaagactt agtcaagcat gggagaagtt   301140
agagctgaaa cccaggtaaa atccttcaag ttacaggcag aaatcattac cagatgtgtg   301200
gtggagtcac acgggggatg tgagtcctaa tgcctgtgca gatgcatggg gaatgcagtg   301260
tcttttttgaa ggactggttt tagcgctgca agaagtaaag taaattctct tttacctgca   301320
ttcttgttcc ctctggtgct tttatgagga cctaggcaag aatagtattg aaccacttat   301380
accatccatc tgttagaaga acctataata cagaaatatt tgctttgggc tgaactccaa   301440
acgtaatact taatgatttc tcttcaagtt tgttgacaca ttctacatct ccacatacaa   301500
tttgctccca gtcgtttctg agatatgcta cagaaagtac aattgatcaa acgttggctg   301560
tagggattca agaacagtcc tgtgactgca ttttcgttcc ttcctgaaac tattccaagg   301620
ccataaaaca cctttttttgt gtgaactgtc tttctgtatc ccatttcaga tgatatcttc   301680
tttcctttaa atacagtctt ttatatttt ctaattgtct gattgccaaa acaatatatc    301740
tgcattgcta taaatttaca gtatcaaaga tcatacagaa gaaaaatctt ttttaacaaa    301800
agaaaaccat tgttgataat ttagtttaca tacatacata tgtacataca tgtatcctct   301860
tagcactctg gggcccggag tagagagcaa acctgtgaaa cagatagata gatagataga   301920
tagatagata gatagataga tagatagaag atatagagat atgttagagc tatagagata   301980
tagtctctag atagatagat aagaatatct gtattctctc tctctagaca aatgattagg   302040
aaacagtcta taagaacgtg tgtgtgtgtg tgtgtgtgtg tgtgtgtgtg tgtatgctct   302100
ctagaggtag aatatatctc tctgtaggga gagagactta tgcatgtgta tgtatgtata   302160
aaacaaagaa acaataaaaa cacaaaggcc caaatatcaa ccagaagaaa ctgaccagct   302220
gtaatgggac aattagaaca tctgtaagaa tatttgtact ggatttaaaa tgataaagac   302280
ataaaagttc atgtattcat catgacaccc agaataaaac tcactggtta tattactagg   302340
ccacgatcgc attttcctga atcttgatca ataaagaat catgattttt tcccactttt    302400
cctatatata ttgaatttca gagtaactaa aaaattggtg attacaagta aaatttcaga   302460
taatatatgc agaaagaaca atactatctg aaaatcatta ttttgtgaaa ctccaaatta   302520
agtaagtata ttaatctgtc ctcacactga tctaaagaac tgctggacac taggtaattt   302580
```

```
attaaggaaa gaggtttact tgacttgcag ttccacatgg ctggggaggc ctcaggaagc   302640
ttacaattgt ggcagaaagg gcagcaaacg tgtctttctt cacatggtgg tggcaggaga   302700
gagaaatgag tgcccattga aaggggaaat cccttataaa accatcagat cttgtgaaaa   302760
ctgactcact accacgagaa caccatgggg gaaactgccc ccatgattca attatctcca   302820
cctggttcct cccacaacat gtggccatgg aactacaatt caagatggga tttgggtggg   302880
gacacagcca aaccatatca ataagagatc taggaaatta tctctgatta tttgaaaagc   302940
ttcgcaggtt tatatatata tatatatata tatatatata tatatatata tatatatata   303000
tgtgtgtatg tatatatata tatatatata tgtgtatgta tatatatata tatatatggt   303060
gggattcatt accaactgaa tgtaattatc aaccactctt aagataatta aaagtaacac   303120
tagcaggtat catgtaagtc cttattaaat tcagtataaa gtacagagca gttcctgggt   303180
gcgttgtttc ctacaaaggg caccataacc ctaaggaaga aaaacaagat gtgattagga   303240
aacattctgt taattctaga acatggggtg ttcttcagca gtaatgttca aaatgtggtt   303300
cacaaagcag caacttgtta gaaatgcaaa atttaagatc ctataccctgg gaggaggctt   303360
cctgaatcta aaattgaggg tgtgggttgc aaactattat ttctttccca aacccatctg   303420
tgatgtttat gcttgataaa atttgatggg acggttcatt gatttccata aggaattaac   303480
gatgtaagaa aatgagaaga agaattgtat tatggaaaag agggtgtcaa tattttcact   303540
tgctttctct ttaaatgtgt ggatcacaag atttgctttt cattaaaagt attcagatat   303600
atatacgtat ttgaaataca tgtgcctata cactaacccc aaaacagctc attaagaatc   303660
tcttccactg ggacataggc atcagtattt gttaaaatat cactaagtgt ttagtgtggt   303720
tgatgagtgt agaagaaata tattttcacc aagcttatga gatgggcagt ttggggccag   303780
gagaagaagg cagtgaaaga acttgggtga taagcagctg tctacttgca aaacaactta   303840
ttattaatga attgggactt taaattttt tttttatttt cataggtttt aggggaacaa   303900
gtggtatttg cttacatgag tcacttcttt agtggtgatt tgtgagattt tggtgcaccc   303960
attacccaag cagtatacac tgaacccaat ttgtagtatt ttatccccca accccctccc   304020
acccttcccc tctgagtccc cagagtccat tgtgtcattc ttatgccttt gcatcctcat   304080
agctcagctc ccacttatga atgagaacat aagatgtttg gttttccatt cctgagttac   304140
ttcacttcca ataatagtct ccagtcccat ccaggtagct gtgaatgcca ttaattcatt   304200
tctttgtatg gctgagtagc attccatcat atatttatgt accacagttt ctttatccgc   304260
tcgttgattt atgggcattg ggttggttcc acattgtgac ccaatgcttt taaaataatg   304320
tgtgtgtttg gccacgaaca taagccagaa cactagaaaa attgtttact gaaagccatc   304380
ttagtttcag gaacacaaag gaaatgaggt aatgtgtgaa aagaacttta aaaattgtaa   304440
ggcattttgc ataaagatgt taggtgcttt ttgaagtttc tatttaaatg tggtcaatta   304500
gagaggtttt ttttttttca ttttatgttt gccttgaaag catttagaag tatgagaata   304560
tataatttca ttttgtaaaa cacaatatgt tgaacctaat aggatctttc ttggaaactg   304620
aacattgtcc tggttttgg aggcatccca ttgaaattta gccatgattc catattcagc   304680
aaattgctgt ggacccagat acatcttcgc tgaccagaag tctttccaga gtggaagatt   304740
ttagtaaatg tacaagtcaa tcttgtagaa ttagataaaa tgcattctgt tttccatcac   304800
ttgccgatat cccccccactg ctaattaaag gaaacacaat cccacaattga tttacttatg   304860
taaatgtaga ttacaaacca acaacatgat tttaagagtc ttaagaagtt gagggctatt   304920
```

```
ttgaatgttt actcttggag acatgtatat ttaggtgtcc tggtcaacaa gatcaattgt   304980
aggaatggtt ggtgcaatca cattggtcat taaatacaga catcacacat aatcaagcag   305040
atttagctca gggtatgggt aactcaacat atgaacacca ttcaaagtat ttccccaaaa   305100
ggctggcatg gtggctgaca tggtttggtt gtgtccccac ccaaatctcg tcttgaattc   305160
ttgtgagagg gacccagcgg gaggcaagtg aatcatgggg gcaggccctt cctgtgctgt   305220
tctcatgata gtgaataagt ctcatgagat ctgatggttt taaaaagggg agtttccctg   305280
cataagctct cttctgttgt ctgctgccat gtgagacatg cctttacct tccaccatga    305340
ttgtgaggcc tccccaggca cgtggaactg ttaagtccat taaacctgtt tcttttgtaa   305400
attgcccagt ctcaggcatg tctctatgag cagtgtgaaa atggactgat atagtggctt   305460
acgcctgtaa tcctagcact tgggagggc aaggcaggca gatcgcttga gctttgcagt    305520
ttgagaccag cctgggcaac atggtgaaac cctgtctcta taaaaatac aaaaattagc    305580
tgggtgcagt ggcacaagtg tgtattccca gctacttggg gacactgggt caggaggatt   305640
gcttgagcac aggattgctt gagctagaga tgcccaatgc atctcaaggg tgcagtgagc   305700
cgagatggcg ccacttcagc ctgggtgaca aagtgagatc ctgtctcaaa aaataaaaaa   305760
atatttcccc aatggggaca tatggcttaa tagttagggt tattgtttgt agtgatgaat   305820
aggtttggaa ataggtagtg gtgataatta taccacattg tgaatgtaat gaatcccact   305880
gaattgtaca ttttaaaatg atcaaaatgg caaacttatc ccacacacaa ataaatagat   305940
atagatatac atagatatct tcatatggtt tttcttgttt tttaattttt tatttttta    306000
ttttatttat ttatttattt gagatggtgc ctccctctgt cgcccaggct ggtgtgcagt   306060
ggcatgatct cggctcactg caacctcctc ctcccaggtt caagcgattc tcctgcctca   306120
gcctctcaag tagctggtat tacaggcctg tgccaccatg ctctgctaat ttttgtattt   306180
ttagtagaga cgaggtttca ccatgttggc caggatgatc tcgaactcct gacctcaggt   306240
gatccgcctg cctcagcctc ccaaagtgct gggattacag gtgtgagcca ctgcgccctg   306300
ccttcatata ggttttaata ttagtttgc ttaatttaaa gacagtttga ggcagtacag    306360
cataaagtac tccccacatt tcatttattt agttttaatt gacaagtaat aattgtacat   306420
atttacgggg tgcatactga tgttccaata catgtaatat acagtgatca gatctaagta   306480
attagcatat ccattatcta aaacatttat catttctttg tgttgggaac attcaatttc   306540
ctccttctag ctatttgaaa ctacatatta tattatttt aactacagtc accctgcagt    306600
gctatggaac acgagaacct atttctcctg tttcccccc tccccacgaa gaaataaaag    306660
aggtgaaatc tgacacacaa agcaaaagga acaaagacat tcaggtactg gagttgagca   306720
taaatttac ctcacaattt ctggcagata agcaaaaag agagagaaaa acaattggtt     306780
ctgggattag tatttccggc aagagaaacc ttctcccttt tccctctgat tcttggtgaa   306840
gagcagttat gatgttggag ataaaaggag aagatggcag tgatggttcc ttgttctttc   306900
cttctgcagt ggctgtcagc ttcgcctgtg atattaacag taagacagga aagcctgaga   306960
ccgcctcact aaagacagac ccttcccatt atgtgtcacg gcagccttca cccttgaatc   307020
tagaaaatac tacctgggcc gtgctaagtt tattcttaaa agcctaacac cgtgtagcta   307080
ccgctgccca atgcatctgc ccaaaacagc actccccaaa tcctgaatat gcatagaaat   307140
aactttcag ttttcatgcc tactgctgaa ttgtaccaac agagattctg atttggaagt    307200
cagcggagga gtctatgcag tttaaatttt tacagacaac tcaaggtttt gtggatatat   307260
cctgagacag ctcagccctc ccaggctgtt ggtaccatag gggctgggag agattgccct   307320
```

```
cacttacccc gcaaacacct tgcaggatgc agaacagctc ttaataaata tgtgttatgg   307380
aaataaagga atgccctgt gcttggaagt attaggctgc ctctctctct ctctgtctct   307440
gtctctcctc tctctctctc tctctctctc tctctctctc tggttcattt              307500
tcaatgccgc tgagtcatac agtgagaagc agcttagggt cattaagaga ttgaaacatc   307560
ggagaaaaaa agtgaatatg ttttcatttg aatctctatt tttaactctt tctgaccttg   307620
tctgtcaaat ttggctacct tgagactgtt gcagtgataa tgaaataagc ctatgctgtt   307680
ctttggaatc attttagaca tatacatgtc taatatatat atatatatat atatgtatat   307740
atatatataa aaaatactta ccatatgtga tcttgtttga catgcctttt ttctatacaa   307800
aagcacatga atcaccatgc ttcagcaatg aagatgttgt gttttggact aaaggcagtg   307860
taaacacaac atgctattag cgttttctt aatcatcact accacccagc cgttgtcttc   307920
ttgcacaaga taataatagc atctcacatt tccatggagc tttataatgc atgaaggtct   307980
ttcacattca tcgttttgtt caatgtcata gggagaggga gcttcagtaa cctcaaagcc   308040
cagtgtgcag aaagagaaac tgggattgat tcaatcattt ggccacagtc ctaggactct   308100
tgaatgtgtg tgtaactcag gcagggtgaa atcccagaa gatacgtccc catcccaagg   308160
gcacctaccc aggttcaata acttggttac aactgacact ctttggatga tgctgcactc   308220
ttcacaaaca cgtatccaaa cctatcatga acccaaacca gagcaaacat caaatcccca   308280
ctcctaccac atattcacat cttgtattaa caccaaagcc tgaagcaccc tgacaacatg   308340
tgtccagaag atgttgaatg tcttccaccc tgactgccac taacctggtt aaagccagga   308400
ccaactttca cctggacaac tgcagtggac ttcttccaaa tgcacgctcc tgcagtcctg   308460
tccaccagtg gctcctgtga gctttacgaa accataaatc ctatcacatc cctgccatgt   308520
tccaactctt atgccttgtc attgctttac aataaattcc aacattttac tctctctttc   308580
aagtgtgaac tcactttgcc tactactgga ataacgttct ttcacatttc cttgctaatt   308640
atgagtcagc tacaccggga ctccttctgt tctcctcacc ctttaaacat atttcccatt   308700
tgaaacttcg caactcgtaa ttcttttcag gaatgtttcc ctttcatcat cttgtagctg   308760
cttcgttgtc atcatttcct ttcatttcca cctcttcaga gaggctttgt ttagaagaaa   308820
acataggagc aaatatttgc cagctagggt tatgcaaaag tttcttacat agaacacaaa   308880
atgtaagaac cgcaagagaa tgtattgacg gggccttcca gacaccatga agaactcaga   308940
gagcaagctt cagattgaga gaaaacattt acaactaata tagcagagaa ttgacttgta   309000
actagaatat ataaaaatat ctcccaactc aatgataagt caggcaacct gcagagcagc   309060
agtcctcaac acttttggca ccagggactg atttcacgga agataatttt ttccaagtag   309120
gggaacggtt tcagtatgaa acttccacct cagatcatca ggcattagat tctcataagg   309180
agcaggcaac ctagatccct cacatgtgca gttcacagta gggttcacac tcctatgaga   309240
atctaatgcc accgctgaac tgacgagagg tggagctcag gtggtaatgt gagtggtagg   309300
gagtggctgt aaatacagat gaagcttccc tcgcttgccc accactcacc tcctgctggc   309360
ccagtcccta accaaaactg gtccatggcc tggggcttgg gaccctgc tgtagaggac   309420 agaataacag cccctacat atgttcacat cctaccttat gcagtaacac ggacttgact   309480
gacgtgataa agattttgag atggggagag tatcttcaag tatctaagtg agctcagtgt   309540
aataaaaata tccttataag acagaaactg gaagcttgga acaatagaag agctgaaggt   309600
gaaacagacg tcagacagag attaagatgc tatgctacat atatatatat attgcccagg   309660
```

```
aggattgctt tgttggagcc tataaaggtt tgtgagataa aagttctgaa gtggagaatt   309720
gttactatga tggttgctta aaatctagtt tttagaacag agatgagttt gactgtagct   309780
actctggtat gtgatccatt taatcatttt tttgtttaat taattctcag agagaaatct   309840
tagccccagc tatttaaatc tctccgtaaa taaagacttc caagcaccac tgggacagtt   309900
accaaaaatg acaaatcatt ggcaattcta acaataaact tcagtatagt aagagatata   309960
atggaactct gtaactgctc tcaaatcaaa catccctcct gcttagtgaa aacagaattg   310020
cactaatttc tctgatgcag tctcaaaatc gagccaccat ttcaggtttt gtaagaaaag   310080
ttgcggactt caggcttaga aaagacatcc cagttatgca ttgtggctga ggataacagg   310140
aagatgagaa ttaggatgta gctatcttca aaaagaaaag tggcaaaaag aaaagaaaaa   310200
ccttaatgtt agaacatata aaaatagtat aaataattaa gaacttaaag aggcagagag   310260
tttggttaaa gcggcaagcc agcaggacaa ttttagtgtg tagcttaagg tacaatacat   310320
gcataatttg cccttcctca attctagaaa atattgtctg tcttcttcaa taacctttct   310380
attcctgaaa ctaagcattc cactgggatt ttagctattt tatgtgctgt catatttact   310440
ttgctagcgt gcatgtgatt acacctaagt tctaattcgt ctaatatatg tgcattactt   310500
tttcattcat ctaatatgaa ttctagttca tctaatatag tgttgtataa gttgtctttt   310560
tacttatgtg cattttacag tgccctgaat agcactgaag tacaaaaatg tatcttaata   310620
tgtgttttat ctccatactt tgatggtgaa aaatattact ttccattcaa atgagtttta   310680
aaatagtctc attaaaaaca aatgaaaacg taaataaaaa aaaaaaaacc ttttctgtaa   310740
tttttcaaga tatctatgga aatgcactga actaccgcat cattttcccc cagattttgc   310800
ttgggtcatc atggctactt catacattgt tgaatgagca tttgccgtaa atctcatagc   310860
ataagtaaaa gctatgatgt gttttttgcc ttgtctttct cttttcactt taaacacata   310920
ataaacactt agtaagcaga ttgaataaat acatccccc tttatgcaaa attattcaca   310980
aataaatggt atctaattca ttctttaaaa taccatcaga gaacacacaa tctcgcttta   311040
ccatctgtat aatttttagag tcagagtcta atttgaccag cagtcaattt tttccctttg   311100
gactcctttc atatatttga aggacatttc tttgttccta gtatgtgtag atgaagcaaa   311160
actaaactgc atggcttctg atattcatga aagcaggcta gtaggtaacc attttttgaac   311220 acattccaca ccaagcgcaa tgctgtttct tgtgcattgt ccagttgagt tcctcagctt   311280
gctatgggag ggctactatt ctcctcccca tttcacatat aaagaaagtg ggactttgaa   311340
atcttaagtc atgtgcttaa ggcttttgcaa tagattccac cacaaggatg tccaactgaa   311400
tccactgcaa gcaataactc caaaagcagt caccaagcaa atgcccttgg tgtaaagtga   311460
tacgttctgt aacagaaatt cattgaaagc catttactgt gccgagagaa taaagataat   311520
cacacaggac acttttggaa aggggcccac attggtagaa agagatggcc aggttctacc   311580
tgagtatgca ggtgaccccct gcggaagatg cagagactga ccttcaggtc acactgacct   311640
ttcaaatggt gctgggtcca tgagctagcc gtgcagcttt gtgtgcggcc atagcccaca   311700
ggaaggtgtg ctcaggcaag gtgttcaggg caatttatgg tcgcccagca gccctgcaga   311760
gggcgcccta gatcttgggg atttttatata aaaaggcaag catatcaaaa tgcaaggcat   311820
attctggaaa tagctagcaa gtgttgtggt ggatttgcag gctccagaac ataagtaggg   311880
catcccttga gaaggtcaca tgggcccaca cagaatgacc cttggattcc cagtaatgaa   311940
tttgtttctc caacacattc actttattgt gtgggtgtga ttgttgttgc taaaaaggga   312000
gatttaaatt atgaactaaa tataaacaga tattagcaat aaaacgtgaa tattccctat   312060
```

```
agtcacatgc ttcgaaataa tcaccctcca ctgtttgaat tccttccaga ttttattttt    312120
taataaaaca aatgggctgg acgcagtggt tcatgcctta atcccaggac tttgggaggc    312180
cgaggcgggt ggatcacttg aagtcaggag ttcaagacta gcctggacaa cattgcaaaa    312240
ccccatctct acaaaatata caaaaattag cagcaaatgg tggcacattc ctgtaatccc    312300
agctatttgg tgggctgagg caggagagtc gcttgaatcc aggaggcaga ggttgtagtg    312360
agctgagatt gcaccactgc actccagtct gggaagcaga gcgaaactct gtctcaaaaa    312420
aaatacataa aaatataaaa taaaataaat gatatgtagt attcagtagc ccactatttt    312480
ttcttgagat accttagatg tgtttctgtg tccatgagtg taaatactcc ttagcactttt    312540 atgcagacaa acagcatctc ataatatgga tccaaccaag acaatccatt caaatctctg    312600
acttgtgaac attcagcttg ctgctattgt ttgttttaa aattacaatc cgtgtgaatt    312660
gtggagcctt gggtggctat ttttatgcat cagaataaag attttcatag aaagcattca    312720
aagaattagg actcctgggt cagaagtttc caattttcat tttcctgggt tttacccatt    312780
ctcttacact ggagaccatc atgatgatgt tgatggtgtg gaaattcaga ggaagctaaa    312840
aggacgtagc acccaaatga gcaggtcctg gggaactgta gttctcatct cagacactag    312900
gatgcagacc cagggaggga caagatgtac aagctctttg aaaactaaaa ccaaaggatg    312960
tgacagccaa ttgaatgaga gtcagcagca aatctggaga aatatctaag gagaaagtgt    313020
tcagttgaaa atactcaaag ttggctgggc atggtggttc acacctgtaa tcccagcact    313080
ttttggaggc tgaggcaggg agatcacttg agctcaggag ttcgagacca gcctggccaa    313140
catgatgaaa ccccgtctct actaaacata caaaaatcag ctgggtgtgg tggcgtgtgc    313200
ctgtaatccc agctactctt gaggctgagg caggagaatt gcttgaatcc aggaagtgga    313260
ggttgcagtg agccaagatc acactgctgc actccagctt aggcgacaga gcgagagtct    313320
gtctcaaaaa caaaaaaaga ctcaaagttg actcaaagag atttgtttcc aggctggcta    313380
ttcccaaatt ttcatttgca tgaaactcat gtatcaatta tcttcagatt ttgatgtttt    313440
attatttaat aaacaagctg tatttattat tttatatttt gttcctaaaa tatgatcaat    313500
ttcagttttt ttttatttca tgtaatttaa actaaagcac ttaaaaaata cctatgcagc    313560
ttaattctag ataaatgtgt ggagatatta tcttttatga aaatactgca aggaatctca    313620
gtagtagttc ataggcccca gagtttggaa acctgtggta taaaaatcat ttgtctctta    313680
taattgtttt agattttctc tactgatatt ggaaatagac tttggttctg tgcaatactg    313740
ctgtgataac atgatacaaa tggagaatgg tctgctagta ctcattccat ttttaagtaa    313800
aaactaaaaa taaaaggcac tgaatttcaa gcagccctgc ctatcaggca acagaatttg    313860
aatgcagtgc atcagcttcc ctccttcca gcccatcctg tgcaatgtgt gcttctgtgt    313920
taaatcctac atgttttcag tcagaaagtt aaaggttcac cttgtaataa atgcatttca    313980
tgaatgattt cctataaccg tcaaagatta gttttgcatc tgtttgactg attttttgttt    314040 tttatgcttc tgcttttcatt ctaaccaaac agatttcttt ttgacctcat ttgcatgatc    314100
taacacaaat tctgtttatt ctcactgaag aatttttatt taaacatttt ctgtttggtg    314160
tcacttcttt agtttaaagg tgcacaaatg tatgtctgtg tacatataca tttatagtca    314220
cacatgcata tatatggtta tatatgcata tatatatata tatacataca tatattatat    314280
atatatacat acacacatat caggtgaatt acacacactg aaatggtgaa agatatttaa    314340
cttctgtatt cacttaatta tctcctggtt acttgtctcc aaaaaatgcc tactgtgttt    314400
```

```
atgcaaggaa tgatctccta aaagaaaatg gattgcagct ttaacgtcat gtaacaatgt   314460
cttttgttaa ttgaaagaaa aacaatatct gacccccattg ggttccttac catttacttg   314520
cagtgcatgg agaaacaaaa gacctgcagt cattctccta agccctgtga tgtaattcaa   314580
aatgagagga aacatctaca ttattatcta taataaaaat tggaaacttt tctgttgtga   314640
caacaatatt aagcctgaat agaaatattc atgtttatat gatattcact tcagtcaaca   314700
tgcagcagga aaaactgtga ttcctatttt tagtcatctt ttccatgaaa cctgtttcta   314760
aataaccata ctaactaaat gtactagtct gttctcatgc tgctaataaa gacatacctg   314820
agactgggta atgtataaag aaaagaagtt taatggactc acagttccac atggctgggg   314880
aggcctcacg atcatggcag aagacaaagg agaagcaaag tcacatctta catggtggca   314940
ggcaagagaa tgtgtccagg ggaactgcca tttataaaac catcagattt catgacactt   315000
attcactatc atgagaacag catgacaaaa acccaccccc atgattcagt tacctcctac   315060
tgggtccctc ccatgacaca tgggattat gggagctaca gttcaagatg agatttgggt   315120
gaggagacag ccaaaccaga tcactgaacg tatctattga tatctcttgt gtgtgtatat   315180
ttgttattgt tgttccttcc aggaccctgg atgaaacttg gcatcaatgt agccattaac   315240
atggattcat tcacatggtc tcttttgcat cttttctttcg ttgttcaatt attggaggag   315300
aggttgctga ttacaagctt catattaggg agagtaaagc tcagaaacca aaatttcatc   315360
ggctaaaatg cttagagagt ttgtagccta aaggacctgt cagttaaagg agccatttgt   315420
tgtaaatctc tggttttaga caatcaagta gcttgttctc ttcattcacc ttgaacatat   315480
atttaaagtt aagtgatcta tccgaggaat gacttctcag gagcagcact catctttggt   315540
atcatgtgtg gctctttcca agttgatgag ctaccatcat tttgctttct acaatcagga   315600
ggcaaaaccc agtggtttag gtttgcagga ttcctaaaaa tattaatttt aatttgctac   315660
aataaatacc aggattcctg gtgtcaaaaa gcttgcaaaa aatcacacca ttagaatttt   315720
ttaagatcac tctttattta cacttaagaa gatagctttg ccaggaaaat gcctgccttc   315780
cttctttcct tccctccttc cttccttcct ttcttccttc cttccttcct tccctccctc   315840
cctcccacct tccttacttc cttccctccc tccctcctac cttccttcct tccttcctcc   315900
tgctctccct ccctccctcc ttccctccct ccctccttcc ctccctccct ccttccctcc   315960
ctccctcctt ccctccctcc ctcctgcctt ccttccttcc ttccttcctc cctcctgctc   316020
tccctccctc cctccttccc tccttccctc tccctgctcc atcacatcac agagctgtag   316080
tgtgctgcct gttccttgcc tccagtctta ttcacaggaa aacctggcca ggtgctgatg   316140
aataaagaag aagacagatt gatagtgaga tctaattttc acagatcagg cgacttggga   316200
aaacaggtct ttttatttc aaatgctaac tttctgggct catagaattc tgtatcagta   316260
agcccacatg cttttttaagt ctgatttata gaaaacatga tttggccctc aaaacaatgt   316320
aacctcccaa cagattcatc tttaccacta cacagataga gctgattagt caagacagaa   316380
gaattgcaat agataaaggg tttaattcct gcagagctgg ctaaatggga gactggagtt   316440
ttattgttac tcaaatcagc cttcccaaaa atttggaggc ttgggttttt ccagaatact   316500
ttggcagaca ggggctaggg aatgagtgct gctgattggt tgaggatgca atgatagggg   316560
tgtggaaaac agccctggtg cacccagtcg gcctctatgt ggggacacag aggagtcact   316620
ggtcctagta ggaccaatca gttgtcagaa atgcaaaagc ctgaaaagac atcttaaaag   316680
gccaatctgt actatgctta ttacctgggt aatgagataa cctgtacatc aaaccccgtg   316740
gacatgcagt tcacctacat aataaaccta caggtatacc cctgaaccta aaataaaagt   316800
```

```
tttaaaaagg caaattttag cttctagtga ttggggaagt tgcaaatctt gtgacctctg    316860
gaataatggc tggtaatcat tcaactaagc ttacatctta gcagaattca ggcctctctc    316920
attctttaac ctggtggcct ttcattactt ttacaaaggt ggtttagttt taagaggggc    316980
tattatcatt taaactacaa gttcaatttc tcccaaagtt agcttggccc gtgcccagga    317040
atgatcaaga acagtatgga ggttaaaggc aagatggagt tggttaggtc agatctcttt    317100
cactgtcata attgtctgac tattgtaagt tttgcaaagg tggtttcaag gtgaaaggac    317160
tatactctta aagagcataa aattattgca ttcattgtgt acctgaaaca ggcactcccc    317220
cttgttgata gtttaaaaag aaaaaaataa taatccctgg atgttgcaat aaatgaaaat    317280
gccatggcag aaactgtgga acaccagcc  tcaaaacacc acattgattt gttaaacttc    317340
agagatccat ggattgtcgt ttccctcagc cagcctgtag gatatttgga agaatttcag    317400
aacctcaaag atcaaaccat ccaataggat gctgttagaa gaactaagat ttttgaaggc    317460
aggggatatt cattagcctg cttttggaaa ggttaaaaca ctctgatttt gctagggagg    317520
aagagtttat ggtggaagaa aggccaatga tttcctgcgt gttgaaaatc ttcatactcc    317580
tccacagaaa caaaataagt caacaagtca ttctgcagaa ttgagaaaga gagaacagtg    317640
agtgaagaaa agacgtgctg aagacagaat cgttctgtta gaaaattgct cgtgccttag    317700
gaattaatca cctctttctt taataggga  agaaagcatt gccctgtggt attataggc    317760 acctaaactg acatgattcg tcattgtcat ataaggatct tcgatctttt ctcccaagca    317820
aagcctgatg cctttatga  acgatcgtgt caaagatata gtgatggaga caggtgttgc    317880
agaacatttt tggcatgaag cactaattag taattgctaa ttaaatgggg gaggaggctt    317940
gggtaatgtc tgatcgcacc cactaatcgt agctaatctc ccgtcacatc cctctgaact    318000
ttaaagaaga tcacattggt aggatgtgtc ttaagtatcc aacctcgcag ttgcgacgct    318060
gcctctcttt gaagctgcag gagatagtga ctcccgattc aggcttggag ttttttattgt    318120 cattgttgaa cgaaaatcgt cctgtgactt tctttggagc caggccattt cctcctttcc    318180
agctcagagc attttttccac aggtgctcag gaaagctcat ggaagaaatg ctggttgact    318240
caattggtat gcagcctcat cctctactct ttttgtttta aaagtagaag ccggcactca    318300
gtcactcctt ggaatgccgt caactttggt tagggacgtg ctttgaggga attggtttga    318360
tgttatttta gggcttaaag cagcctgtct tcatacaaac atgactgcag gtggccataa    318420
taatgtgctg agcatccctt gaaatgagtg aatgacatgg ctcttggaaa aaagaaattg    318480
tatagaaggg gcaaatatca tagttgggta gttgggggaag gctcaaataa ggacgtgaaa    318540
atggttaaaa aaaaaaactt ttaaaaattc tttgtctttt tggaaggcat atccagtaca    318600
gatttggaca taaagttgga ttaaagttta tgcaatgaac taaacttgca ggaggcctta    318660
gaaaatattc ctagttttga atctgagtag gagagtgtat gtcttcccaa acttgacttc    318720
aaaacatcag aagaaagcag ttttttccagg tcaagctatt tttcaataca gaaggaacaa    318780
aaaataaaat agattaactc ataactttgc tatcattaat accaaaattg ccattttttca   318840 actactaagg agaaattaag aatcgtatgc cttgagtaaa atctagatcc tcaactcaca    318900
gaatccttct ttttaaaata aggaaggcca gttcctgata ttttgggaac agttggggag    318960
atgtgaatat tcattagctt ttgggtgagg ttcaataatt acatttttttt gtatgtgact    319020 aatattttcg ctatgtagga aaatagaggt gtatactatt tacgagtcgg atctagtgga    319080
gtctgtaact tacgttgttt cttaagcatt gaaaggagtt aaaacaaaat gttaataact    319140
```

```
aattcagtga gaaagacagg cgcacactgc ctttgtatac atgcacatat tcttagacac   319200
agacacacat gtgcacttac gcccctccc ccccccacac acgtactgtt ttccctgaaa    319260
aatttcttgt aggagtctgt tgcatttttc aaaaagaaa atgaaaatgt gcacagaaat    319320
gataccttga acctagtaaa atttacgacg tcttctggga ttgcttcatg ttattaatat   319380
tttagattca ttttgccttc tctattagcc acatatatac acaaagatgc catggtatca   319440
taacatcaac ctaaaataac cattatttat ataattattt ctgccacaaa attttttctc   319500
ctgttcttcc tctaattggt gggggtgaga gttgaggaga gagagaatga agaagacaag   319560
ctatgagata tcttttcaaa tagcagagac acgtatgcac ttttctatt tggccaccaa    319620 aaatatcttg tgttcttttg tagggttttt aagtaccggt gaccaggcag caaaaggcaa   319680
ctatgggctc ctggatcaga ttcaagcact gcggtggatt gaggagaatg tgggagcctt   319740
tggcggggac cccaagagag tgaccatctt tggctcgggg gctggggcct cctgtgtcag   319800
cctgttgacc ctgtcccact actcagaagg taataatggc accccaggg tgggcgggca    319860 aatacccctga accaagaaat gaatggtcag agttcatatc tcagatgcat gtcctggtta  319920
ccagaagtca ctctggcaac agaaaatgcc caaaagatca aatgaatcca tcttcatgtc   319980
ttttaactca gcttttgttc catttgctct gtcacccagg ctggagtgca gtggtatgat   320040
catagctcat tgtagcttcc aactcctggg cttaaggctt ctcccatctc agtctcctga   320100
atacctggga ctactggctg cttttaaaa ttttttatag agaagtggtc ttgctatgtt    320160
tgcctgggct ggtctcaaac tccaggactc aagcgatcct cctgccttgg cctctcaaag   320220 tgctgggat acagatgtga gccaccatgc ttgatcagta atattttct cctaatttaa     320280 atgtgtgaca attaggtgtt ggttacaatg attggaacaa aataactact ttagaagtcc   320340
tgacactttt gttttttttt gccattctga ctgtatttga ctatttgaaa ttttattaac   320400
ttctagctac aacttagtaa aagtagtatg gaagagagac agtatgtcga taagggatgc   320460
gggtgtatag attttgtaac catcagggct tttagccaca tgttttttaa gaagtcgctc   320520
ctctctctaa ttcatattaa ttctttaaat cttctggaaa tattgaaaca cgtctggtgc   320580 attcattttag aagtagattc tgggtagaag tagattctac ccagaggaat agtgtctctc  320640
tccctgatgg tctccctccc tcccttgctc ttcccctccc attcttctct ttccctctct   320700
cgtcctctct gtctctctcc ctctctatgt cctcctccct ctacctctct cctgctccct   320760
ctctctcttt tgctctgtct ctcaccctct ctctcccct ccttccactg tctctcctcc    320820
ctccctctct ctctcccct cacactgtcc ccccactctc cctgtctttc tccctctctc    320880
tctcttcctc tctctccttt tctctgtctc cccactctct tactcactat ctccttttcct  320940 ctctctcttt ccccccttc cctctgtccc tctctctctt tgtttcttc tctctctctc     321000 cctccctttc ttcttctcct gcaaatatga ctttcaccaa aggacctcct tcctggtcag   321060
gtcagcatgc agcactaggg agtgtccaga gtttgctttc ccctctccct tcctctctct   321120
ctctcctgca aatatgactt tcacgaagga cctccttgct gggccagtca gcacgaggtc   321180
ctctgcttgt ccccgtggga gctccaaacc ctccctgggg ccctgctatt aacctggaaa   321240
aagctgatgt tggcaaagtg gagaaagagg aaaccacaaa aacacatgtg catcatgtta   321300
cctcaaccag atgtgcactt gaacgtgtag tcagcatagg cacccgtacc caaccagatg   321360
tgcacttgga cgcctaagca gtagatggtt atgctgccta agtaatggtc agcataggca   321420
gccacacccc tgagccctgc tggagtgcct gaggctttcc ccggaggctc actcagtgga   321480
ttcccagctg tcccttttgtg aaggaggctc cctgcagtat ccgatgagag acttcaaaga  321540
```

```
ggagtccaca ggaatttgag gcaattggtt ctggaagcag gatcacaaat tcctggctgt  321600
ggcctaaaag gaagaggcag gaaaatctgc agtgcagatc cagccctggg ttgcctggcc  321660
acacgcaagt gaatattcct aatagccgtc tcagtcatca agacagcttt gtaatttgtt  321720
ctgtgttgtc agtggtcttc agaatggcac cacactgact gaacctgaag ttctcaaaac  321780
cttcatggaa ttttttttt ttttcaggga gtctcactct gtctcccagg caggagtgca  321840
gtggcacaat cttggcttac cgcaacatcc accttctgga ttcaaagcga ttctcctgcc  321900
tcagcctccc gagttgctgg gattacaggc gcccaccact gtgcccggct aattttttgta 321960 tttttagtag agatgggctt tcaccgtgtt ggccaggcta gtctcgaact tcctgacctc  322020
aagtggccca cccacctcga cctcccgaat gattatttt aaagttatca gctggatatg  322080
gtggctcatg gctgttatcc cagcactttg ggaggctgag cggggaggat ggcttgagcc  322140
caggagtttg agaccagcct ggtcaacata gcgagacccc gtttgtacaa aaatgaaaat  322200
aaaaaccagc tgggcctggt ggcgcatgct tgtggtccca gttacttggg gggctgaggt  322260
gggaggatcg cttgagccag ggatgtcgag gctgcagtga gctgtgaggt tccactccag  322320
cctgggtgac agagtgagac cctgtctcaa catacataca tacatacata aaattaaaaa  322380
gtatctttct ttagagtaac tgcaggactt tcttcacttc ggcaccgtct ggacaagttt  322440
ctggatcgct gtgctcctca gtgtcttcat tggcaagata ggacagatga gggtttcctg  322500
aaatcctcca aactctgaat tccttgagtt tttagttcat aatgttttgc ccatgagacc  322560
aaatggcctt tgatttctta ctagtgctaa tgagaggaaa ggctcatatt tgtattaact  322620
ttatttcaaa aacacgataa gtgaagaatc tgatgaacca tttggtagag agatttctat  322680 ggcattttg aaaataccct gattttcact tttctcaatt gatataatca caattgtaga  322740
tttagaaagc agtcagaacc aacttcagga gtaatcaaac acatgtaagc cacattaatt  322800
ggagggaggt gttaattatt taagtcaata ggttggaaat tattatactt ttgcatcggt  322860
catttctgca aggcatgctt ctaaacagcc catcaatata atcacgaatt atgaaaaata  322920
caagccaggc actgaggctc ctgcctgtct atcatcccag caatttggga ggccaaggtg  322980
ggcagattgc ttgagtccag gagttcaaga caagcctgaa caacatggcg aaaccccgtc  323040
tctacaaaaa agagacgcat ctgttgtccc agctacttgg gaggctgagg tggaaggatc  323100
atttgagcct ggaaggcaga ggctccagcg agccaagatc ccgccactgc actccagcct  323160
gggtagcaga gtgataccct gtctaaaata aaaataaata tagccagact gtttgcctta  323220
ggaattcctt gcctggttat atggtctaat gaagacaaag tacacgtgga aagtgatagt  323280
tttatgaaga tgttcaccac agtattagta tcgtagcaaa gaatgaaatg aaaagctaca  323340
agatcaaaag gagaggaaaa ttataatgaa ccatatgtat ttactcaata ataatttaag  323400
aatttaccta agatatacat cagctggaaa aacagtttag acagctatat aaatattggg  323460
ctcagctatg caaaacagac atttgaatgg agggaaagag ctaagaatta tgtgaactcc  323520
tagcatactc attacgctaa ggtgagttgt gtttaaagta tgaattctgg gtgatttttt  323580
tcattatcca actatttag tcttatcagg agttctgtta cttccctaac atacaaataa  323640 atgtttatg tatgttactt tatatacact actgcctaaa ttattgccag tacttatgag  323700
aagggcggga aaggaacttc tcacagcatt ttttccaatt ctgaatgttt taactaatga  323760
aagtatccaa tagaatacat attgactttc tcttttggtt ttttttttt tggacatttt  323820 aaaataatct tcagagccaa gcactcaagt caatacttgc acatttctga cagaaacgtt  323880
```

```
cccaggatgg ctttgatgac atactggtca aagccatatt ggtttcaagt tgcggtcctg  323940
tgtgtcatct ttgggcaatc ctccagtctt taaaatcacg tcttcctgat gacagttata  324000
ttttcctcat atttgattgc ttctgtgacc ttaaaaatcg acagggcatg aacttctgga  324060
ctcacaactg aatgccttat tctttagtgc ccgactcggg ctgggattca cggaaatggc  324120
aggaagcaag tgtaaatgga atgctgattt ttacagcgca cctctcttgt cctatcgtag  324180
ttaaaaatac agattttata cttctggaca tccgtgtagt agactgaact catggagaat  324240
tttaagctac acagaatttt actcctaaaa ttgcccatgc ttttcaagt ttctcagcaa  324300
gtggagcatt tttatatgtg gcaaaataaa atatacacat ctctgagttt ccaatggatg  324360
tagttttgaa agaagtgacc taaaaaatac tccttacttg ggcacccagt tgaggatttc  324420
tttaagcata gctagctgaa tgtatttatt ttaattggca aatcttaata tcttcattag  324480
actcaaggta gaagtagaaa tgcgctcctg aattagcact ctgaagttga ttcaagtgga  324540
tttctttttt tcccataatg aagagatacc tagttttgct tgtgagacaa gagggccttt  324600
gaactggtac tagcttaaag cattttttt cttggaaatg gggaatgcag ttgctcttgg  324660
agttttata tatggcatct ggaggcaagg aagcaaaaac gacactaaat tgtggaagga  324720
aaagaaatc acatgtattt taccagtgca ggagaagtgt caatgtggtt tcatttcctt  324780
aaactcgtgt gtgtgtgtgt gtgtgtagaa taacattccc taaaatgaat gttcaggagg  324840
aggggtgaag ggggaatgga aatgaaaatg ggtaaagggg cccctgacag agctgaatgc  324900
tactacatcc agaaactcac atgcctgaga gacaatcaca gccttcattg ctcagtaaaa  324960
gctgcatttc tgtcctgtgg gttttcattt gcatgtccac aattttgcac ctgcaggtct  325020
cttccagaag gccatcattc agagcggcac cgccctgtcc agctgggcag tgaactacca  325080
gccgccaag tacactcgga tattggcaga caaggtcggc tgcaacatgc tggacaccac  325140
ggacatggta gaatgcctgc ggaacaagaa ctacaaggag ctcatccagc agaccatcac  325200
cccgccacc taccacatag ccttcgggcc ggtgatcgac ggcgacgtca tcccagacga  325260
ccccagatc ctgatggagc aaggcgagtt cctcaactac gacatcatgc tgggcgtcaa  325320
ccaaggggaa ggcctgaagt tcgtggacgg catcgtggat aacgaggacg tgtgacgcc  325380
caacgacttt gacttctccg tgtccaactt cgtggacaac ctttacggct accctgaagg  325440
gaaagacact ttgcgggaga ctatcaagtt catgtacaca gactgggccg ataaggaaaa  325500
ccgggagacg cggcggaaaa ccctggtggc tctctttact gaccaccagt gggtggcccc  325560
cgccgtggcc accgccgacc tgcacgcgca gtacggctcc cccacctact tctatgcctt  325620
ctatcatcac tgccaaagcg aaatgaagcc cagctgggca gattcggccc atggtgatga  325680
ggtcccctat gtcttcggca tcccccatgat cggtcccacc gagctcttca gttgtaactt  325740
ttccaagaac gacgtcatgc tcagcgccgt ggtcatgacc tactggacga acttcgccaa  325800
aactgggtac gttcatcttc gtgttgggt atcactatcc ttgccacttg tttgtgtcct  325860
caatataggt gttgcttcta ctgccacgtg caggagcaca cacgcataca cacacataca  325920
catgcatgca cacacataca cacagacaca cgcttacaca cacagcagta acaggcagct  325980
tctcccccaa catctatggc aactcatttt tttctttact cctaaagtgt tataggagta  326040
aaacacttaa ctgtcaaacc agattttac tagagttcta attgcccatt gggaattcca  326100
gagttcctac ctgcaggtgc aggactcata catatatgat ggttctgtta acagctgatt  326160
aaacggtttt gttttttgtcc ttgttgtttt agagacacag tctcactctg ttgcccacac  326220
tggagtgcag tggtgcaaca gtagctcact acagcctcct tgaactccta ggctcaagcc  326280
```

```
atcctcctgc ctcagcctcc tgagtagctg ggactacagg tgcctgccac catgcctggc  326340
taatttttaa ttttttttttt ttggtagaaa gagggtctca ctctgttgcc taggctggag  326400
tatagtggcg caatcatagc tcactgaagc ctcgagctca tgggttcatg tgatcctccc  326460
atctcagcct cttgagtagc tgggactaca ggcgtgcacc accatgccct tacatggatt  326520
tttgtagaca cagggtttgc tatgttgccc aggcttctct caaactcctg gctcaaggg  326580 atcctcccac atcagccttc tgaatagctg gactacagg tgcacaccac cttactcagc  326640
taattttatt ttgttagaga cagggttttg ctgtgtcacc cgagctggtc tcaaactctt  326700
gggctcaagt gatcttccca cctcagcctc caaaagtgct gagattacag gtgtgagcca  326760
tcacaccagc cctcattaca gagttttaag tctaatttca accatatctc ttttgttaat  326820
ttgcaaggat atcacagcac atgtaccact tggggaactg tgttgattgc ctggccatag  326880
gaatgaaaac aaatatcata ataattataa agaaatataa atatatattc ctatatatat  326940
ttaatgtcta tataaaaata tagatattcc tatttgtata atatagtaca tttatatttg  327000
tatttgtata tatatacaca caaatatatt tgtatataca aatacaaata tatatacaaa  327060
tactatatat atacaatata tatacaaata caaatatata tatacacaaa tacgtttgta  327120
ttttctctgc tatataaata actagagaga gaaaatgaaa atatatgata tttgtatcat  327180
attgctatat gtcatgcata cataaacaca cacacacaaa cacacataca tgtgtatctc  327240
acaggaaagc tcatttattg gcctaaatat agtagaaaat ataaatata caaaaagcat  327300 atatacaaca gagtctgcca atattctgct gagcggattc tctgcaaacc atgggagaaa  327360
agaacccaaa acaacctaaa tagctccaaa cattgtggca ttttttcatt ttctcttgtc  327420
taataatgta actgtggaaa tggatggggt gtcattctgt tctaccagtg tgtgcctcca  327480
tcatcaccct gagcctcttt acactgaatg agagagaaag atgtgcctgt cgcccaggga  327540
gggtaaatct tcccgtgcgg aatgaggctc tgagactgca gtggccctgc cacacatgag  327600
ttatgcacag taatccttag aagatctggg gatgctggtg gtttcaatgc ctacgtgttt  327660
agcagctggc atactgtaca aagattccaa agtggtttgg gtagggagtg gtttgagaat  327720
gttttgtgcc cttggcgaaa gtacagcatg tttttggagt ggaaaaggta tcacctggat  327780
accacctttc aataatcaga cttttgtagat ttggtctgag aaaggctacc cagaggagaa  327840
gagaggaggg acccacattt gatgcaaatg cttgtctatc actcaacggt tcttttttgt  327900
gtgaagaaat gattgaaatc aaattaatac ttttttttaaa gtaaaccttg tttattagtt  327960 tgtttgggact gctgttatca gagtatccaa aactgtatgg ctatgctggg cgcagtggct  328020
catgcctgta accccagcac tttgggaggc cgaggcagga ggatcacctg aggaggccaa  328080
gagtttaaga ccagcctagg caacatagtg agagtccgtc tctacaaaac aaatgaaaaa  328140
atttagctgt gcatggtagc atatgccgag agtctcagct tctcaggagg ctgaggcaga  328200
gggatcactt gagctcagga ggtcaaggct gcagtgggcc atgtttgcac cactgcactc  328260
caacctgggt gacagaccga aacctttatc tttaaaaaaaa aaaaaaaaaa aaaaaaaaaa  328320
aagcaccaaa aacggtgtgt cttataacaa cagaaatgta tcggttcacg ctttctaagg  328380
ccagaagttg caaatgaagg tgcttgcagg gccaagttcc ctccaaatct gtaggggag  328440 ggtatttcct tgctccttct tagttactgg tgtttgggtg cagtcttggg cattcctacc  328500
ttgcaggtgc accatcccac tctgtgtctt tgtcatctta cggcctccct gtgtgtctct  328560
gtctccacat ggccgtcttc atataagagc atctgccaag gtgcattaga agctcaccct  328620
```

```
actctagtat gacctcaact taacataaat agtcatatct gcagttaccc tatttccaaa    328680
taagctcaca tactgagata ctggggttat gacttcagcg tatcttaatt tatggggaga    328740
cagtattcaa tctctaatac cctgtgaaat cagggccagg ccctcttttg tgacagcact    328800
gagataggcg gtgtctgccc ttgcagagaa tttcatcctc ttgaagccta aagacttcca    328860
tgagagtttc ccaacatggc tatactcatt caatcttcgc tacattggca tccaaacgta    328920
ttaccgactt ggtctgcaaa cactctcttt acttactctc attaaaaaca tatgcttttt    328980
cttttcctcc ttacatgatt tgaaaataaa ctttatatga ttatcttaag tggaaagcta    329040
gaatcattcc tcatacattt tatggaacca ttaaaacaat agtgaaatct aaataatgct    329100
gttaaattct cattagctct tcctgacttc caaaggctat gagactgagg ctggctctct    329160
cattattaaa aaaaaataaa aaaaaaaaa aaggaaaaaa gacagaaaaa gataaaggaa     329220
gttaattagt tccatgaggt gatcgttatc actgctgaca ccaaatggac gcttttacca    329280
agacatcacg aaggtctgag agagccgtga aagagaata ccacaatgat ctctctgtta     329340
ttgagtgctt ttaatgccat gaatctgttt cttaaaatca cttggcttag agcctgtgat    329400
ttccaccctg catttaggga atacattcac gttgccattc atggtctgtg ttgagggtgc    329460
ttctagcttt catgaaggcc ctgacatggc tggaagagat gaggaaggaa taactgctag    329520
aacttggaga gacgctctga tgctactgaa atcaaaagct gcaggtagag agagttcatt    329580
gaggtaccca gagctcgaat gtcagtccgt ctgaagcctc tatttttgtt tcttccgccc    329640
atgggaaaca tccctgaaat aacactgagt gtattaatgc agtgagctct tttaattcat    329700
tggaaaggta ttagaatgac tcaaatgatt cctcaaggaa gttactcaga acttacatct    329760
catgtgaaat gcaacgtgtg gattcaaata caaatagttt aagtgatcac acctccatgg    329820
cagccccata aagaaggaa atggggaatt tcactgtcgg gcacagtctg gtgagctagg     329880
tattcgtcag tggatgacaa ggacttcagt tgcagttggt agttatttgt ttattgtaaa    329940
ttgggtggtg gcccgatcac tccagggcag agaaggattc cctggtcacc aggtgcagag    330000
aatgaaccaa actgatgccc gcaaggagaa agtatgggat gcaccttatc tgctgtcatg    330060
gtgtgagctg ccaagtttaa cgccattttg cagagcacac actcagatga tgactcacag    330120
aacaggaggg catatttctg cataccatca ctgttcccct ccagcactgg aggtgacagg    330180
aggaaacaag aatagctccc agcgtgtctg tcactacacg gtgccgtgga aaaggatcg     330240
cattgtgcca ggacatactt caccactctc agtgggcgtt aagtcaagcg ttctaaacct    330300
gcaggcacag ccagtctctc gatggcgcat gtgtttgcca agatgaagtg gatggggtct    330360
ggatgcttct atatagacat ctcaaagtag atggttctga cctttagtct aggtttgaag    330420
gcacatatac ctggtataca taaaccttg gttttgggat gagcacagaa aaatgatgtt     330480
gggatgtgca tggcggagaa aaggaaggaa ggagggaggg aatggaggaa agagagttca    330540
gacaaaggaa cgaagggagg gaaggaggga gggaggaggg aaaagaaaag gagggcggga    330600
gggaatcaag aaaggagtaa aggaagggag gaagggagga agaaagagg taaggggga     330660
ggagaggaag gaaagaagaa ggaaggaag gagggagga aggtgaaagg aagaaaggga     330720
ggaaggaaga aaagatggaa ggaaggaaag gaaagagaga aaagagggaa gagaggaagg    330780
gagaagggag aaagaagaga ggaaggaagg aaagtagcga gggaaggaag gaaaaaatgg    330840
agggagagag aaagaaggaa gggaggggag aaggaagagg gaggaaaaag ggaatggagg    330900
aggagaggaa gaagggaggg agggaaagaa ggaaaacagg gaaaaggagg gtaagagaga    330960
gaaaagaggg aaggggggaga ggaggaagga aagaaggagg gagggaggga caattggatc   331020
```

```
tttgcttata aattatgtca cctgtatatt ttcatggtag cattaggtga gagggctctc  331080
ccatcttaga aaggcggagt cagcgagtac gcatagtaga aatgaggagg aagtccctac  331140
ggaggctcta aattatgaaa accttgatca agaaaggatg ttgaaatcat tgaatgccag  331200
ggcctcaagt aatccttgct atttcttttt tattattatt ttgaataggg aagcagttgc  331260
ccaggcctgt gcctgagggg gatcctcccc tgtagcaagg aggtgtttca atgttagtcc  331320
aggtcagagg actaaaatca tgctggaaga gaaccgtgtg agcccaaaca tgcagaggca  331380
ttgtagaaat aaggtagatt gagaccgttt ttggaaatca gctgcagtgt caaggagaag  331440
tgaaaactaa ctctaaagtt tcaaaagggt tctagagcat taaagtcctt ttcctggaaa  331500
attactttgg aataggaga aaagggttc gtccaagctg atcaatgaaa ttcaggtgct  331560
cagtgatcca ggattctttc attttgagct ctgtgtggaa agagatggac aaaaaggagt  331620
ggggaatctt ggtttattta aaggtatga caaagaacag tgctttaaag taaccaaaca  331680
atgcattata atatagaata gaagaccta tgtgctattg gaagtcagat atgagaagag  331740
agttttgtaa tggaaaatca gatcaacaca tattttgatt ttttatgtt gttccatcga  331800
gtctgggtt tgtacggcag attgatttct gtcctgtttg catcagctac catcactgct  331860
tttgaatgtg ctggtatcct atgattaatt tacgttcaac tattgttaaa tctttgggaa  331920
aaaaagaag ttccaatgag gtatttagtg gggatgggtt acagagagtt gcagcgtaat  331980
tctggctgta aaggcgacct ttattaccaa aaaggaattt taagctgaat gaatgaacat  332040
ccccacctgg tgtggaagag gagtcactga atgcataata aactagtccg gtaataatcg  332100
ttaactgcga acaatgtttt gggtatgagg aaaacctgta ctacttaaag gaacagctga  332160
gaggattcac agatattttt agagagatca tagtactata tccatctcca gctaaagaaa  332220
tgaactagac cttagaaagg cacttgagtc tctgctgcca agatgacatc tcaaataaaa  332280
caggacaggt ggaaatggct gtgttaggtg ctggggata aggaggaaga catgcattga  332340
gtcttttact agagagacca acttgtgttt ctgtcctcaa tcattatagt ctttaatttt  332400
actcacagga gtttaaacac ttcttaggct gaataaagtc taaaaaacaa aacactgata  332460
ccccacatct agacctcact gtctggaggg tttggtaagg gagaatgact tgggctatca  332520
taatctccac aagtttatct ggctttaaga attctggctg tgcatctccg agatctttaa  332580
tagacagacg gtatcaggtg gcagctcatt tatatggatt ttccaaatcc tctgcttat  332640
tcttcaagaa caaatataa tgtgttttct ttacctttca aatatacct gagttccttc  332700
gaaaatagcc ttgtacccaa catgaacaga atactccttt tcctagatgc tcactgctta  332760
atagatgagg tagccacaca tctaatagat ccaattcagt aaaattggat ccatggaaaa  332820
aaaggtagaa tcttcacttc catttgtttc tttagaatat taaaatcaa taactaatat  332880
tagtggattt ttttcctaaa atattcattc acttattttt ctttcagtac acgttaaata  332940
actgaaaatt ttaaaattat ttcagaggac ttaaagagca aaagaaacat gagttgctgc  333000
attgaatcca acatttttc aaaccatgt aagaatacat gcataataaa taaaaaagc   333060
agaagacttt tcaaatatat tgtttatcag taaataagaa aactcatggt attagaacct  333120
atgagattat atatatttgt tctcacccta ttagtaaagt gaaaacacag cagttagtgt  333180
gcattcaact aaagggtaga ggtcaacttt cttttctcc tgtattatgt tatacatcta  333240
atatctatat ctatagatag atatacacat acacatatat acacatgaca tacatatata  333300
tactgcatat agtatatagt tagtatgcag tataaactgt ggtatgcagt atacttgtat  333360
```

```
atagtatgta atatacaata tacttttatg cactctacaa tgtatacaat atagaaattc 333420
agtatgtact ctgatataca gtatatcact ccctacttct ccctcccttg caatattata 333480
ggtgttctat tttttatatt ggaagagagg gggtaatatt tcctgaattc ttaccatatg 333540
ccagacatct tgtcattatc tttcaacctt catcacttac ctccaaccct gatattttca 333600
tcagccatgt agaggagtaa gttaaggcca atactggctg gaaaacttgc ttaagatttc 333660
acagctctta actagccaga gctgcagaaa gttgaataca gggaaatgat ttattttatc 333720
accaccacag actcagactg aggggataaa atcttccttc agcaagtgtg gcgcctctgg 333780
ctcaagtata ttgtttgaat cctgcacagt gtctggtaat ggctacagat acatgatctt 333840
ccttggtcct gcagccttct gccatgcagg ccatgcaatg actggaggca gtttcacaga 333900
agtcccgcca aggagaagtt acctggaaga tagcccttag ctcacacctg gagccattga 333960
tcaggatgtt gcaactccct gcttgcctgg ttctgcacat cacatctcaa tgctcagtgc 334020
taactagtac ataacatttt gccatgcata atctcaaatc gttttataa caaataaacc 334080 ttaagacgta attgtttttt agcttacttt acaagccata aaaaaaatgg aagaaatgag 334140
catttggtaa tttattttt gaaggggaag tgttatccta aaagagtcag ttgcaaagat 334200
gtttattaaa ggcccctatgt tttatgaatt atctccaaat tttatgatt ctccttctac 334260 ctgtgaccac ttgtgcaaat aataagaaga taattctttg gctcatagtt tccaagcaca 334320
acttagcatc tgtaacagcc cttgacttgt ttctgggtgt cttttttatc ttaaacatgt 334380
taacctcatc ataactatat gtaccatttt agcaaacttc ttacagctaa catagcgtgc 334440
tttcatcttt ttaccttcaa atagagagca aacacatggt gcatatgtct atttacaaac 334500
actttgtaat tataaagcct atttttattt ctactgttaa tatcaatttt cattgctaaa 334560 actgcaaacat ttattcattt acttcaaaag caattcttga gcaagaaaga gaatacccat 334620
ttcttggaca atagcttctt aatcagaatt tctcaacctc agtactgtta acatttgggt 334680
ccagataact tctttgctgt gggggtctct cctgtgcacc agagggtatt tagtagcatc 334740
cctcacctcc acccttcata gaacaaccct tcgtctacgg aaaccaaaag tgtctccaga 334800
tactgccaaa tatcccttgt gagcaaatca gtcctggatg agttttacag ttcgacaaga 334860
gtgaaacttg aaatactgaa attttttccta gagacactta gttttccttc tttcccttta 334920
tttttgaaga tcatttgatg ccttaaaaaa tagtaaacat gttataaaaa ttgcataatg 334980
ctgctatcag gatttatatt taaaagaaaa ataagagcaa ttttttaaagg aaaagacaac 335040 atggtagaca ggtctaggat taaagcagaa tgtacctttg ctgcttgggt atttttgtgct 335100 cattgataaa tatatatgaa gagcagattg taacttcctg atttattggt ttaagataat 335160
ttcacgtcac atgtggaaga gtatgacctt tctttttttc ttccttctat cctcagtgat 335220
ccaaatcaac cagttcctca ggataccaag ttcattcaca caaaacccaa ccgctttgaa 335280
gaagtggcct ggtccaagta taatcccaaa gaccagctct atctgcatat tggcttgaaa 335340
cccagagtga gagatcacta ccgggcaacg aaagtggctt tctggttgga actcgttcct 335400
catttgcaca acttgaacga gatattccag tatgtttcaa caaccacaaa ggttcctcca 335460
ccagacatga catcatttcc ctatggcacc cggcgatctc ccgccaagat atggccaacc 335520
accaaacgcc cagcaatcac tcctgccaac aatcccaaac actctaagga ccctcacaaa 335580
acagggcctg aggacacaac tgtcctcatt gaaaccaaac gagattattc caccgaatta 335640
agtgtcacca ttgccgtcgg ggcgtcgctc ctcttcctca acatcttagc ttttgcggcg 335700
ctgtactaca aaaaggacaa gaggcgccat gagactcaca ggcgccccag tccccagaga 335760
```

```
aacaccacaa atgatatcgc tcacatccag aacgaagaga tcatgtctct gcagatgaag    335820
cagctggaac acgatcacga gtgtgagtcg ctgcaggcac acgacacact gaggctcacc    335880
tgcccgccag actacaccct cacgctgcgc cggtcgccag atgacatccc acttatgacg    335940
ccaaacacca tcaccatgat tccaaacaca ctgacgggga tgcagccttt gcacactttt    336000
aacaccttca gtggaggaca aaacagtaca aatttacccc acggacattc caccactaga    336060
gtatagcttt gccctatttc ccttcctatc cctctgccct acccgctcag caacataaga    336120
gagggaagga aagagagaag gaaagagaga gagaaagaaa gtctccagac caggaatgtt    336180
tttgtcccac tgacttaaga caaaaatgca aaaaggcagt catcccatcc cggcagaccc    336240
ttatcgttgg tgttttccag tattacaaga tcaacttctg accctgtgaa atgtgagaag    336300
tacacatttc tgttaaaata actgctttaa gatctctacc actccaatcg atgtttagtg    336360
tgataggaca tcaccatttc aaggccccgg gtgtttccaa cgtcatggaa gcagctgaca    336420
cttctgaaac tcagccaagg acacttgata tttttaatt acaatggaag tttaaacatt    336480
tctttctgtg ccacacaatg gatggctctc cttaagtgaa gaaagagtca atgagatttt    336540
gcccagcaca tggagctgta atccagagag aaggaaacgt agaaatttat tattaaaaga    336600
atggactgtg cagcgaaatc tgtacggttc tgtgcaaaga ggtgttttgc cagcctgaac    336660
tatatttaag agactttgta aaaagaaaa atgtatatag ctgtgagttt aaacaaaaac    336720
cacaaacaga caaacaagaa aaaagctttt tattggtgtt ttcactttga aagagctttt    336780
agcaaggttg tgcttttcat tgtgctctgt acgtatataa atatatatat atatacacac    336840
acacacacac attagtcata tcacctctgt ttcctcccca acaaaagagg ctttcttct    336900 taattacttg tggtaaacaa agacatggga ttttcttaca tgagattctc atttgtagga    336960
ggatgtgatg tcccacagaa gacccagacg gtctgtgtgg cctatttccc ccgtcaggtt    337020
gcacaggtgc atgcaagagc attcttagga gaccactgtt ttgaaaaact tttgacttgt    337080
acgtgttagc cttcatgaaa ttgcagtaca gagatgggtc cccaaagtgg agtgtattta    337140
cagcttgtta aattagagac atgcacacac aaagaatcag tagggagaaa caaaaataca    337200
agtcccgttc tgtagctctg gccctttgaa tatgtttagg aagagttgct tcccatttca    337260
gggccctgcc aaaaaaagaa gaaagcttgc ctttggtggg gctatgcccc ttggagtaaa    337320
tacggctctg tgttccctag cagctgcggg agggtttggc cgatgaagta cctgctcagc    337380
ttagctaatc agattgaagg aagacatgtg tctttccttt ttgtttaagc actcggtccc    337440
ttatttatca gtaagcaggt ttttaaaaat ctttatatc atttatggga tcaaacatat    337500
gattgtctga aaacatcact ttttgtggat ttgtgtatcc ggtcaccaaa cggtgaatat    337560
tatagaagaa tgggggaaga aaggatagaa tattaaaact gctttgcatg ggttttctgg    337620
gaaattagga taacttcact gagaagacat tgaatggaaa ttattcaccc atttaaatt    337680 ggtgacctag ggatcagaga tttgtctttc caacagcttg tcatttttc atttctcttc    337740 tcattttca ggaaagtttt gagtgttata aggtggaagg aaacatagta gcaatggata    337800
cttttttgaa aaattattgc attaccaaga aacagtagcc aaagatattt gaagatcatg    337860
ttcctcggct ccattgtggg ttattctaga atccagtct taaatctctc cgctaaagtg    337920
gacattcccc ataaaaattg tccagctgcc tggctctttt gcaataacaa cctttgatta    337980
ctgaatccct acactcaaac tatagtgata tatcagtgtt tgagagtgac ctctagaaaa    338040
aagaaaagtg ttttagaaa tgcgtacaag tcacccccaa atcctattgc ttatcttggg    338100
```

| | |
|---|---|
| ttaaatttga gagtgattct ctgtatataa atatgtgaaa tattattatc tcaacttagc | 338160 |
| acacgtgaag caacatttct ttcctacaga gaggtgtcat ggtaagattt cattccgaat | 338220 |
| tcattgtttc atagagctat gatcaggcca tttctgcaag caatgtatga ccccacctga | 338280 |
| gcaaccacaa ataggctctc tgtgaaacta caaaggaagt tatgtgtggc atccatgttg | 338340 |
| gtttcgtctg tctgtaatgt gaattccagt atttgtttag tatttccagt tgtctcctgc | 338400 |
| tagcaatatg tacagtaacg cgtcaggctt gtgacatttg aataaggaaa aacagagttc | 338460 |
| ctgttaagtg aataacttta gcttttacag gggattatga tcaaaagtga ttttagtaca | 338520 |
| tcttaaatga tatcttattt ctacatggaa agaagttata gaatcttcat agagttctat | 338580 |
| gagaaaaaat atacttgcta tctataaaaa agagaaaaaa gaaaaaaaat gagaaaaaag | 338640 |
| taagaaaaaa aaaaatcctg tcctaggctt ttactcttga tcttcaaagg cacgcagggt | 338700 |
| ttaatggttc cttgggttat tattttgcag ttttgttttt tattttgcct taagtaatga | 338760 |
| tagaagatat atatggccgg acacatatgt ataaacttt cagcagcatt tttaataata | 338820 |
| aaatatcaca gtattttcta atgctttgtg caaataa | 338857 |

<210> SEQ ID NO 2
<211> LENGTH: 5672
<212> TYPE: DNA
<213> ORGANISM: Homo sapiens

<400> SEQUENCE: 2

| | |
|---|---|
| agaaggggaa ggctcctggg ctttcaatac atcctcctga atcatacctc gtttcgggtt | 60 |
| ccctagaaaa atctggacgt gtaaaaagaa ctcttaacgg ccgatgcagc tcttccaaag | 120 |
| ctaaggctgc cttggagttt tcataagaaa ttgtccctgg aggtgttgga tgatcacagc | 180 |
| ttccttggag cattgcagtt gctggaatcc agtttcagga ttaagggagg gctgcctcct | 240 |
| tgcaatgggc tgccaagaaa acggctgtgc ttgttcttaa cctcaggctc tgtctgtgat | 300 |
| cagtctgaga gtctctccca ggtctactgc tccctggaaa gccctatctc tctgcaggct | 360 |
| cgcctctggg ctttgtctcc ttggagccac atcactggga cagctgtgga tgtggatgca | 420 |
| gatttgaacc atgtcacggc cccagggact gctatggctt cctttgttgt tcaccccggt | 480 |
| ctgcgtcatg ttaaactcca atgtcctcct gtggttaact gctcttgcca tcaagttcac | 540 |
| cctcattgac agccaagcac agtatccagt tgtcaacaca aattatggca aaatccgggg | 600 |
| cctaagaaca ccgttaccca atgagatctt gggtccagtg gagcagtact tagggtccc | 660 |
| ctatgcctca cccccactg gagagaggcg gtttcagccc ccagaacccc cgtcctcctg | 720 |
| gactggcatc cgaaatacta ctcagtttgc tgctgtgtgc cccagcacc tggatgagag | 780 |
| atccttactg catgacatgc tgcccatctg gtttaccgcc aatttggata ctttgatgac | 840 |
| ctatgttcaa gatcaaaatg aagactgcct ttacttaaac atctacgtgc ccacggaaga | 900 |
| tgatattcat gatcagaaca gtaagaagcc cgtcatggtc tatatccatg ggggatctta | 960 |
| catggagggc accggcaaca tgattgacgg cagcattttg gcaagctacg gaaacgtcat | 1020 |
| cgtgatcacc attaactacc gtctgggaat actagggttt ttaagtaccg gtgaccaggc | 1080 |
| agcaaaaggc aactatgggc tcctggatca gattcaagca ctgcggtgga ttgaggagaa | 1140 |
| tgtgggagcc tttggcgggg accccaagag agtgaccatc tttggctcgg ggctggggc | 1200 |
| ctcctgtgtc agcctgttga cctgtccca ctactcagaa ggtctcttcc agaaggccat | 1260 |
| cattcagagc ggcaccgccc tgtccagctg ggcagtgaac taccagccgg ccaagtacac | 1320 |
| tcggatattg gcagacaagg tcggctgcaa catgctggac accacggaca tggtagaatg | 1380 |

```
cctgcggaac aagaactaca aggagctcat ccagcagacc atcaccccgg ccacctacca   1440
catagccttc gggccggtga tcgacggcga cgtcatccca gacgacccc  agatcctgat   1500
ggagcaaggc gagttcctca actacgacat catgctgggc gtcaaccaag gggaaggcct   1560
gaagttcgtg gacggcatcg tggataacga ggacggtgtg acgcccaacg actttgactt   1620
ctccgtgtcc aacttcgtgg acaaccttta cggctaccct gaagggaaag acactttgcg   1680
ggagactatc aagttcatgt acacagactg gccgataag  gaaaacccgg agacgcggcg   1740
gaaaaccctg gtggctctct ttactgacca ccagtgggtg gccccgccg  tggccaccgc   1800
cgacctgcac gcgcagtacg gctcccccac ctacttctat gccttctatc atcactgcca   1860
aagcgaaatg aagcccagct gggcagattc ggcccatggt gatgaggtcc cctatgtctt   1920
cggcatcccc atgatcggtc ccaccgagct cttcagttgt aacttttcca agaacgacgt   1980
catgctcagc gccgtggtca tgacctactg gacgaacttc gccaaaactg gtgatccaaa   2040
tcaaccagtt cctcaggata ccaagttcat tcacacaaaa cccaaccgct ttgaagaagt   2100
ggcctggtcc aagtataatc ccaaagacca gctctatctg catattggct gaaacccag   2160
agtgagagat cactaccggg caacgaaagt ggctttctgg ttggaactcg ttcctcattt   2220
gcacaacttg aacgagatat ccagtatgt  ttcaacaacc acaaaggttc ctccaccaga   2280
catgacatca tttccctatg cacccggcg  atctcccgcc aagatatggc caaccaccaa   2340
acgcccagca atcactcctg ccaacaatcc caaacactct aaggaccctc acaaaacagg   2400
gcctgaggac acaactgtcc tcattgaaac caaacgagat tattccaccg aattaagtgt   2460
caccattgcc gtcggggcgt cgctcctctt cctcaacatc ttagcttttg cggcgctgta   2520
ctacaaaaag acaagaggc  gccatgagac tcacaggcgc cccagtcccc agagaaacac   2580
cacaaatgat atcgctcaca tccagaacga agagatcatg tctctgcaga tgaagcagct   2640
ggaacacgat cacgagtgtg agtcgctgca ggcacacgac acactgaggc tcacctgccc   2700
gccagactac accctcacgc tgcgccggtc gccagatgac atcccactta tgacgccaaa   2760
caccatcacc atgattccaa acacactgac ggggatgcag cctttgcaca cttttaacac   2820
cttcagtgga ggacaaaaca gtacaaattt accccacgga cattccacca ctagagtata   2880
gctttgccct atttcccttc ctatccctct gccctacccg ctcagcaaca tagaagaggg   2940
aaggaaagag agaaggaaag agagagagaa agaaagtctc cagaccagga atgttttgt   3000
cccactgact taagacaaaa atgcaaaaag gcagtcatcc catcccggca gacccttatc   3060
gttggtgttt tccagtatta caagatcaac ttctgaccct gtgaaatgtg agaagtacac   3120
atttctgtta aaataactgc tttaagatct ctaccactcc aatcgatgtt tagtgtgata   3180
ggacatcacc atttcaaggc cccgggtgtt tccaacgtca tggaagcagc tgacacttct   3240
gaaactcagc caaggacact tgatattttt taattacaat ggaagtttaa acatttcttt   3300
ctgtgccaca caatggatgg ctctccttaa gtgaagaaag agtcaatgag attttgccca   3360
gcacatggag ctgtaatcca gagagaagga aacgtagaaa tttattatta aaagaatgga   3420
ctgtgcagcg aaatctgtac ggttctgtgc aaagaggtgt tttgccagcc tgaactatat   3480
ttaagagact ttgtaaaaaa gaaaatgta  tatagctgtg agtttaaaca aaaccacaa    3540
acagacaaac aagaaaaaaa gcttttattg gtgttttcac tttgaaagag cttttagcaa   3600
ggttgtgctt ttcattgtgc tctgtacgta tataaatata tatatatata cacacacaca   3660
cacacattag tcatatcacc tctgtttcct ccccaacaaa agaggctttt cttcttaatt   3720
```

```
acttgtggta aacaaagaca tgggattttc ttacatgaga ttctcatttg taggaggatg    3780
tgatgtccca cagaagaccc agacggtctg tgtggcctat ttcccccgtc aggttgcaca    3840
ggtgcatgca agagcattct taggagacca ctgttttgaa aaactttga cttgtacgtg     3900 ttagccttca tgaaattgca gtacagagat gggtccccaa agtggagtgt atttacagct    3960
tgttaaatta gagacatgca cacacaaaga atcagtaggg agaaacaaaa atacaagtcc    4020
cgttctgtag ctctggccct ttgaatatgt ttaggaagag ttgcttccca tttcagggcc    4080
ctgccaaaaa aagaagaaag cttgcctttg gtggggctat gccccttgga gtaaatacgg    4140
ctctgtgttc cctagcagct gcgggagggt ttggccgatg aagtacctgc tcagcttagc    4200
taatcagatt gaaggaagac atgtgtcttt ccttttgtt taagcactcg gtcccttatt     4260
tatcagtaag caggttttta aaatctttt atatcattta tgggatcaaa catatgattg     4320
tctgaaaaca tcactttttg tggatttgtg tatccggtca ccaaacggtg aatattatag    4380
aagaatgggg gaagaaagga tagaatatta aaactgcttt gcatgggttt tctgggaaat    4440
taggataact tcactgagaa gacattgaat ggaaattatt cacccatttt aaattggtga    4500
cctagggatc agagatttgt cttttccaaca gcttgtcatt ttttcatttc tcttctcatt    4560
tttcaggaaa gttttgagtg ttataaggtg aaggaaaca tagtagcaat ggatacttttt    4620 ttgaaaaatt attgcattac caagaaacag tagccaaaga tatttgaaga tcatgttcct    4680
cggctccatt gtgggttatt ctagaaatcc agtcttaaat ctctccgcta aagtggacat    4740
tccccataaa aattgtccag ctgcctggct cttttgcaat aacaaccttt gattactgaa    4800
tccctacact caaactatag tgatatatca gtgtttgaga gtgacctcta gaaaaaagaa    4860
aagtgttttt agaaatgcgt acaagtcacc cccaaatcct attgcttatc ttgggttaaa    4920
tttgagagtg attctctgta tataaatatg tgaaatatta ttatctcaac ttagcacacg    4980
tgaagcaaca tttctttcct acagagaggt gtcatggtaa gatttcattc cgaattcatt    5040
gtttcataga gctatgatca ggccatttct gcaagcaatg tatgaccca cctgagcaac     5100 cacaaatagg ctctctgtga aactacaaag gaagttatgt gtggcatcca tgttggtttc    5160
gtctgtctgt aatgtgaatt ccagtatttg tttagtattt ccagttgtct cctgctagca    5220
atatgtacag taacgcgtca ggcttgtgac atttgaataa ggaaaaacag agttcctgtt    5280
aagtgaataa ctttagcttt tacagggggat tatgatcaaa agtgatttta gtacatctta    5340
aatgatatct tatttctaca tggaaagaag ttatagaatc ttcatagagt tctatgagaa    5400
aaaatatact tgctatctat aaaaaagaga aaaagaaaa aaatgagaa aaagtaaga      5460 aaaaaaaaaa tcctgtccta ggcttttact cttgatcttc aaaggcacgc agggtttaat    5520
ggttccttgg gttattattt tgcagttttg tttttttattt tgccttaagt aatgatagaa    5580
gatatatatg gccggacaca tatgtataaa cttttcagca gcattttttaa taataaaata    5640 tcacagtatt ttctaaaaaa aaaaaaaaa aa                                   5672
```

<210> SEQ ID NO 3
<211> LENGTH: 21
<212> TYPE: DNA
<213> ORGANISM: Artificial sequence
<220> FEATURE:
<223> OTHER INFORMATION: polynucleotide

<400> SEQUENCE: 3

```
cggctgcaac ttctcgcgca a                                              21
```

<210> SEQ ID NO 4
<211> LENGTH: 816
<212> TYPE: PRT
<213> ORGANISM: Homo sapiens

<400> SEQUENCE: 4

```
Met Ser Arg Pro Gln Gly Leu Leu Trp Leu Pro Leu Leu Phe Thr Pro
1               5                   10                  15

Val Cys Val Met Leu Asn Ser Asn Val Leu Leu Trp Leu Thr Ala Leu
            20                  25                  30

Ala Ile Lys Phe Thr Leu Ile Asp Ser Gln Ala Gln Tyr Pro Val Val
        35                  40                  45

Asn Thr Asn Tyr Gly Lys Ile Arg Gly Leu Arg Thr Pro Leu Pro Asn
    50                  55                  60

Glu Ile Leu Gly Pro Val Glu Gln Tyr Leu Gly Val Pro Tyr Ala Ser
65                  70                  75                  80

Pro Pro Thr Gly Glu Arg Arg Phe Gln Pro Pro Glu Pro Pro Ser Ser
                85                  90                  95

Trp Thr Gly Ile Arg Asn Thr Thr Gln Phe Ala Ala Val Cys Pro Gln
            100                 105                 110

His Leu Asp Glu Arg Ser Leu Leu His Asp Met Leu Pro Ile Trp Phe
        115                 120                 125

Thr Ala Asn Leu Asp Thr Leu Met Thr Tyr Val Gln Asp Gln Asn Glu
    130                 135                 140

Asp Cys Leu Tyr Leu Asn Ile Tyr Val Pro Thr Glu Asp Asp Ile His
145                 150                 155                 160

Asp Gln Asn Ser Lys Lys Pro Val Met Val Tyr Ile His Gly Gly Ser
                165                 170                 175

Tyr Met Glu Gly Thr Gly Asn Met Ile Asp Gly Ser Ile Leu Ala Ser
            180                 185                 190

Tyr Gly Asn Val Ile Val Ile Thr Ile Asn Tyr Arg Leu Gly Ile Leu
        195                 200                 205

Gly Phe Leu Ser Thr Gly Asp Gln Ala Ala Lys Gly Asn Tyr Gly Leu
    210                 215                 220

Leu Asp Gln Ile Gln Ala Leu Arg Trp Ile Glu Glu Asn Val Gly Ala
225                 230                 235                 240

Phe Gly Gly Asp Pro Lys Arg Val Thr Ile Phe Gly Ser Gly Ala Gly
                245                 250                 255

Ala Ser Cys Val Ser Leu Leu Thr Leu Ser His Tyr Ser Glu Gly Leu
            260                 265                 270

Phe Gln Lys Ala Ile Ile Gln Ser Gly Thr Ala Leu Ser Ser Trp Ala
        275                 280                 285

Val Asn Tyr Gln Pro Ala Lys Tyr Thr Arg Ile Leu Ala Asp Lys Val
    290                 295                 300

Gly Cys Asn Met Leu Asp Thr Thr Asp Met Val Glu Cys Leu Arg Asn
305                 310                 315                 320

Lys Asn Tyr Lys Glu Leu Ile Gln Gln Thr Ile Thr Pro Ala Thr Tyr
                325                 330                 335

His Ile Ala Phe Gly Pro Val Ile Asp Gly Asp Val Ile Pro Asp Asp
            340                 345                 350

Pro Gln Ile Leu Met Glu Gln Gly Glu Phe Leu Asn Tyr Asp Ile Met
        355                 360                 365

Leu Gly Val Asn Gln Gly Glu Gly Leu Lys Phe Val Asp Gly Ile Val
    370                 375                 380
```

```
Asp Asn Glu Asp Gly Val Thr Pro Asn Asp Phe Asp Phe Ser Val Ser
385                 390                 395                 400

Asn Phe Val Asp Asn Leu Tyr Gly Tyr Pro Glu Gly Lys Asp Thr Leu
            405                 410                 415

Arg Glu Thr Ile Lys Phe Met Tyr Thr Asp Trp Ala Asp Lys Glu Asn
        420                 425                 430

Pro Glu Thr Arg Arg Lys Thr Leu Val Ala Leu Phe Thr Asp His Gln
        435                 440                 445

Trp Val Ala Pro Ala Val Ala Thr Ala Asp Leu His Ala Gln Tyr Gly
    450                 455                 460

Ser Pro Thr Tyr Phe Tyr Ala Phe Tyr His His Cys Gln Ser Glu Met
465                 470                 475                 480

Lys Pro Ser Trp Ala Asp Ser Ala His Gly Asp Glu Val Pro Tyr Val
            485                 490                 495

Phe Gly Ile Pro Met Ile Gly Pro Thr Glu Leu Phe Ser Cys Asn Phe
            500                 505                 510

Ser Lys Asn Asp Val Met Leu Ser Ala Val Val Met Thr Tyr Trp Thr
            515                 520                 525

Asn Phe Ala Lys Thr Gly Asp Pro Asn Gln Pro Val Pro Gln Asp Thr
530                 535                 540

Lys Phe Ile His Thr Lys Pro Asn Arg Phe Glu Glu Val Ala Trp Ser
545                 550                 555                 560

Lys Tyr Asn Pro Lys Asp Gln Leu Tyr Leu His Ile Gly Leu Lys Pro
            565                 570                 575

Arg Val Arg Asp His Tyr Arg Ala Thr Lys Val Ala Phe Trp Leu Glu
            580                 585                 590

Leu Val Pro His Leu His Asn Leu Asn Glu Ile Phe Gln Tyr Val Ser
            595                 600                 605

Thr Thr Thr Lys Val Pro Pro Pro Asp Met Thr Ser Phe Pro Tyr Gly
            610                 615                 620

Thr Arg Arg Ser Pro Ala Lys Ile Trp Pro Thr Thr Lys Arg Pro Ala
625                 630                 635                 640

Ile Thr Pro Ala Asn Asn Pro Lys His Ser Lys Asp Pro His Lys Thr
            645                 650                 655

Gly Pro Glu Asp Thr Thr Val Leu Ile Glu Thr Lys Arg Asp Tyr Ser
            660                 665                 670

Thr Glu Leu Ser Val Thr Ile Ala Val Gly Ala Ser Leu Leu Phe Leu
            675                 680                 685

Asn Ile Leu Ala Phe Ala Ala Leu Tyr Tyr Lys Lys Asp Lys Arg Arg
            690                 695                 700

His Glu Thr His Arg Arg Pro Ser Pro Gln Arg Asn Thr Thr Asn Asp
705                 710                 715                 720

Ile Ala His Ile Gln Asn Glu Glu Ile Met Ser Leu Gln Met Lys Gln
            725                 730                 735

Leu Glu His Asp His Glu Cys Glu Ser Leu Gln Ala His Asp Thr Leu
            740                 745                 750

Arg Leu Thr Cys Pro Pro Asp Tyr Thr Leu Thr Leu Arg Arg Ser Pro
            755                 760                 765

Asp Asp Ile Pro Leu Met Thr Pro Asn Thr Ile Thr Met Ile Pro Asn
            770                 775                 780

Thr Leu Thr Gly Met Gln Pro Leu His Thr Phe Asn Thr Phe Ser Gly
785                 790                 795                 800

Gly Gln Asn Ser Thr Asn Leu Pro His Gly His Ser Thr Thr Arg Val
```

<210> SEQ ID NO 5
<211> LENGTH: 21
<212> TYPE: DNA
<213> ORGANISM: Artificial sequence
<220> FEATURE:
<223> OTHER INFORMATION: Primer

<400> SEQUENCE: 5
aaagccctat ctctctgcag g                                                 21

<210> SEQ ID NO 6
<211> LENGTH: 22
<212> TYPE: DNA
<213> ORGANISM: Artificial sequence
<220> FEATURE:
<223> OTHER INFORMATION: Primer

<400> SEQUENCE: 6
tgagtagtat ttcggatgcc ag                                                22

<210> SEQ ID NO 7
<211> LENGTH: 22
<212> TYPE: DNA
<213> ORGANISM: Artificial sequence
<220> FEATURE:
<223> OTHER INFORMATION: Primer

<400> SEQUENCE: 7
aagaacaccg ttacccaatg ag                                                22

<210> SEQ ID NO 8
<211> LENGTH: 23
<212> TYPE: DNA
<213> ORGANISM: Artificial sequence
<220> FEATURE:
<223> OTHER INFORMATION: Primer

<400> SEQUENCE: 8
gagacattat aaaaccctcc tag                                               23

<210> SEQ ID NO 9
<211> LENGTH: 22
<212> TYPE: DNA
<213> ORGANISM: Artificial sequence
<220> FEATURE:
<223> OTHER INFORMATION: Primer

<400> SEQUENCE: 9
ttagcattgg tgagtcagtg tg                                                22

<210> SEQ ID NO 10
<211> LENGTH: 22
<212> TYPE: DNA
<213> ORGANISM: Artificial sequence
<220> FEATURE:
<223> OTHER INFORMATION: Primer

<400> SEQUENCE: 10
ccgtcaaaac gagaagtgga ct                                                22

<210> SEQ ID NO 11
<211> LENGTH: 20
<212> TYPE: DNA
<213> ORGANISM: Artificial sequence -continued

```
<220> FEATURE:
<223> OTHER INFORMATION: Primer

<400> SEQUENCE: 11 cttttctat ttggccacca                                        20

<210> SEQ ID NO 12
<211> LENGTH: 21
<212> TYPE: DNA
<213> ORGANISM: Artificial sequence
<220> FEATURE:
<223> OTHER INFORMATION: Primer

<400> SEQUENCE: 12
ttcttggttc agggtatttg c                                     21

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13
agctgcattt ctgtcctgtg                                       20

<210> SEQ ID NO 14
<211> LENGTH: 20
<212> TYPE: DNA
<213> ORGANISM: Artificial sequence
<220> FEATURE:
<223> OTHER INFORMATION: Primer

<400> SEQUENCE: 14
tctcccgcaa agtgtctttc                                       20

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
ccaacttcgt ggacaacctt                                       20

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
accccaacac gaagatgaac                                       20

<210> SEQ ID NO 17
<211> LENGTH: 20
<212> TYPE: DNA
<213> ORGANISM: Artificial sequence
<220> FEATURE:
<223> OTHER INFORMATION: Primer

<400> SEQUENCE: 17
cacgtcacat gtggaagagt                                       20
```

```
<210> SEQ ID NO 18
<211> LENGTH: 20
<212> TYPE: DNA
<213> ORGANISM: Artificial sequence
<220> FEATURE:
<223> OTHER INFORMATION: Primer

<400> SEQUENCE: 18
gacggcaatg gtgacactta                                                  20

<210> SEQ ID NO 19
<211> LENGTH: 20
<212> TYPE: DNA
<213> ORGANISM: Artificial sequence
<220> FEATURE:
<223> OTHER INFORMATION: Primer

<400> SEQUENCE: 19
tcctcattga aaccaaacga                                                  20

<210> SEQ ID NO 20
<211> LENGTH: 20
<212> TYPE: DNA
<213> ORGANISM: Artificial sequence
<220> FEATURE:
<223> OTHER INFORMATION: Primer

<400> SEQUENCE: 20
aacattcctg gtctggagac                                                  20
```

MODULATION OF NLGN4 EXPRESSION, NK CELL ACTIVITY IN NON-ALCOHOLIC FATTY LIVER DISEASE (NAFLD)

CROSS REFERENCE TO RELATED APPLICATIONS

This application claims priority from U.S. Provisional application Ser. No. 61/884153 filed on Sep. 30, 2013.

FIELD OF THE INVENTION

The present invention relates to the involvement of NK cells in Nonalcoholic-Fatty-Liver-Disease (NAFLD), mediated by a novel Neuroligin-4 (NLGn4) synaptic pathway. The present invention provides compositions and methods for modulating the action of NLGn4 to attenuate Nonalcoholic-Fatty-Liver-Disease (NAFLD).

BACKGROUND OF THE INVENTION

Nonalcoholic fatty-liver disease (NAFLD) is one of the most prevalent liver diseases in western countries. The full pathophysiology of NAFLD is still unknown. Both obesity and insulin resistance are considered to play a strong role in the disease process. Indeed, the rising rates of obesity and diabetes mellitus correlate with the increasing incidence of NAFLD, which is the hepatic and early manifestation of metabolic syndrome. Estimates suggest that about 20% to 30% of adults in developed countries have excess fat accumulation in the liver, 50% among people with diabetes, and about 80% in the obese and morbidly obese individuals.

Non-alcoholic steatohepatitis (NASH) is the most severe form of NAFLD, and can progress to more severe forms of liver disease, including fibrosis progression, cirrhosis, and even hepatocellular carcinoma.

The disease begins with the aberrant accumulation of triglycerides in the liver, resulting in simple steatosis; most patients who develop steatosis are stable and further disease does not develop. However, some individuals progress to NASH, the severe form of NAFLD. In NASH, up to 20% of patients' progress into cirrhosis.

The normal liver is composed of hepatocytes and non-parenchymal cells, which include kupffer cells, sinusoidal endothelial cells, and myofibroblasts known as Hepatic Stellate Cells (HSCs). HSCs are considered to be involved in the pathogenesis of liver fibrosis from any etiology, including NASH-related hepatic fibrosis. In normal liver, HSCs are described as being in a quiescent state and serve to store retinoids (vitamin A). Quiescent stellate cells represent 5-8% of the total number of liver cells. When the liver is damaged, HSCs can change into an activated state characterized by contractions, loss of lipid droplets and enhanced of proliferation, cell migration as well as cellular adhesion. HSCs are also unequivocally the main cells involved in the production of excessive ECM seen in liver fibrosis. Since activated HSCs themselves secrete inflammatory chemokines, a vicious cycle is formed, whereby fibrogenic and inflammatory cells stimulate each other and perpetuate a process of liver damage and repair.

Natural killer (NK) cells are a key component of the innate immune system, and play a critical role in the early stages of the immune response against tumor cells, as well as those infected by viral and microbial pathogens.

In humans, two NK-cell subsets have been characterized according to the cell-surface density of CD56 and expression of CD16. $CD56^{dim}CD16^{bright}$ NK cells (hereinafter $CD56^{dim}$) compose approximately 90% of circulating NK cells; $CD56^{bright}CD16^{dim}$ NK cells (hereinafter $CD56^{bright}$) constitute approximately 10%. $CD56^{bright}$ NK cells proliferate and produce interferon in response to stimulation with interleukin-12 (IL-12), whereas $CD56^{dim}$ NK cells are more cytolytic and produce significant amounts of cytokine when their activating receptors are engaged.

In a paper published by some of the inventors it was found that, as opposed to CD8 immune cells, NK cells have anti-fibrotic activity through stimulation of HSC killing. (Melhhem et al., J.Hepatology; 2006; 45: 60-71). It has also been reported that the function of NK cells decreases when the liver disease progresses into cirrhosis, suggesting that attenuating NK function is a prerequisite for the progression of the disease (Seki et al.; Clin Dev Immunol.; 2011; Article ID 868345).

Human neuroligin-4 (NLG4, NLGn4, NLGn4X) encodes a member of a family of neuronal cell surface proteins called the Neuroligins. FIG. 1 illustrates the neuroligins and their interactions. Members of this family may act as splice site-specific ligands for beta-neurexins and may be involved in the formation and remodeling of central nervous system synapses. The encoded protein interacts with discs, large (*Drosophila*) homolog 4 (DLG4). Mutations in this gene have been associated with autism and Asperger syndrome. NLGn4 is also detected with high levels of expression in heart and lower in liver, skeletal muscle and pancreas.

The clinical implications of NAFLD are derived mostly from its potential to progress to cirrhosis and liver failure. There is an unmet medical for compositions and methods for treating NAFLD and preventing the progression to cirrhosis. Nowhere in the art has it been suggested that disease progression of NAFLD can be modulated by attenuating NLGn4 expression and thereby NK cell activity.

SUMMARY OF THE INVENTION

The present invention relates to preventing, treating and attenuating liver disease by inhibiting NLGn4 expression and thereby modulating the activity of NK cells. The invention, according to some embodiments relates to attenuation of the progression of NAFLD into cirrhosis and liver failure by modulating the expression of human neuroligin-4 (NLGn4, NLGn4, NLGn4X) and thereby activating cytotoxic NK cells.

There is provided herein according to some embodiments, a method of treating, attenuating and/or preventing progression of a liver disorder in a subject, the method comprising administering to the subject a composition comprising a therapeutically effective amount of an agent capable of inhibiting expression of a NLGn4 gene product, thereby treating, attenuating and/or preventing progression of the liver disorder.

According to some embodiments, the human NLGn4 gene product is encoded by a nucleic acid sequence comprising SEQ ID NO: 1. According to some embodiments, the NLGn4 gene product is encoded by a nucleic acid sequence with the accession number NM_020742. According to some embodiments, the NLGn4 gene product is encoded by a nucleic acid sequence with the accession number NM_181332. According to some embodiments, the NLGn4 gene product is encoded by a nucleic acid sequence with the accession number NM_001282145. According to some embodiments, the NLGn4 gene product is encoded by a nucleic acid sequence with the accession number NM_001282146.

According to some embodiments, the NLGn4 gene product comprises an mRNA sequence set forth in SEQ ID NO: 2. According to some embodiments, the accession number of the NLGn4 mRNA is AY358562. According to some embodiments, the accession number of the NLGn4 mRNA is BC032567. According to some embodiments, the accession number of the NLGn4 mRNA is BC034018.

According to some embodiments, the NLGn4 gene product comprises a peptide sequence set forth in SEQ ID NO: 4. According to some embodiments, the accession number of the NLGn4 polypeptide is NP_001269075.1. According to some embodiments, the accession number of the NLGn4 polypeptide is NP_001269074.1. According to some embodiments, the accession number of the NLGn4 polypeptide is NP_851849.1. According to some embodiments, the accession number of the NLGn4 polypeptide is NP_065793.1.

According to some embodiments, the agent comprises one or more inhibitory nucleic acids complementary to at least a portion of SEQ ID NO: 2.

According to some embodiments, the one or more inhibitory nucleic acids is selected from the group consisting of: an antisense molecule, an siRNA, and an shRNA. Each possibility is a separate embodiment of the invention.

According to some embodiments, the siRNA comprises a sequence set forth in SEQ ID NO: 3. According to some embodiments, the accession number of the siRNA sequence is SI03083395.

According to some embodiments, the liver disorder is selected from the group consisting of: non-alcoholic fatty liver disease (NAFLD), non-alcoholic steatohepatitis (NASH), cirrhosis, hepatitis, liver adenoma, insulin hypersensitivity, liver cancer and any combination thereof. Each possibility is a separate embodiment of the invention.

According to some embodiments, the liver disorder is characterized by NLGn4 overexpression. According to some embodiments, NLGn4 overexpression comprises a 2,3,4,5-10 fold or more increase in NLGn4 expression relative to the expression level obtained in normal subjects. According to some embodiments, the overexpression attenuates NK cell activity, inhibits the expression of NLGn4 and modulates and/or activates the function of the NK cell.

According to some embodiments, administering to the subject the composition comprising a therapeutically effective amount of an agent capable of inhibiting expression of a NLGn4 gene product comprises administering the composition to an immune cell population of the subject. According to some embodiments, administering the composition to an immune cell population comprises infecting the immune cell population with a vector comprising the agent capable of inhibiting NLGn4 expression.

According to some embodiments, inhibiting the expression of the NLGn4 gene product reduces the activity of hepatic stellate cells. According to some embodiments, inhibiting the expression of the NLGn4 gene product increases apoptosis of the hepatic stellate cells.

According to some embodiments, the composition further comprises a GLUT4 antagonist. According to some embodiments, NLGn4 expression is regulated by a specific type of ionotropic glutamate receptor N-methyl-D-aspartate (NMDA or GLUT4 receptor; NMDAR). According to some embodiments, NLGn4 is linked to NMDR and both localize and bind PSD-95; a post synaptic density protein (PSD) According to some embodiments, the composition comprises an NMDAR antagonist selected from the group consisting of: Ketamin, Amantadine, Phencyclidine, Nitrous oxide, Dextromethorphan (and dextrorphan), Memantine, Ethanol, Riluzole, Xenon, HU-211, Lead (Pb2+), Conantokins, and Huperzine A.

According to an alternative embodiment, administering an N-methyl D aspartate receptor (NMDAR) agonist can increase NMDAR-mediated NLGn4 expression and as a result attenuate NK cell activity. Non-limiting examples of NMDAR agonists are Aminocyclopropanecarboxylic acid, D-Cycloserine, cis-2,3-Piperidinedicarboxylic acid, L-aspartate, L-alanine, Quinolinate, Homocysterate, D-serine, and ACPL.

There is provided herein according to some embodiments, a pharmaceutical composition for the use in treating, attenuating and/or preventing progression of a liver disorder in a subject, the composition comprising a therapeutically effective amount of an agent capable of inhibiting expression of a NLGn4 gene product, wherein the composition is capable of treating, attenuating and/or preventing progression of the liver disorder.

According to some embodiments, the pharmaceutical composition further comprises a pharmaceutically acceptable carrier.

There is provided herein according to some embodiments, a method of diagnosing and/or monitoring a liver disorder in a subject, the method comprising: isolating an immune cell population from a biological sample of the subject; detecting expression level of an NLGn4 gene product in the immune cell population and diagnosing and/or monitoring the liver disorder according to the NLGn4 gene product expression level.

According to some embodiments, the NLGn4 gene product is encoded by a nucleic acid sequence comprising SEQ ID NO: 1. According to some embodiments, the NLGn4 gene product comprises SEQ ID NO: 2.

According to some embodiments, the agent comprises one or more inhibitory nucleic acids complementary to at least a portion of SEQ ID NO: 2. According to some embodiments, the one or more inhibitory nucleic acids are selected from the group consisting of: an antisense molecule, an siRNA, and an shRNA. Each possibility is a separate embodiment of the invention.

According to some embodiments, the siRNA comprises a sequence set forth in SEQ ID NO: 3.

According to some embodiments, the liver disorder is selected from the group consisting of: non-alcoholic fatty liver disease (NAFLD), non-alcoholic steatohepatitis (NASH), cirrhosis, hepatitis, liver adenoma, insulin hypersensitivity, liver cancer and any combination thereof. Each possibility is a separate embodiment of the invention.

According to some embodiments, the immune cell population is a natural killer (NK) cell population. Additionally or alternatively, the immune cell population is a subpopulation of NK cells According to some embodiments; the NK subpopulation is the $CD56^{dim}$ subpopulation. According to some embodiments; the NK subpopulation is the $CD56^{bright}$ subpopulation. According to some embodiments, the method comprises modulating the activity of the NK cells and/or a subpopulation of NK cells. According to some embodiments, modulating the activity of NK cells comprises enhancing the cytotoxicity of the NK cells. According to some embodiments, enhancing the cytotoxicity of NK cells comprises, but is not limited to, elevating CD107a expression in the NK cell and/or NK subpopulation.

According to some embodiments, the NK cell is a liver NK cell, and the activity of the NK cell is attenuated in patients with a liver disorder. According to yet another embodiment, NK cells from patients with a liver disorder, overexpresses NLGn4.

According to some embodiments, the biological sample comprises a blood sample, a tissue sample, a biological fluid, or any combination thereof.

According to some embodiments, the NLGn4 gene product expression level is detected by Polymerase Chain Reaction (PCR), Reverse-Transcriptase-PCR (RT-PCR), Northern Blot, Real-time PCR, hybridization to an oligonucleotide or any combination thereof. Each possibility is a separate embodiment of the invention.

According to some embodiments, the oligonucleotide comprises deoxyribonucleic acid (DNA), RNA, complementary deoxyribonucleic acid (cDNA), genomic DNA, synthetic oligonucleotide, or any combination thereof. Each possibility is a separate embodiment of the invention.

There is provided herein according to some embodiments, a kit for diagnosing a liver disorder, the kit comprising: means for isolating an immune cell population from a biological sample of a patient; and at least one reagent capable of detecting NLGn4 gene product expression level.

According to some embodiments, the reagent comprises NLGn4 specific primers.

According to some embodiments, the NLGN4 primers were designed to specifically amplify the NLGN4 copy on the X chromosome (Xp22.32-p22.31).

DETAILED DESCRIPTION

Figure 1:
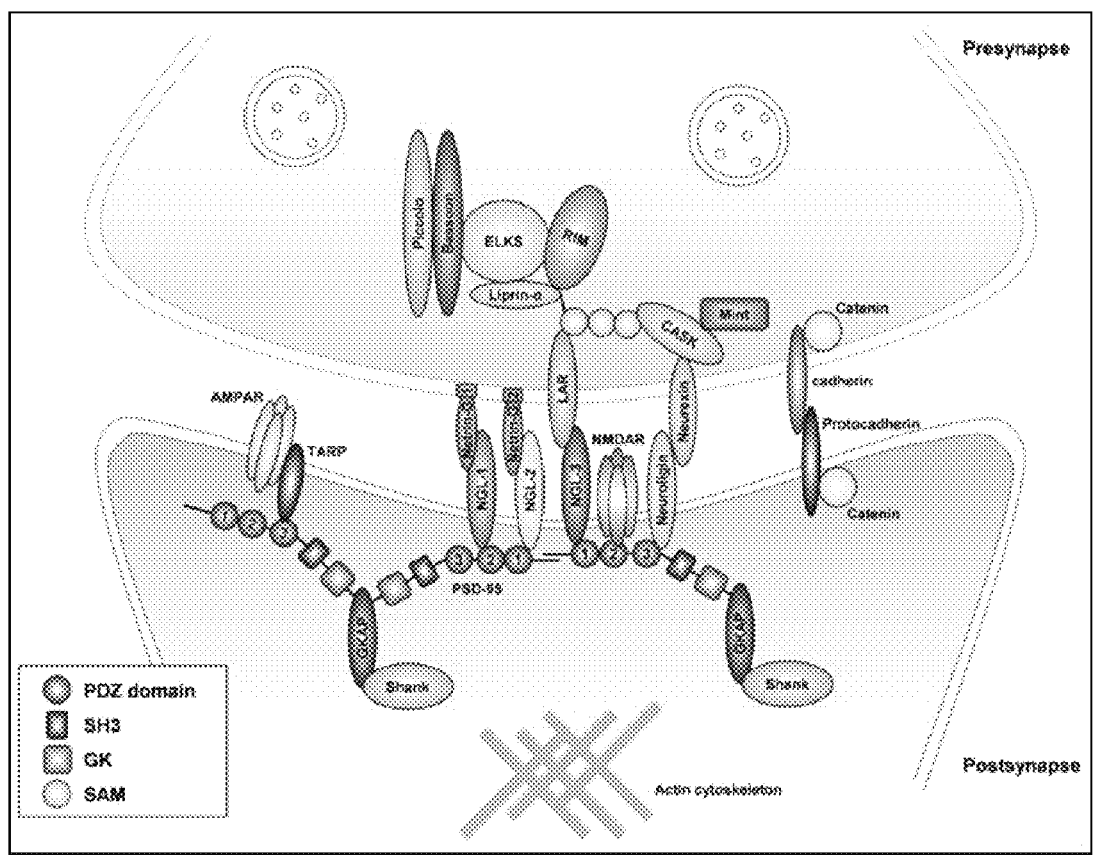
FIG. 1 shows a schematic representation of the Neuroligins and NLG interactions.

The present invention provides methods and compositions for treating and diagnosing liver disorders by activating attenuated natural killer (NK) cells and thereby reducing Hepatic stellate cell (HCSs) induced fibrosis.

In the following description, various aspects of the invention will be described. For the purpose of explanation, specific details are set forth in order to provide a thorough understanding of the invention. However, it will also be apparent to one skilled in the art that the invention may be practiced without specific details being presented herein.

Furthermore, well-known features may be omitted or simplified in order not to obscure the invention.

The following are terms which are used throughout the description and which should be understood in accordance with the various embodiments to mean as follows:

As referred to herein, the terms "liver disorder", "liver disease" and "hepatic disease" are used interchangeably and refer to diseases and disorders that cause the liver to function improperly or stop functioning.

As referred to herein, the term "gene product" refers to a DNA sequence that is transcribed into mRNA that is then translated into a sequence of amino acids characteristic of a specific polypeptide. Hence it is understood by the skilled in the art that the term gene product encompasses non-processed RNA, mRNA, splice variants thereof, corresponding cDNA sequences, polypeptides and proteins.

As used herein the terms "polynucleotide" "polynucleotide molecules", "oligonucleotide", "nucleic acid" and "nucleotide" may interchangeably be used. The terms are directed to polymers of deoxyribonucleotides (DNA), ribonucleotides (RNA), and modified forms thereof in the form of a separate fragment or as a component of a larger construct, linear or branched, single stranded, double stranded, triple stranded, or hybrids thereof. The term also encompasses RNA/DNA hybrids. The polynucleotides may include sense and antisense oligonucleotide or polynucleotide sequences of DNA or RNA. The DNA or RNA molecules may be, for example, but not limited to: complementary DNA (cDNA), genomic DNA, synthesized DNA, recombinant DNA, or a hybrid thereof or an RNA molecule such as, for example, mRNA, shRNA, siRNA, miRNA, and the like. Accordingly, as used herein, the terms "polynucleotide molecules", "oligonucleotide", "polynucleotide", "nucleic acid" and "nucleotide" sequences are meant to refer to both DNA and RNA molecules and refers to nucleic acid or ribonucleic acid sequence.

As used herein the term "complementary" is directed to base pairing between strands of nucleic acids. As known in the art, each strand of a nucleic acid may be complementary to another strand in that the base pairs between the strands are non-covalently connected via two or three hydrogen bonds. Two nucleotides on opposite complementary nucleic acid strands that are connected by hydrogen bonds are called a base pair. According to the Watson-Crick DNA base pairing, adenine (A) forms a base pair with thymine (T) and guanine (G) with cytosine (C). In RNA, thymine is replaced by uracil (U). The degree of complementarity between two strands of nucleic acid may vary, according to the number (or percentage) of nucleotides that form base pairs between the strands. For example, "100% complementarity" indicates that all the nucleotides in each strand form base pairs with the complement strand. For example, "95% complementarity" indicates that 95% of the nucleotides in each strand from base pair with the complement strand. The term sufficient complementarity may include any percentage of complementarity from about 30% to about 100%.

As used herein the term "short hairpin RNA" and "shRNA are used interchangeably and refer to, refer to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region.

As used herein the term "small interfering RNA" and "siRNA" are used interchangeably and refer to a nucleic acid molecule mediating RNA interference or gene silencing. The siRNA inhibits expression of a target gene and provides effective gene knock-down.

As used herein the term "antisense oligonucleotide" refer to nucleic acids, preferably, DNA, RNA or its derivatives, that are complementary to the nucleotide sequences of a target mRNA, characterized in that they binds to the target mRNA and interfere its translation to protein.

As used herein the term "vector" refers to expression constructs engineered to express shRNAs such as, but not limited to, retroviral and lentiviral vectors. Such expression constructs may include one or more inducible promoters, RNA Pol III promoter systems such as U6 snRNA promoters or H1 RNA polymerase III promoters, or other promoters known in the art.

According to an aspect of the invention, provided is a method of treating, attenuating or preventing a liver disorders such as Non-alcoholic fatty liver disease (NAFLD), and Non-alcoholic steatohepatitis (NASH) in a patient in need thereof. Alternatively other disorders such as cirrhosis, hepatitis, liver adenoma, insulin resistance, and liver cancer, or any NK related inflammatory or neoplastic disorder, can be the subject of treatment as well. The clinical implications of NAFLD are derived mostly from its potential to progress to Non-alcoholic steatohepatitis, cirrhosis and liver failure. In accordance, the invention, addresses the long felt need to attenuate the progression of NAFLD into cirrhosis and liver failure by inhibiting NLGn4 expression and thereby modulating the cytotoxic activity of NK cells. According to some embodiments, the invention provides a method for modulating the activity of a natural killer (NK) cell.

According to some embodiments, the method comprises administering to the patient in need thereof, a composition comprising a therapeutically effective amount of an agent capable of inhibiting the expression of the ribonucleic acid (RNA) encoded by NLGn4 nucleic acid molecule. The agent can for example be one or more polynucleotides, capable of hybridizing with the NLGn4 nucleic acid, such an inhibitory nucleic acid that is complementary and specific to at least a portion of NLGn4. The inhibitory nucleic acid can for example be an antisense molecule, an siRNA, or an shRNA. According to some embodiments, the siRNA comprises the sequence set forth in SEQ ID NO: 3. CGGCTGCAACT-TCTCGCGCAA.

The NLGn4 mRNA sequence is set forth in the following sequence SEQ ID NO:2:

```
agaaggggaaggctcctgggctttcaatacatcctcctgaatcatacctcgtttcgggttccctagaaaaatctggacgtgtaaa aagaactcttaacggccgatgcagctcttccaaagctaaggctgccttggagttttcataagaaattgtccctggaggtgttgga tgatcacagcttccttggagcattgcagttgctggaatccagtttcaggattaagggagggctgcctccttgcaatgggctgcc aagaaaacggctgtgcttgttcttaacctcaggctctgtctgtgatcagtctgagagtctctcccaggtctactgctccctggaaa gccctatctctctgcaggctcgcctctgggctttgtctccttggagccacatcactgggacagctgtggatgtggatgcagattt gaaccatgtcacggcccagggactgctatggcttcctttgttgttcacccggtctgcgtcatgttaaactccaatgtcctcctg tggttaactgctcttgccatcaagttcaccctcattgacagccaagcacagtatccagttgtcaacacaaattatggcaaaatcc ggggcctaagaacaccgttacccaatgagatcttgggtccagtggagcagtacttaggggtcccctatgcctcacccccact ggagagaggcggtttcagcccccagaaccccgtcctcctggactggcatccgaaatactactcagtttgctgctgtgtgccc ccagcacctggatgagagatccttactgcatgacatgctgcccatctggtttaccgccaatttggatactttgatgacctatgttc aagatcaaaatgaagactgccttacttaaacatctacgtgccacggaagatgatattcatgatcagaacagtaagaagcccg tcatggtctatatccatggggatcttacatggagggcaccggcaacatgattgacggcagcattttggcaagctacggaaac gtcatcgtgatcaccattaactaccgtctgggaatactagggttttttaagtaccggtgaccaggcagcaaaaggcaactatggg ctcctggatcagattcaagcactgcggtggattgaggagaatgtgggagcctttggcggggaccccaagagagtgaccatct ttggctcgggggctggggcctcctgtgtcagcctgttgaccctgtcccactactcagaaggtctcttccagaaggccatcattc agagcggcaccgccctgtccagctgggcagtgaactaccagccggccaagtacactcggatattggcagacaaggtcggc tgcaacatgctggacaccacggacatggtagaatgcctgcggaacaagaactacaaggagctcatccagcagaccatcacc ccggccacctaccacatagccttcgggccggtgatcgacggcgacgtcatcccagacgaccccagatcctgatggagca aggcgagttcctcaactacgacatcatgctgggcgtcaaccaaggggaaggcctgaagttcgtggacggcatcgtggataa cgaggacggtgtgacgcccaacgactttgacttctccgtgtccaacttcgtggacaacctttacggctaccctgaagggaaag acactttgcgggagactatcaagttcatgtacacagactgggccgataaggaaaacccggagacgcggcggaaaaccctg gtggctctctttactgaccaccagtgggtggccccgccgtggccaccgccgacctgcacgcgcagtacggctcccccacc tacttctatgccttctatcatcactgccaaagcgaaatgaagcccagctgggcagattcggcccatggtgatgaggtcccctat gtcttcggcatcccccatgatcggtcccaccgagctcttcagttgtaacttttccaagaacgacgtcatgctcagcgccgtggtca tgacctactggacgaacttcgccaaaactggtgatccaaatcaaccagttcctcaggataccaagttcattcacacaaaaccca accgctttgaagaagtggcctggtccaagtataatcccaaagaccagctctatctgcatattggcttgaaacccagagtgaga
```

-continued

```
gatcactaccgggcaacgaaagtggctttctggttggaactcgttcctcatttgcacaacttgaacgagatattccagtatgtttc aacaaccacaaaggttcctccaccagacatgacatcatttccctatggcacccggcgatctcccgccaagatatggccaacc accaaacgcccagcaatcactcctgccaacaatcccaaacactctaaggaccctcacaaaacagggcctgaggacacaact gtcctcattgaaaccaaacgagattattccaccgaattaagtgtcaccattgccgtcggggcgtcgctcctcttcctcaacatctt agcttttgcggcgctgtactacaaaaaggacaagaggcgccatgagactcacaggcgccccagtccccagagaaacacca caaatgatatcgctcacatccagaacgaagagatcatgtctctgcagatgaagcagctggaacacgatcacgagtgtgagtc gctgcaggcacacgacacactgaggctcacctgcccgccagactacaccctcacgctgcgccggtcgccagatgacatcc cacttatgacgccaaacaccatcaccatgattccaaacacactgacggggatgcagccttttgcacacttttaacaccttcagtg gaggacaaaacagtacaaatttaccccacggacattccaccactagagtatagctttgccctatttcccttcctatccctctgccc tacccgctcagcaacatagaagagggaaggaaagagagaaggaaagagagagagaaagaaagtctccagaccaggaat gttttttgtcccactgacttaagacaaaaatgcaaaaaggcagtcatcccatcccggcagacccttatcgttggtgttttccagtatt acaagatcaacttctgaccctgtgaaatgtgagaagtacacatttctgttaaaataactgctttaagatctctaccactccaatcga tgtttagtgtgataggacatcaccatttcaaggccccgggtgtttccaacgtcatggaagcagctgacacttctgaaactcagcc aaggacacttgatatttttaattacaatggaagtttaaacatttctttctgtgccacacaatggatggctctccttaagtgaagaaa gagtcaatgagattttgcccagcacatggagctgtaatccagagagaaggaaacgtagaaatttattattaaaagaatggactg tgcagcgaaatctgtacggttctgtgcaaagaggtgttttgccagcctgaactatatttaagagactttgtaaaaagaaaaatgt atatagctgtgagtttaaacaaaaaccacaaacagacaaacaagaaaaaaagcttttattggtgttttcactttgaaagagcttta gcaaggttgtgcttttcattgtgctctgtacgtatataaatatatatatatacacacacacacacacattagtcatatcacctctgt ttcctccccaacaaaagaggcttttcttcttaattacttgtggtaaacaaagacatgggattttcttacatgagattctcatttgtagg aggatgtgatgtcccacagaagacccagacggtctgtgtggcctattcccccgtcaggttgcacaggtgcatgcaagagcat tcttaggagaccactgttttgaaaaacttttgacttgtacgtgttagccttcatgaaattgcagtacagagatgggtccccaaagt ggagtgtatttacagcttgttaaattagagacatgcacacacaaagaatcagtagggagaaacaaaaatacaagtcccgttctg tagctctggcccttttgaatatgtttaggaagagttgcttcccatttcagggccctgccaaaaaagaagaaagcttgcctttggtg gggctatgcccttggagtaaatacggctctgtgttccctagcagctgcgggagggtttggccgatgaagtacctgctcagctt agctaatcagattgaaggaagacatgtgtctttcctttttgtttaagcactcggtccctatttatcagtaagcaggtttttaaaaatct tttatatcatttatgggatcaaacatatgattgtctgaaaacatcacttttttgtggatttgtgtatccggtcaccaaacggtgaatatta tagaagaatgggggaagaaaggatagaatattaaaactgctttgcatgggttttctgggaaattaggataacttcactgagaag acattgaatggaaattattcacccatttttaaattggtgacctagggatcagagatttgtctttccaacagcttgtcattttttcatttctc ttctcattttttcaggaaagttttgagtgttataaggtggaaggaaacatagtagcaatggatacttttttgaaaaattattgcattacc aagaaacagtagccaaagatatttgaagatcatgttcctcggctccattgtgggttattctagaaatccagtcttaaatctctccgc taaagtggacattccccataaaaattgtccagctgcctggctcttttgcaataacaacctttgattactgaatccctacactcaaac tatagtgatatcagtgtttgagagtgacctctagaaaaagaaaagtgtttttagaaatgcgtacaagtcaccccccaaatccta ttgcttatcttgggttaaatttgagagtgattctctgtatataaatatgtgaaatattattatctcaacttagcacacgtgaagcaacat ttctttcctacagagaggtgtcatggtaagatttcattccgaattcattgtttcatagagctatgatcaggccatttctgcaagcaat gtatgacccacctgagcaaccacaaataggctctctgtgaaactacaaaggaagttatgtgtggcatccatgttggtttcgtct gtctgtaatgtgaattccagtatttgtttagtattttccagttgtctcctgctagcaatatgtacagtaacgcgtcaggcttgtgacattt gaataaggaaaaacagagttcctgttaagtgaataacttagcttttacaggggattatgatcaaaagtgattttagtacatcttaa atgatatcttatttctacatggaaagaagttatagaatcttcatagagttctatgagaaaaatatacttgctatctataaaaaagag aaaaagaaaaaaaatgagaaaaaaagtaagaaaaaaaaaaatcctgtcctaggcttttactcttgatcttcaaaggcacgcag
```

-continued

```
ggtttaatggttccttgggttattattttgcagttttgttttttattttgccttaagtaatgatagaagatatatatggccggacacatatg tataaacttttcagcagcatttttaataataaaatatcacagtattttctaaaaaaaaaaaaaaaaaa
```

Additionally or alternatively, the method comprises administering to the patient in need thereof, a composition comprising a therapeutically effective amount of an agent (such as for example an antibody) capable of inhibiting the expression and/or function of NLGn4 protein.

The NLGn4 polypeptide sequence is set forth in the following sequence SEQ ID NO: 4:

According to another aspect of the invention, there is provided a method of modulating the expression of the ribonucleic acid (RNA) encoded by NLGn4 nucleic acid. According to one embodiment, modulating the expression NLGn4 can serve to treat, attenuate or prevent a liver disorder, such as Non-alcoholic fatty liver disease (NAFLD), Non-alcoholic steatohepatitis (NASH), cirrhosis,

```
MSRPQGLLWLPLLFTPVCVMLNSNVLLWLTALAIKFTLIDSQAQYPVVNTNYGKIRGLRTPLPNEILGPV

EQYLGVPYASPPTGERRFQPPEPPSSWTGIRNTTQFAAVCPQHLDERSLLHDMLPIWFTANLDTLMTYVQ

DQNEDCLYLNIYVPTEDDIHDQNSKKPVMVYIHGGSYMEGTGNMIDGSILASYGNVIVITINYRLGILGF

LSTGDQAAKGNYGLLDQIQALRWIEENVGAFGGDPKRVTIFGSGAGASCVSLLTLSHYSEGLFQKAIIQS

GTALSSWAVNYQPAKYTRILADKVGCNMLDTTDMVECLRNKNYKELIQQTITPATYHIAFGPVIDGDVIP

DDPQILMEQGEFLNYDIMLGVNQGEGLKFVDGIVDNEDGVTPNDFDFSVSNFVDNLYGYPEGKDTLRETI

KFMYTDWADKENPETRRKTLVALFTDHQWVAPAVATADLHAQYGSPTYFYAFYHHCQSEMKPSWADSAHG

DEVPYVFGIPMIGPTELFSCNFSKNDVMLSAVVMTYWTNFAKTGDPNQPVPQDTKFIHTKPNRFEEVAWS

KYNPKDQLYLHIGLKPRVRDHYRATKVAFWLELVPHLHNLNEIFQYVSTTTKVPPPDMTSFPYGTRRSPA

KIWPTTKRPAITPANNPKHSKDPHKTGPEDTTVLIETKRDYSTELSVTIAVGASLLFLNILAFAALYYKK

DKRRHETHRRPSPQRNTTNDIAHIQNEEIMSLQMKQLEHDHECESLQAHDTLRLTCPPDYTLTLRRSPDD

IPLMTPNTITMIPNTLTGMQPLHTFNTFSGGQNSTNLPHGHSTTRV
```

According to some embodiments, the NK cells are liver NK cells which are attenuated in patients having a liver disorder. According to yet another embodiment, the liver disorder is characterized by overexpression of NLGn4 RNA. Such overexpression can attenuate NK cell activity.

According to some embodiments inhibiting the expression of NLGn4 modulates the function of the NK cell for example by activating the NK cell and/or the CD56$^{dim}$ NK cell subset. As a result of NK activation, the activity of hepatic stellate cells (HSCs) and hence fibrosis is reduced. In addition, and according to yet another embodiment, modulating and/or activating the NK cells increases the apoptosis of the HSCs.

According to yet another embodiment there is provided a method for modulating the activity of a natural killer (NK) cell and/or treating, preventing and/or attenuating a liver disorder by administering to a patient a composition comprising a GLUT4 antagonist. Such antagonist can according to the present invention inhibit GLUT4 mediated NLGn4 expression. The antagonist can be selected from the group comprising Ketamine, Amantadine, Phencyclidine, Nitrous oxide, Dextromethorphan (and dextrorphan), Memantine, Ethanol, Riluzole (used in ALS), Xenon, HU-211 (also a cannabinoid), Lead (Pb2+), Conantokins, and Huperzine A. According to an alternative embodiment administering a NMDAR (also known as GLUT4) agonist can increase GLUT4 mediated NLGn4 expression and as a result attenuate NK cell activity. Examples of a GLUT4 agonists are Aminocyclopropanecarboxylic acid, D-Cycloserine, cis-2, 3-Piperidinedicarboxylic acid, L-aspartate, L-alanine, Quinolinate, Homocysterate, D-serine, and ACPL.

hepatitis, liver adenoma, insulin resistance, a liver cancer, any NK related inflammatory or neoplastic disorder, or any combination thereof.

According to another embodiment, modulating the expression of NLGn4 comprises contacting the immune cell, such as an NK cell and/or a CD56$^{dim}$ NK cell subset, with a composition comprising an effective amount of an agent that inhibits NLGn4 expression. Such agent can for example be an inhibitory nucleic acid that is complementary and specific to at least a portion of the NLGn4 nucleic acid molecule.

According to yet another embodiment, the inhibitory nucleic acid can for example be an antisense molecule, an siRNA, or an shRNA.

Inhibiting NLGn4 can according to the present invention enhance the cytotoxicity of the NK cells and or specific NK cell subpopulations. According to certain embodiments enhancing the cytotoxicity comprises enhancing the expression of CD107a on said NK cell.

In certain liver disorders NK cell function can be attenuated. According to the present invention such attenuation can be a result of NLGn4 overexpression. In accordance, inhibiting the expression of NLGn4 modulates and/or activates the function of attenuated NK cell. In turn, activating the NK cell may reduce HSC activity and/or increase their apoptosis.

According to yet another aspect of the invention there is provided a method of diagnosing or monitoring a liver disorder and/or the severity of a liver disorder in a patient such as Non-alcoholic fatty liver disease (NAFLD), Non-alcoholic steatohepatitis (NASH), cirrhosis, hepatitis, a liver adenoma, insulin resistance, a liver cancer, any NK related inflammatory or neoplastic disorder, or any combination thereof. The method comprises, according to one embodiment, detecting the expression level of a ribonucleic acid (RNA) encoded by NLGn4 nucleic acid molecule in a biological sample, such as a blood sample, a tissue sample and/or a biological fluid, of a patient.

According to some embodiments, the method further comprises isolating the RNA from the biological sample prior to detecting the NLGn4 RNA expression level. The detection of NLGn4 expression comprises Polymerase Chain Reaction (PCR), Reverse-Transcriptase-PCR (RT-PCR), Northern Blot, Real-time PCR, Flow Cytometry (FACS) or any combination thereof.

Alternatively, the expression level of NLGn4 is detected by hybridization to an oligonucleotide such as a deoxyribonucleic acid (DNA), an RNA, complementary deoxyribonucleic acid (cDNA), a genomic DNA, a synthetic oligonucleotide, or any combination thereof.

According to yet another aspect of the invention, there is provided a pharmaceutical composition comprising a therapeutically effective amount of an agent that inhibits the expression or function of NLGn4.

The agent can be one or more polynucleotides, capable of hybridizing with said nucleic acid. For example the agent can be an inhibitory nucleic acid, such as an antisense molecule, an siRNA, or an shRNA that is complementary and specific to at least a portion of said NLGn4 nucleic acid molecule According to some embodiments, the pharmaceutical composition further comprises a vector capable of expressing the inhibitory nucleic acid molecule. Non-limiting examples of vectors comprise lentiviral vectors, retroviral vectors, plasmids as well as other suitable vectors.

According to another embodiment, the composition comprises or additionally comprises a GLUT4 antagonist. Such antagonist can according to the present invention inhibit GLUT4 mediated NLGn4 expression. The antagonist can be selected from the group consisting of Ketamin, Amantadine, Phencyclidine, Nitrous oxide, Dextromethorphan (and dextrorphan), Memantine, Ethanol, Riluzole (used in ALS), Xenon, HU-211 (also a cannabinoid), Lead (Pb2+), Conantokins, and Huperzine A. According to an alternative embodiment administering a GLUT4 agonist can increase GLUT4 mediated NLGn4 expression and as a result attenuate NK cell activity. Examples of a GLUT4 agonists are alanine, Aminocyclopropanecarboxylic acid, D-Cycloserine, cis-2,3-Piperidinedicarboxylic acid, L-aspartate, L-alanine, Quinolinate, Homocysterate, D-serine, and ACPL.

According to yet another aspect of the invention, there is provided a kit for prevention, treatment or attenuation of a liver disorder such as, but not limited to, Non-alcoholic fatty liver disease (NAFLD), Non-alcoholic steatohepatitis (NASH), cirrhosis, hepatitis, a liver adenoma, insulin resistance, a liver cancer, any NK related inflammatory or neoplastic disorder, or any combination thereof. The kit comprises the pharmaceutical composition as essentially described above and a pharmaceutically acceptable carrier.

According to yet another aspect of the invention, there is provided a kit for diagnosing a liver disorder such as but not limited to Non-alcoholic fatty liver disease (NAFLD), Non-alcoholic steatohepatitis (NASH), cirrhosis, hepatitis, a liver adenoma, insulin hypersensitivity, a liver cancer or any combination thereof. The kit comprises at least one reagent capable of detecting the expression of a nucleic acid in a biological sample such as a blood sample, a tissue sample, and/or a biological fluid.

According to some embodiments, the reagent comprises NLGn4 specific primers. According to some embodiments, the NLGn4 specific primers are selected from the group set forth in table 1 below.

TABLE 1

| NLGn4 specific primers | | |
|---|---|---|
| Exon | Forward | Reverse |
| 2.1 | AAAGCCCTATCTCTCTGCAGG (SEQ ID NO: 5) | TGAGTAGTATTTCGGATGCCAG (SEQ ID NO: 6) |
| 2.2 | AAGAACACCGTTACCCAATGAG (SEQ ID NO: 7) | GAGACATTATAAAACCCTCCTAG (SEQ ID NO: 8) |
| 3 | TTAGCATTGGTGAGTCAGTGTG (SEQ ID NO: 9) | CCGTCAAAACGAGAAGTGGACT (SEQ ID NO: 10) |
| 4 | CTTTTTCTATTTGGCCACCA (SEQ ID NO: 11) | TTCTTGGTTCAGGGTATTTGC (SEQ ID NO: 12) |
| 5.1 | AGCTGCATTTCTGTCCTGTG (SEQ ID NO: 13) | TCTCCCGCAAAGTGTCTTTC (SEQ ID NO: 14) |
| 5.2 | CCAACTTCGTGGACAACCTT (SEQ ID NO: 15) | ACCCAACACGAAGATGAAC (SEQ ID NO: 16) |
| 6.1 | CACGTCACATGTGGAAGAGT (SEQ ID NO: 17) | GACGGCAATGGTGACACTTA (SEQ ID NO: 18) |
| 6.2 | TCCTCATTGAAACCAAACGA (SEQ ID NO: 19) | AACATTCCTGGTCTGGAGAC (SEQ ID NO: 20) |

The following examples are presented to provide a more complete understanding of the invention. The specific techniques, conditions, materials, proportions and reported data set forth to illustrate the principles of the invention are exemplary and should not be construed as limiting the scope of the invention.

EXAMPLES

Example 1

Methods used for evaluating the role of NLGn4 in NK activity a) Knockdown of NLGn4: Lentivirus expressing NLGn4 siRNA were used to infect NK cells of either mouse or human origin and thereby inhibiting NLGn4 expression.

b) NLGn4 expression: NLGn4 expression level was evaluated by real-time PCR. In short, RNA was extracted from the cells using Tri Reagent. The extracted RNA was converted to cDNA using random hexamers and reverse transcriptase. NLGn4 expression level was assessed by real time PCR using NLGn4 specific primers. The results were normalized to the expression levels of α-actin using α-actin specific primers.

c) Isolation of NK cells from human blood samples: Blood samples obtained from patients were centrifuged at 4000 rpm for 5 min. After centrifugation, the buffy coat fraction of the blood containing most of the leukocytes was collected and NK cells were isolated using the RosetteSep NK isolation kit according to manufactures instruction.

d) Flow cytometry using FACS analysis of CD107a, NLGn4, α-SMA, annexin.

Example 2

NLGn4 is Overexpressed in Patients with Cirrhosis and in a Non-alcoholic Fatty Liver Disease (NAFLD) Mouse Model Human peripheral blood cells (PBLs) were isolated in accordance with Example 1c from cirrhotic patients and healthy controls, as well as from NAFLD/control mice. RNA was extracted and converted into cDNA and a gene array analysis was performed using an Affymetrix expression array. The results were collated in order to identify the genes having an at least two-fold change in the expression profile. It was found that NLGn4 showed the most significant change in that an approximately 4-fold up-regulation was observed among the cirrhotic patients.

Example 3

NLGn4 Expression Can Be Reduced Using siRNA

Figure 2:
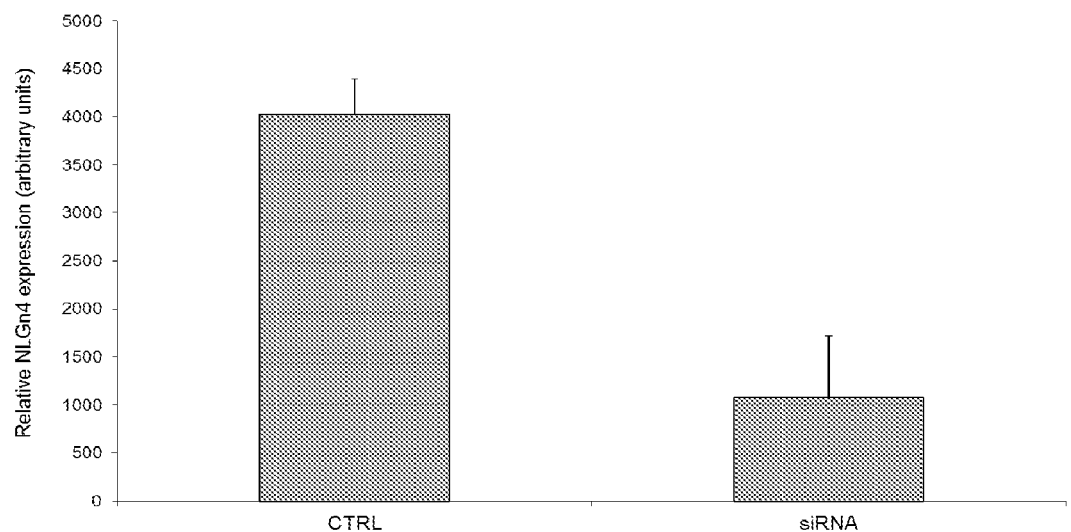
FIG. 2 shows NLGn4 expression upon NLGn4 siRNA expression in mouse NK cells.

Mouse liver NK cells were infected with a lentiviral vector expressing an siRNA against NLGn4 or a scrambled control. 48 hours post infection, the cells were harvested, RNA extracted and converted into cDNA in accordance with example 1b. NLGn4 Expression levels in cells infected with the NLGn4 siRNA or the scrambled control were evaluated using real-time PCR using primes specific for NLGn4. The expression levels obtained were normalized to those obtained for α-actin. As seen in FIG. 2, a significant reduction in NLGn4 expression is observed in cells infected with the siRNA expressing vector, as compared to the control.

Example 4

Figure 3A:
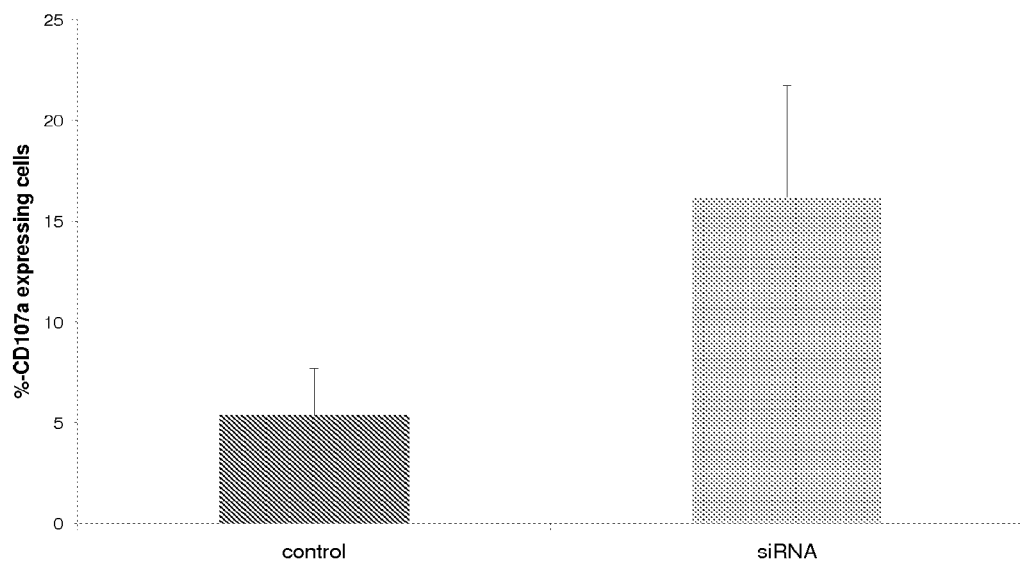
FIG. 3A presents the percentage of viable NK cells expressing CD107a (control or infected with NLGn4 siRNA) co-cultured with HSCs isolated from a WT mouse.

NLGn4 Knockdown (KD) Increases NK Activation and Hepatic Stellate Cell (HSC) Apoptosis and Reduces HSC Activity NK cells obtained from mice livers were pre-incubated with IL2 in order to obtain a mature NK cell population. Following infection with the NLGn4 siRNA or with the scrambled control, the cells were co-cultured with freshly isolated HSC from a NAFLD mouse model. The activity of the NK cells was evaluated by the expression of CD107a, a marker of active NK cells. The percentage of viable NK cells expressing CD107a was evaluated by FACS using an anti-CD107a antibody and gating annexin negative cells. As seen in FIG. 3A, as a result of the KD of NLGn4 a significant increase in CD107a positive cells amongst the viable NK cell population was observed.

Figure 3B:
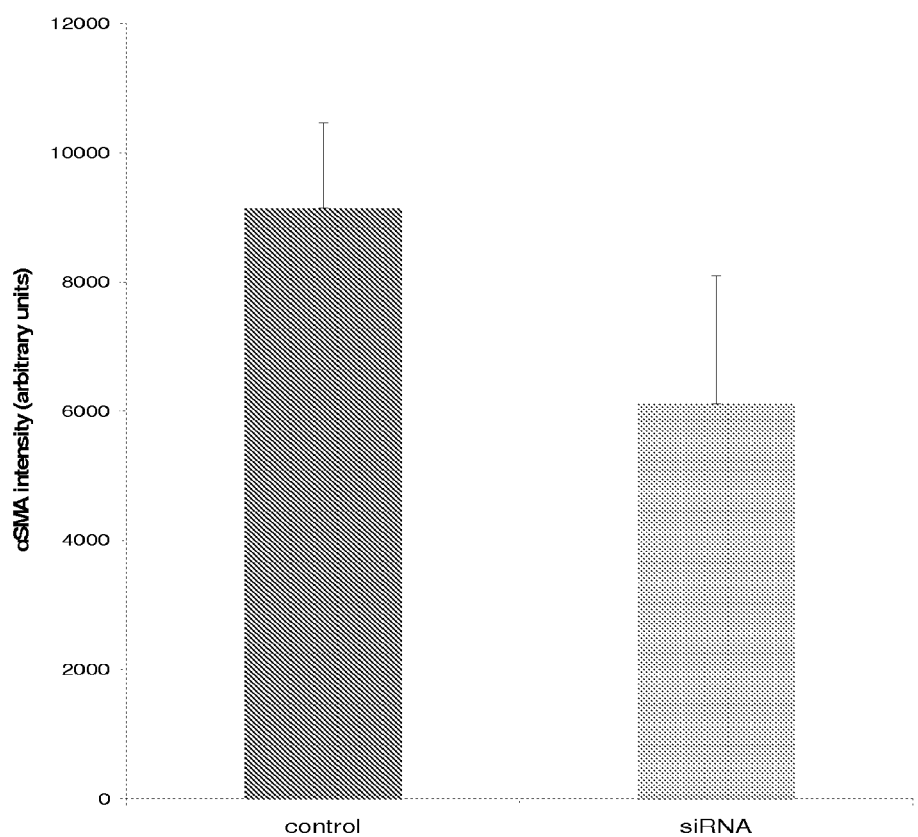
FIG. 3B presents αSMA intensity of HSCs co-cultured with control or NLGn4 siRNA infected NK cells.
Figure 3C:
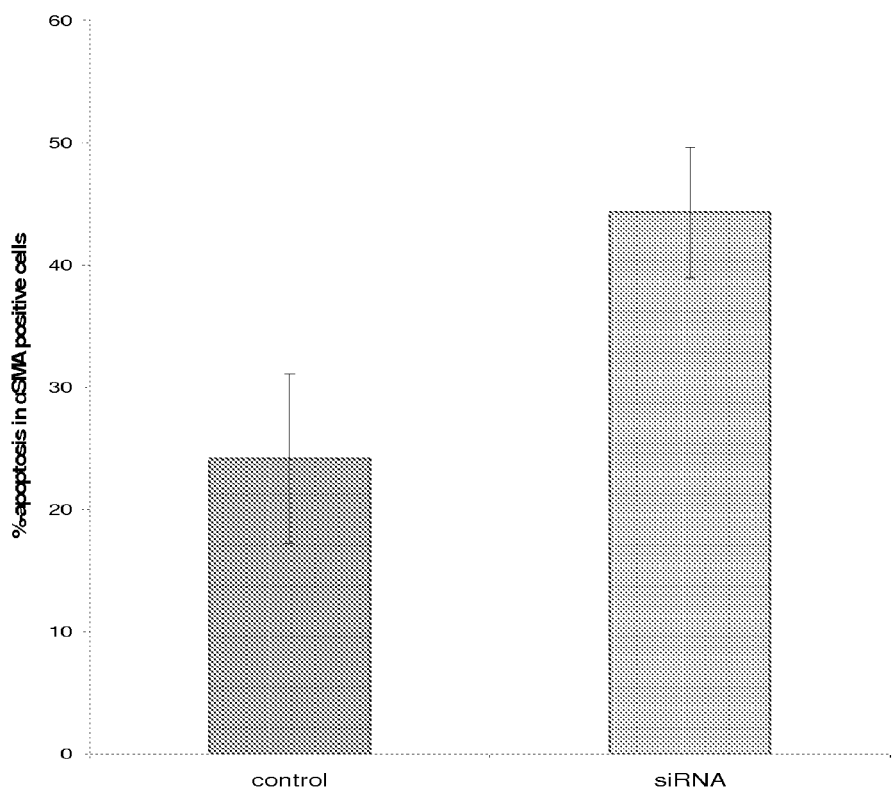
FIG. 3C shows apoptosis of HCS upon co-culturing with control or NLGn4 siRNA infected NK cells.

The impact of NK cell activation by NLGn4 KD on HCSs was evaluated by co-culturing the HSCs with the control or the NLGn4 KD NK cells and assessing αSMA intensity (marker of HSC activation). α-SMA intensity was significantly decreased upon co-culture with NLGn4 KD NK cells (FIG. 3B) and amongst the α-SMA expressing cells an increase in apoptosis was observed (FIG. 3C).

Example 5

Figure 4:
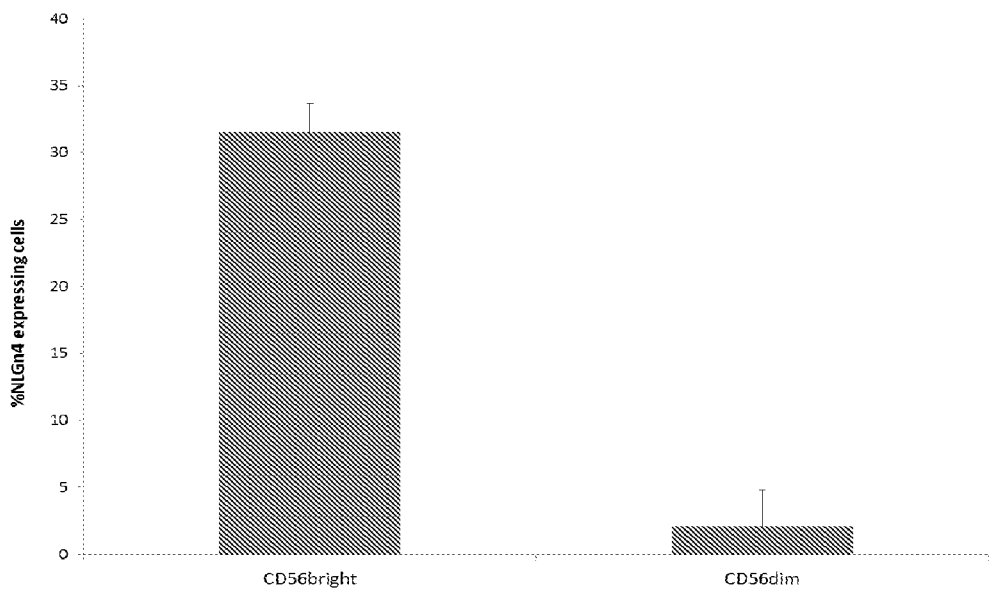
FIG. 4 presents NLGn4 expression in the $CD56^{bright}$ and $CD56^{dim}$ NK subpopulation.

NLGn4 is Expression is High in the CD56$^{bright}$ NK Subpopulation and Low in the CD56$^{dim}$ NK Subpopulation Human peripheral blood cells (PBLs) were isolated in accordance with Example 1c. The isolated NK cells were then co-stained with an anti-CD56 antibody and with an anti-NLGn4 antibody. FACS analysis of the cells showed that NLGn4 is significantly more abundant in the CD56$^{bright}$ cell population as compared to the CD56$^{dim}$ cell population (FIG. 4).

Example 6

Figure 5:
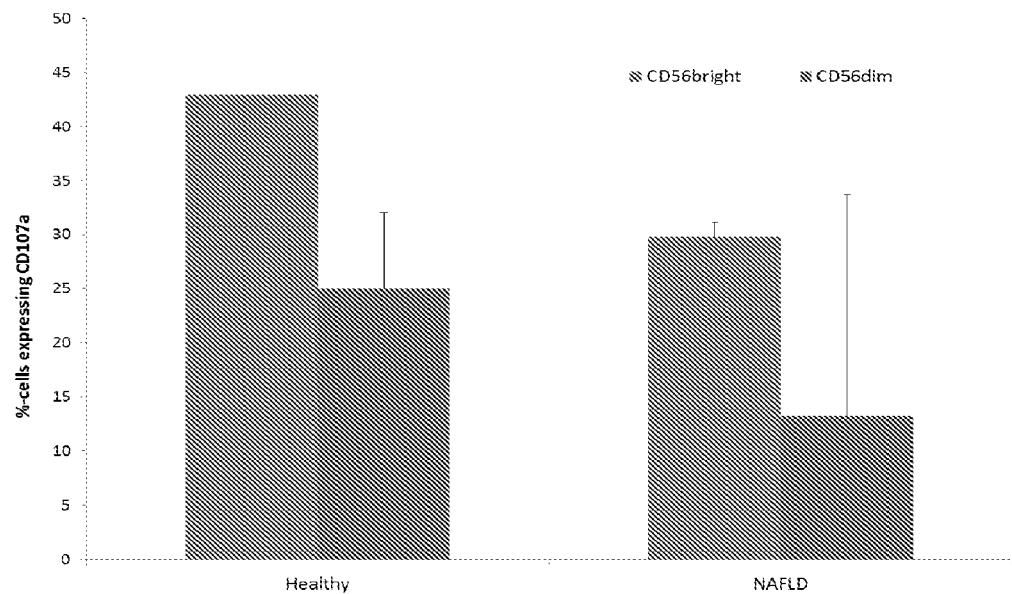
FIG. 5 presents CD107a expression in NAFLD patients and healthy controls.

NK activity as Assessed by CD107a Expression is Attenuated in NAFLD Patients Human peripheral blood cells (PBLs) from NAFLD patients (n=9) and healthy controls (n=3) were isolated in accordance with Example 1c. The isolated NK cells were then co-stained with an anti-CD56 antibody and with an anti-CD107a antibody. FACS analysis showed that CD107a expression was reduced, corresponding to an attenuated NK activity in NAFLD patients (FIG. 5).

Example 7

Figure 6:
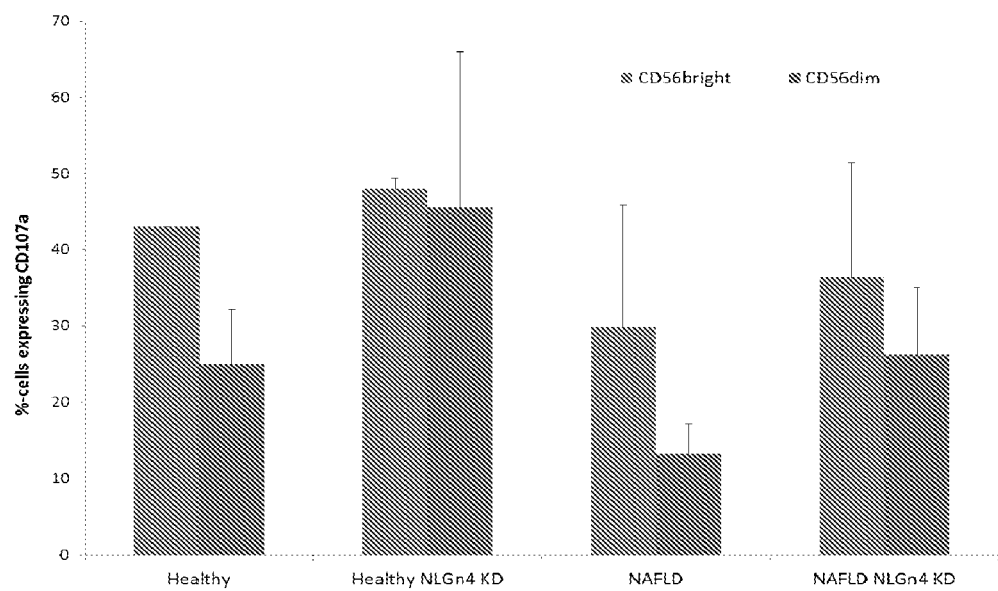
FIG. 6 presents on NK cell activity as assessed by CD107a expression.

NLGn4 KD Increases CD56$^{dim}$ NK Cell Activity as Assessed by CD107a Expression Human peripheral blood cells (PBLs) from NAFLD patients (n=9) and healthy controls (n=3) were isolated in accordance with Example 1c. The isolated NK cells were then infected with a lentiviral vector expressing an siRNA against human NLGn4 or a scrambled control. NK activity in response to NLGn4 KD was assessed by CD107a expression. That is, the isolated NK cells were co-stained with an anti-CD56 antibody and with an anti-CD 107a antibody. As seen from FIG. 6, CD107a expression was significantly elevated in the CD56$^{dim}$ subpopulation. This might suggest that reducing the expression of NLGn4 can effectively enhance NK cytotoxicity. Since NLGn4 is primarily expressed in CD 56$^{bright}$ cells it may be suggested that overexpression of NLGn4 by CD56$^{bright}$ cells inhibits the cytotoxicity of CD56$^{dim}$ cells.

Example 8

NLGn4 KD Does Not Alter NK Viability

Figure 7A:
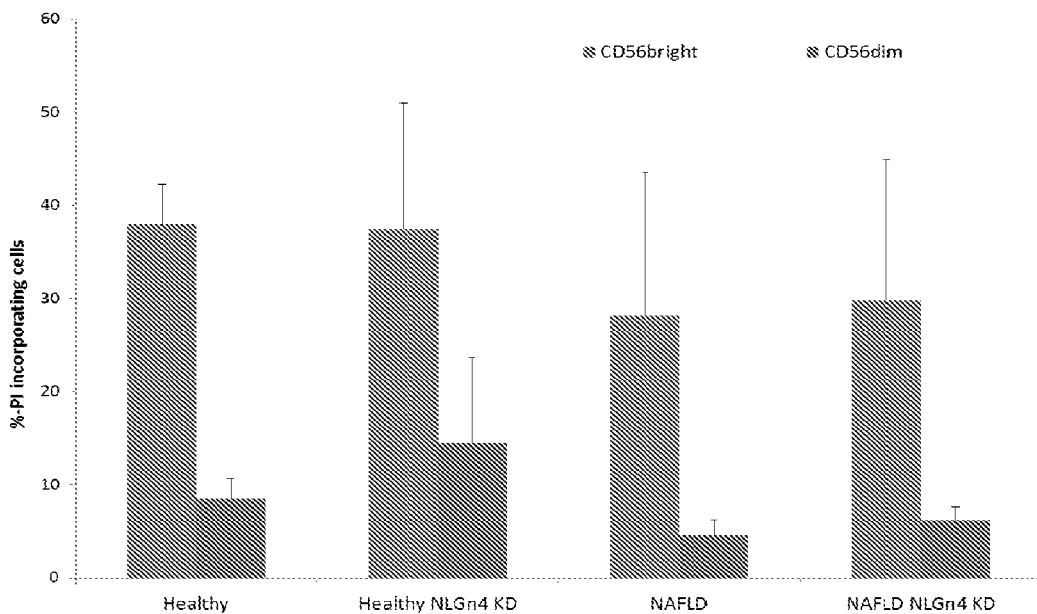
FIG. 7A presents the effects of NLGn4 KD on NK cell viability, as estimated by PI incorporation.
Figure 7B:
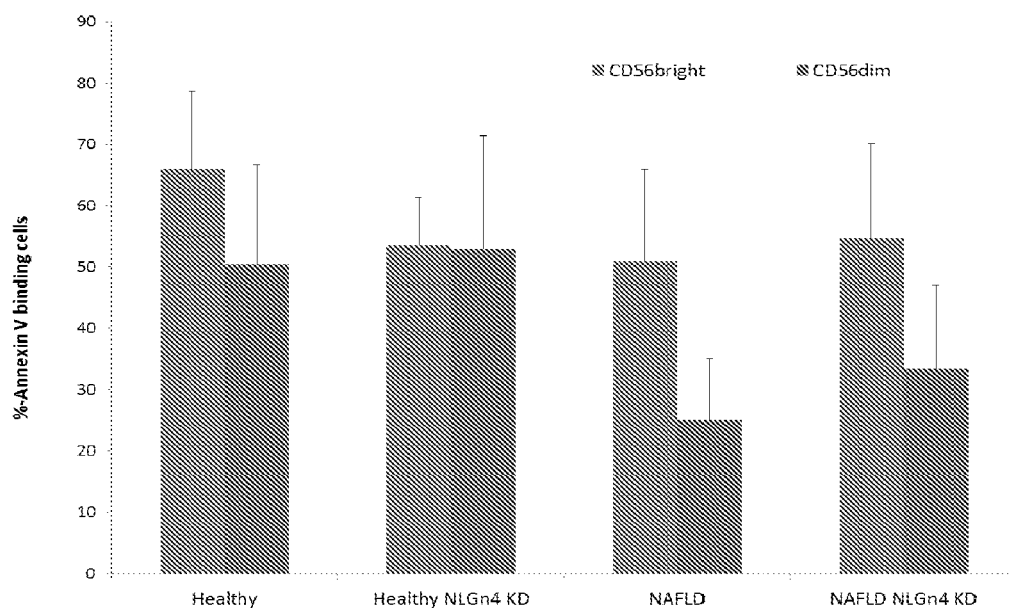
FIG. 7B presents the effects of NLGn4 KD on NK cell viability, as estimated by annexin binding.

Human peripheral blood cells (PBLs) from NAFLD patients (n=9) and healthy controls (n=3) were isolated in accordance with Example 1c. The isolated NK cells were then infected with a lentiviral vector expressing an siRNA against human NLGn4 or a scrambled control. The viability of the NK cells was assessed by FACS analysis estimating annexin binding and PI incorporation. As seen in FIGS. 7A and B, NLGn4 knockdown did not alter cellular viability neither of CD56$^{bright}$ nor of CD56$^{dim}$ NK cells in either NAFLD patients or healthy controls. This indicates that CD56$^{dim}$ cytotoxicity toward foreign cells is elevated without compromising self-recognition.

Example 9

NLGn4 Overexpression Correlates with High Insulin Levels

Figure 8:
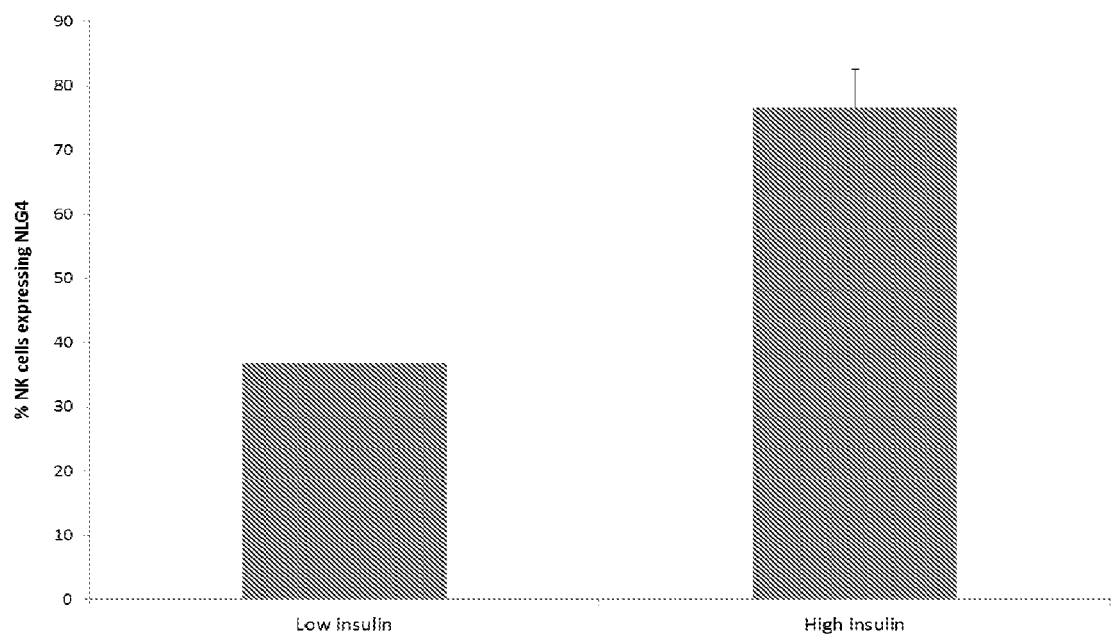
FIG. 8 shows the correlation between insulin and NLGn4 expression.

Human peripheral blood cells (PBLs) from patients with low insulin levels (n=3) and patients with high insulin levels controls (n=3) were isolated in accordance with Example 1c. The isolated NK cells were stained with an anti-NLGn4 antibody. FACS analysis of the cells showed that NLGn4 was significantly higher in NK cells from patients with high insulin levels as compared to those with low insulin levels (FIG. 8). This may suggest that the increased prevalence of NAFLD among insulin resistant subjects may be due to insulin mediated NLGn4 overexpression.

Example 10

Treatment of Mice With a GLUT4 Agonist Elevates NLGn4 Expression

NK cells from livers of mice treated with the GLUT4 agonist alanine or control mice are isolated. The isolated NK cells are then co-stained with an anti-CD56 antibody and with an anti-NLGn4 antibody.

Example 11

Treatment of Mice With a GLUT4 Antagonist Reduces NLGn4 Expression

NK cells from livers of mice treated with the GLUT4 agonist or control mice are isolated. The isolated NK cells are then co-stained with an anti-CD56 antibody and with an anti-NLGn4 antibody.

The invention claimed is:

1. A method of treating and/or attenuating hepatocellular carcinoma in a subject, the method comprising administering to the subject a composition comprising a therapeutically effective amount of an agent capable of specifically inhibiting expression of a human NLGn4 gene product, said human NLGn4 gene product comprising SEQ ID NO: 2, and said agent comprising one or more siRNAs having a length of 20-25 base pairs and a sequence with at least 95% complementarity to at least a portion of SEQ ID NO: 2, thereby treating and/or attenuating the hepatocellular carcinoma.

2. The method of claim 1, wherein the siRNA has a sequence set forth in SEQ ID NO: 3.

3. The method of claim 1, wherein the NLGn4 gene product is encoded by a nucleic acid sequence comprising SEQ ID NO: 1.

4. The method of claim 1, wherein inhibiting the expression of the NLGn4 gene product reduces activity of hepatic stellate cells.

5. The method of claim 1, wherein inhibiting the expression of the NLGn4 gene product increases apoptosis of the hepatic stellate cells.

6. The method of claim 1, wherein said composition further comprises a GLUT4 antagonist.

* * * * *